(12) United States Patent
Fleury et al.

(10) Patent No.: US 9,593,110 B2
(45) Date of Patent: *Mar. 14, 2017

(54) NEPRILYSIN INHIBITORS

(71) Applicants: Melissa Fleury, San Francisco, CA (US); Anne-Marie Beausoliel, San Mateo, CA (US); Adam D. Hughes, Belmont, CA (US); Daniel D. Long, San Francisco, CA (US); Donna A. A. Wilton, San Francisco, CA (US)

(72) Inventors: Melissa Fleury, San Francisco, CA (US); Anne-Marie Beausoliel, San Mateo, CA (US); Adam D. Hughes, Belmont, CA (US); Daniel D. Long, San Francisco, CA (US); Donna A. A. Wilton, San Francisco, CA (US)

(73) Assignee: Theravence Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/608,686

(22) Filed: Jan. 29, 2015

(65) Prior Publication Data

US 2015/0210690 A1    Jul. 30, 2015

Related U.S. Application Data

(60) Provisional application No. 62/016,742, filed on Jun. 25, 2014, provisional application No. 61/933,406, filed on Jan. 30, 2014.

(51) Int. Cl.
*C07D 249/04*    (2006.01)
*C07D 231/14*    (2006.01)
*C07D 263/34*    (2006.01)
*C07D 271/07*    (2006.01)
*C07D 213/81*    (2006.01)
(Continued)

(52) U.S. Cl.
CPC .......... *C07D 471/04* (2013.01); *A61K 31/415* (2013.01); *A61K 31/4192* (2013.01); *A61K 31/4196* (2013.01); *A61K 31/42* (2013.01); *A61K 31/421* (2013.01); *A61K 31/425* (2013.01); *A61K 31/4245* (2013.01); *A61K 31/437* (2013.01); *A61K 31/44* (2013.01); *A61K 31/4985* (2013.01); *A61K 31/505* (2013.01); *A61K 45/06* (2013.01); *C07C 229/34* (2013.01); *C07C 271/22* (2013.01); *C07D 213/81* (2013.01); *C07D 231/14* (2013.01); *C07D 231/18* (2013.01); *C07D 231/20* (2013.01); *C07D 233/70* (2013.01); *C07D 233/90* (2013.01); *C07D 235/08* (2013.01); *C07D 237/14* (2013.01); *C07D 239/28* (2013.01); *C07D 239/34* (2013.01); *C07D 249/04* (2013.01); *C07D 249/10* (2013.01); *C07D 249/12* (2013.01); *C07D 249/18* (2013.01); *C07D 261/12* (2013.01); *C07D 261/18* (2013.01); *C07D 263/18* (2013.01); *C07D 263/34* (2013.01); *C07D 271/07* (2013.01); *C07D 275/03* (2013.01); *C07D 295/10* (2013.01); *C07D 309/40* (2013.01); *C07D 319/06* (2013.01); *C07D 401/04* (2013.01); *C07D 403/04* (2013.01); *C07D 403/06* (2013.01); *C07D 403/12* (2013.01); *C07D 405/12* (2013.01); *C07D 405/14* (2013.01)

(58) Field of Classification Search
CPC .. C07D 249/06; C07D 249/04; C07D 487/04; C08K 5/3472; A61Q 17/04
USPC ............ 548/255, 266.8; 514/210.2; 546/323
See application file for complete search history.

(56) References Cited

U.S. PATENT DOCUMENTS 4,189,604 A    2/1980    Umezawa et al.
4,206,232 A    6/1980    Ondetti et al.
(Continued)

OTHER PUBLICATIONS

Ksander et al., "Dicarboxylic acid dipeptide neutral endopeptidase inhibitors", Journal of Medicinal Chemistry, 38(10): 1689-1700 (1995).
(Continued)

*Primary Examiner* — Alicia L Otton
*Assistant Examiner* — Sagar Patel
(74) *Attorney, Agent, or Firm* — Jeffrey A. Hagenah; Wendy Petka

(57) ABSTRACT

In one aspect, the invention relates to compounds having the formula I:

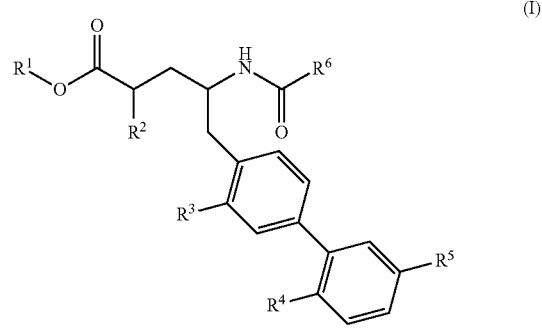

where $R^1$-$R^6$ are as defined in the specification, or a pharmaceutically acceptable salt thereof. These compounds have neprilysin inhibition activity. In another aspect, the invention relates to pharmaceutical compositions comprising these compounds; methods of using these compounds; and processes and intermediates for preparing these compounds.

25 Claims, No Drawings

(51) Int. Cl.

| | | |
|---|---|---|
| A61K 31/422 | (2006.01) | |
| A61K 31/4192 | (2006.01) | |
| A61K 31/4196 | (2006.01) | |
| A61K 31/42 | (2006.01) | |
| A61K 31/4245 | (2006.01) | |
| C07D 471/04 | (2006.01) | |
| C07D 261/18 | (2006.01) | |
| C07D 249/10 | (2006.01) | |
| A61K 31/415 | (2006.01) | |
| A61K 31/421 | (2006.01) | |
| A61K 31/44 | (2006.01) | |
| C07D 239/28 | (2006.01) | |
| A61K 31/505 | (2006.01) | |
| C07D 275/03 | (2006.01) | |
| A61K 31/425 | (2006.01) | |
| A61K 31/437 | (2006.01) | |
| C07D 403/04 | (2006.01) | |
| A61K 31/4985 | (2006.01) | |
| C07D 403/12 | (2006.01) | |
| A61K 45/06 | (2006.01) | |
| C07D 405/14 | (2006.01) | |
| C07D 309/40 | (2006.01) | |
| C07C 271/22 | (2006.01) | |
| C07D 319/06 | (2006.01) | |
| C07D 231/18 | (2006.01) | |
| C07D 231/20 | (2006.01) | |
| C07D 233/70 | (2006.01) | |
| C07D 233/90 | (2006.01) | |
| C07D 401/04 | (2006.01) | |
| C07D 235/08 | (2006.01) | |
| C07D 403/06 | (2006.01) | |
| C07D 237/14 | (2006.01) | |
| C07D 239/34 | (2006.01) | |
| C07D 405/12 | (2006.01) | |
| C07C 229/34 | (2006.01) | |
| C07D 249/12 | (2006.01) | |
| C07D 249/18 | (2006.01) | |
| C07D 261/12 | (2006.01) | |
| C07D 263/18 | (2006.01) | |
| C07D 295/10 | (2006.01) | |

(56) References Cited

U.S. PATENT DOCUMENTS

| | | |
|---|---|---|
| 4,374,829 A | 2/1983 | Harris et al. |
| 4,513,009 A | 4/1985 | Roques et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 12/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 9,126,956 B2* | 9/2015 | Fleury ............... A61K 31/415 |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0213806 A1* | 8/2012 | Fleury ............... C07D 295/10 424/184.1 |
| 2012/0289710 A1 | 11/2012 | Hook et al. |
| 2012/0309724 A1 | 12/2012 | Fleury et al. |
| 2013/0323271 A1 | 12/2013 | Mammen et al. |
| 2013/0330365 A1 | 12/2013 | Hughes et al. |
| 2013/0330366 A1 | 12/2013 | Hughes et al. |
| 2014/0045906 A1 | 2/2014 | Fleury et al. |
| 2014/0256702 A1 | 9/2014 | Fenster et al. |
| 2015/0209352 A1* | 7/2015 | Fleury ............... A61K 31/505 514/256 |

OTHER PUBLICATIONS

Misawa et al., "Structure-based design of dipeptide derivatives for the human neutral endopeptidase", Bioorganic & Medicinal Chemistry, 19: 5935-5947 (2011).

* cited by examiner

NEPRILYSIN INHIBITORS

CROSS-REFERENCE TO RELATED APPLICATIONS

This application claims the benefit of U.S. Provisional Application No. 61/933,406 filed on Jan. 30, 2014 and U.S. Provisional Application No. 62/016,742 filed on Jun. 25, 2014; the entire disclosures of which are incorporated herein by reference.

BACKGROUND OF THE INVENTION

Field of the Invention

The present invention relates to novel compounds having neprilysin-inhibition activity. The invention also relates to pharmaceutical compositions comprising these compounds, processes and intermediates for preparing these compounds and methods of using these compounds to treat diseases such as hypertension, heart failure, pulmonary hypertension, and renal disease.

State of the Art

Neprilysin (neutral endopeptidase, EC 3.4.24.11) (NEP), is an endothelial membrane bound $Zn^{2+}$metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) Exp. Opin. Ther. Patents 9(12): 1665-1677.

In spite of these compounds however, there remains a need for NEP inhibitors that have improved potency, different metabolic and cleavage properties, and/or having improved oral absorption. This invention is directed to that need.

SUMMARY OF THE INVENTION

The present invention provides novel compounds that have been found to possess neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

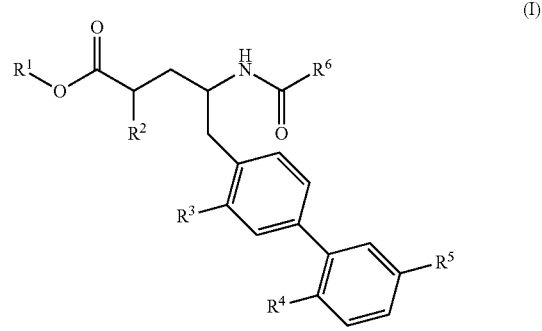

(I)

where:

$R^1$ is H, —$C_{1-8}$alkyl, —$CH(CH_3)OC(O)$—O-cyclohexyl, —$(CH_2)_2$-morpholinyl, or —$CH_2$-5-methyl-[1,3]dioxol-2-one;

$R^2$ is —$CH_2$—O—$R^{20}$, —$C_{0-1}$alkylene-NHC(O)—$R^{21}$, —$C_{0-3}$alkylene-$NR^{22}R^{23}$, —$CH_2$—$R^{24}$, oxetane, 2-pyridine, 3-pyridine, thiophene, tetrahydropyran, or piperidine and having H or —$C(O)CH_3$ on the nitrogen, said tetrahydropyran and piperidine being attached at the 4-position; where $R^{20}$ is —$C_{1-6}$alkyl, —$CH_2NR^{27}CHR^{28}$—, —$C_{2-3}$alkylene-OH, or —$C_{2-3}$alkylene-$NR^{29}R^{30}$; —$R^{21}$ is —$C_{1-6}$alkyl, —O—$C_{1-6}$alkyl, —$C_{0-6}$alkylene-$NR^{25}R^{25}$, —CH$(NH_2)$—$R^{26}$, —$C_{1-4}$alkylene-NHC(O)O—$C_{1-6}$alkyl, —OCH$(CH_3)$OC(O)CH$(CH_3)_2$, or pyrrolidine attached at a carbon atom; $R^{22}$ is H or —$C_{1-6}$alkyl; $R^{23}$ is H, —$C_{1-6}$alkyl, —$C_{1-6}$alkyl substituted with 1 to 6 fluoro atoms, —$SO_2$—$C_{1-6}$alkyl, —$CH_2OC(O)$—$C_{1-6}$alkyl, —$C_{2-4}$alkylene-OH, —$C_{2-4}$alkylene-O—$CH_3$, or cyclopropyl optionally substituted with one or two $R^{31}$ groups; or $R^{22}$ and $R^{23}$ are taken together to form —$(CH_2)_2$—O—$(CH_2)_2$—, a 2-oxa-6-azaspiro[3.3]heptane ring, or an azetidine ring optionally substituted with one or two $R^{31}$ groups; $R^{24}$ is —$CH_2OH$, —CN, —$C(O)NH_2$, triazole or imidazole attached at a nitrogen atom, or oxadiazolone or tetrazole attached at the carbon atom; each $R^{25}$ is independently H or —$CH_3$; $R^{26}$ is —$C_{1-4}$alkylene-$NH_2$, —$CH_2OH$, or benzyl; $R^{27}$ is H, —$C_{1-6}$alkyl, —$C_{1-6}$alkyl substituted with 1 to 6 fluoro atoms, —$(CH_2)_2OH$, or —$(CH_2)_2OC_{1-6}$alkyl; $R^{28}$ is H, —$C_{1-6}$alkyl, —$C_{1-2}$alkylene-OH, or —$C_{1-2}$alkylene-O$C_{1-6}$alkyl; $R^{29}$ and $R^{30}$ are independently H, —$C_{1-6}$alkyl, —$C_{1-6}$alkyl substituted with 1 to 6 fluoro atoms, —$(CH_2)_2OH$, or —$(CH_2)_2OC_{1-6}$alkyl; or $R^{29}$ and $R^{30}$ are taken together to form —$CH_2$—$CH_2$—$CH_2$—; and each $R^{31}$ is independently halo, —$C_{1-6}$alkyl, —$C_{0-2}$alkylene-OH, —$C_{0-2}$alkylene-O$C_{1-6}$alkyl, —CN, or —$CONH_2$;

$R^3$, $R^4$ and $R^5$ are independently H or halo;

$R^6$ is a heterocycle selected from the group consisting of 3H-oxazol-2-one, [1,2,4]oxadiazol-5-one, [1,2,3,5]oxatriazole, dihydro-[1,2,4]triazol-3-one, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an $R^{60}$ group selected from the group consisting of —OH, —$(CH_2)_2OH$, —$C_{0-2}$alkylene-O—$C_{1-6}$alkyl, —$C_{1-6}$alkyl, —$CHF_2$, —$CF_3$, and phenyl; and each carbon atom in the heterocycle is unsubstituted or substituted with an $R^{61}$ group independently selected from the group consisting of halo, —OH, —$C_{1-6}$alkyl, —$C_{0-2}$alkylene-O—$C_{1-6}$alkyl, —C(O)

$CH_3$, —$C(O)NH(CH_3)$, —$C(O)N(CH_3)_2$, —$C_{3-6}$cycloalkyl, —$CF_3$, —$CH_2SO_2CH_3$, —$NH_2$, —$CH_2NH_2$, —$CH_2N(CH_3)_2$, pyrazine, and phenyl substituted with methyl or halo;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents.

Compounds of the invention possess NEP enzyme inhibition activity, and are therefore expected to be useful as therapeutic agents for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of a compound of the invention. Another aspect of the invention relates to a method of treating hypertension, heart failure, or renal disease, comprising administering to a patient a therapeutically effective amount of a compound of the invention. Still another aspect of the invention relates to a method for inhibiting a NEP enzyme in a mammal comprising administering to the mammal, a NEP enzyme-inhibiting amount of a compound of the invention.

Since compounds of the invention possess NEP inhibition activity, they are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of formula I, comprising the step of coupling a compound of formula 1 with a compound of formula 2:

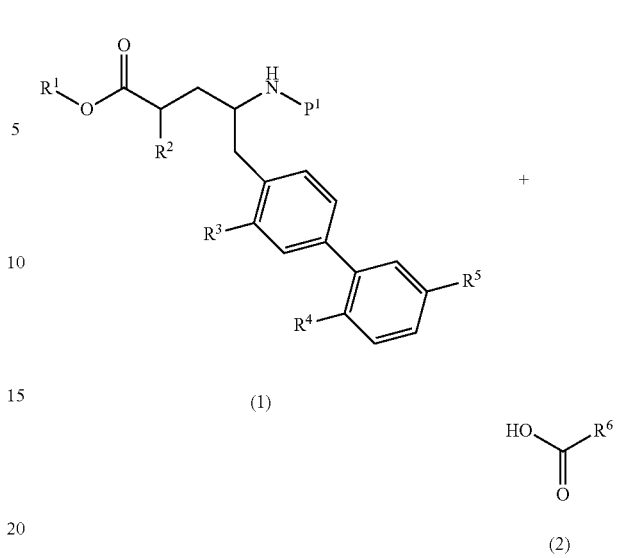

to produce a compound of formula I; where $P^1$ is H or an amino-protecting group selected from the group consisting of t-butoxycarbonyl, trityl, benzyloxycarbonyl, 9-fluorenylmethoxycarbonyl, formyl, trimethylsilyl, and t-butyldimethylsilyl; and where the process further comprises deprotecting the compound of formula 1 when $P^1$ is an amino protecting group; and where $R^1$-$R^6$ are as defined for formula I. In other aspects, the invention relates to products prepared by any of the processes described herein, as well as novel intermediates used in such process. In one aspect of the invention novel intermediates have formula 1, or a salt thereof, as defined herein.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal Still another aspect of the invention relates to the use of a compound of the invention as a research tool. Other aspects and embodiments of the invention are disclosed herein.

DETAILED DESCRIPTION OF THE INVENTION

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-6}$alkyl, meaning an alkyl group having from 1 to 6 carbon atoms where the carbon atoms are in any acceptable configuration. Representative alkyl groups include, by way of example, methyl, ethyl, n-propyl, isopropyl, n-butyl, s-butyl, isobutyl, t-butyl, n-pentyl, n-hexyl, and the like.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene-, —$C_{0-2}$alkylene-, —$C_{1-2}$alkylene-, —$C_{1-6}$alkylene-, and so form. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —$C_{0-2}$alkylene-, such terms are intended to include the absence of carbon atoms, that is, the alkylene group is not present except for a covalent bond attaching the groups separated by the alkylene term.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like.

The term "halo" means fluoro, chloro, bromo and iodo.

The term "heterocycle" is intended to include monovalent unsaturated (aromatic) heterocycles having a single ring or two fused rings as well as monovalent saturated and partially unsaturated groups having a single ring or multiple condensed rings. The heterocycle ring can contain from 3 to 15 total ring atoms, of which 1 to 14 are ring carbon atoms (e.g., —$C_{1-7}$heterocycle, —$C_{3-5}$heterocycle, —$C_{2-6}$heterocycle, —$C_{3-12}$heterocycle, —$C_{5-9}$heterocycle, —$C_{1-9}$heterocycle, —$C_{1-11}$heterocycle, and —$C_{1-14}$heterocyle), and 1 to 4 are ring heteroatoms selected from nitrogen, oxygen or sulfur. Typically, however, the heterocycle ring contains from 3 to 10 total ring atoms, of which 1 to 9 are ring carbon atoms, and 1 to 4 are ring heteroatoms. Exemplary heterocycles include, for example, —$C_{1-7}$heterocycle, —$C_{3-5}$heterocycle, —$C_{2-6}$heterocycle, —$C_{3-12}$heterocycle, —$C_{5-9}$heterocycle, —$C_{1-9}$heterocycle, —$C_{1-11}$heterocycle, and —$C_{1-14}$heterocyle. Exemplary heterocycles include 3H-oxazol-2-one, 4H-[1,2,4]oxadiazol-5-one, dihydro-[1,2,4]triazol-3-one, [1,2,3,5]oxatriazole, triazole, pyrazole, oxazole, isoxazole, isothiazole, pyridine, oxadiazole, and pyrimidine.

When a heterocycle is described as being "attached at a carbon atom," it means that the point of attachment is at any available carbon ring atom. Examples of heterocycles attached at a carbon atom are the triazole rings illustrated below:

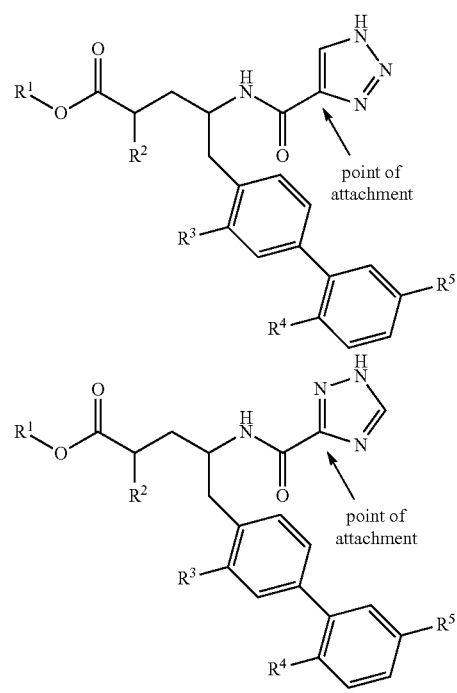

The term "optionally substituted" means that group in question may be unsubstituted or it may be substituted one or several times, such as 1 to 3 times, or 1 to 5 times, or 1 to 8 times. For example, a heterocycle that is "optionally substituted" with one or two halo or hydroxyl groups, may be unsubstituted, or it may contain one halo group, one hydroxyl group, two halo groups, two hydroxyl group, or one halo group and one hydroxyl group. Generally, such groups can be positioned on any available atom provided that the normal valency of the designated atom is not exceeded and that the substitution results in a stable moiety. Such groups may be specified as being on an available nitrogen atom or an available carbon atom.

When a nitrogen atom in a heterocycle is described as being "substituted," it means that the hydrogen atom on the nitrogen is replaced with a selected moiety, provided that the normal valency of the nitrogen is not exceeded, and that the substitution results in a stable ring. Similarly, when a nitrogen atom in a heterocycle is described as being "unsubstituted," it means that a hydrogen atom is on the nitrogen or the valency of the nitrogen has already been met without substitution (for example the nitrogen atom in a pyridine ring). For example, triazole has three nitrogen atoms present. The first triazole depicted has all unsubstituted nitrogen atoms since two nitrogen atoms have their valency met without substitution and one nitrogen atom has a hydrogen present. On the other hand, the second triazole depicted is substituted on the nitrogen atom with an $R^{60}$ group:

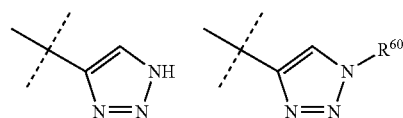

There are instances where the heterocycle will not be substituted with an $R^{60}$ group. For example, pyridine has one nitrogen atom present, but the valency of the nitrogen atom is met without substitution:

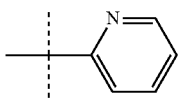

Similarly, triazole has two carbon atoms present, with one forming the point of attachment to the remainder of the compound. The first triazole has an "unsubstituted" carbon atom, while the second triazole is substituted on the carbon atom with an $R^{61}$ group, and the third triazole is substituted on the carbon atom with an $R^{61}$ group and on the nitrogen atom with an $R^{60}$ group:

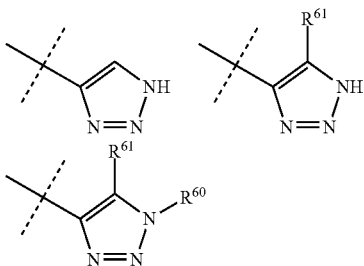

When a carbon atom in a heterocycle is described as being "substituted," it means that the hydrogen atom on the carbon is replaced with a selected moiety, provided that the normal valency of the carbon is not exceeded, and that the substitution results in a stable ring. Similarly, when a carbon atom in a heterocycle is described as being "unsubstituted," it means that a hydrogen atom is on the carbon atom or its valency has already been met without substitution (for example the oxo group on 4H-[1,2,4]oxadiazol-5-one). For example, pyrazole has three carbon atoms present, with one forming the point of attachment to the remainder of the compound, such that it is not available for substitution. The first pyrazole has two "unsubstituted" carbon atoms, while the second pyrazole has a first "unsubstituted" carbon atom and a second carbon atom that is substituted with an $R^{61}$ group, the third pyrazole is substituted on both carbon atoms with an $R^{61}$ group (which may be the same or different; depicted at $R^{61a}$ and $R^{61b}$), and the fourth pyrazole is substituted on both carbon atoms with an $R^{61}$ group:

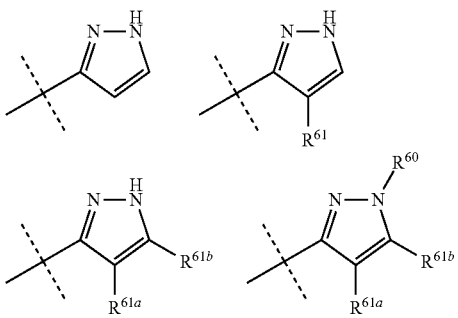

There are instances where the heterocycle will not be substituted with an $R^{61}$ group. For example, although 4H-[1,2,4]oxadiazol-5-one has two carbon atoms present, one carbon atom forms the point of attachment to the remainder of the compound and the other carbon atom is already substituted with an oxo group and so is not available for substitution with an $R^{61}$ group:

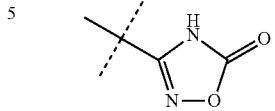

Similarly, [1,2,3,5]oxatriazole has one carbon atom present, but it forms the point of attachment to the remainder of the compound:

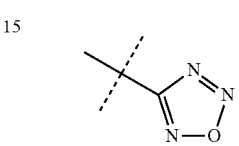

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) ameliorating the disease or medical condition, i.e., eliminating or causing regression of the disease or medical condition in a patient; (b) suppressing the disease or medical condition, i.e., slowing or arresting the development of the disease or medical condition in a patient; or (c) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which compounds of the invention are being evaluated or being used in an assay, for example an animal model.

All other terms used herein are intended to have their ordinary meaning as understood by those of ordinary skill in the art to which they pertain.

In one aspect, the invention relates to compounds of formula I:

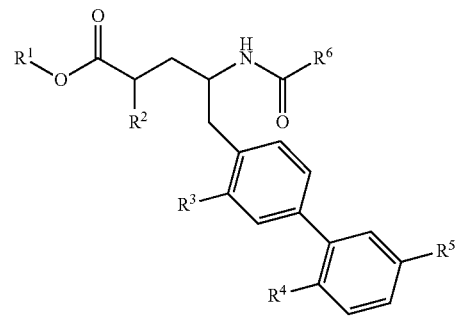

or a pharmaceutically acceptable salt thereof.

As used herein, the term "compound of the invention" includes all compounds encompassed by formula I and species thereof. Similarly, reference to compound of a given formula is intended to include all species. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of the invention contain one or more chiral centers and therefore, these compounds may be prepared and used in various stereoisomeric forms. In some embodiments, in order to optimize the therapeutic activity of the compounds of the invention, e.g., to treat hypertension, it may be desirable that the carbon atoms have a particular (R,R), (S,S), (S,R), or (R,S) configuration or are enriched in a stereoisomeric form having such configuration. In other embodiments, the compounds of the invention are present as racemic mixtures. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified. For example, if triazole is depicted as ($R^{60}$ being hydrogen):

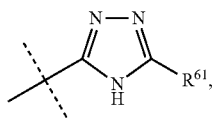

is understood that the compound may also exist in a tautomeric form such as:

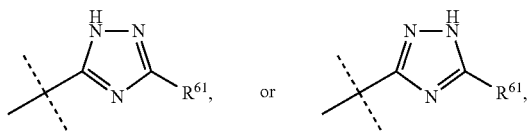

and that all such forms are covered by the invention.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest are compounds of formula I enriched in tritium or carbon-14 which can be used, for example, in tissue distribution studies; compounds of the invention enriched in deuterium especially at a site of metabolism resulting, for example, in compounds having greater metabolic stability; and compounds of formula I enriched in a positron emitting isotope, such as $^{11}C$, $^{18}F$, $^{15}O$ and $^{13}N$, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

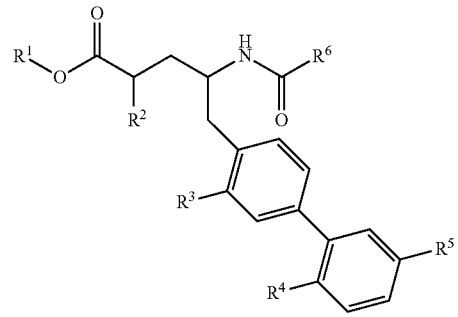

$R^1$ is selected from the group consisting of H, —$C_{1-8}$ alkyl, —CH(CH$_3$)OC(O)—O—cyclohexyl, —(CH$_2$)$_2$-morpholinyl, and —CH$_2$-5-methyl-[1,3]dioxol-2-one. In one embodiment, $R^1$ is H. In one embodiment, $R^1$ is —$C_{1-8}$ alkyl, for example —CH$_2$CH$_3$, —CH(CH$_3$)$_2$, —(CH$_2$)$_3$CH$_3$, and —(CH$_2$)$_5$CH$_3$. When $R^1$ is —$C_{1-8}$alkyl, the compound of formula I can be referred to as an alkyl ester, for example an ethyl ester. In one embodiment, $R^1$ is —CH(CH$_3$)OC(O)—O—cyclohexyl:

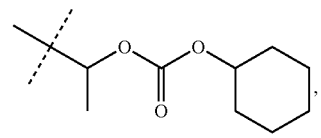

and the compound of formula I can be referred to as a cilexetil ester. In another embodiment, $R^1$ is —(CH$_2$)$_2$-morpholinyl:

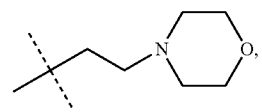

and the compound of formula I can be referred to as a 2-morpholinoethyl or mofetil ester. In yet another one embodiment, $R^1$ is —CH$_2$-5-methyl-[1,3]dioxol-2-one:

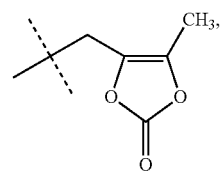

and the compound of formula I can be referred to as a medoxomil ester. In one particular embodiment, $R^1$ is H, —CH$_2$CH$_3$, —CH(CH$_3$)$_2$, —(CH$_2$)$_3$CH$_3$, or —(CH$_2$)$_5$CH$_3$.

$R^2$ is —CH$_2$—O—$R^{20}$, —$C_{0-1}$alkylene-NHC(O)—$R^{21}$, —$C_{0-3}$alkylene-NR$^{22}$R$^{23}$, —CH$_2$—$R^{24}$, oxetane, 2-pyridine, 3-pyridine, thiophene, tetrahydropyran, or piperidine and having H or —C(O)CH$_3$ on the nitrogen, where the tetrahydropyran and piperidine rings are attached at the 4-position. The $R^{20}$ moiety is —$C_{1-6}$alkyl, —CH$_2$NR$^{27}$CHR$^{28}$—, —$C_{2-3}$alkylene-OH, or —$C_{2-3}$alkylene-NR$^{29}$R$^{30}$. The $R^{21}$ moiety is —$C_{1-6}$alkyl, —O—$C_{1-6}$ alkyl, —C$_{0-6}$alkylene-NR$^{25}$R$^{25}$, —CH(NH$_2$)—R$^{26}$, —C$_{1-4}$alkylene-NHC(O)O—C$_{1-6}$alkyl, —OCH(CH$_3$)OC(O)CH(CH$_3$)$_2$, or pyrrolidine attached at a carbon atom. The R$^{22}$ moiety is H or —C$_{1-6}$alkyl. The R$^{23}$ moiety is H, —C$_{1-6}$alkyl, —C$_{1-6}$alkyl substituted with 1 to 6 fluoro atoms, —SO$_2$—C$_{1-6}$alkyl, —CH$_2$OC(O)—C$_{1-6}$alkyl, —C$_{2-4}$alkylene-OH, —C$_{2-4}$alkylene-O—CH$_3$, or cyclopropyl optionally substituted with one or two R$^{31}$ groups. In addition, R$^{22}$ and R$^{23}$ can be taken together to form —(CH$_2$)$_2$—O—(CH$_2$)$_2$—, a 2-oxa-6-aza-spiro[3.3]heptane ring, or an azetidine ring optionally substituted with one or two R$^{31}$ groups. The R$^{24}$ group is —CH$_2$OH, —CN, —C(O)NH$_2$, triazole or imidazole attached at a nitrogen atom, or oxadiazolone or tetrazole attached at the carbon atom. Each of the R$^{25}$ groups are independently H or —CH$_3$. The R$^{26}$ group is —C$_{1-4}$alkylene-NH$_2$, —CH$_2$OH, or benzyl. The R$^{27}$ group is H, —C$_{1-6}$alkyl, —C$_{1-6}$alkyl substituted with 1 to 6 fluoro atoms, —(CH$_2$)$_2$OH, or —(CH$_2$)$_2$OC$_{1-6}$alkyl. The R$^{28}$ group is H, —C$_{1-6}$alkyl, —C$_{1-2}$alkylene-OH, or —C$_{1-2}$alkylene-OC$_{1-6}$alkyl. The R$^{29}$ and R$^{30}$ groups are independently H, —C$_{1-6}$alkyl, —C$_{1-6}$alkyl substituted with 1 to 6 fluoro atoms, —(CH$_2$)$_2$OH, or —(CH$_2$)$_2$OC$_{1-6}$alkyl. In addition, R$^{29}$ and R$^{30}$ can be taken together to form —CH$_2$—CH$_2$—CH$_2$—. Each R$^{31}$ group is independently halo (for example, fluoro or chloro), —C$_{1-6}$alkyl, —C$_{0-2}$alkylene-OH, —C$_{0-2}$alkylene-OC$_{1-6}$alkyl, —CN, or —CONH$_2$.

In one embodiment, R$^2$ is —CH$_2$—O—R$^{20}$ and R$^{20}$ is —C$_{1-6}$alkyl, for example, —CH$_2$—O—CH$_3$ or —CH$_2$—O—CH$_2$CH$_3$. In another embodiment, R$^2$ is —CH$_2$—O—R$^{20}$ and R$^{20}$ is —CH$_2$NR$^{27}$CHR$^{28}$—, where R$^{27}$ is H, —C$_{1-6}$alkyl, —C$_{1-6}$alkyl substituted with 1 to 6 fluoro atoms (e.g., —CH$_2$CH$_2$CHF$_2$, —CH$_2$CH$_2$CH$_2$F, and —CH$_2$CH$_2$CF$_3$), —(CH$_2$)$_2$OH, or —(CH$_2$)$_2$OC$_{1-6}$alkyl, and R$^{28}$ is H, —C$_{1-6}$alkyl, —C$_{1-2}$alkylene-OH, or —C$_{1-2}$alkylene-OC$_{1-6}$alkyl (e.g., —CH$_2$OCH$_3$, —CH$_2$OCH$_2$CH$_3$, and —(CH$_2$)$_2$OCH$_3$), for example,

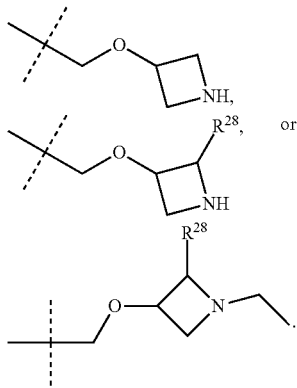

In one particular embodiment, R$^{28}$ is H.

In still another embodiment, R$^2$ is —CH$_2$—O—R$^{20}$ and R$^{20}$ is —C$_{2-3}$alkylene-OH, for example, —CH$_2$—O—(CH$_2$)$_2$ OH or —CH$_2$—O—(CH$_2$)$_3$OH. In yet another embodiment, R$^2$ is —CH$_2$—O—R$^{20}$ and R$^{20}$ is —C$_{2-3}$alkylene-NR$^{29}$R$^{30}$, where R$^{29}$ and R$^{30}$ are independently H, —C$_{1-6}$ alkyl, —C$_{1-6}$alkyl substituted with 1 to 6 fluoro atoms, —(CH$_2$)$_2$OH, or —(CH$_2$)$_2$OC$_{1-6}$alkyl, for example, —CH$_2$—O—(CH$_2$)$_2$NH$_2$, —CH$_2$—O—(CH$_2$)$_3$NH$_2$, —CH$_2$—O—(CH$_2$)$_2$NHCH$_3$, —CH$_2$—O—(CH$_2$)$_3$NHCH$_3$, —CH$_2$—O—(CH$_2$)$_2$N(CH$_3$)$_2$, or —CH$_2$—O—(CH$_2$)$_2$NH(CH$_2$CHF$_2$). In yet another embodiment, R$^2$ is —CH$_2$—O—R$^{20}$ and R$^{20}$ is —C$_{2-3}$alkylene-NR$^{29}$R$^{30}$, where R$^{28}$ and R$^{29}$ are taken together to form are taken together to form —CH$_2$—CH$_2$—CH$_2$—, for example,

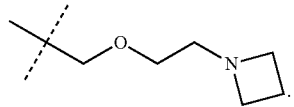

In one embodiment, R$^2$ is —C$_{0-1}$alkylene-NHC(O)—R$^{21}$ and R$^{21}$ is —C$_{1-6}$alkyl, for example, —NHC(O)CH$_3$, —NHC(O)CH$_2$CH$_3$, or —CH$_2$NHC(O)CH$_3$. In another embodiment, R$^2$ is —C$_{0-1}$alkylene-NHC(O)—R$^{21}$ and R$^{21}$ is —O—C$_{1-6}$alkyl, for example, —NHC(O)OCH$_3$. In still another embodiment, R$^2$ is —C$_{0-1}$alkylene-NHC(O)—R$^{21}$ and R$^{21}$ is —C$_{0-6}$alkylene-NR$^{25}$R$^{25}$ (where each R$^{25}$ group is independently H or —CH$_3$), for example, —NHC(O)CH$_2$NH$_2$, —CH$_2$NHC(O)CH$_2$NH$_2$, —NHC(O)(CH$_2$)$_2$NH$_2$, —NHC(O)(CH$_2$)$_3$NH$_2$, —CH$_2$NHC(O)(CH$_2$)$_3$NH$_2$, —NHC(O)(CH$_2$)$_4$NH$_2$, —NHC(O)(CH$_2$)$_5$NH$_2$, —NHC(O)CH(CH$_3$)NH$_2$, —CH$_2$NHC(O)C(CH$_3$)$_2$NH$_2$, —NHC(O)CH$_2$NH(CH$_3$), —NHC(O)CH$_2$N(CH$_3$)$_2$, —NHC(O)(CH$_2$)$_3$NH(CH$_3$), —NHC(O)(CH$_2$)$_3$N(CH$_3$)$_2$, —NHC(O)C(CH$_3$)$_2$NH$_2$, —NHC(O)CH(NH$_2$)—CH(CH$_3$)$_2$, or —CH$_2$NHC(O)C(CH$_3$)$_2$NH$_2$.

In yet another embodiment, R$^2$ is —C$_{0-1}$alkylene-NHC(O)—R$^{21}$ and R$^{21}$ is —CH(NH$_2$)—R$^{26}$ (where R$^{26}$ is —C$_{1-4}$alkylene-NH$_2$, —CH$_2$OH, or benzyl), for example, —NHC(O)CH(NH$_2$)—(CH$_2$)$_4$NH$_2$, —NHC(O)CH(NH$_2$)—CH$_2$OH, or —NHC(O)CH(NH$_2$)-benzyl. In one embodiment, R$^2$—C$_{0-1}$alkylene-NHC(O)—R$^{21}$ is and R$^{21}$ is —C$_{1-4}$alkylene-NHC(O)O—C$_{1-6}$alkyl, for example, —NHC(O)—CH$_2$—NHC(O)O—CH$_3$ and —NHC(O)—CH[CH(CH$_3$)$_2$]-NHC(O)O—CH$_3$.

In another embodiment, R$^2$ is —C$_{0-1}$alkylene-NHC(O)—R$^{21}$ and R$^{21}$ is —OCH(CH$_3$)OC(O)CH(CH$_3$)$_2$, for example, —NHC(O)OCH(CH$_3$)OC(O)CH(CH$_3$)$_2$ and —CH$_2$NHC(O)OCH(CH$_3$)OC(O)CH(CH$_3$)$_2$. In still another embodiment, R$^2$ is —C$_{0-1}$alkylene-NHC(O)—R$^{21}$ and R$^{21}$ is pyrrolidine, for example: (shown without stereochemistry and as the (S) isomer)

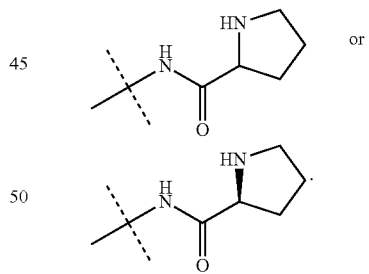

In another embodiment, R$^2$ is —C$_{0-3}$alkylene-NR$^{22}$R$^{23}$ (where R$^{22}$ is H or —C$_{1-6}$alkyl, and R$^{23}$ is H, —C$_{1-6}$alkyl, —C$_{1-6}$alkyl substituted with 1 to 6 fluoro atoms, —SO$_2$—C$_{1-6}$alkyl, —CH$_2$OC(O)—C$_{1-6}$alkyl, —C$_{2-4}$alkylene-OH, —C$_{2-4}$alkylene-O—CH$_3$, or cyclopropyl optionally substituted with one or two R$^{31}$ groups, where each R$^{31}$ is independently halo, —C$_{1-6}$alkyl, —C$_{0-2}$alkylene-OH, —C$_{0-2}$ alkylene-OC$_{1-6}$alkyl, —CN, or —CONH$_2$. Examples of this embodiment include, for example, —NH$_2$, —CH$_2$NH$_2$, —CH(CH$_3$)NH$_2$, —C(CH$_3$)$_2$NH$_2$, —(CH$_2$)$_2$NH$_2$, —(CH$_2$)$_3$ NH$_2$, —CH$_2$NH(CH$_3$), —CH$_2$N(CH$_3$)$_2$, —CH$_2$NH—CH$_2$CH$_2$F, —CH$_2$NH—CH$_2$CHF$_2$, —NH—SO$_2$CH$_3$, —NHCH₂OC(O)CH₃, —NHCH₂OC(O)CH(CH₃)₂, —CH₂NHCH₂OC(O)CH(CH₃)₂, —CH₂—NH—(CH₂)₂—OH, —CH₂—NH—(CH₂)₃—OH, —CH₂—N(CH₃)—(CH₂)₂—OH, —NH—(CH₂)₂—O—CH₃, —CH₂—NH—(CH₂)₂—O—CH₃, —CH₂—N(CH₃)—(CH₂)₂—O—CH₃, —NH—(CH₂)₃—O—CH₃, —CH₂—NH—(CH₂)₃—O—CH₃,

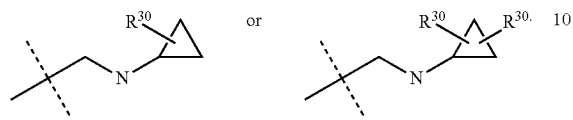

In another embodiment $R^2$ is —$C_{0-3}$alkylene-$NR^{22}R^{23}$ and $R^{22}$ and $R^{23}$ taken together to form —(CH₂)₂—O—(CH₂)₂—, a 2-oxa-6-aza-spiro[3.3]heptane ring, or an azetidine ring optionally substituted with one or two $R^{31}$ groups, where each $R^{31}$ group is independently halo, —$C_{1-6}$alkyl, —$C_{0-2}$alkylene-OH, —$C_{0-2}$alkylene-O$C_{1-6}$alkyl, —CN, or —CONH₂. Examples of this embodiment include:

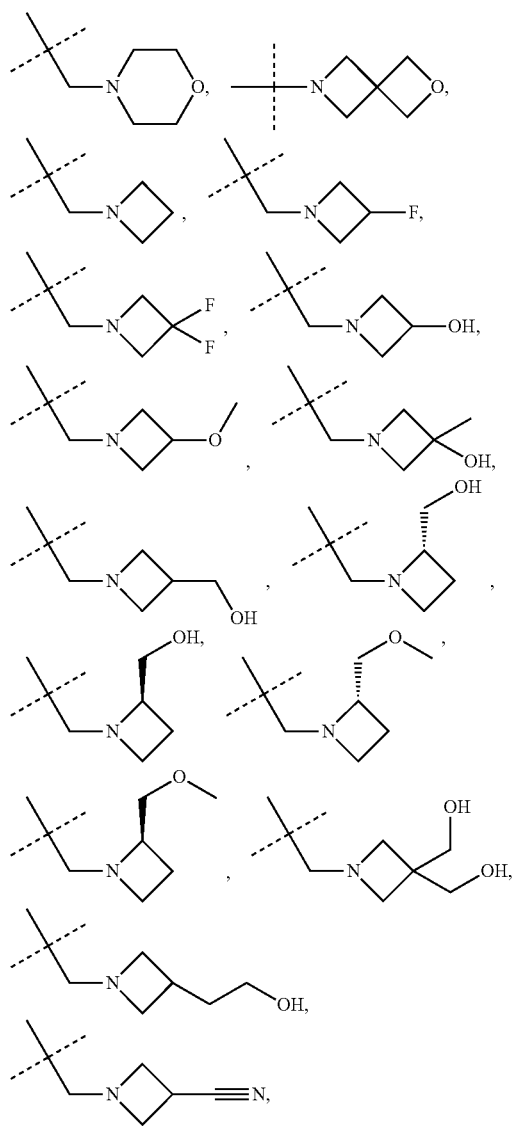

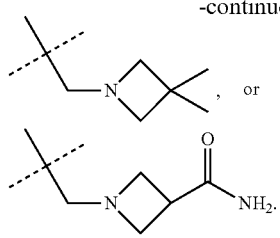

In still another embodiment, $R^2$ is —CH₂—$R^{24}$ and $R^{24}$ is —CH₂OH, —CN, —C(O)NH₂, triazole or imidazole attached at a nitrogen atom, or oxadiazolone or tetrazole attached at the carbon atom, for example, —(CH₂)₂OH, —CH₂CN, —CH₂—C(O)NH₂,

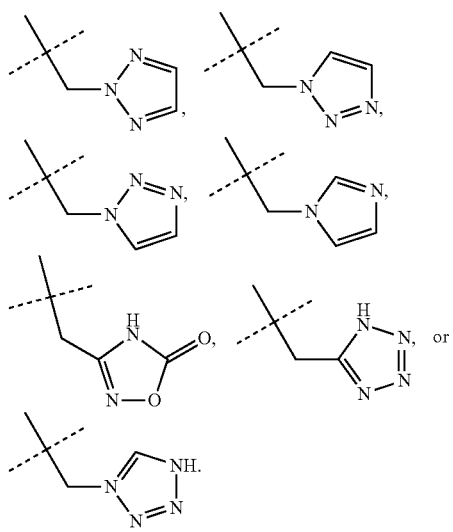

In one embodiment, $R^2$ is oxetane, for example,

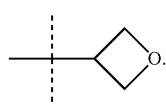

In another embodiment, $R^2$ is 2-pyridine or 3-pyridine:

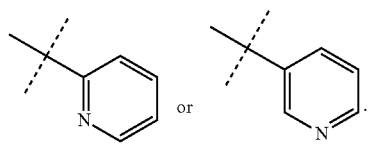

In yet another embodiment, $R^2$ is thiophene, for example,

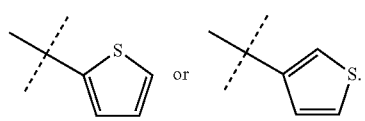

In another embodiment, $R^2$ is tetrahydropyran (attached at the 4-position), for example,

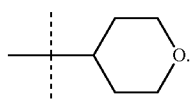

In yet another embodiment, $R^2$ is piperidine (attached at the 4-position) having H or —C(O)CH$_3$ on the nitrogen, for example,

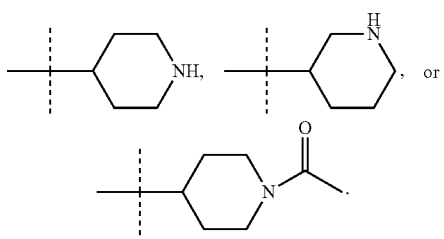

$R^3$ is selected from the group consisting of H and halo, and in one embodiment, $R^3$ is H or Cl. $R^4$ is selected from the group consisting of H and halo, and in one embodiment, $R^4$ is H or F. $R^5$ is selected from the group consisting of H and halo, and in one embodiment, $R^5$ is H, Br, or Cl, and in another embodiment $R^5$ is H or Cl. In other embodiments, $R^3$ is H, $R^4$ is F, and $R^5$ is Cl; or $R^3$ and $R^4$ are H and $R^5$ is Br or Cl; or $R^3$, $R^4$, and $R^5$ are H; or $R^3$ is Cl, $R^4$ is F, and $R^5$ is Cl; or $R^3$ is H, $R^4$ is F, and $R^5$ is H.

$R^6$ is a heterocycle selected from the group consisting of 3H-oxazol-2-one, [1,2,4]oxadiazol-5-one, [1,2,3,5]oxatriazole, dihydro-[1,2,4]triazol-3-one, [1,2,4]triazolo[1,5-α]pyridine, triazole, pyrazole, imidazole, oxazole, isoxazole, isothiazole, pyridine, oxadiazole, and pyrimidine, where the heterocycle is attached at a carbon atom. In one embodiment, $R^6$ is 3H-oxazol-2-one, 4H-[1,2,4]oxadiazol-5-one, [1,2,3,5]oxatriazole, [1,2,3]triazole, [1,2,4]triazole, pyrazole, imidazole, oxazole, isoxazole, isothiazole, pyridine, oxadiazole, or pyrimidine. In another embodiment, $R^6$ is 3H-oxazol-2-one, 4H-[1,2,4]oxadiazol-5-one, [1,2,4]triazolo[1,5-α]pyridine, [1,2,3]triazole, [1,2,4]triazole, pyrazole, oxazole, isoxazole, isothiazole, pyridine, or pyrimidine.

Each nitrogen atom in the heterocycle is unsubstituted or substituted with an $R^{60}$ group selected from the group consisting of —OH, —(CH$_2$)$_2$OH, —C$_{0-2}$alkylene-O—C$_{1-6}$alkyl (e.g., —OCH$_3$ or —OCH$_2$CH$_3$), —C$_{1-6}$alkyl (e.g., —CH$_3$), —CHF$_2$, —CF$_3$, and phenyl. In one embodiment, the nitrogen atoms in the heterocycle are unsubstituted. In another embodiment, $R^{60}$ is —OH, —(CH$_2$)$_2$OH, —OCH$_3$, —OCH$_2$CH$_3$, —CH$_3$, —CHF$_2$, or —CF$_3$; in another embodiment $R^{60}$ is phenyl; and in yet another embodiment, one nitrogen atom in the heterocycle is substituted with an $R^{60}$ moiety.

Each carbon atom in the heterocycle is unsubstituted or substituted with an $R^{61}$ group independently selected from the group consisting of halo, —OH, —C$_{1-6}$alkyl, —C$_{0-2}$alkylene-O—C$_{1-6}$alkyl, —C(O)CH$_3$, —C(O)NH(CH$_3$), —C(O)N(CH$_3$)$_2$, —C$_{3-6}$cycloalkyl (e.g., cyclopropyl, cyclobutyl, cyclopentyl, and cyclohexyl), —CF$_3$, —CH$_2$SO$_2$CH$_3$, —NH$_2$, —CH$_2$NH$_2$, —CH$_2$N(CH$_3$)$_2$, pyrazine, and phenyl substituted with methyl. In one embodiment, the carbon atoms in the heterocycle are unsubstituted; and in another embodiment, one carbon atom in the heterocycle is substituted with an $R^{61}$ group. In another embodiment, $R^{61}$ is chloro, fluoro, —OH, —CH$_3$, —CH$_2$CH$_3$, —(CH$_2$)$_2$CH$_3$, —CH(CH$_3$)$_2$, —OCH$_3$, —OCH$_2$CH$_3$, —CH$_2$—OCH$_3$, —C(O)CH$_3$, —C(O)NH(CH$_3$), —C(O)N(CH$_3$)$_2$, cyclopropyl, —CF$_3$, —CH$_2$SO$_2$CH$_3$, —NH$_2$, —CH$_2$NH$_2$, —CH$_2$N(CH$_3$)$_2$, pyrazine, or phenyl substituted with methyl or fluoro; and in one particular embodiment, $R^{61}$ is chloro, fluoro, —OH, —CH$_3$, —CH$_2$CH$_3$, —(CH$_2$)$_2$CH$_3$, —CH(CH$_3$)$_2$, —OCH$_3$, —OCH$_2$CH$_3$, —C(O)CH$_3$, —C(O)NH(CH$_3$), —C(O)N(CH$_3$)$_2$, cyclopropyl, —CF$_3$, or phenyl substituted with methyl or fluoro.

In another embodiment, two carbon atoms in the heterocycle are substituted with $R^{61}$ groups, which may be the same or different; and in one specific embodiment, the $R^{61}$ moiety on a first carbon is selected from the group consisting of fluoro, —OH, —CH$_3$, —C$_{0-2}$alkylene-O—C$_{1-6}$alkyl, —C(O)CH$_3$, —C$_{3-6}$cycloalkyl, —CF$_3$, —CH$_2$SO$_2$CH$_3$, —NH$_2$, and —CH$_2$N(CH$_3$)$_2$, and the $R^{61}$ moiety on a second carbon is selected from the group consisting of halo, —OH, —CH$_3$, —O—CH$_2$CH$_3$, —C(O)CH$_3$, cyclopropyl, —CF$_3$, —CH$_2$SO$_2$CH$_3$, —NH$_2$, —CH$_2$N(CH$_3$)$_2$, and phenyl substituted with methyl or halo. In one particular embodiment, a first carbon atom in the heterocycle is substituted with an $R^{61}$ group selected from the group consisting of fluoro and —CH$_3$; and a second carbon atom in the heterocycle is substituted with an $R^{61}$ group selected from the group consisting of —CH$_3$, —O—CH$_2$CH$_3$, cyclopropyl, and phenyl substituted with methyl.

In one embodiment, $R^6$ is 3H-oxazol-2-one, for example:

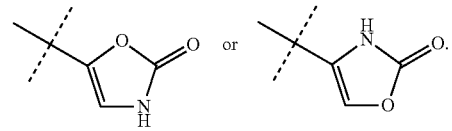

In one embodiment, $R^6$ is [1,2,4]oxadiazol-5-one, for example 4H-[1,2,4]oxadiazol-5-one or 2H-[1,2,4]oxadiazol-5-one:

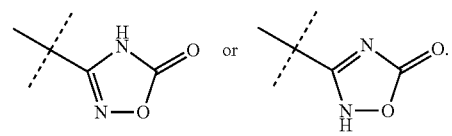

In one embodiment, $R^6$ is [1,2,3,5]oxatriazole, for example:

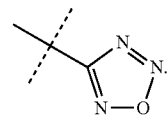

In one embodiment, $R^6$ is dihydro-[1,2,4]triazol-3-one, for example 2,4-dihydro-[1,2,4]triazol-3-one or 4,5-dihydro-[1,2,4]triazol-3-one:

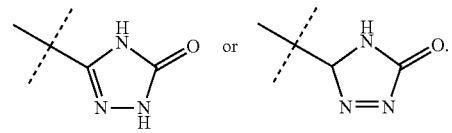

In one particular embodiment, $R^6$ is a 2,4-dihydro-[1,2,4]triazol-3-one ring such as:

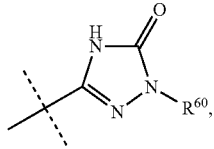

specific examples of which include:

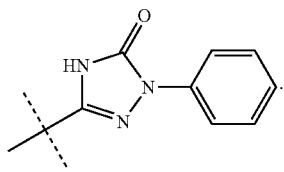

In one embodiment, $R^6$ is [1,2,4]triazolo[1,5-α]pyridine, for example:

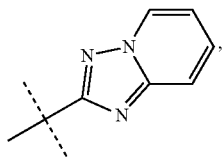

In one particular embodiment, $R^6$ is a [1,2,4]triazolo[1,5-α]pyridine ring such as:

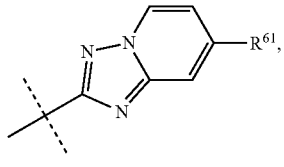

specific examples of which include:

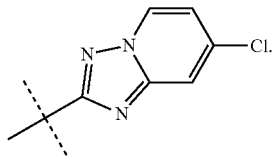

In one embodiment, $R^6$ is [1,2,3]triazole or [1,2,4]triazole, for example:

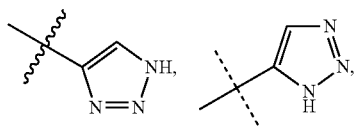

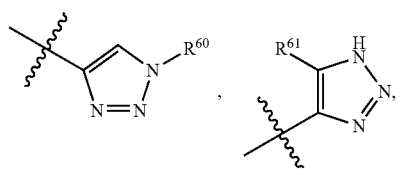

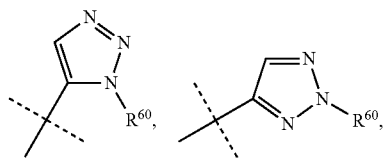

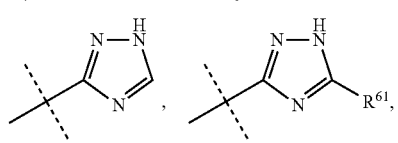

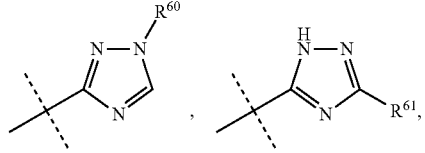

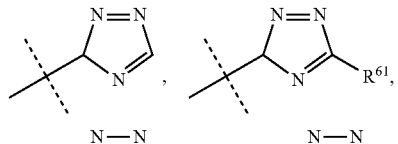

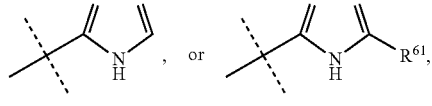

specific examples of which include:

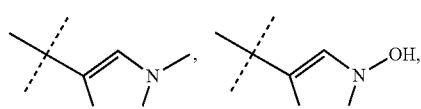

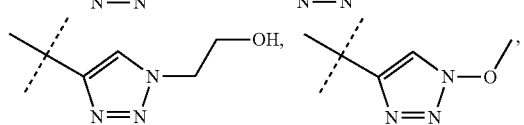

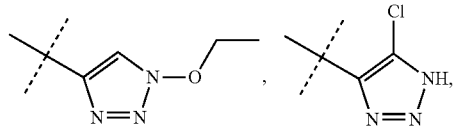

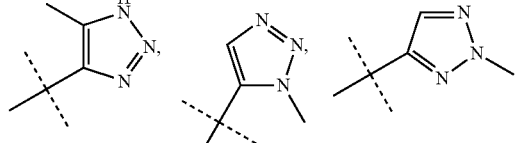

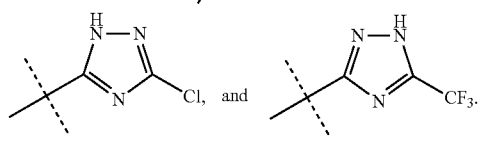

In one particular embodiment, $R^6$ is a triazole ring such as:
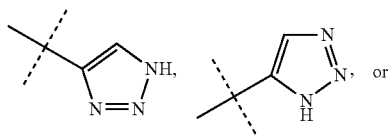 or
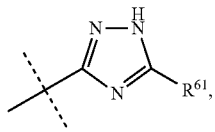
specific examples of which include:
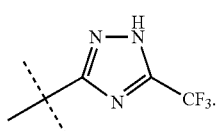
In one embodiment, $R^6$ is a pyrazole ring, for example:
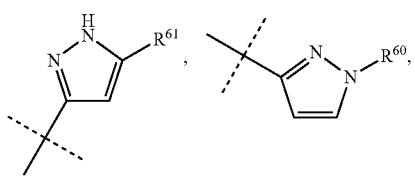
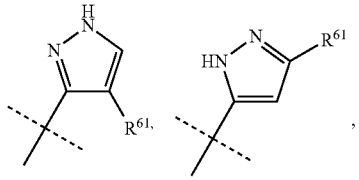
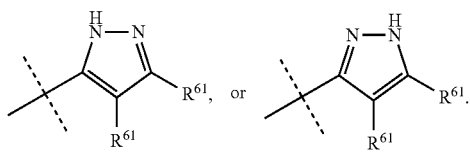
In one particular embodiment, $R^6$ is a pyrazole ring such as:
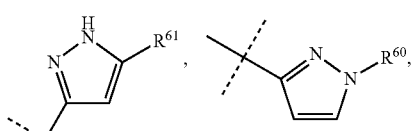
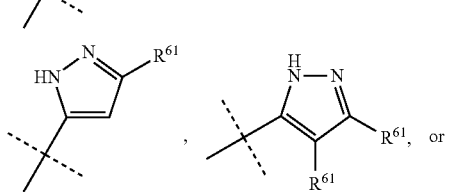
-continued
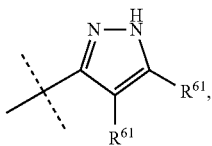
specific examples of which include:
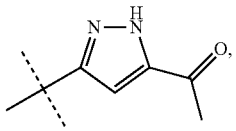
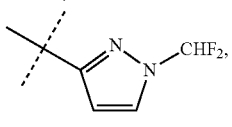
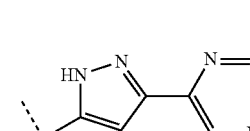
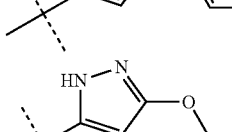
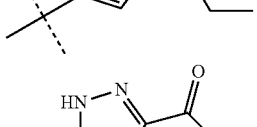
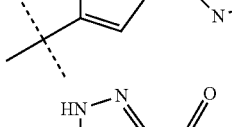
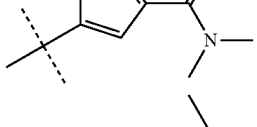
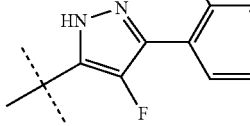
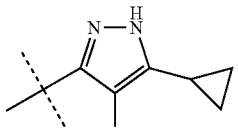
In one embodiment, $R^6$ is an imidazole ring, for example:
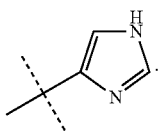

In one particular embodiment, $R^6$ is an imidazole ring such as:

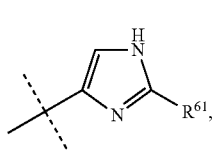

specific examples of which include:

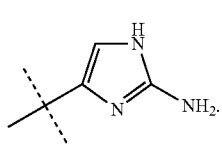

In one embodiment, $R^6$ is an oxazole ring, for example:

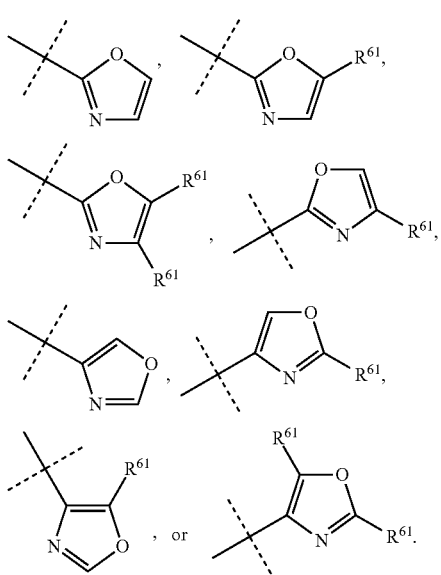

In one particular embodiment, $R^6$ is an oxazole ring such as:

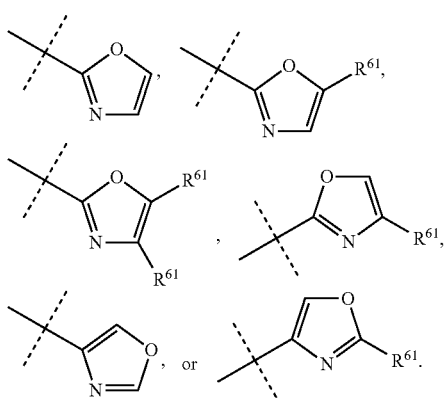

specific examples of which include:

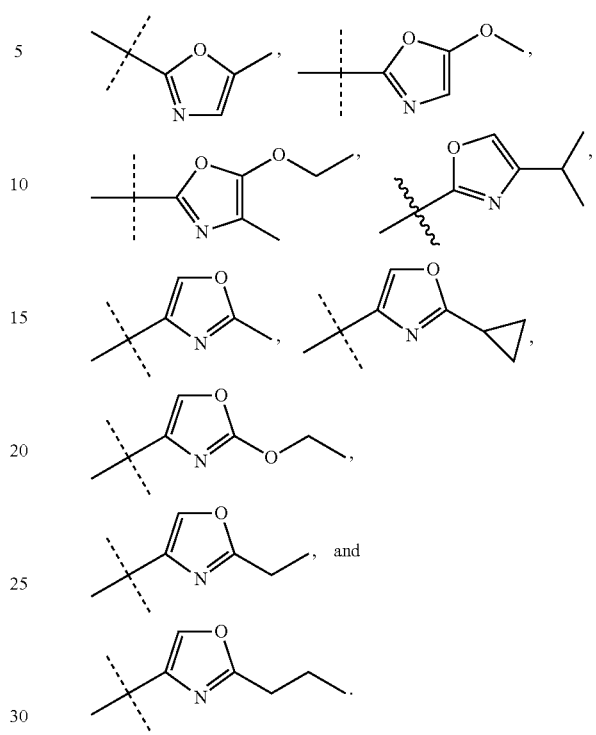

In one embodiment, $R^6$ is an isoxazole ring, for example:

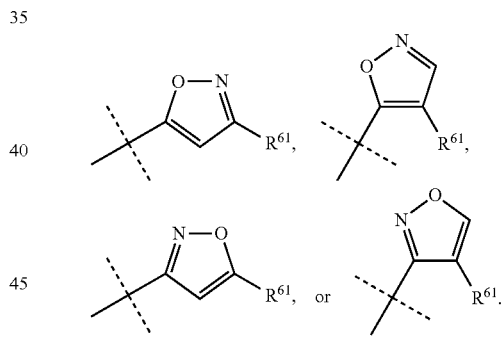

In one particular embodiment, $R^6$ is an isoxazole ring such as:

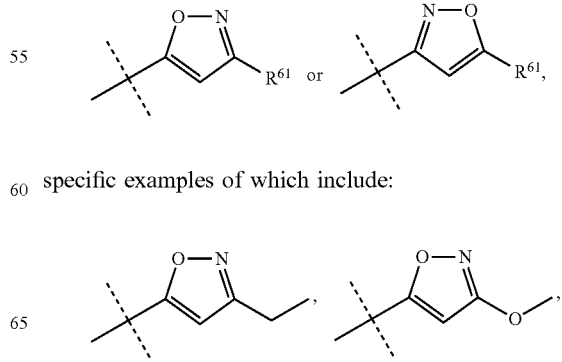

specific examples of which include:

-continued

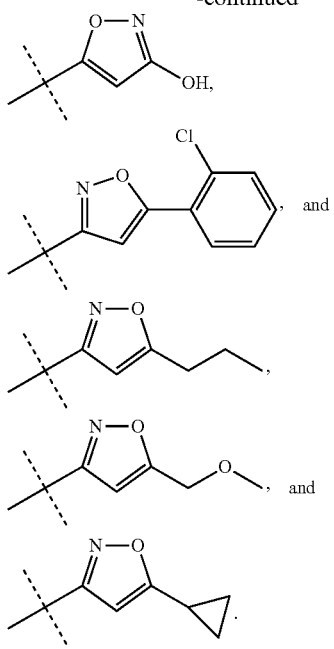

In one embodiment, $R^6$ is an isothiazole ring, for example:

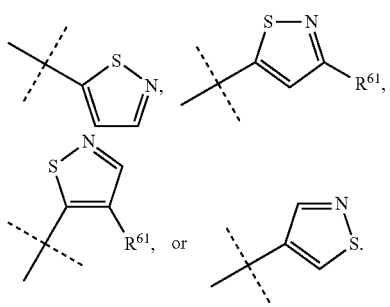

In one particular embodiment, $R^6$ is an isothiazole ring such as:

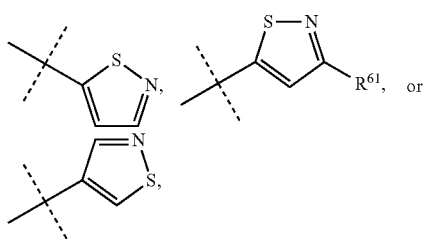

specific examples of which include:

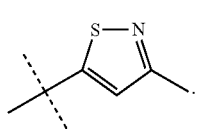

In one embodiment, $R^6$ is a pyridine ring, for example:

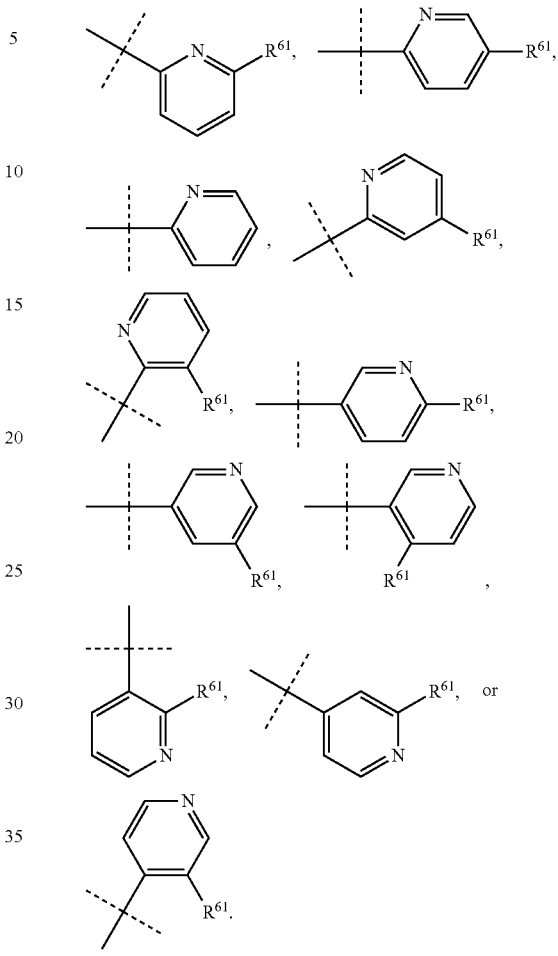

In one particular embodiment, $R^6$ is a pyridine ring such as:

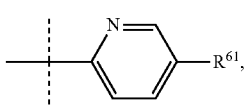

specific examples of which include:

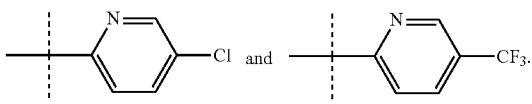

In one embodiment, $R^6$ isoxadiazole, for example [1,2,4]oxadiazole or [1,3,4]oxadiazole:

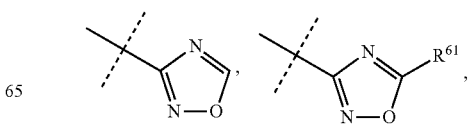

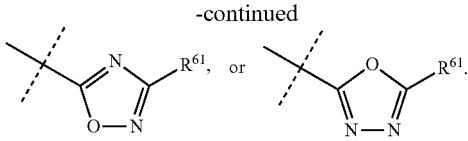

In one embodiment, R⁶ is a pyrimidine ring, for example:

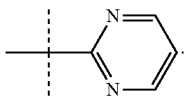

In addition, particular compounds of formula I that are of interest include those set forth in the Examples below, as well as pharmaceutically acceptable salts thereof.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Fourth Edition, Wiley, New York, 2006, and references cited therein.

Carboxy-protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino-protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Hydroxyl-protecting groups are suitable for preventing undesired reactions at a hydroxyl group, and examples include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like.

Standard deprotection techniques and reagents are used to remove the protecting groups, and may vary depending upon which group is used. For example, a BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C").

Suitable bases for use in these schemes include, by way of illustration and not limitation, potassium carbonate, calcium carbonate, sodium carbonate, triethylamine ($Et_3N$), pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform ($CHCl_3$), carbon tetrachloride ($CCl_4$), 1,4-dioxane, methanol, ethanol, water, diethyl ether, acetone, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), 1,3-dicyclohexylcarbodiimide (DCC), N-(3-dimethylaminopropyl)-N'-ethylcarbodiimide (EDC), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated aqueous $NaHCO_3$, $Na_2CO_3$ (5%), $CHCl_3$ or 1M NaOH); drying (for example, over $MgSO_4$, over Na₂SO₄, or in vacuo); filtering; crystallizing (for example, from EtOAc and hexanes); being concentrated (for example, in vacuo); and/or purification (e.g., silica gel chromatography, flash chromatography, preparative HPLC, reverse phase-HPLC, or crystallization).

By way of illustration, compounds of formula I, as well as their salts, can be prepared as shown in Schemes I and II.

Scheme I

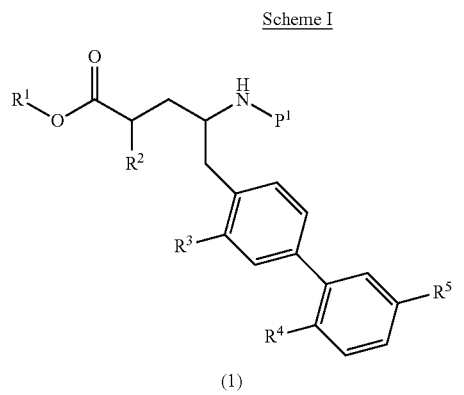

(1)

+

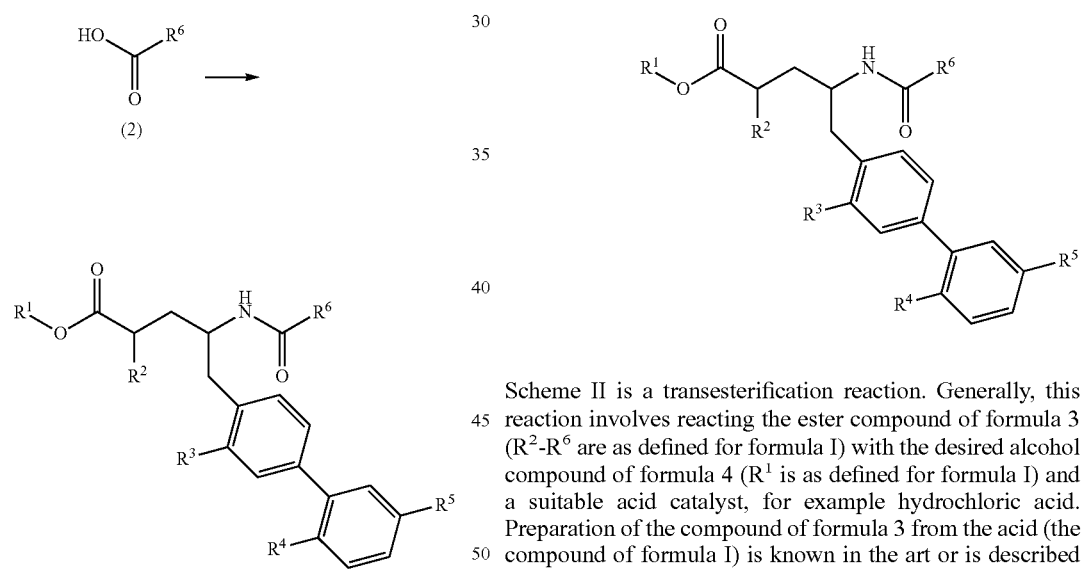

Scheme II

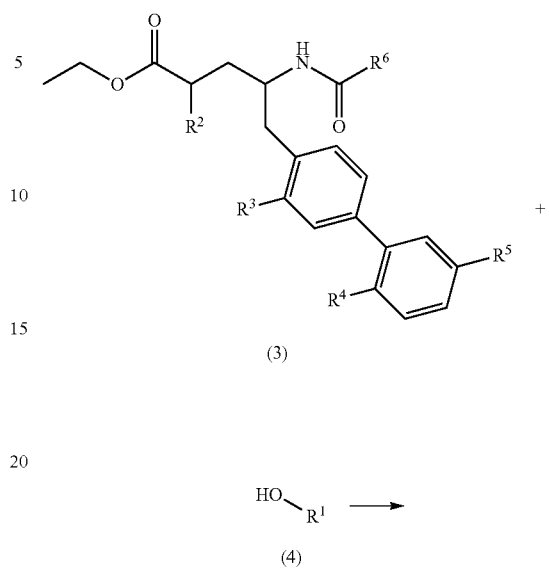

Scheme I is a is a coupling reaction between a compound of formula 1 ($R^1$-$R^5$ are as defined for formula I and $P^1$ is H or a suitable amino-protecting group) and a compound of formula 2 ($R^6$ is as defined for formula I). When $P^1$ is an amino protecting group, the process further comprises deprotecting the compound, before or in situ with the coupling step. Exemplary coupling reagents include HATU, and HOBt with EDC. Generally, this reaction is conducted in the presence of a base such as DIPEA or 4-methylmorpholine, and an inert diluent or solvents such as DMF or DMA. Preparation of various amine starting materials (Compound 1) are illustrated in the Examples. The carboxylic acid starting materials (Compound 2) are generally commercially available or can be prepared using procedures that are known in the art.

Scheme II is a transesterification reaction. Generally, this reaction involves reacting the ester compound of formula 3 ($R^2$-$R^6$ are as defined for formula I) with the desired alcohol compound of formula 4 ($R^1$ is as defined for formula I) and a suitable acid catalyst, for example hydrochloric acid. Preparation of the compound of formula 3 from the acid (the compound of formula I) is known in the art or is described herein. The HO—$R^1$ alcohols are either commercially available or can be prepared by techniques that are known in the art or described herein. Exemplary HO—$R^1$ groups include:

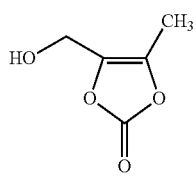

Certain intermediates described herein are believed to be novel and accordingly, such compounds are provided as further aspects of the invention including, for example, the compounds of formula 1 or a salt thereof:

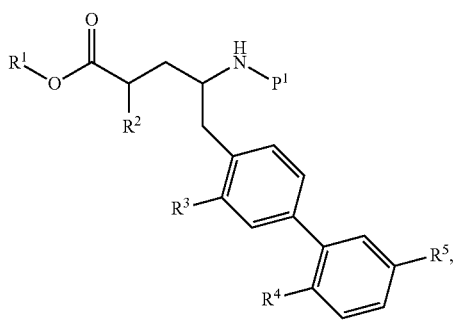

(1)

where $R^1$-$R^5$ are as defined for formula I and $P^1$ is H or a suitable amino-protecting group selected from the group consisting of t-butoxycarbonyl, trityl, benzyloxycarbonyl, 9-fluorenylmethoxycarbonyl, formyl, trimethylsilyl, and t-butyldimethylsilyl; or a salt thereof.

Further details regarding specific reaction conditions and other procedures for preparing representative compounds of the invention or intermediates thereof are described in the Examples set forth below.

Utility

Compounds of the invention possess neprilysin (NEP) inhibition activity, that is, the compounds are able to inhibit enzyme-catalytic activity. In another embodiment, the compounds do not exhibit significant inhibitory activity of the angiotensin-converting enzyme. One measure of the ability of a compound to inhibit NEP activity is the inhibition constant ($pK_i$). The $pK_i$ value is the negative logarithm to base 10 of the dissociation constant ($K_i$), which is typically reported in molar units. Compounds of the invention of particular interest are those having a $pK_i$ at NEP greater than or equal to 7.0, and even more particularly those having a $pK_i$ greater than or equal to 8.0; and in still another embodiment, compounds of interest have a $pK_i$ in the range of greater than or equal to 9.0. Such values can be determined by techniques that are well known in the art, as well as in the assays described herein.

Another measure of the ability of a compound to inhibit NEP activity is the apparent inhibition constant ($IC_{50}$), which is the molar concentration of compound that results in half-maximal inhibition of substrate conversion by the NEP enzyme. The $pIC_{50}$ value is the negative logarithm to base 10 of the $IC_{50}$. Compounds of the invention that are of particular interest, include those that exhibit a $pIC_{50}$ for NEP greater than or equal to about 7.0. In another embodiment, compounds of interest have a $pIC_{50}$ for NEP within the range of about 7.0-10.0.

It is noted that in some cases, compounds of the invention may possess weak NEP inhibition activity. In such cases, those of skill in the art will recognize that these compounds still have utility as research tools.

Exemplary assays to determine properties of compounds of the invention, such as the NEP inhibiting activity, are described in the Examples and include by way of illustration and not limitation, assays that measure NEP inhibition (described in Assay 1). Useful secondary assays include assays to measure ACE inhibition (also described in Assay 1) and aminopeptidase P (APP) inhibition (described in Sulpizio et al. (2005) JPET 315:1306-1313). A pharmacodynamic assay to assess the in vivo inhibitory potencies for ACE and NEP in anesthetized rats is described in Assay 2 (see also Seymour et al. (1985) Hypertension 7(Suppl I):I-35-I-42 and Wigle et al. (1992) Can. J. Physiol. Pharmacol. 70:1525-1528), where ACE inhibition is measured as the percent inhibition of the angiotensin I pressor response and NEP inhibition is measured as increased urinary cyclic guanosine 3',5'-monophosphate (cGMP) output.

There are many in vivo assays that can be used to ascertain further utilities of the compounds of the invention. The conscious spontaneously hypertensive rat (SHR) model is a renin dependent hypertension model, and is described in Assay 3. See also Intengan et al. (1999) Circulation 100 (22):2267-2275 and Badyal et al. (2003) Indian Journal of Pharmacology 35:349-362. The conscious desoxycorticosterone acetate-salt (DOCA-salt) rat model is a volume dependent hypertension model that is useful for measuring NEP activity, and is described in Assay 4. See also Trapani et al. (1989) J. Cardiovasc. Pharmacol. 14:419-424, Intengan et al. (1999) Hypertension 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensitive (DSS) hypertensive rat model is a model of hypertension that is sensitive to dietary salt (NaCl), and is described in Assay 5. See also Rapp (1982) Hypertension 4:753-763. The rat monocrotaline model of pulmonary arterial hypertension described, for example, in Kato et al. (2008) J. Cardiovasc. Pharmacol. 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) J. Amer. Soc. Nephrol. 7:1038-1044. Other animal models, such as the hot plate, tail-flick and formalin tests, can be used to measure the analgesic properties of compounds of the invention, as well as the spinal nerve ligation (SNL) model of neuropathic pain. See, for example, Malmberg et al. (1999) Current Protocols in Neuroscience 8.9.1-8.9.15. Other properties and utilities of the compounds can be demonstrated using various in vitro and in vivo assays well known to those skilled in the art.

Depending upon the intended route of administration, oral bioavailability may be an important characteristic, as well as potency as a neprilysin inhibitor. One means of measuring oral bioavailability is by the rat PO cassette assay, where the % F is a measure of the amount of the oral drug dose that actually gets into the blood stream; an exemplary assay is described in Assay 6. Compounds tested in this assay and having a % F<10% are likely to be poorly absorbed. Similarly, compounds tested in this assay and having a % F>10% are likely to be better absorbed. Therefore, compounds of the invention having a % F>10% are of particular interest as orally administered drugs.

Compounds of the invention are expected to inhibit the NEP enzyme in any of the assays listed above, or assays of a similar nature. Thus, the aforementioned assays are useful in determining the therapeutic utility of compounds of the invention, for example, their utility as antihypertensive agents or antidiarrheal agents. Other properties and utilities of compounds of the invention can be demonstrated using other in vitro and in vivo assays well-known to those skilled in the art. Compounds of formula I may be active drugs as well as prodrugs. Thus, when discussing the activity of compounds of the invention, it is understood that any such prodrugs may not exhibit the expected activity in an assay, but are expected to exhibit the desired activity once metabolized.

Compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compounds are expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, these compounds are expected to have other physiological actions, for example, on the renal, central nervous, reproductive and gastrointestinal systems.

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Rogues et al. (1993) *Pharmacol. Rev.* 45:87-146 and Dempsey et al. (2009) *Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension. When used to treat hypertension, the compound may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $β_1$-adrenergic receptor antagonists, dual-acting β-adrenergic receptor antagonist/$α_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a calcium channel blocker, a diuretic, or a combination thereof, and used to treat primary hypertension. In another particular embodiment of the invention, a compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic receptor antagonists, $β_1$-adrenergic receptor antagonists, $β_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $β_1$-adrenergic receptor antagonists, dual-acting β-adrenergic receptor antagonist/$α_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a $β_1$-adrenergic receptor antagonist, an $AT_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marcais-Collado (1987) *Eur. J. Pharmacol.* 144(2): 125-132. When used to treat diarrhea, compounds of the invention may be combined with one or more additional antidiarrheal agents.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury (caused, for example, by cardiovascular surgery, chemotherapy, or the use of contrast dyes in medical imaging) or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, $AT_1$ receptor antagonists, and diuretics.

Preventative Therapy

By potentiating the effects of the natriuretic peptides, compounds of the invention are also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional antiglaucoma agents.

Pain Relief

As NEP inhibitors, compounds of the invention are expected to inhibit the degradation of endogenous enkephalins and thus such compounds may also find utility as analgesics. See, for example, Rogues et al. (1980) *Nature* 288:286-288 and Thanawala et al. (2008) *Current Drug Targets* 9:887-894. When used to treat pain, the compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, $5-HT_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) J. Investigative Med. 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since compounds of the invention possess NEP enzyme inhibition activity, such compounds are also useful as research tools for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, compounds of the invention can be used as research tools for evaluating other chemical compounds, and thus are also useful in screening assays to discover, for example, new compounds having NEP-inhibiting activity. In this manner, a compound of the invention is used as a standard in an assay to allow comparison of the results obtained with a test compound and with compounds of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay.

Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: *The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more $\alpha$-D-glucopyranose units linked at the 1,4 positions by a linkages as in amylase, $\beta$-cyclodextrin or cycloheptaamylose. Exemplary cyclodextrins include cyclodextrin derivatives such as hydroxypropyl and sulfobutyl ether cyclodextrins such as hydroxypropyl-$\beta$-cyclodextrin and sulfobutyl ether $\beta$-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, $\alpha$-adrenergic receptor antagonists, $\beta_1$-adrenergic receptor antagonists, $\beta_2$-adrenergic receptor agonists, dual-acting $\beta$-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $β_1$-adrenergic receptor antagonist ("$β_1$-blockers"). Representative $β_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $β_1$-antagonist is selected from atenolol, bisoprolol, metoprolol, propranolol, sotalol, and combinations thereof. Typically, the $β_1$-blocker will be administered in an amount sufficient to provide from about 2-900 mg per dose.

In one embodiment, compounds of the invention are administered in combination with a $β_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $β_2$-adrenergic receptor agonist will be administered in an amount sufficient to provide from about 0.05-500 μg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof.

In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day. In another embodiment, compounds of the invention are administered in combination with a dual-acting angiotensin-converting enzyme/neprilysin (ACE/NEP) inhibitor, examples of which include, but are not limited to: AVE-0848 ((4S,7S,12bR)-7-[3-methyl-2(S)-sulfanylbutyramido]-6-oxo-1,2,3,4,6,7,8,12b-octahydro-pyrido[2,1-a][2]-benzazepine-4-carboxylic acid); AVE-7688 (ilepatril) and its parent compound; BMS-182657 (2-[2-oxo-3 (S)-[3-phenyl-2 (S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentyl-carbonyl]-L-tryptophan); fasidotril; fasidotrilate; enalaprilat; ER-32935 ((3R,6S,9aR)-6-[3 (S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2 (S)-(mercaptomethyl)-3 (R)-phenylbutyl]-L-alanine); sampatrilat; SA-898 ((2R,4R)—N-

[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-yalyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth subsalicylate.

In yet another embodiment, a compound of the invention is administered in combination with an anti-glaucoma agent. Representative anti-glaucoma agents include, but are not limited to: α-adrenergic agonists such as brimonidine; β₁-adrenergic receptor antagonists; topical β₁-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin; and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buproprion and the buproprion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9 (R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-(β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl) propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl) ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a 5-$HT_{1D}$ serotonin receptor agonist, examples of which include, by way of illustration and not limitation, triptans such as almotriptan, avitriptan, eletriptan, frovatriptan, naratriptan, rizatriptan, sumatriptan, and zolmitriptan.

In one embodiment, compounds of the invention are administered in combination with a sodium channel blocker, examples of which include, by way of illustration and not limitation, carbamazepine, fosphenytoin, lamotrigine, lidocaine, mexiletine, oxcarbazepine, phenytoin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation For Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% NaHCO$_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
Bn benzyl
BOC t-butoxycarbonyl (—C(O)OC(CH$_3$)$_3$)
(BOC)$_2$O di-t-butyl dicarbonate
Cbz carbobenzyloxy (—C(O)O-benzyl)
DCC 1,3-dicyclohexylcarbodiimide
DCM dichloromethane or methylene chloride
DIPEA N,N-diisopropylethylamine
DMAP 4-dimethylaminopyridine
DMF N,N-dimethylformamide
DMSO dimethylsulfoxide
EDC 1-(3-dimethylaminopropyl)-3-ethylcarbodiimide
EDTA ethylenediaminetetraacetic acid
Et$_3$N triethylamine
EtOAc ethyl acetate
EtOH ethanol
Et$_2$O diethyl ether
HATU N,N,N',N'-tetramethyl-O-(7-azabenzotriazol-1-yl) uronium hexafluorophosphate
HOBt 1-hydroxybenzotriazole
HMPA Hexamethylphosphoramide
LDA Lithium diisopropylamide
LiHMDS lithium hexamethyl disilazide
MeCN acetonitrile
MeOH methanol
MTBE methyl t-butyl ether
NaHMDS sodium bis(trimethylsilyl)amide
Pd(dppf)$_2$Cl$_2$ 1,1-bis(diphenylphosphino)ferrocene palladium chloride
PdOH$_2$/C palladium hydroxide on carbon (Pearlman's catalyst)
Pd(PPh$_3$)$_4$ tetrakis(triphenylphosphine)palladium(0)
PPh$_3$ Triphenylphosphine
PE petroleum ether
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

It is understood that many of the compounds described in the Preparations and Examples can exist in a tautomer form, and that both forms are intended to be covered. For example, (2S,4S)-5-(5'-chloro-2'-fluorobiphenyl-4-yl)-2-methoxymethyl-4-[(1H-[1,2,3]triazole-4-carbonyl)amino]pentanoic acid is depicted in Example 2-1 but it is understood that this compound can exist in a tautomer form, for example, as (2S,4S)-5-(5'-chloro-2'-fluorobiphenyl-4-yl)-2-methoxymethyl-4-[(3H-[1,2,3]triazole-4-carbonyl)amino]pentanoic acid.

Preparation 1: (2S,4S)-5-(4-Bromophenyl)-4-t-butoxycarbonylamino-2-hydroxymethylpentanoic Acid Ethyl Ester

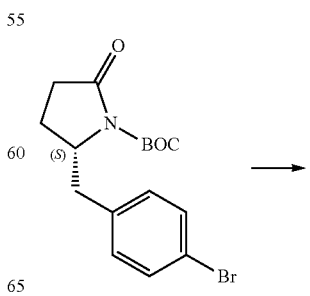

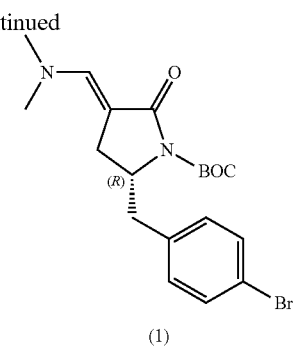

(1)

A mixture of (S)-2-(4-bromobenzyl)-5-oxopyrrolidine-1-carboxylic acid t-butyl ester (52 g, 147 mmol) and t-butoxy-N,N,N',N'-tetramethylmethanediamine (50 g, 286 mmol) was stirred at 80° C. for 4 hours under argon. The mixture was diluted with EtOAc (500 mL) and washed with water (300 mL) and saturated aqueous NaCl (300 mL), dried over $NaSO_4$, and concentrated to yield Compound 1 (60 g) as a red oil. LC-MS: [M+H]+:410.

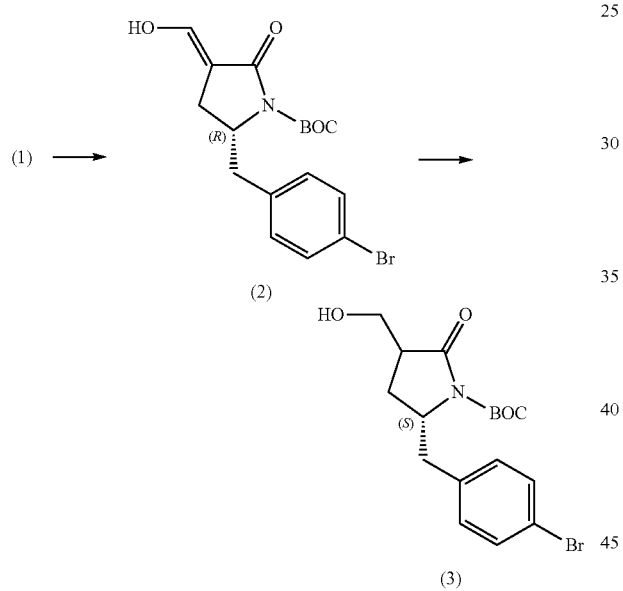

To a solution of Compound 1 (60 g, 147 mmol) in THF (600 mL) was added 1 M HCl (175 mL, 175 mmol) at 0° C. under nitrogen. After stirring for 1 hour at room temperature, the mixture was diluted with EtOAc (500 mL) and adjusted with saturated aqueous $NaHCO_3$ to pH 7. The aqueous layer was extracted with EtOAc (2×300 mL) and the combined organic layers were washed with water (2×500 mL) and saturated aqueous NaCl (500 mL), dried over $NaSO_4$, and concentrated to yield Compound 2 (56 g) as a yellow solid. LC-MS: [2M+Na]+: 787

To a solution of Compound 2 (20 g, 52 mmol) in MeOH (600 mL) was added 1M HCl (210 mL, 210 mmol) at 0° C. under nitrogen. The mixture was stirred at 0° C. for 1 hour, then $NaBH_3CN$ (13.2 g, 210 mmol) was added in small portions over 30 minutes. After stirring for 2 hours at 0° C., the mixture was adjusted with saturated aqueous $NaHCO_3$ to pH 7 and concentrated. The aqueous layers were extracted with EtOAc (3×200 mL) and the combined organic layers were washed with water (2×100 mL) and saturated aqueous NaCl (100 mL), dried over $Na_2SO_4$, filtered, and concentrated to yield the crude residue, which was further purified by silica gel chromatography (PE:EtOAc=5:1) to yield Compound 3 (10 g) as a white solid. LC-MS: [2M+Na]+: 791

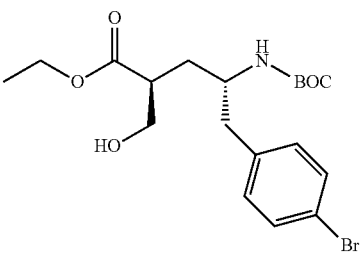

(3)

To a solution of Compound 3 (10 g, 26 mmol) in anhydrous EtOH (800 mL) was added anhydrous $K_2CO_3$ (14.3 g, 104 mmol) at 0° C. under nitrogen. After stirring for 1 hour at 0° C., the mixture was warmed to room temperature and stirred for 16 hours. After filtration, the filtrate was concentrated and the reside was purified by silica gel chromatography (PE:EtOAc=5:1 to 2:1) to yield the title compound (2.5 g) as a colorless oil. LC-MS: [M+Na]+: 453

Preparation 2: (2S,4S)-4-t-Butoxycarbonylamino-5-(5'-chloro-2'-fluoro-biphenyl-4-yl-2-hydroxymethyl-pentanoic Acid Ethyl Ester

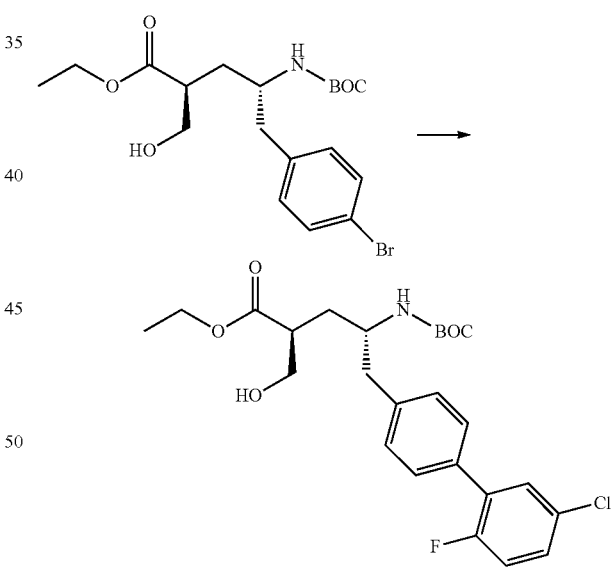

(2S,4S)-5-(4-Bromophenyl)-4-t-butoxycarbonylamino-2-hydroxymethylpentanoic acid ethyl ester (6 g, 13.9 mmol), 5-chloro-2-fluorophenylboronic acid (2.7 g, 15.3 mmol), $Pd(dppf)Cl_2$ (500 mg, 683 µmol), and KF (1.6 g, 27.8 mmol) in dioxane (50 mL) and water (50 mL) were combined in a flask that had been evacuated and back-filled with nitrogen. The mixture was stirred at 80° C. for 4 hours, then extracted with EtOAc (2×50 mL), and the organic layers were concentrated and purified by silica gel chromatography (PE:EtOAc=5:1) to yield the title compound (4 g) as a yellow oil. LC-MS: [2M+Na]+: 982; $^1$H NMR (300 MHz, $CDCl_3$): δ ppm 7.05~7.44 (m, 7H), 4.4 (s, 1H), 4.1~4.2 (m, 2H), 3.85 (s, 1H), 3.76 (m, 2H), 2.7~2.85 (m, 3H), 1.94~2.02 (m, 2H), 1.59 (s, 1H), 1.40 (s, 9H), 1.24~1.29 (t, 3H); $^{13}$C NMR (75 MHz, CDCl$_3$): δ ppm 174.65, 159.98, 156.71, 155.50, 138.16, 129.87, 129.04, 128.61, 117.78, 117.45, 79.63, 63.77, 61.16, 50.34, 44.91, 41.73, 33.30, 28.70, 14.54.

Preparation 3: (2S,4S)-4-Amino-5-(5'-chloro-2'-fluorobiphenyl-4-yl)-2-methoxymethylpentanoic Acid Ethyl Ester

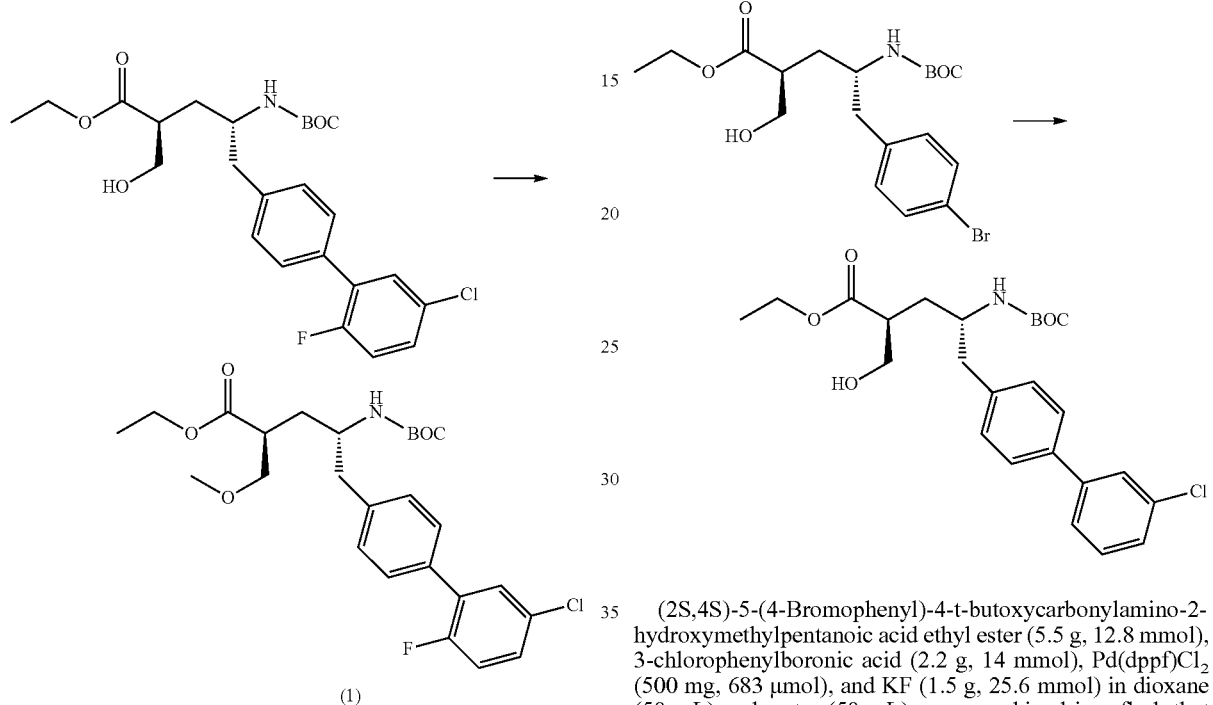

(2S,4S)-4-t-Butoxycarbonylamino-5-(5'-chloro-2'-fluorobiphenyl-4-yl)-2-hydroxymethylpentanoic acid ethyl ester (1.5 g, 3.1 mmol) was combined with 10N NaOH (2.2 mL, 21.9 mmol), DCM (12 mL), and tetrabutylammonium hydrogen sulfate (212 mg, 625 µmol). Dimethyl sulfate (512 mg, 4.1 mmol) was added, the reaction flask was capped and stirred vigorously overnight. The DCM layer was extracted and concentrated under reduced pressure. The residue was purified by normal phase chromatography (0-80% EtOAc/hexanes) to yield Compound 1 (630 mg).

Compound 1 (292 mg, 591 µmol) was dissolved in MeCN (2 mL) and 4N HCl in dioxane (0.6 mL) and stirred for 10 minutes. The mixture was concentrated under reduced pressure to yield the title compound as an HCl salt, which was used without further purification.

Preparation 4: (2S,4S)-4-t-Butoxycarbonylamino-5-(3'-chlorobiphenyl-4-yl)-2-hydroxymethylpentanoic Acid Ethyl Ester

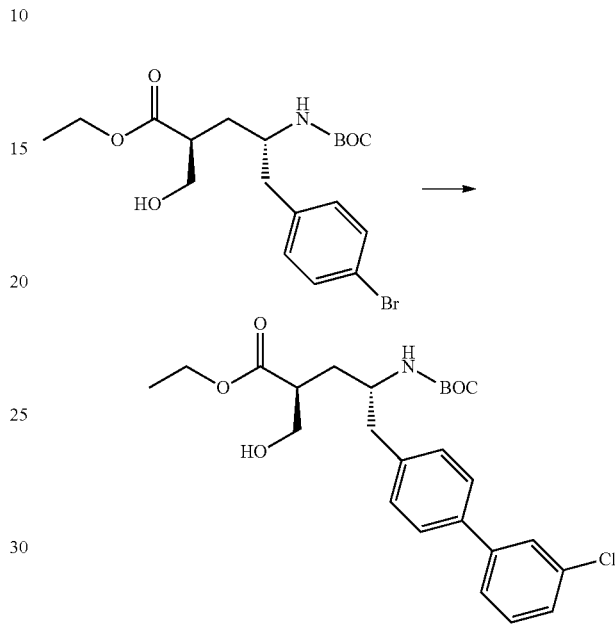

(2S,4S)-5-(4-Bromophenyl)-4-t-butoxycarbonylamino-2-hydroxymethylpentanoic acid ethyl ester (5.5 g, 12.8 mmol), 3-chlorophenylboronic acid (2.2 g, 14 mmol), Pd(dppf)Cl$_2$ (500 mg, 683 µmol), and KF (1.5 g, 25.6 mmol) in dioxane (50 mL) and water (50 mL) were combined in a flask that had been evacuated and back-filled with nitrogen. The mixture was stirred at 80° C. for 4 hours, then extracted with EtOAc (2×50 mL), and the organic layers were concentrated and purified by silica gel chromatography (PE:EtOAc=5:1) to yield the title compound (3.3 g) as a yellow oil. LC-MS: [2M+Na]$^+$: 947; 1H NMR (300 MHz, CDCl$_3$): δ ppm 7.23~7.54 (m, 8H), 4.4 (s, 1H), 4.1~4.2 (m, 2H), 3.85 (s, 1H), 3.7 (m, 2H), 2.69~2.85 (m, 3H), 1.93~2.09 (m, 2H), 1.59 (s, 1H), 1.40 (s, 9H), 1.24~1.29 (t, 3H).

Preparation 5: (2S,4S)-4-Amino-5-(3'-chlorobiphenyl-4-yl)-2-methoxymethylpentanoic Acid Ethyl Ester

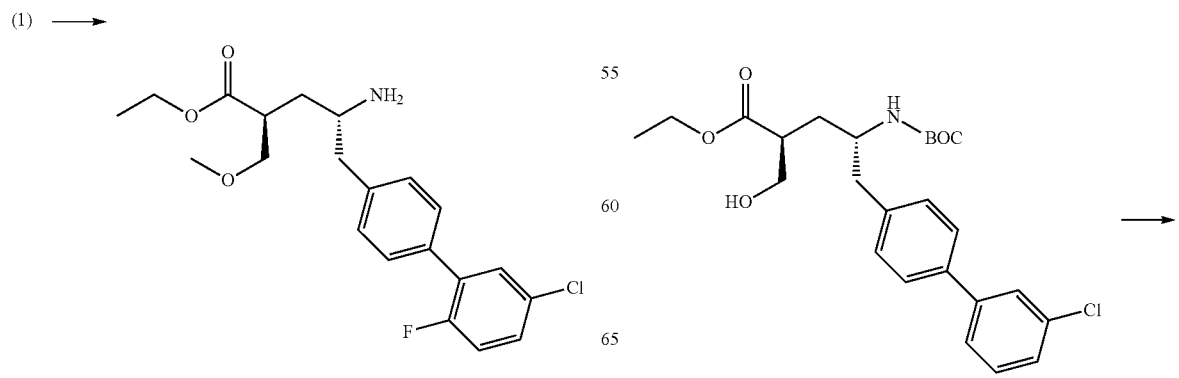

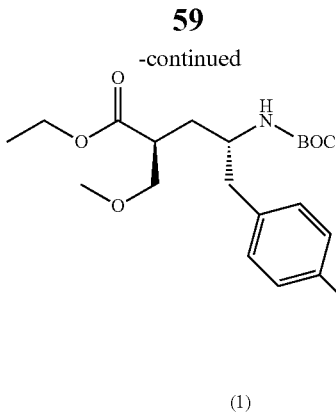

(1)

(2S,4S)-4-t-Butoxycarbonylamino-5-(3'-chlorobiphenyl-4-yl)-2-hydroxymethylpentanoic acid ethyl ester (1.4 g, 3.1 mmol) was combined with 10N NaOH (2.2 mL, 21.9 mmol), DCM (12 mL), and tetrabutylammonium hydrogen sulfate (212 mg, 625 µmol). Dimethyl sulfate (512 mg, 4.1 mmol) was added, the reaction flask was capped and stirred vigorously overnight. The DCM layer was extracted and concentrated under reduced pressure. The residue was purified by normal phase chromatography (0-80% EtOAc/hexanes) to yield Compound 1 (650 mg).

(1) ⟶

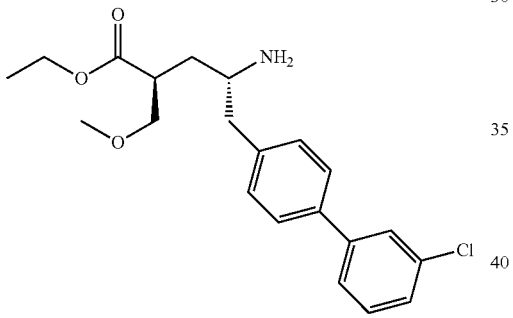

Compound 1 (281 mg, 591 µmol) was dissolved in MeCN (2 mL) and 4N HCl in dioxane (0.6 mL) and stirred for 10 minutes. The mixture was concentrated under reduced pressure to yield the title compound as an HCl salt, which was used without further purification.

Preparation 6: (2S,4S)-5-Biphenyl-4-yl-4-t-butoxycarbonylamino-2-hydroxymethylpentanoic Acid Ethyl Ester

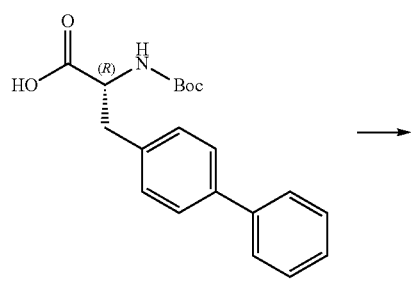

⟶

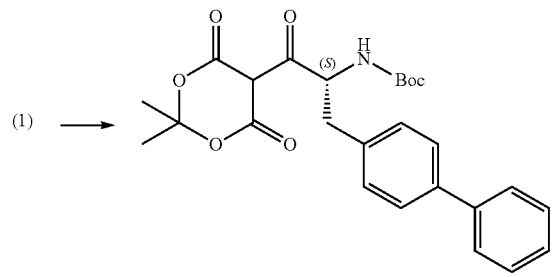

(1)

To a solution of (R)-3-biphenyl-4-yl-2-t-butoxycarbonylamino-propionic acid (50 g, 146 mmol), Meldrum's acid (23.3 g, 161 mmol) and DMAP (27.8 g, 227 mmol) in anhydrous DCM (500 mL) was added a solution of DCC (33.3 g, 161 mmol) in anhydrous DCM (200 mL) over 1 hour at −5° C. under nitrogen. The mixture was stirred at −5° C. for 8 hours, then refrigerated overnight, during which time, tiny crystals of dicyclohexylurea precipitated. After filtration, the mixture was washed with 5% KHSO$_4$ (4×200 mL) and saturated aqueous NaCl (200 mL), then dried under refrigeration with MgSO$_4$ overnight. The solution was filtered and evaporated to yield Compound 1 (68 g) as a light yellow solid, which was used without further purification. LC-MS: 490 [M+Na], 957 [2M+Na].

(1) ⟶

(2)

To a solution of crude Compound 1 (68 g, 147 mmol) in anhydrous DCM (1 L) was added AcOH (96.7 g, 1.6 mol) at −5° C. under nitrogen. The mixture was stirred at −5° C. for 0.5 hour, then NaBH$_4$ (13.9 g, 366 mmol) was added in small portions over 1 hour. After stirring for an additional one hour at −5° C., saturated aqueous NaCl (300 mL) was added. The organic layer was washed with saturated aqueous NaCl (2×300 mL) and water (2×300 mL), dried over MgSO$_4$, filtered, and evaporated to yield the crude residue, which was further purified by chromatography (hexanes: EtOAc=5:1) to yield Compound 2 (46 g) as a light yellow solid. LC-MS: 476 [M+Na], 929 [2M+Na].

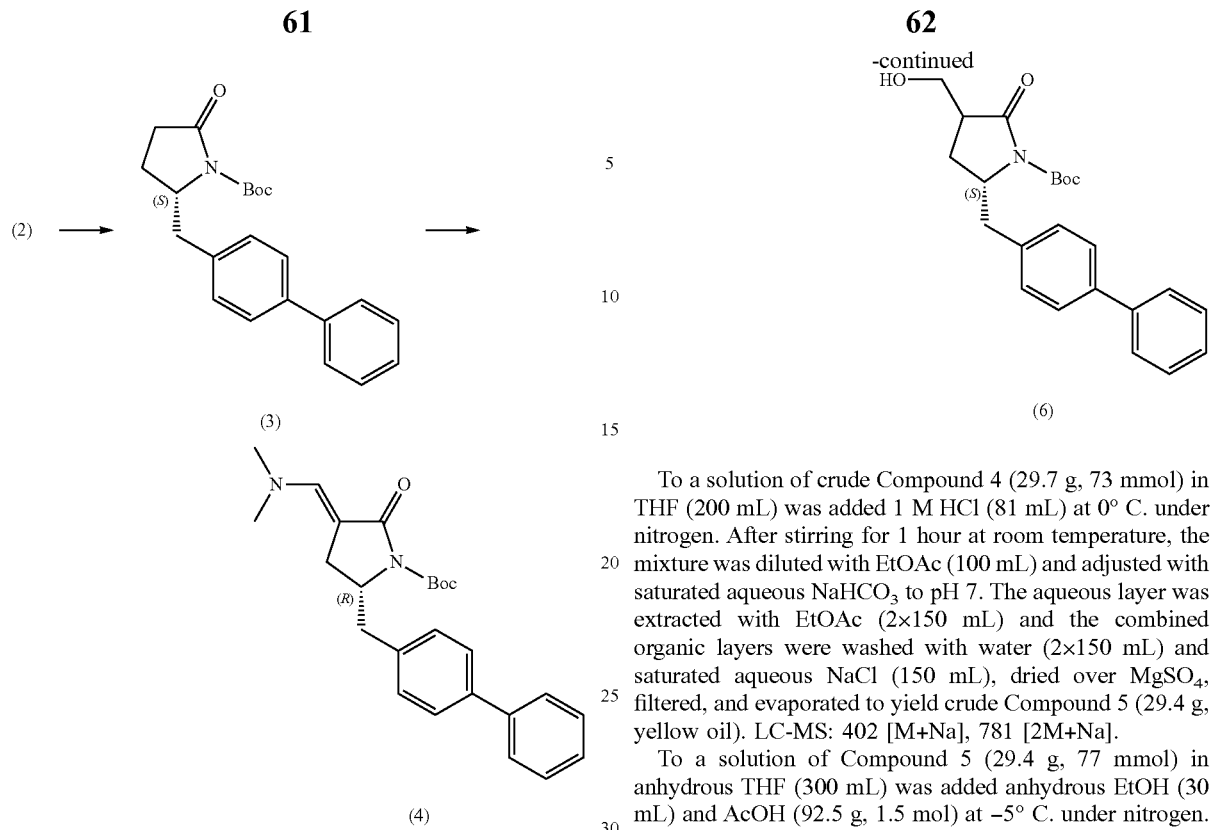

A solution of Compound 2 (46 g, 101 mmol) in anhydrous toluene (300 mL) was refluxed under nitrogen for 3 hours. After evaporation of the solvent, the residue was purified by chromatography (hexanes:EtOAc=10:1) to yield Compound 3 (27 g) as a light yellow solid. LC-MS: 374 [M+Na], 725 [2M+Na]. $^1$H NMR (300 MHz, CDCl$_3$): δ7.64-7.62 (m, 4H), 7.51-7.46 (m, 2H), 7.42-7.39 (m, 1H), 7.39-7.30 (m, 2H), 4.50-4.43 (m, 1H), 3.27-3.89 (m, 1H), 2.88-2.80 (m, 1H), 2.48-2.42 (m, 2H), 2.09-1.88 (m, 2H), 1.66 (s, 9H).

A mixture of Compound 3 (27 g, 77 mmol) and t-butoxy-N,N,N',N'-tetramethylmethanediamine (40.3 g, 231 mmol) was heated to 80° C. under nitrogen. After stirring for 3 hours at 80° C., the mixture was diluted with EtOAc (300 mL), washed with water (2×150 mL) and saturated aqueous NaCl (2×150 mL), dried over MgSO$_4$, filtered, and evaporated to yield crude Compound 4 (29.7 g, light yellow oil). LC-MS: 425 [M+H], 835 [2M+H].

To a solution of crude Compound 4 (29.7 g, 73 mmol) in THF (200 mL) was added 1 M HCl (81 mL) at 0° C. under nitrogen. After stirring for 1 hour at room temperature, the mixture was diluted with EtOAc (100 mL) and adjusted with saturated aqueous NaHCO$_3$ to pH 7. The aqueous layer was extracted with EtOAc (2×150 mL) and the combined organic layers were washed with water (2×150 mL) and saturated aqueous NaCl (150 mL), dried over MgSO$_4$, filtered, and evaporated to yield crude Compound 5 (29.4 g, yellow oil). LC-MS: 402 [M+Na], 781 [2M+Na].

To a solution of Compound 5 (29.4 g, 77 mmol) in anhydrous THF (300 mL) was added anhydrous EtOH (30 mL) and AcOH (92.5 g, 1.5 mol) at -5° C. under nitrogen. The mixture was stirred at -5° C. for 0.5 hour, then NaBH$_3$CN (19.4 g, 308 mmol) was added in small portions over 1 hour. After stirring for one additional hour at -5° C., the mixture was adjusted with saturated aqueous NaHCO$_3$ to pH 7. The aqueous layers were extracted with EtOAc (2×200 mL) and the combined organic layers were washed with water (2×150 mL) and saturated aqueous NaCl (150 mL), dried over MgSO$_4$, filtered, and concentrated to yield the crude residue, which was further purified by chromatography (hexanes:EtOAc=5:1) to yield Compound 6 (11.2 g) as a light yellow solid. LC-MS: 404 [M+Na], 785 [2M+Na].

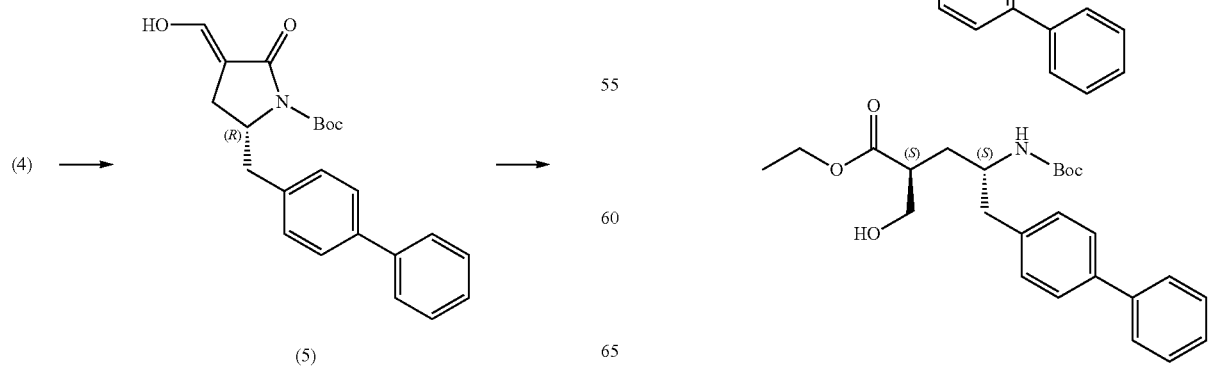

To a solution of Compound 6 (11.2 g, 29 mmol) in anhydrous EtOH (500 mL) was added anhydrous K$_2$CO$_3$ (8.0 g, 58 mmol) at 0° C. under nitrogen. After stirring for 1 hour at 0° C., the mixture was warmed to room temperature and stirred for 16 hours. After filtration, the filtrate was concentrated and the residue was diluted with water (150 mL), DCM (200 mL) and saturated aqueous NaCl (50 mL). After separation, the aqueous layer was extracted with DCM (2×150 mL). The combined organic layers were washed with saturated aqueous NaCl (2×200 mL), dried over MgSO$_4$, and concentrated to yield the crude residue which was further purified by column chromatography (hexanes:EtOAc=5:1) to yield the (S,S) title compound (8.3 g) as a light yellow solid, as well as the (R,S) isomer.

(S,S) title compound: LC-MS: 450 [M+Na], 877 [2M+Na]. $^1$H NMR (300 MHz, CDCl$_3$): δ7.58-7.23 (m, 9H), 4.46-4.43 (d, 1H), 4.20-4.13 (m, 2H), 3.94 (s, 1H), 3.82-3.70 (m, 2H), 2.85-2.70 (m, 3H), 2.25-2.22 (d, 1H), 2.01-1.92 (m, 1H), 1.47 (s, 9H), 1.26-1.24 (m, 3H).

(R,S) isomer: LC-MS: 450 [M+Na], 877 [2M+Na]. $^1$H NMR (300 MHz, CDCl$_3$): δ7.58-7.55 (m, 4H), 7.50-7.43 (m, 2H), 7.40-7.30 (m, 1H), 7.26-7.23 (m, 1H), 4.46 (m, 1H), 4.21-4.13 (m, 2H), 3.94 (m, 1H), 3.82-3.77 (m, 2H), 2.83-2.81 (d, 2H), 2.66-2.63 (m, 1H), 2.24 (m, 1H), 1.83-1.81 (m, 2H), 1.38 (s, 9H), 1.30-1.25 (m, 3H).

Preparation 7: (2S,4S)-4-Amino-5-biphenyl-4-yl-2-methoxymethylpentanoic Acid Ethyl Ester

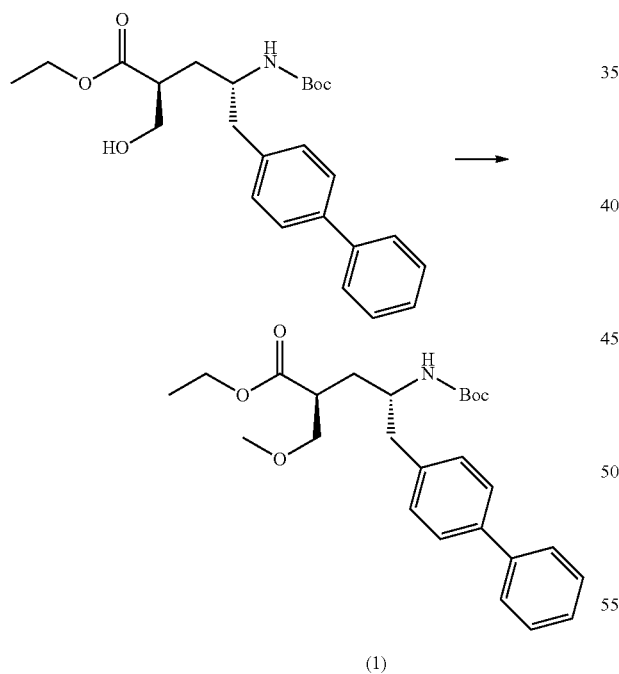

(2S,4S)-5-Biphenyl-4-yl-4-t-butoxycarbonylamino-2-hydroxymethylpentanoic acid ethyl ester (69 mg, 140 µmol) was combined with DCM (1 mL), 10N NaOH (98 µL, 982 µmol), tetrabutylammonium hydrogen sulfate (9.5 mg, 28 µmol) and dimethyl sulfate (54 µL, 561 µmol). The mixture was stirred overnight and the DCM layer was purified by normal phase chromatography (0-100% EtOAc/hexanes) to yield Compound 1 (30 mg).

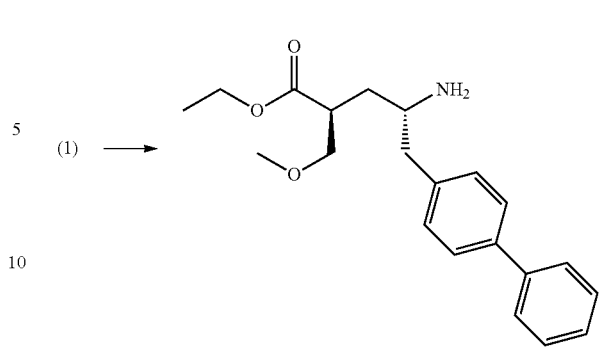

Compound 1 (21.7 mg, 49 µmol) was dissolved in MeCN (0.3 mL) and 4N dioxane (0.3 mL) and stirred for 10 minutes. The mixture was concentrated under reduced pressure to yield the title compound as an HCl salt.

Preparation 8: (2S,4S)-4-Amino-5-(5'-chloro-2'-fluorobiphenyl-4-yl)-2-ethoxymethylpentanoic Acid Ethyl Ester

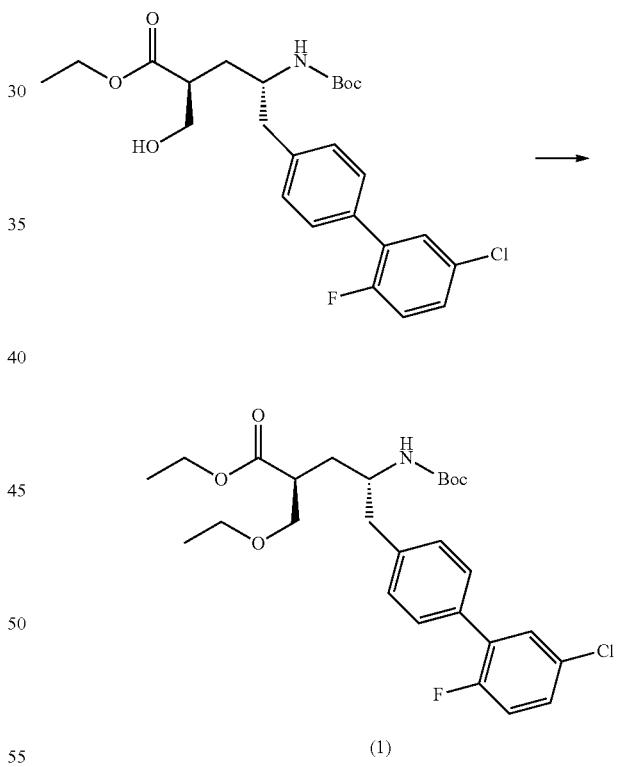

(2S,4S)-4-t-Butoxycarbonylamino-5-(5'-chloro-2'-fluorobiphenyl-4-yl)-2-hydroxymethylpentanoic acid ethyl ester (1.5 g, 3.1 mmol) was combined with 10N NaOH (2.2 mL, 21.9 mmol), DCM (12 mL), and tetrabutylammonium hydrogen sulfate (212 mg, 625 µmol). Diethyl sulfate (626 mg, 4.1 mmol) was added, the reaction flask was capped and stirred vigorously overnight. The DCM layer was extracted and concentrated under reduced pressure. The residue was purified by normal phase chromatography (0-80% EtOAc/hexanes) to yield Compound 1 (300 mg).

(1) →

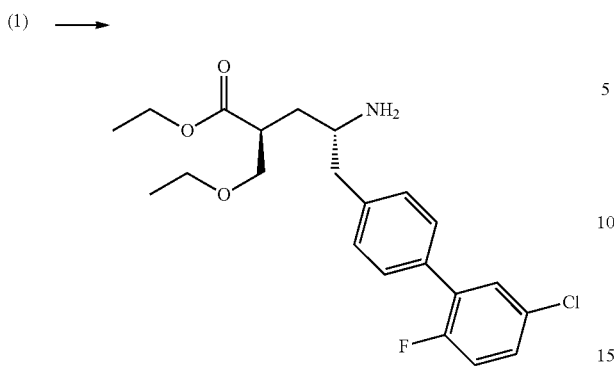

Compound 1 (300 mg, 591 μmol) was dissolved in MeCN (2 mL) and 4N HCl in dioxane (0.6 mL) and stirred for 10 minutes. The mixture was concentrated under reduced pressure to yield the title compound as an HCl salt, which was used without further purification.

Preparation 9: (2S,4S)-4-Amino-5-(3'-chlorobiphenyl-4-yl)-2-ethoxymethylpentanoic Acid Ethyl Ester

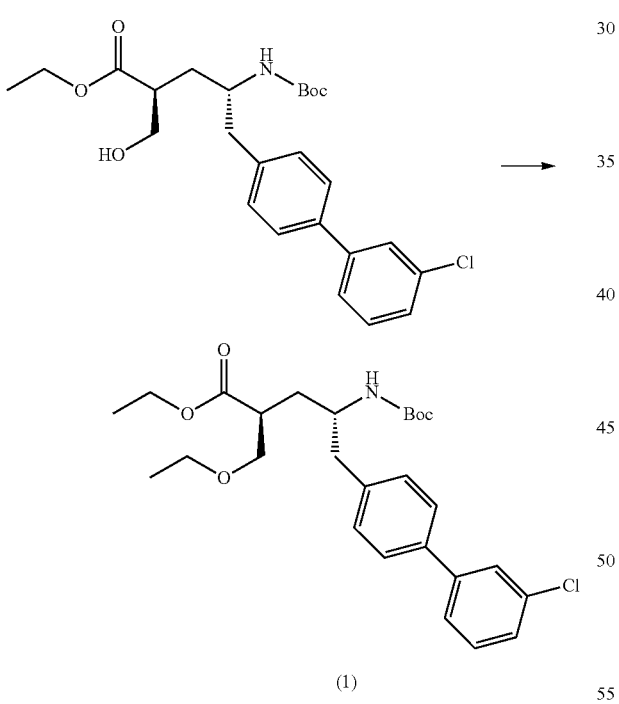

(2S,4S)-4-t-Butoxycarbonylamino-5-(3'-chlorobiphenyl-4-yl)-2-hydroxymethylpentanoic acid ethyl ester (1.4 g, 3.1 mmol) was combined with 10N NaOH (2.2 mL, 21.9 mmol), DCM (12 mL), and tetrabutylammonium hydrogen sulfate (212 mg, 625 μmol). Diethyl sulfate (626 mg, 4.1 mmol) was added, the reaction flask was capped and stirred vigorously overnight. The DCM layer was extracted and concentrated under reduced pressure. The residue was purified by normal phase chromatography (0-80% EtOAc/hexanes) to yield Compound 1 (350 mg).

(1) →

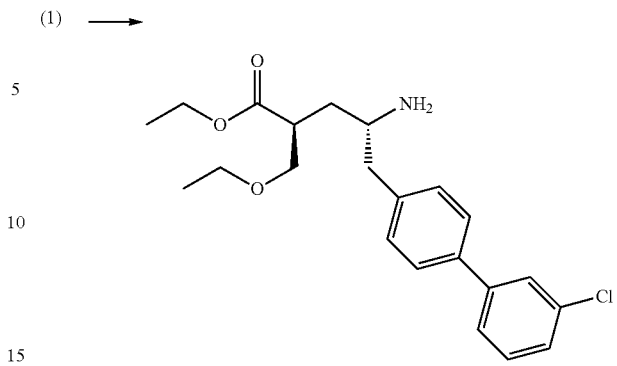

Compound 1 (289 mg, 591 μmol) was dissolved in MeCN (2 mL) and 4N HCl in dioxane (0.6 mL) and stirred for 10 minutes. The mixture was concentrated under reduced pressure to yield the title compound, which was used without further purification.

Preparation 10: (2S,4S)-4-Amino-5-biphenyl-4-yl-2-ethoxymethylpentanoic Acid Ethyl Ester

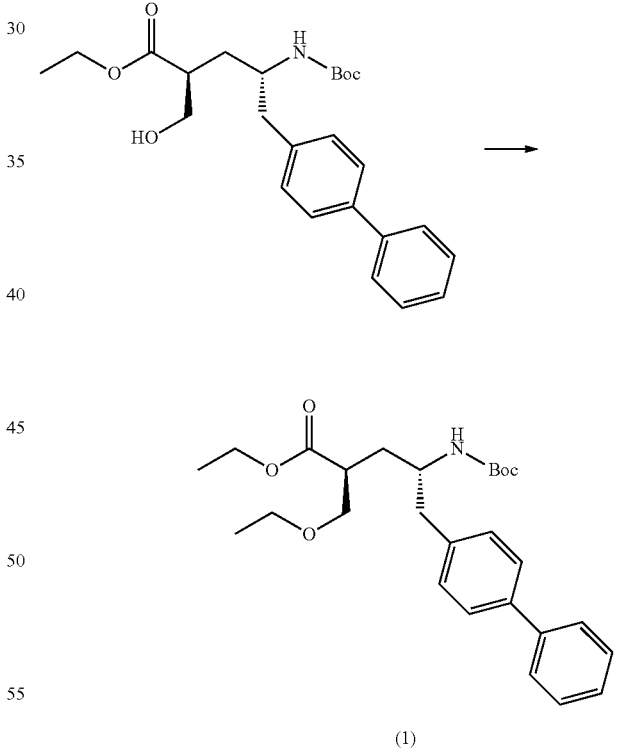

(2S,4S)-5-Biphenyl-4-yl-4-t-butoxycarbonylamino-2-hydroxymethylpentanoic acid ethyl ester (60 mg, 140 μmol) was combined with 10N NaOH (98 μL, 982 μmol), DCM (1 mL), tetrabutylammonium hydrogen sulfate (9.5 mg, 28 μmol), and diethyl sulfate (87 mg, 561 μmol). The mixture was stirred overnight and the DCM layer was purified by normal phase chromatography (0-100% EtOAc/hexanes) to yield Compound 1 (15 mg).

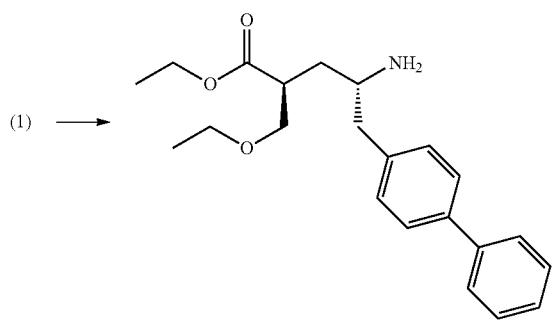 [SMILES: CCOC[C@H](C[C@H](N)Cc1ccc(-c2ccccc2)cc1)C(=O)OCC]

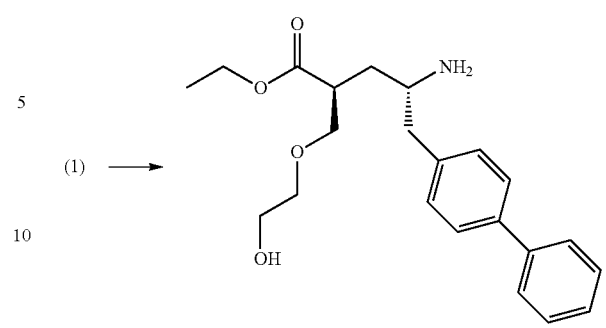

Compound 1 (22.4 mg, 49 µmol) was dissolved in MeCN (0.3 mL) and 4N HCl in dioxane (0.3 mL) and stirred for 10 minutes. The mixture was concentrated under reduced pressure to yield the title compound as an HCl salt, which was used without further purification.

Compound 1 (23.2 mg, 49 µmol) was dissolved in MeCN (0.3 mL) and 4N HCl in dioxane (0.3 mL) and stirred for 10 minutes. The mixture was concentrated under reduced pressure to yield the title compound as an HCl salt, which was used without further purification.

Preparation 11: (2S,4S)-4-Amino-5-biphenyl-4-yl-2-(2-hydroxyethoxymethyl)pentanoic Acid Ethyl Ester Preparation 12: (2S,4S)-4-Amino-5-biphenyl-4-yl-2-(3-hydroxypropoxymethyl)pentanoic Acid Ethyl Ester

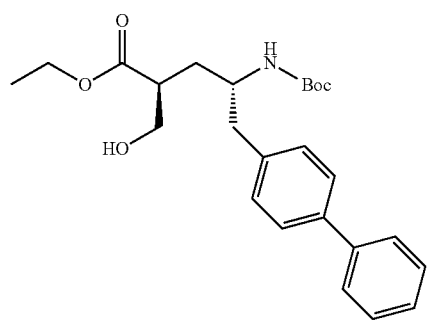

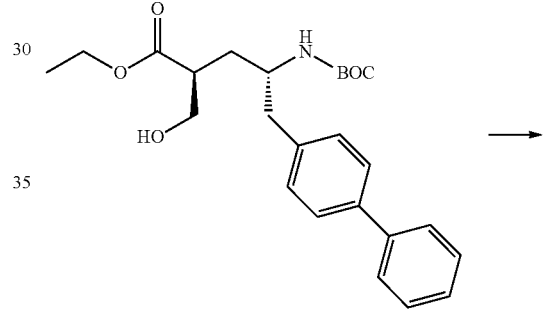

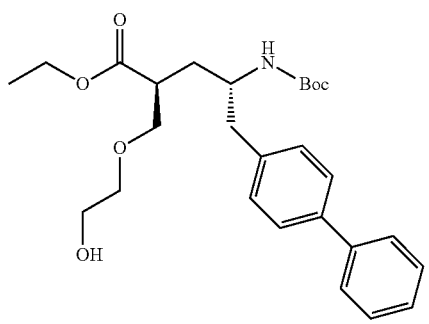

(1)

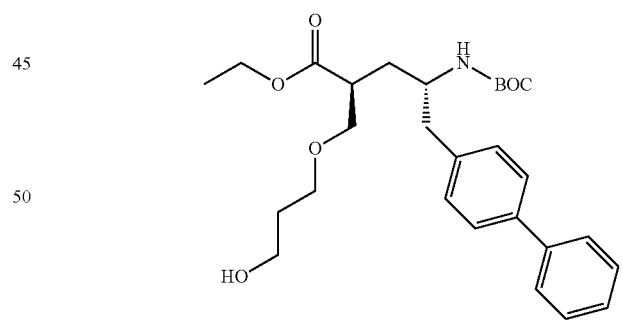

(1)

(2S,4S)-5-Biphenyl-4-yl-4-t-butoxycarbonylamino-2-hydroxymethylpentanoic acid ethyl ester (60 mg, 140 µmol) was combined with 10N NaOH (98 µL, 982 µmol), DCM (1 mL), tetrabutylammonium hydrogen sulfate (9.5 mg, 28 µmol), and [1,3,2]dioxathiolane 2,2-dioxide (70 mg, 561 µmol). The mixture was stirred overnight and the DCM layer was separated, dried over $Na_2SO_4$, and purified by normal phase chromatography (0-100% EtOAc/hexanes) to yield Compound 1 (8 mg).

(2S,4S)-5-Biphenyl-4-yl-4-t-butoxycarbonylamino-2-hydroxymethylpentanoic acid ethyl ester (60 mg, 140 µmol) was combined with 10N NaOH (98 µL, 982 µmol), DCM (1 mL), tetrabutylammonium hydrogen sulfate (9.5 mg, 28 µmol), and [1,3,2]dioxathiane 2,2-dioxide (78 mg, 561 µmol). The mixture was stirred overnight and the DCM layer was separated, dried over $Na_2SO_4$, and purified by normal phase chromatography (0-100% EtOAc/hexanes) to yield Compound 1 (9 mg).

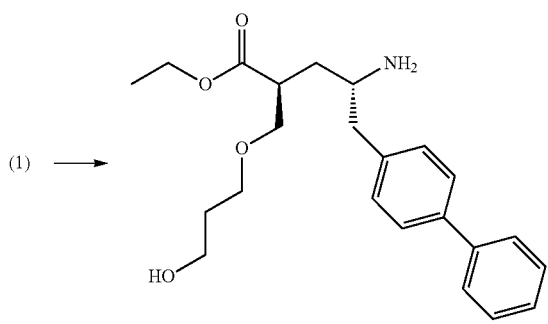 [SMILES: CCOC(=O)[C@H](COCCCO)C[C@H](N)Cc1ccc(-c2ccccc2)cc1]

Compound 1 (23.9 mg, 49 μmol) was dissolved in MeCN (0.3 mL) and 4N HCl in dioxane (0.3 mL) and stirred for 10 minutes. The mixture was concentrated under reduced pressure to yield the title compound as an HCl salt, which was used without further purification.

Preparation 13: (2R,4R)-4-t-Butoxycarbonylamino-5-(5'-chloro-2'-fluorobiphenyl-4-yl)-2-hydroxypentanoic Acid Ethyl Ester

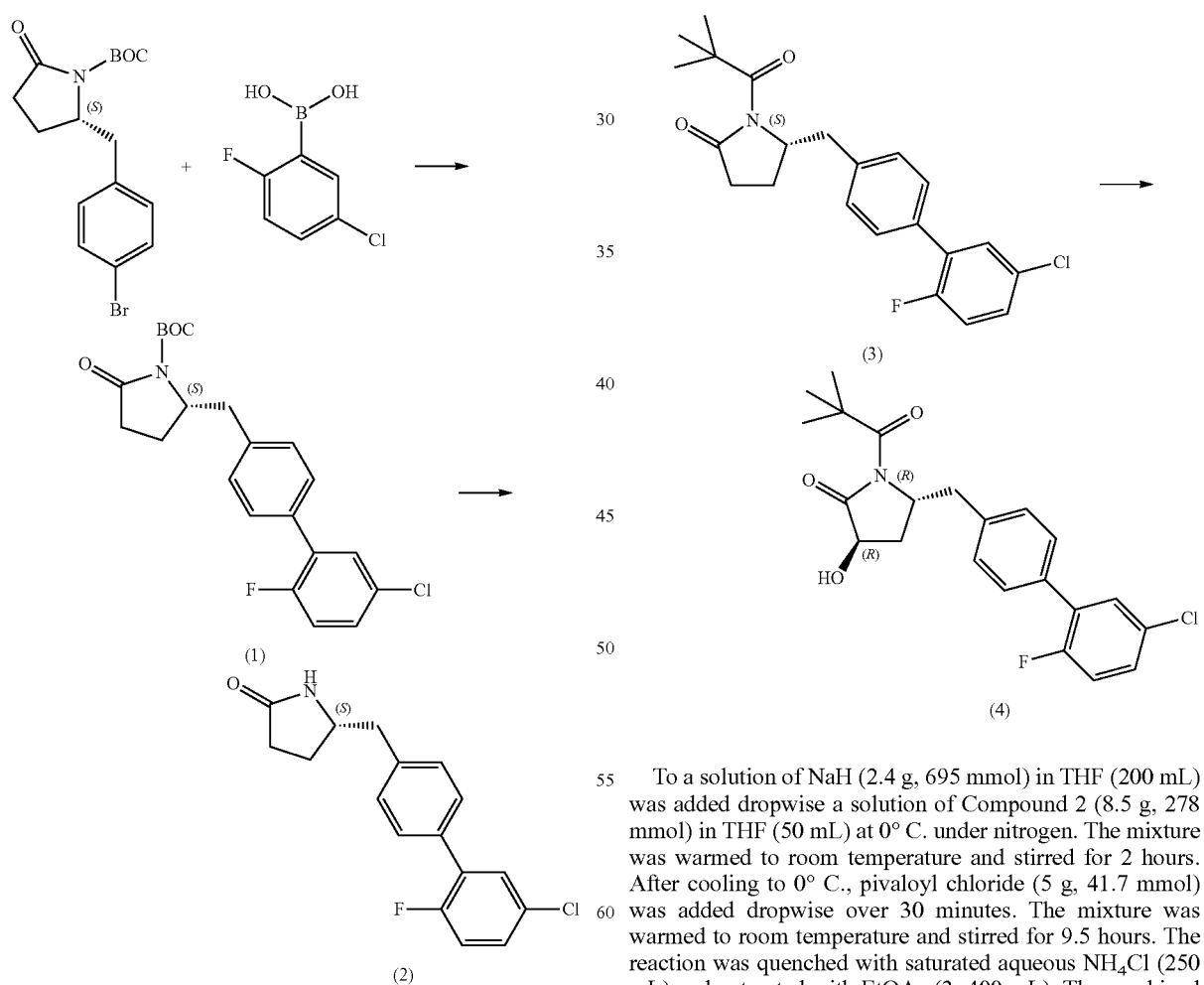

To a solution of (S)-2-(4-bromobenzyl)-5-oxopyrrolidine-1-carboxylic acid t-butyl ester (25 g, 70.6 mmol) in 1,4-dioxane (500 mL) was added 5-chloro-2-fluorophenylboronic acid (24.6 g, 141 mmol), Pd(PPh$_3$)$_4$ (4.1 g, 3.5 mmol) and a solution of K$_2$CO$_3$ (17.8 g, 141 mmol) in water (90 mL), at room temperature under nitrogen. The mixture was heated to 60° C. and stirred overnight. Water (500 mL) was added and the solvent evaporated. The mixture was extracted with EtOAc (3×200 mL). The combined organic layers were washed with saturated aqueous NaCl (300 mL) and filtered. The filtrate was concentrated to yield the crude residue which was purified by chromatography to yield Compound 1 (22.7 g) as a light yellow solid. LC-MS: 829.2 [2M+Na$^+$].

To a solution of Compound 1 (4.9 g, 12.1 mol) in DCM (100 mL) was added TFA (4.5 mL, 60.7 mmol) at 0° C. under nitrogen, and stirred for 1 hour. The mixture was warmed to room temperature for 1.5 hours. After evaporation of the solvent, the residue was diluted with EtOAc (100 mL), then washed with saturated aqueous NaHCO$_3$ (3×100 mL), water (2×100 mL), saturated aqueous NaCl (100 mL), then dried over Na$_2$SO$_4$. The mixture was filtered and the filtrate was concentrated to yield crude Compound 2. LC-MS: 304 [M+H]$^+$.

To a solution of NaH (2.4 g, 695 mmol) in THF (200 mL) was added dropwise a solution of Compound 2 (8.5 g, 278 mmol) in THF (50 mL) at 0° C. under nitrogen. The mixture was warmed to room temperature and stirred for 2 hours. After cooling to 0° C., pivaloyl chloride (5 g, 41.7 mmol) was added dropwise over 30 minutes. The mixture was warmed to room temperature and stirred for 9.5 hours. The reaction was quenched with saturated aqueous NH$_4$Cl (250 mL) and extracted with EtOAc (3×400 mL). The combined organic layers were dried over Na$_2$SO$_4$ and concentrated to yield the crude residue which was purified by chromatography to yield Compound 3 (18 g) as a yellow solid. LC-MS: 388 [M+H].

To a solution of Compound 3 (9 g, 23.2 mmol) in THF (200 mL) was added dropwise NaHMDS (20.9 mL, 41.8 mmol) at −78° C. under nitrogen. After stirring for 1 hour at −78° C., a solution of (+)-(8,8-dichlorocamphorylsulfonyl) oxaziridine (10.4 g, 34.8 mmol) in THF (50 mL) was added dropwise. After stirring at −78° C. for 1 hour, the reaction was quenched with saturated aqueous NH$_4$Cl (50 mL) and extracted with EtOAc (3×400 mL). The combined organic layers were washed with 1M HCl (400 mL), saturated aqueous NaHCO$_3$ (400 mL), and saturated aqueous NaCl (400 mL), dried over Na$_2$SO$_4$, and concentrated to give the crude residue which was purified by chromatography to yield Compound 4 (8.8 g) as a white semi-solid. LC-MS: 426.1 [M+Na$^{3\circ}$].

(4) →

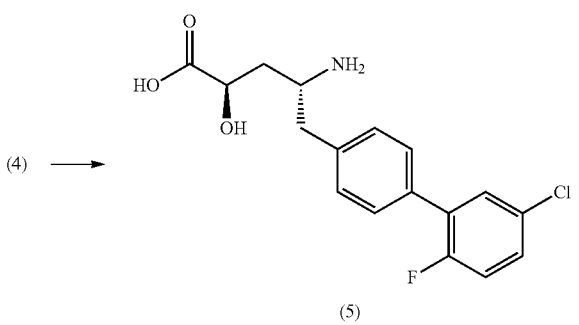 [SMILES: N[C@H](Cc1ccc(-c2cc(Cl)ccc2F)cc1)C[C@@H](O)C(=O)O]

(5)

A solution of Compound 4 (8.8 g, 21.8 mmol) in EtOH (12 mL) was added to concentrated HCl (200 mL) and heated at 100° C. and stirred overnight. The mixture was then concentrated to give the crude residue which was purified by washing with Et$_2$O (100 mL) to yield Compound 5 (7.5 g) as a solid HCl salt. LC-MS: 338 [M+H].

(5) →

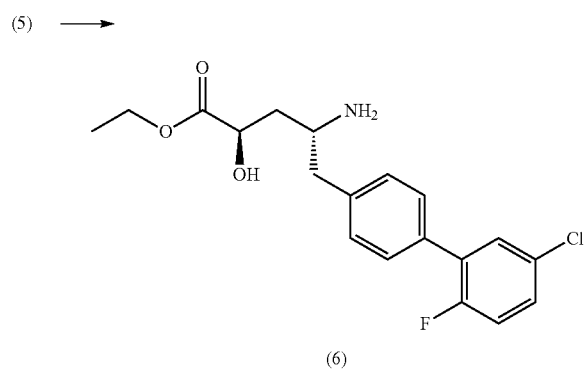

(6)

A solution of Compound 5 (7.5 g, 20.1 mmol) in EtOH/HCl (100 mL) was heated at 50° C. overnight. The mixture was concentrated and the crude residue was purified by washing with Et$_2$O (200 mL) to yield Compound 6 (6.5 g) as a white solid HCl salt. LC-MS: 366.1 [M+H$^{3\circ}$].

(6) →

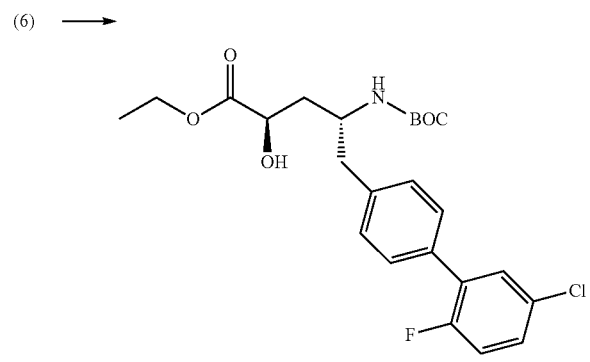

Compound 6 (2 g, 5.5 mmol) and di-t-butyl dicarbonate (1.5 mL, 6.6 mmol) were mixed in DCM (10 mL) followed by DIPEA (1.9 mL, 10.9 mmol). The mixture was stirred at room temperature for 3 hours, at which time LCMS indicated the mass of the desired compound. The solvent was removed and the residue was purified by normal phase column chromatography (20-100% EtOAc/hexanes) to yield the title compound (2.5 g).

Preparation 14: (2R,4R)-4-Amino-2-azido-5-(5'-chloro-2'-fluorobiphenyl-4-yl)pentanoic Acid Ethyl Ester

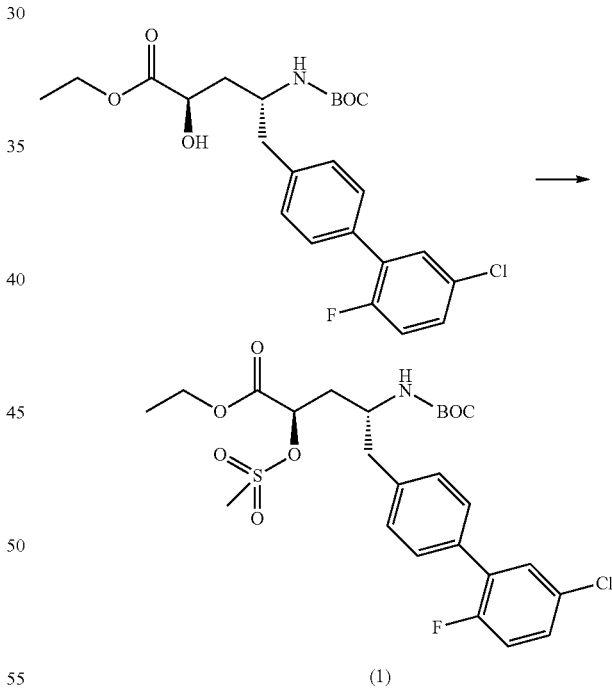

(1)

(2R,4R)-4-t-Butoxycarbonylamino-5-(5'-chloro-2'-fluorobiphenyl-4-yl)-2-hydroxypentanoic acid ethyl ester (2.5 g, 5.4 mmol) was dissolved in DCM (10 mL). Methanesulfonyl chloride (460 µL, 6.0 mmol) was added, followed by Et$_3$N (1.5 mL, 10.8 mmol). The mixture was stirred at room temperature for 10 minutes, at which time LCMS indicated the mass of the desired compound. EtOAc and a saturated aqueous NH$_4$Cl were added. The organic layer was extracted, separated, dried over MgSO$_4$, filtered, and evaporated to yield crude Compound 1, which was used directly in the next step.

(1) →

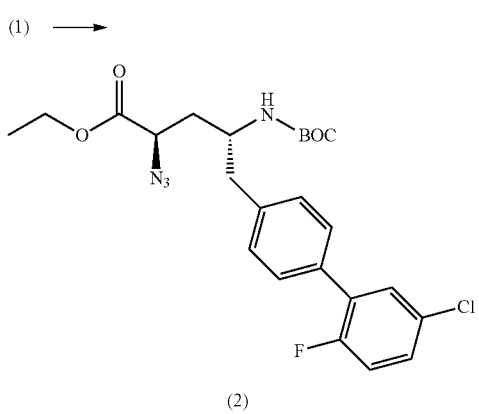

(2)

Compound 1 (2.9 g, 5.4 mmol) in DMF (6 mL) was combined with sodium azide (422 mg, 6.5 mmol), and the resulting mixture was stirred at 50° C. for 4 hours, at which time LCMS indicated the mass of the desired compound. EtOAc and water were added. The organic layer was extracted, separated and dried over $MgSO_4$, filtered, and evaporated. The residue was purified by normal phase column chromatography (20-100% EtOAc/hexanes) to yield Compound 2 (2.1 g) as a yellow oil.

(2) →

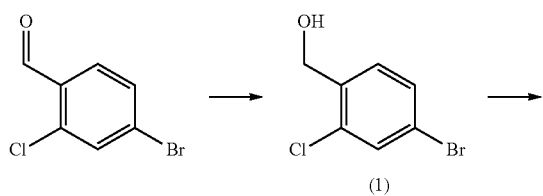

Compound 2 (2.1 g, 4.2 mmol) was dissolved in MeCN (6 mL). A solution of 4N HCl in dioxane (10.5 mL, 42.2 mmol) was added, and the mixture was stirred at room temperature for 20 minutes then concentrated in vacuo to yield the crude title compound as an HCl salt, which was used without further purification.

Preparation 15: (2R,4R)-4-Amino-5-(4-bromo-2-chlorophenyl)-2-hydroxypentanoic Acid Ethyl Ester

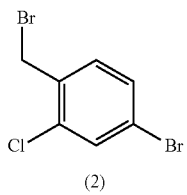

(2)

To a suspension of 4-bromo-2-chlorobenzaldehyde (50 g, 22.8 mmol) in MeOH (500 mL) was added $NaBH_4$ (17.3 g, 45.6 mmol) in portions at 0° C. The mixture was stirred for 30 minutes and then aqueous $NH_4Cl$ was added to quench the reaction. The mixture was concentrated in vacuo. The residue was extracted with EtOAc (200 mL×2) and the combined organic layers were dried over $Na_2SO_4$, and concentrated in vacuo to yield Compound 1 (48 g) as a white solid.

To a solution of Compound 1 (46.8 g, 21.1 mmol) in dry DCM (500 mL) was added phosphorous tribromide (68.6 g, 25.3 mmol) dropwise at 0° C. under nitrogen. The mixture was stirred for 2 hours and then washed with saturated aqueous $NaHCO_3$ (200 mL×2) and saturated aqueous NaCl (200 mL), dried over $Na_2SO_4$, concentrated in vacuo to yield Compound 2 (36 g) as a colorless oil.

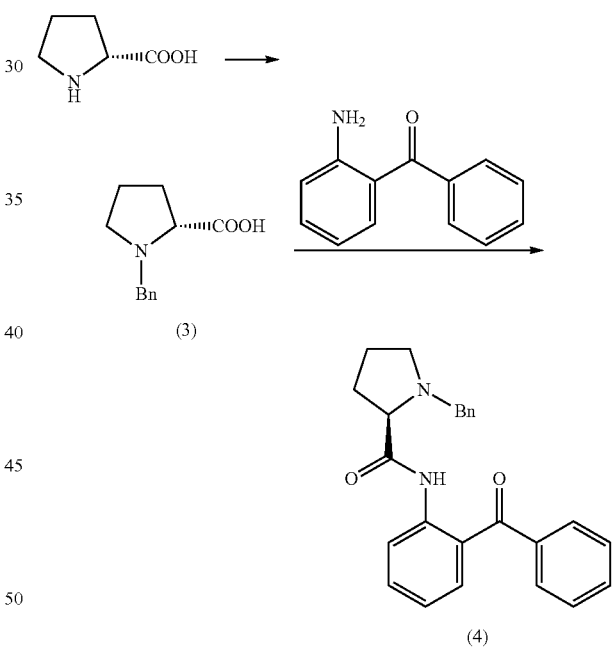

To a stirred solution of (R)-pyrrolidine-2-carboxylic acid (57.7 g, 0.5 mol) and KOH (84 g, 1.5 mol) in isopropyl alcohol (330 mL) was added benzyl chloride (70 mL, 0.6 mol) dropwise at 0° C. over 3 hours. The mixture was then stirred overnight at the same temperature. The resulting mixture was neutralized with concentrated HCl to pH 6, followed by the addition of chloroform (200 mL). The mixture was stirred for 30 minutes, then filtered and the precipitate was washed with chloroform (100 mL×3). The combined chloroform solutions were dried over $Na_2SO_4$, and concentrated in vacuo to yield Compound 3 (52 g) as a white solid. LC-MS: 206 [M+H]$^+$.

To a solution of Compound 3 (10 g, 48.8 mmol) in dry DCM (50 mL) was added $SO_2Cl_2$ (7.3 g, 61 mmol) at −20°

C. under nitrogen. The mixture was stirred at −20° C. for 3 hours followed by the addition of a solution of (2-aminophenyl)(phenyl)methanone (6 g, 30.5 mmol) in dry DCM (25 mL) and the mixture was stirred overnight at room temperature. A solution of Na$_2$CO$_3$ (10.3 g) in water (40 mL) was added at 0° C. The organic layer was separated and the aqueous layer was extracted with DCM (50 mL×3). The combined organic layers were dried over Na$_2$SO$_4$ and concentrated in vacuo. The residue was washed with MTBE (50 mL×2) to yield Compound 4 (8.5 g) as a yellow solid. LC-MS: 385 [M+H]$^+$.

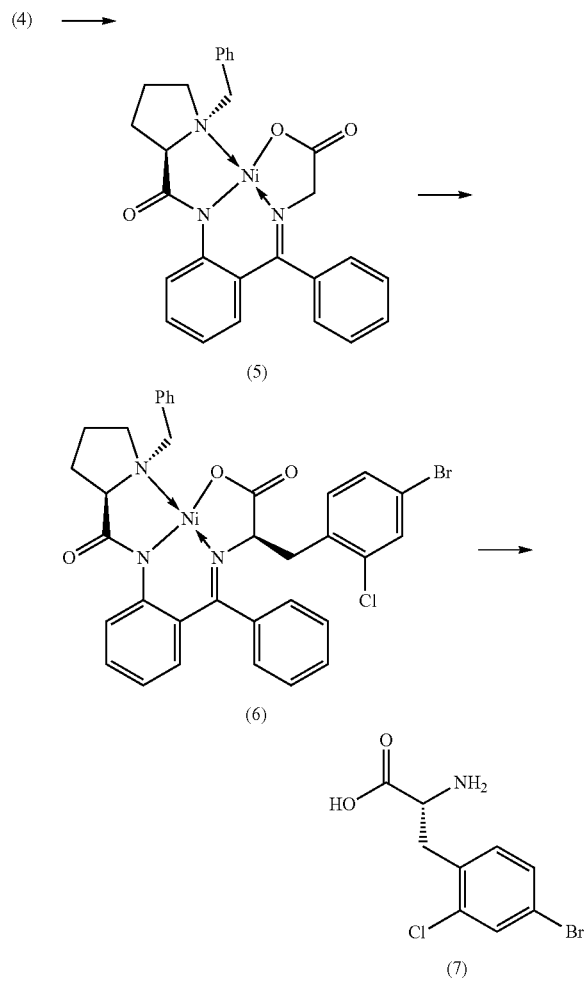

To a solution of Compound 4 (29.4 g, 76.5 mmol), glycine (28.7 g, 382.4 mmol) and Ni(NO$_3$)$_2$.6H$_2$O (44.5 g, 152.9 mmol) in MeOH (280 mL) was added a solution of KOH (30 g, 535.3 mmol) in MeOH (100 mL) at 45° C. under nitrogen. The mixture was stirred at 60° C. for an hour. The resulting solution was neutralized with AcOH (31 mL) and poured into ice water (380 mL). The resulting solid was filtered and dissolved in DCM (450 mL), which was washed with saturated aqueous NaCl (150 mL), dried over Na$_2$SO$_4$ and concentrated. The residue was washed with EtOAc (50 mL×2) to yield compound 5 (38 g) as a red solid. LC-MS: 498 [M+H]$^+$.

Compound 5 (14.3 g, 28.7 mmol) and NaOH (3.4 g, 81.6 mmol) were added to a flask which was purged with nitrogen twice. Anhydrous DMF (100 mL) was added and the mixture was stirred for 5 minutes at 0° C. before a solution of Compound 2 (8.6 g, 30.1 mmol) in DMF (20 mL) was added. The reaction mixture was stirred at room temperature for 30 minutes until complete consumption of Compound 4 (checked by TLC). The resulting mixture was poured into a 5% AcOH aqueous solution (120 mL) which was then extracted with DCM (150 mL×3) and the combined organic layers were washed with saturated aqueous NaCl (150 mL), dried over Na$_2$SO$_4$ and concentrated in vacuo. The residue was recrystallized with DCM/Et$_2$O (1:1) to yield Compound 6 (15.5 g) as a red solid. LC-MS: 702 [M+H]$^+$.

To a solution of Compound 6 (46 g, 65.6 mmol) in MeOH (300 mL) was added 3N HCl (200 mL). The mixture was refluxed until the red color turned green. The resulting solution was concentrated in vacuo before concentrated NH$_3$H$_2$O (100 mL) was added. The solution was extracted with DCM (200 mL×2) and the aqueous phase was concentrated in vacuo and subjected to the cation exchange resin (eluted with NH$_3$H$_2$O/EtOH, 1:1) to yield Compound 7 (15 g) as a white solid. LC-MS: 280 [M+H]$^+$.

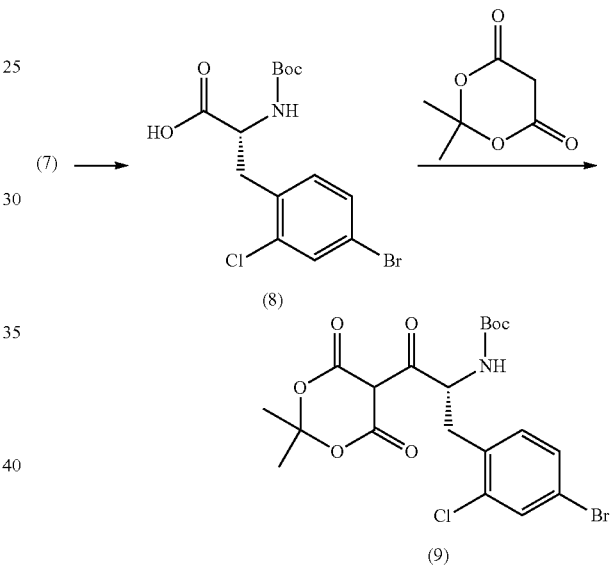

To a suspension of Compound 7 (15 g, 53.9 mmol) in MeCN (150 mL) was added a solution of NaOH (4.3 g, 107.7 mmol) in water (150 mL) at 0° C., followed by the addition of (BOC)$_2$O (17.6 g, 80.8 mmol). The mixture was stirred overnight at room temperature. The resulting solution was concentrated in vacuo, followed by extraction with DCM (150 mL×2). The layers were separated and the aqueous phase was acidified with 1N HCl to pH 3 and extracted with EtOAc (150 mL×3). The combined organic layers were washed with saturated aqueous NaCl (150 mL), dried over Na$_2$SO$_4$, filtered and concentrated in vacuo to yield Compound 8 (12.3 g, 60%) as a white solid. LC-MS: 402 [M+Na]$^+$.

To a suspension of Compound 8 (18.4 g, 48.5 mmol) and Meldrum's acid (8.4 g, 58.2 mmol) in DCM (400 mL) was added DMAP (9.5 g, 77.6 mmol) at −5° C. After stirring for 10 minutes, a solution of DCC (12 g, 58.2 mmol) in DCM (100 mL) was added dropwise at −5° C. The mixture was stirred overnight at room temperature. The resulting solution was cooled to 0° C. and filtered. The filtrate was washed with aqueous citric acid (200 mL×3) and saturated aqueous NaCl (200 mL), dried over Na$_2$SO$_4$, filtered, and concentrated in vacuo. The residue was triturated with Et$_2$O (50 mL×2) to yield Compound 9 (22 g) as a light yellow solid.

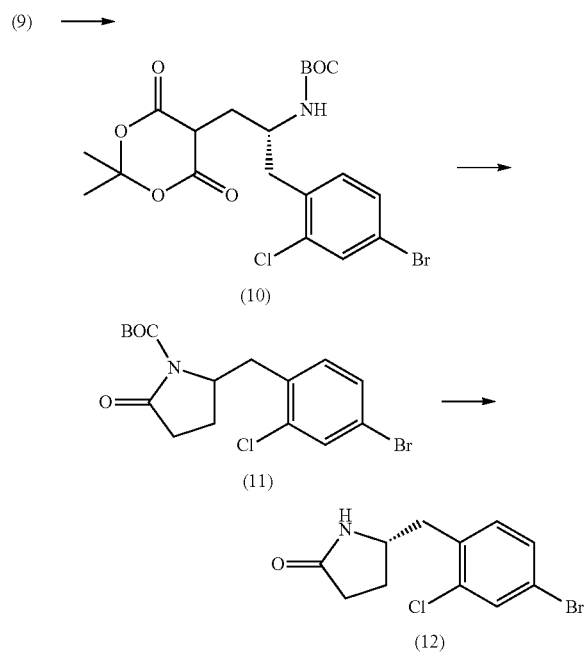

To a solution of Compound 9 (22 g, 43.6 mmol) in DCM (400 mL) was added AcOH (28.8 g, 479.4 mmol) at 0° C. After stirring for 10 minutes, NaBH$_4$ (4.1 g, 109 mmol) was added in portions. The mixture was stirred for an hour at 0° C. The resulting solution was washed with saturated aqueous NaHCO$_3$ (200 mL×2) and saturated aqueous NaCl (200 mL), dried over Na$_2$SO$_4$ and concentrated in vacuo. The residue was washed with ether (100 mL×2) to yield Compound 10 (18.6 g) as an off-white solid. LC-MS: 514 [M+Na]$^+$.

A solution of Compound 10 (18.6 g, 37.9 mmol) in toluene (350 mL) was heated under reflux for 2 hours. Upon cooling, the mixture was evaporated to dryness to yield Compound 11 (14 g) as a yellow syrup. LC-MS: 334 [M−tBu+H]$^+$.

To a solution of Compound 11 (14 g, 36.0 mmol) in DCM (250 mL) was added TFA (20 mL). The mixture was stirred for 4 hours at 0° C. The resulting solution was concentrated in vacuo to remove TFA. The residue was dissolved in DCM (400 mL) and washed with saturated aqueous NaHCO$_3$ (200 mL×2), dried over Na$_2$SO$_4$ and concentrated to yield Compound 12 (10 g) as a yellow solid. LC-MS: 290 [M+H]$^+$.

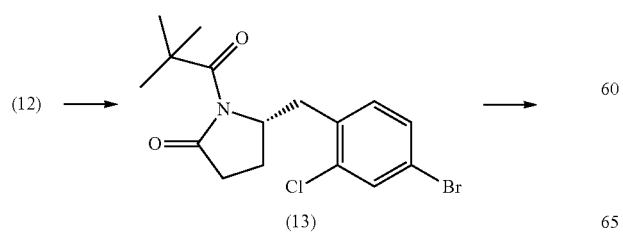

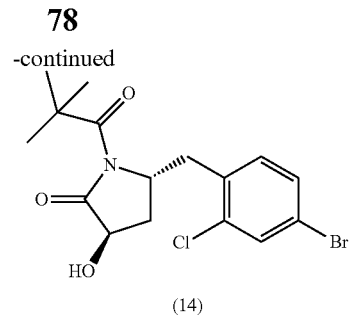

To a solution of Compound 12 (10 g, 34.7 mmol) in dry THF (250 mL) was added NaH (2.4 g, 69.3 mmol, 70%) at 0° C. The mixture was stirred for one hour at 0° C. under nitrogen, then pivaloyl chloride (5 g, 41.6 mmol) was added. After stirring for another 2 hours, saturated aqueous NaHCO$_3$ (100 mL) was added to quench the reaction. The resulting mixture was concentrated and extracted with EtOAc (100 mL×3) and the combined organic layers were washed with saturated aqueous NaCl (100 mL), dried over Na$_2$SO$_4$ and concentrated in vacuo. The residue was purified by silica gel chromatography (hexanes/EtOAc, 5:1) to yield Compound 13 (11.8 g) as a white solid. LC-MS: 374[M+H]$^+$.

To a solution of Compound 13 (11.8 g, 31.8 mmol) in dry THF (70 mL) was added NaHMDS (24 mL, 47.7 mmol, 2.0 M in THF) dropwise at −78° C. under nitrogen. After stirring for 30 minutes, a solution of (+)-(8,8-dichlorocamphorylsulfonyl)-oxaziridine (15.2 g, 50.8 mmol) in THF (70 mL) was added dropwise at −78° C. The mixture was stirred for another hour at the same temperature before aqueous NH$_4$Cl (70 mL) was added to quench the reaction. The resulting mixture was extracted with EtOAc (150 mL×3) and the combined organic layers were washed with saturated aqueous NaCl (150 mL), dried over Na$_2$SO$_4$, filtered, and concentrated in vacuo. The crude residue was purified by silica gel chromatography (hexanes/EtOAc, 20:1~5:1) to yield the crude residue (5 g), which was further purified by preparative HPLC to yield Compound 14 (4 g) as a yellow solid. LC-MS: 390 [M+H]$^+$.

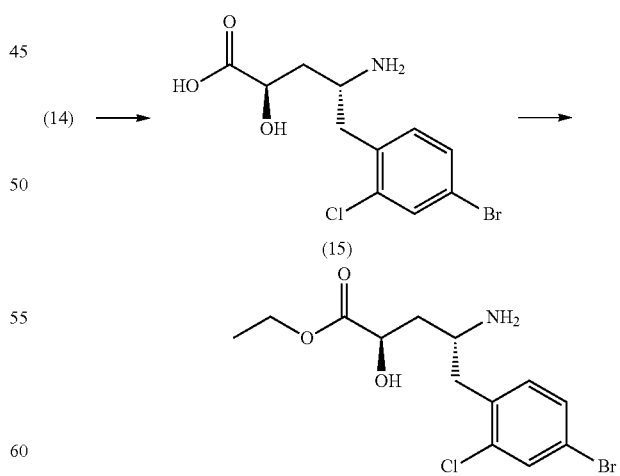

A solution of Compound 14 (4 g, 10.3 mmol) in concentrated HCl (50 mL) was heated under reflux overnight. The mixture was concentrated in vacuo and the resulting solid was washed with Et$_2$O (50 mL×2) to yield Compound 15 (3.1 g) as a white solid HCl salt. LC-MS: 324 [M+H]$^+$.

A solution of Compound 15 (3.1 g, 8.6 mmol) in HCl/EtOH (6.7M, 40 mL) was stirred overnight at 50° C. The resulting mixture was concentrated in vacuo and the residue was washed with ether (50 mL×2) to yield the title compound (2.9 g) as an off-white solid HCl salt. LC-MS: 352 [M+H]+. ¹H NMR: (CD₃OD) 1.268 (t, J=6.9 Hz, 3H), 1.862-1.946 (m, 1H), 2.068-2.143 (m, 1H), 3.104-3.199 (m, 2H), 3.769-3.809 (m, 1H), 4.162-4.209 (m, 2H), 4.274-4.881 (m, 1H), 7.325 (dd, J=8.1, 2.1 Hz, 1H), 7.522 (dd, J=8.3, 3.0 Hz, 1H), 7.696 (d, J=1.8 Hz, 1H).

Preparation 16: (2R,4R)-5-(4-Bromo-2-chlorophenyl)-4-t-butoxycarbonylamino-2-hydroxypentanoic Acid Ethyl Ester

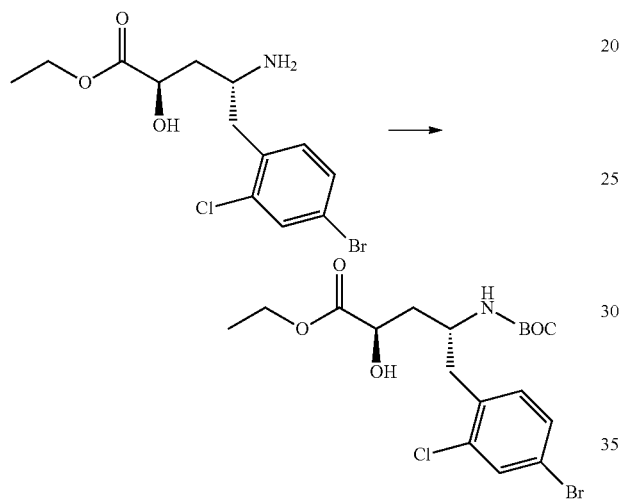

(2R,4R)-4-Amino-5-(4-bromo-2-chlorophenyl)-2-hydroxypentanoic acid ethyl ester (160 mg, 460 µmol) and di-t-butyl dicarbonate (99.6 mg, 456 µmol) were mixed in DCM (5 mL) followed by the addition of DIPEA (120 µL, 680 µmol). The mixture was stirred at room temperature for 1 hour. EtOAc was added and the mixture was washed with 1N HCl (10 mL) followed by aqueous NaHCO₃ (10 mL) and saturated aqueous NaCl (10 mL). The organic layer was retained and dried over MgSO₄, then filtered and dried in vacuo to yield the title compound (200 mg).

Preparation 17: (2R,4R)-4-Amino-2-azido-5-(3,5'-dichloro-2'-fluorobiphenyl-4-yl)pentanoic Acid Ethyl Ester

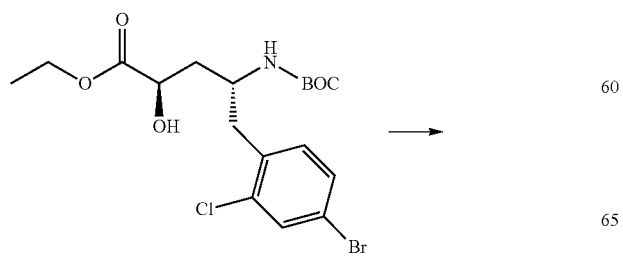

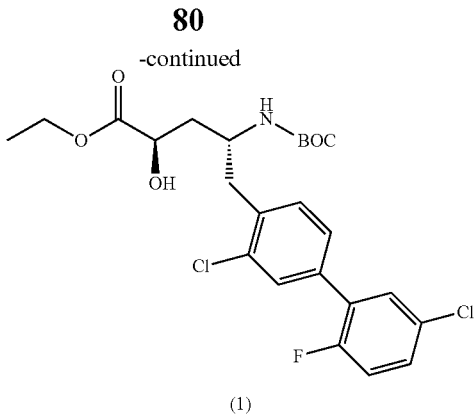

(1)

A microwave flask was charged with (2R,4R)-5-(4-Bromo-2-chlorophenyl)-4-t-butoxycarbonylamino-2-hydroxypentanoic acid ethyl ester (400 mg, 887 µmol), 5-chloro-2-fluorophenylboronic acid (170 mg, 976 µmol), Na₂CO₃ (282 mg, 2.7 mmol), Pd(PPh₃)₄ (154 mg, 133 µmol), EtOH (4 mL) and water (1 mL), then placed under nitrogen. The mixture was microwaved for 45 minutes at 110° C., at which time LCMS indicated the mass of the desired compound. The solvent was removed in vacuo and the crude residue was purified by normal phase column chromatography (20-100% EtOAc/hexanes) to yield Compound 1 (218 mg).

(1) →

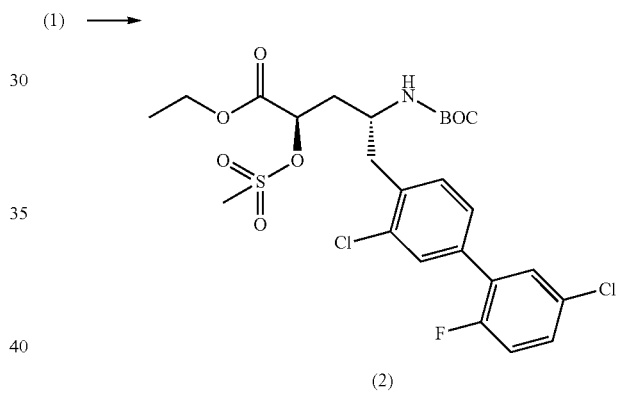

(2)

Compound 1 (218 mg, 436 µmol) was dissolved in DCM (5 mL). Methanesulfonyl chloride (37 µL, 479 µmol) was added, followed by Et₃N (152 µL, 1.1 mmol). The mixture was stirred at room temperature for 10 minutes. EtOAc and a saturated aqueous NH₄Cl were added. The organic layer was extracted, separated, dried over MgSO₄, filtered, and evaporated, to yield crude Compound 2, which was used directly in the next step without purification.

(2) →

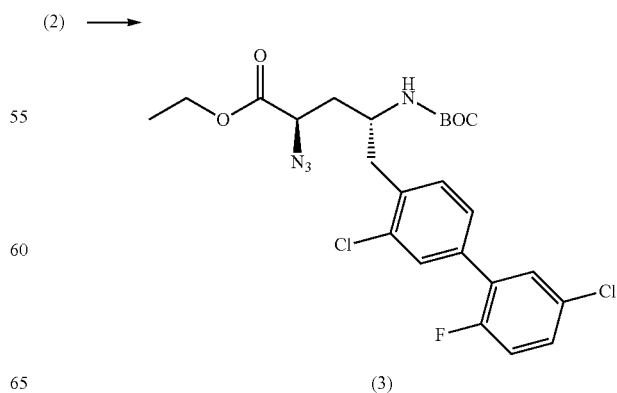

(3)

Compound 2 (252 mg, 436 µmol) in DMF (4 mL) was combined with sodium azide (85 mg, 1.3 mmol), and the resulting mixture was stirred at 50° C. for 7 hours. EtOAc and water were added. The organic layer was extracted, separated and dried over MgSO₄, filtered, and evaporated. The solvent was evaporated and the residue was purified by normal phase column chromatography (20-100% EtOAc/hexanes) to yield Compound 3 (181 mg) as a yellow oil.

(3) ⟶

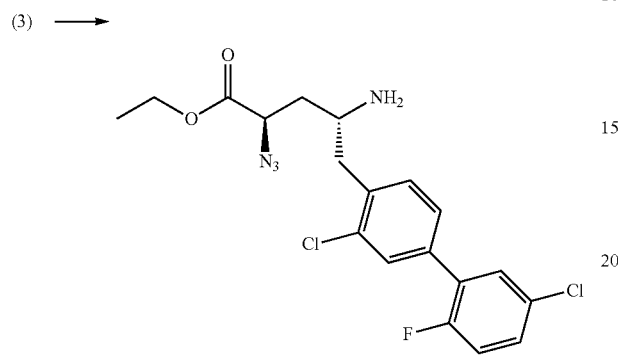

Compound 3 (162 mg, 308 µmol) was dissolved in MeCN (3 mL). A solution of 4N HCl in dioxane (1.2 mL, 4.6 mmol) was added, and the mixture was stirred at room temperature for 20 minutes, at which time LCMS indicated the mass of the desired compound. The mixture was then concentrated in vacuo to yield the crude title compound as an HCl salt, which was used without further purification.

Preparation 18: Oxodiperoxymolybdenum(pyridine)-(hexamethylphosphorictriamide)

$$MoO_3 \rightarrow MoO_5 \cdot H_2O \cdot (Me_2N)_3PO \rightarrow MoO_5 \cdot (Me_2N)_3PO \rightarrow MoO_5 \cdot Py \cdot (Me_2N)_3PO$$

Molybdenum oxide (MoO₃; 30 g, 0.2 mol) and 30% hydrogen peroxide (150 mL) were combined, with stirring. The reaction flask was placed in an oil bath equilibrated at 40° C. and heated until the internal temperature reached 35° C. The heating bath was then removed and replaced by a water bath to control the mildly exothermic reaction so that an internal temperature of 35-40° C. was maintained. After the initial exothermic period (~30 minutes), the reaction flask was returned to the 40° C. oil bath and stirred for a total of 3.5 hours to form a yellow solution with a small amount of suspended white solid. After cooling to 20° C., the solution was filtered and the resulting yellow filtrate was cooled to 10° C. (with stirring) and hexamethylphosphoric triamide ((Me₂N)₃PO; HMPA; 37.3 g, 0.2 mol) was added dropwise over 5 minutes, resulting in the formation of a yellow crystalline precipitate. Stirring was continued for a total of 15 minutes at 10° C., and the residue was filtered and pressed dry. After 30 minutes in vacuo, the filter cake was dissolved in MeOH (20 mL) and stirred at 40° C. Additional MeOH was slowly added until the solids dissolved. The saturated solution was cooled in the refrigerator, yielding a yellow solid (appeared as needles). The solid mass was physically broken, filtered and washed with cold MeOH (20-30 mL) to yield oxodiperoxymolybdenum(aqua) (hexamethylphosphoric triamide) (MoO₅·H₂O·HMPA, 46-50 g).

MoO₅·H₂O·HMPA was dried over phosphorus oxide in a vacuum desiccator, shielded from the light, for 24 hours at 0.2 mm Hg to yield a somewhat hygroscopic yellow solid, MoO₅·HMPA. MoO₅·HMPA (36.0 g, 0.1 mol) was dissolved in THF (150 mL) and the solution was filtered to remove any precipitate. The filtrate was then stirred at 20° C. while dry pyridine (8.0 g, 0.1 mol) was added over 10 minutes. The crystalline, yellow residue was collected, washed with dry THF (25 mL) and anhydrous ether (200 mL) and dried in a vacuum desiccator (1 hour, 0.2 mm Hg) to yield the title compound (36-38 g; MoO₅·Py·HMPA) as a finely divided yellow solid.

Preparation 19: (2R,4R)-4-Amino-5-biphenyl-4-yl-2-hydroxypentanoic Acid Ethyl Ester and (2R,4S)-4-Amino-5-biphenyl-4-yl-2-hydroxypentanoic Acid Ethyl Ester

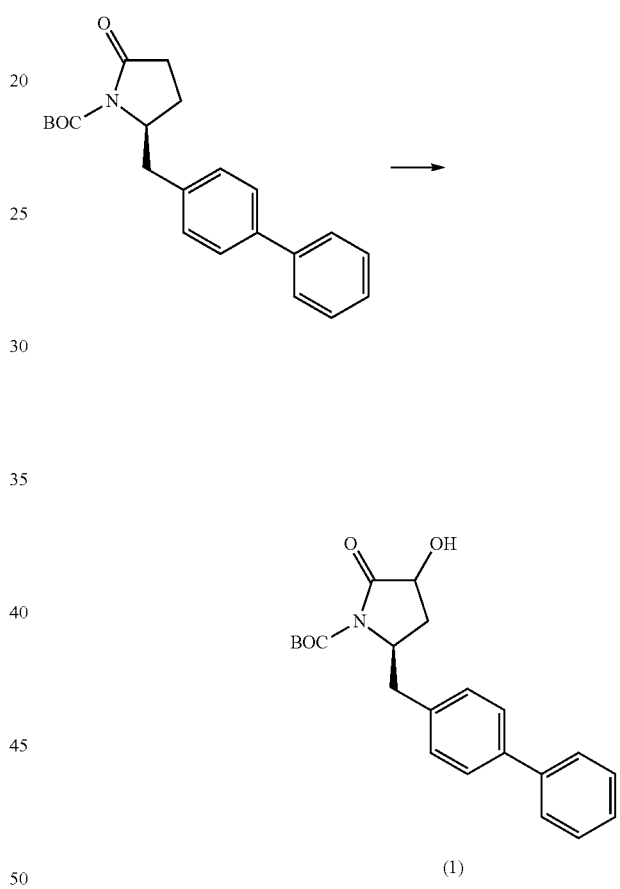

(1)

To a stirred solution of (S)-2-biphenyl-4-ylmethyl-5-oxopyrrolidine-1-carboxylic acid t-butyl ester (4.4 g, 12.4 mmol) in anhydrous THF (70 mL) was added a solution of 1 M LiHMDS in THF (28 mL) over 15 minutes at −65° C. under nitrogen. After stirring for 3 hours at −65° C., oxodiperoxymolybdenum (pyridine) (hexamethylphosphorictriamide) (9 g, 18.6 mmol) was added. The mixture was stirred for another 2 hours at −35° C., then saturated aqueous Na₂S₂O₃ (60 mL) was added. The organic layer was collected and washed with saturated aqueous NH₄Cl (3×60 mL) and saturated aqueous NaCl (2×60 mL), then dried over Na₂SO₄, and the solvent was removed under reduced pressure to yield the crude residue which was further purified by chromatography (hexanes:EtOAc=5:1) to yield Compound 1 (1.8 g) as a white solid. LC-MS: [2M+Na]:757.

(1) →

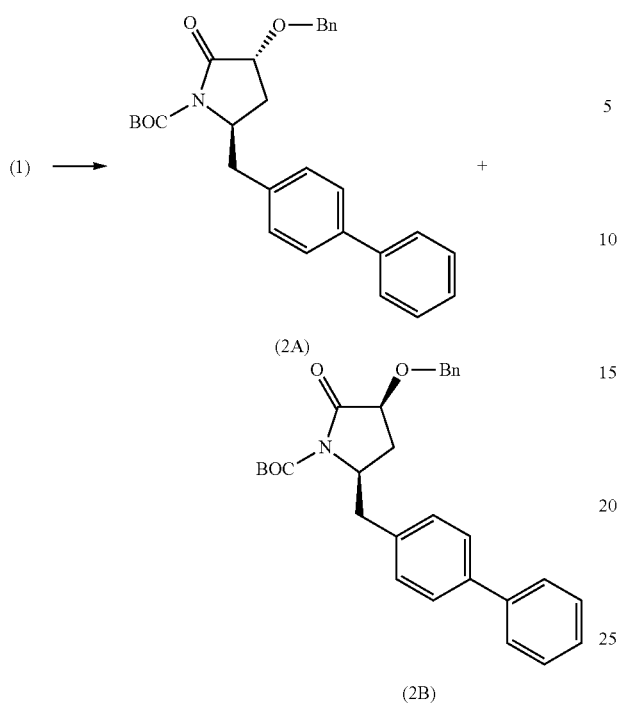

(2A)

(2B)

To a solution of Compound 1 (1.8 g, 5.0 mmol) in anhydrous DCM (50 mL) was added DMAP (122 mg, 1 mmol) and Et₃N (1.5 g, 14.9 mmol) at 0° C. under nitrogen. After stirring for 0.5 hour at 0° C., benzyl chloride (1.0 g, 7.4 mmol) was added over 15 minutes. The mixture was stirred for an additional 2 hours at 0° C., then saturated aqueous NaHCO₃ (50 mL) was added. The organic layer was collected and washed with saturated aqueous NaHCO₃ (2×50 mL) and saturated aqueous NaCl (50 mL), then dried over Na₂SO₄. The mixture was filtered and the filtrate was concentrated to yield the crude residue which was further purified by chromatography (hexanes:EtOAc=4:1) to yield Compound 2A (471 mg) and Compound 2B (883 mg) as white solids. LC-MS: [M+Na]:494; [2M+Na]:965.

Compound 2A: ¹H NMR (300 MHz, CDCl₃): δ (ppm)= 8.02 (m, 2H), 7.57-7.25 (m, 12H), 5.42 (m, 1H), 4.50 (m, 1H), 3.26-3.21 (m, 1H), 2.90 (m, 1H), 2.58 (m, 1H), 2.15-2.05 (m, 1H), 1.62 (m, 9H)

Compound 2B: ¹H NMR (300 MHz, CDCl₃): δ (ppm)= 8.06 (m, 2H), 7.58-7.18 (m, 12H), 5.53-5.41 (m, 1H), 4.39 (m, 1H), 3.57-3.54 (m, 1H), 2.87-2.80 (m, 1H), 2.48-2.44 (m, 1H), 1.98 (m, 1H), 1.63 (m, 9H).

(2A) →

(3)

To a stirred solution of Compound 2A (471 mg, 1 mmol) in anhydrous EtOH (10 mL) was added anhydrous K₂CO₃ (691 mg, 5 mmol) at room temperature under nitrogen. After stirring for 20 hours at room temperature, the mixture was filtered. To the filtrate was added water (30 mL), DCM (30 mL) and saturated aqueous NaCl (5 mL). The aqueous layer was separated and extracted with DCM (30 mL×3). The combined organic layers were washed with saturated aqueous NaCl (50 mL), dried over Na₂SO₄, and concentrated to yield the crude residue which was further purified by chromatography (hexanes:EtOAc=6:1) to yield Compound 3 (275 mg) as a white solid. LC-MS: [M+Na]⁺:436, [2M+Na]⁺:849.

(3) →

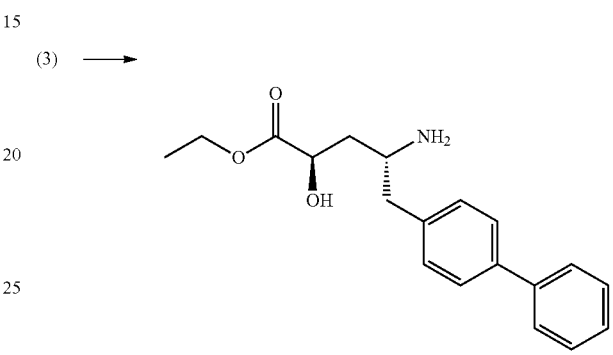

To EtOH (5 mL) was added acetyl chloride (685 mg) at −30° C. After stirring for 1 hour at −30° C., a solution of Compound 3 (275 mg, 665 μmol) in anhydrous EtOH (5 mL) was added. The mixture was heated to 25° C. and stirred for 3 hours at 25° C. After evaporation of the solvent, the residue was washed with cold anhydrous Et₂O (10 mL) to yield (2R,4R)-4-amino-5-biphenyl-4-yl-2-hydroxypentanoic acid ethyl ester (207 mg) as a white solid HCl salt. LC-MS: [M+H]⁺:314, [2M+Na]⁺:649.

¹H NMR (300 MHz, CDCl₃): δ (ppm)=7.99 (m, 3H), 7.66-7.64 (m, 4H), 7.48-7.35 (m, 5H), 6.08 (m, 1H), 4.21 (m, 1H), 4.09-4.05 (m, 2H), 3.52 (m, 1H), 2.97-2.95 (m, 2H), 1.89-1.87 (m, 2H), 1.19-1.14 (m, 3H).

(2B) →

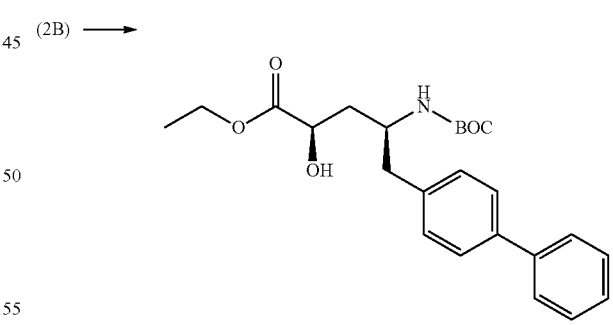

(4)

To a stirred solution of Compound 2B (883 mg, 1.9 mmol) in anhydrous EtOH (15 mL) was added anhydrous K₂CO₃ (1293 mg, 9.4 mmol) at room temperature under nitrogen. After stirring for 20 hours at room temperature, the mixture was filtered. To the filtrate was added water (30 mL), DCM (30 mL) and saturated aqueous NaCl (5 mL). The aqueous layer was separated and extracted with DCM (30 mL×3). The combined organic layers were washed with saturated aqueous NaCl (50 mL), dried over Na₂SO₄, and concentrated to yield the crude residue which was further purified by chromatography (hexanes:EtOAc=6:1) to yield Compound 4 (524 mg) as a white solid. LC-MS: [M+Na]⁺:436, [2M+Na]⁺:849.

(4) →

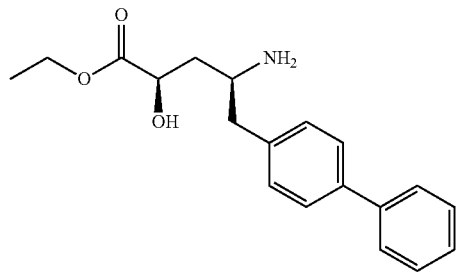

To EtOH (8 mL) was added acetyl chloride (1.3 g) at −30° C. After stirring for 1 hour at −30° C., a solution of Compound 4 (524 mg, 1.3 mmol) in anhydrous EtOH (8 mL) was added. The mixture was heated to 25° C. and stirred for 3 hours at 25° C. After evaporation of the solvent, the residue was washed with cold anhydrous Et₂O (10 mL) to yield (2R,4S)-4-amino-5-biphenyl-4-yl-2-hydroxypentanoic acid ethyl ester (395 mg) as a white solid HCl salt. LC-MS: [M+H]⁺:314, [2M+Na]⁺:649.

$^1$H NMR (300 MHz, CDCl₃): δ (ppm)=8.14 (m, 3H), 7.66-7.62 (m, 4H), 7.47-7.31 (m, 5H), 5.87-5.85 (m, 1H), 4.34 (m, 1H), 4.08-4.00 (m, 2H), 3.48 (m, 1H), 3.09 (m, 1H), 2.85-2.81 (m, 1H), 1.88 (m, 1H), 1.76 (m, 1H), 1.15-1.10 (m, 3H).

Preparation 20: (2R,4R)-2-Amino-5-(2'-fluoro-biphenyl-4-yl)-4-[(1H-[1,2,3]triazole-4-carbonyl)amino]pentanoic Acid 1H-1,2,3-triazole-4-carboxylic acid (50.8 mg, 449 μmol) and HATU (171 mg, 449 μmol) were dissolved in DMF (3 mL) and stirred for 15 minutes at room temperature. (2R,4R)-4-Amino-2-azido-5-(5'-chloro-2'-fluorobiphenyl-4-yl)pentanoic acid ethyl ester (160 mg, 409 μmol) and DIPEA (214 μL, 1.2 mmol) were added, and the mixture was stirred at room temperature for 15 minutes, at which time LCMS indicated the mass of the desired compound. The mixture was then concentrated in vacuo to yield Compound 1, which was used in the next step without purification.

(1) →

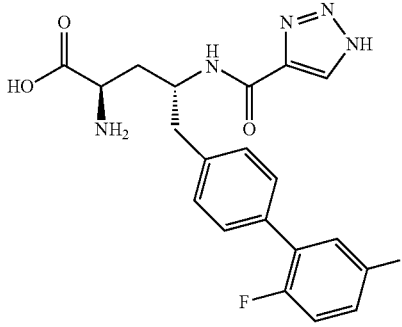

+

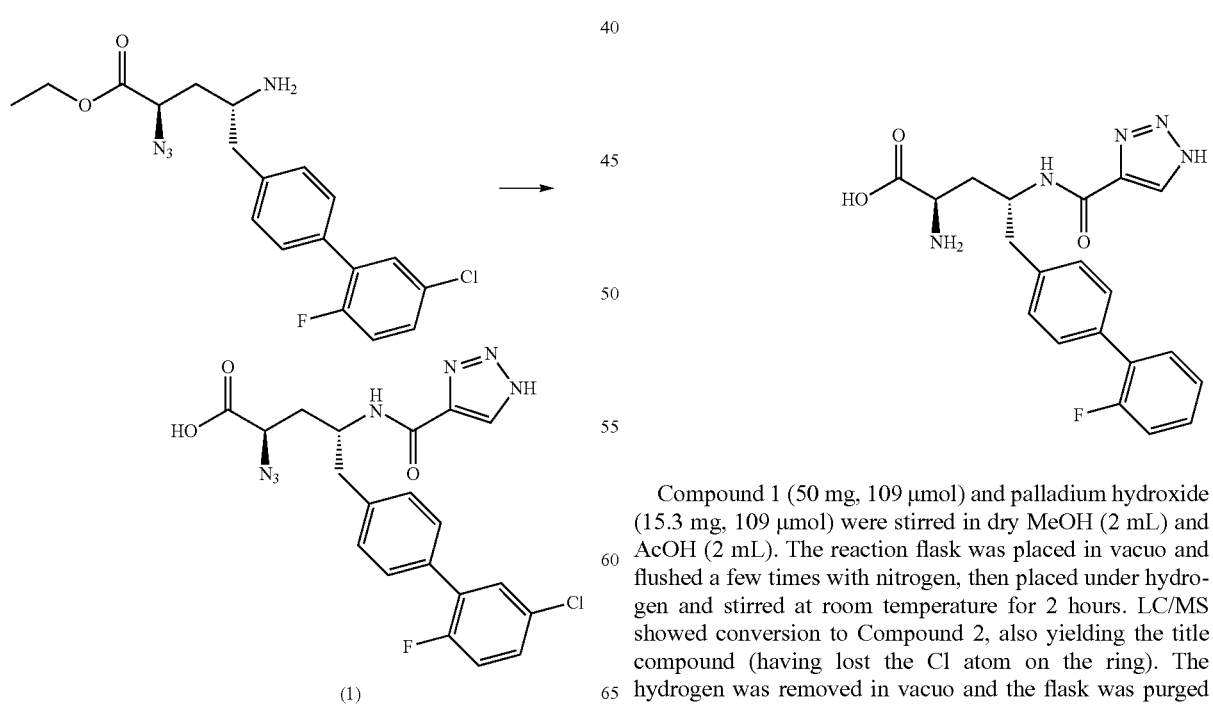

Compound 1 (50 mg, 109 μmol) and palladium hydroxide (15.3 mg, 109 μmol) were stirred in dry MeOH (2 mL) and AcOH (2 mL). The reaction flask was placed in vacuo and flushed a few times with nitrogen, then placed under hydrogen and stirred at room temperature for 2 hours. LC/MS showed conversion to Compound 2, also yielding the title compound (having lost the Cl atom on the ring). The hydrogen was removed in vacuo and the flask was purged with nitrogen. The mixture was filtered and the solution was concentrated in vacuo to yield the crude title compound.

Preparation 21: (2R,4R)-4-Amino-5-(5'-chloro-2'-fluorobiphenyl-4-yl)-2-methoxycarbonylaminopentanoic Acid Ethyl Ester Compound 2 was prepared as described herein.

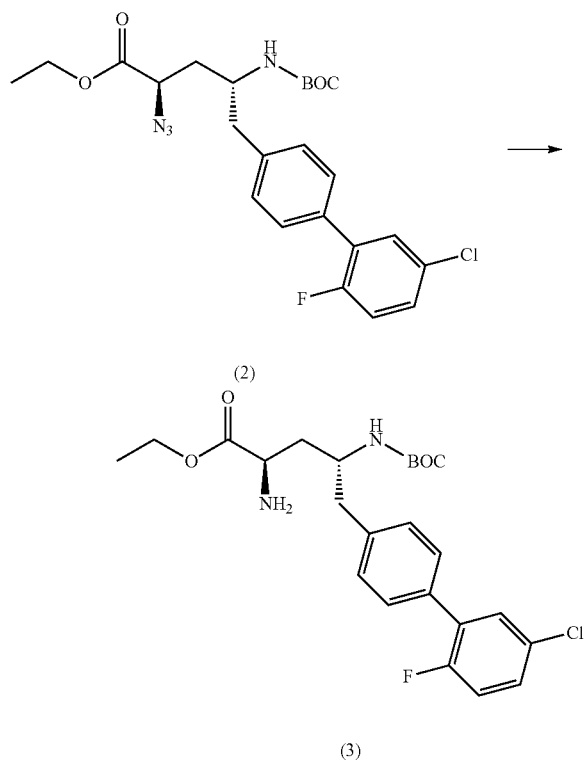

Compound 2 (210 mg, 428 μmol) and palladium hydroxide (60.1 mg, 428 μmol) were dissolved in dry MeOH (5 mL) and AcOH (5 mL). The reaction flask was placed in vacuo and flushed a few times with nitrogen, then placed under hydrogen and stirred at room temperature for 1 hour. LC/MS showed reaction completion. The hydrogen was removed in vacuo and the flask was purged with nitrogen. The mixture was filtered and the solution was concentrated in vacuo to yield crude Compound 3, which was used in the next step without purification.

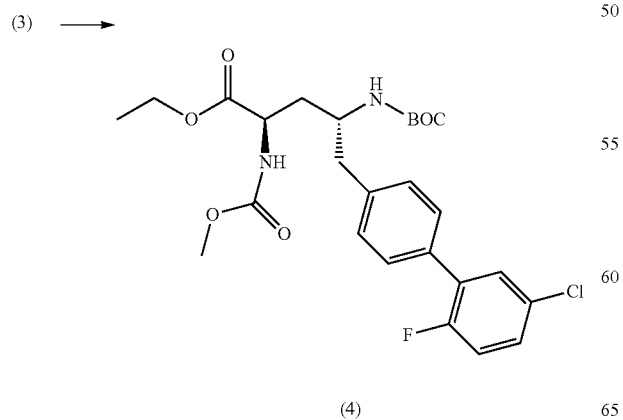

Compound 3 (199 mg, 428 μmol) was dissolved in DCM (5 mL). Methyl chloroformate (36.5 μL, 471 μmol) was added, followed by DIPEA (187 μL, 1.2 mmol). The resulting mixture was stirred at room temperature for 10 minutes (LC/MS showed reaction completion) then concentrated in vacuo and the residue was purified by normal phase column chromatography (20-100% EtOAc/hexanes) to yield Compound 4.

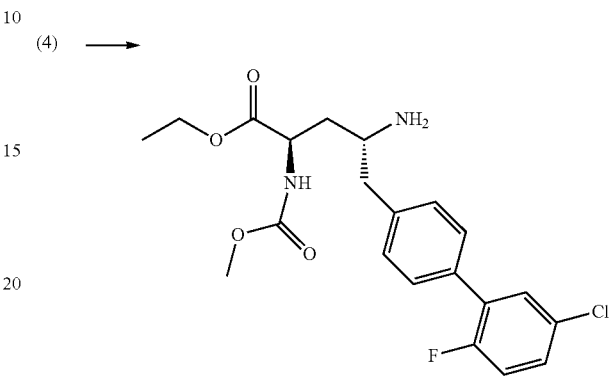

Compound 4 (30 mg, 57 μmol) was dissolved in MeCN (3 mL). A solution of 4N HCl in dioxane (215 μL, 860 μmol) was added and the resulting mixture was stirred at room temperature for 10 minutes (LC/MS showed reaction completion) then concentrated in vacuo to yield the crude title compound as an HCl salt, which was used without further purification.

Preparation 22: (2S,4S)-4-Amino-5-biphenyl-4-yl-2-cyanomethylpentanoic Acid Ethyl Ester

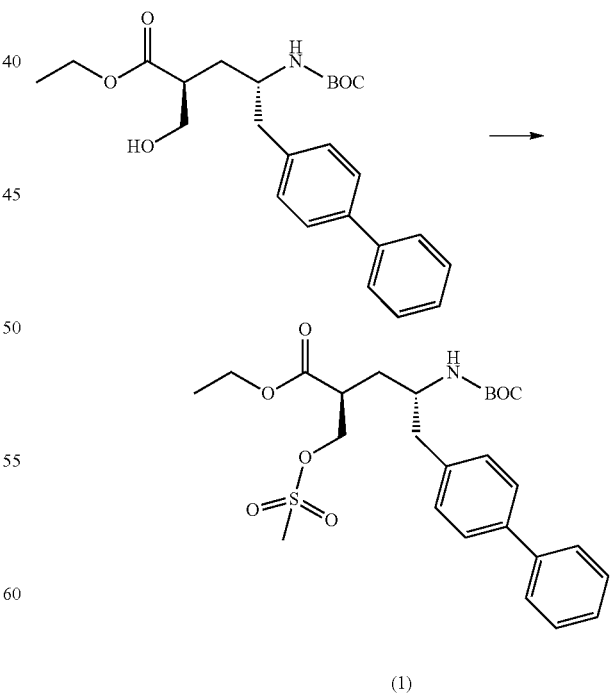

(2S,4S)-5-Biphenyl-4-yl-4-t-butoxycarbonylamino-2-hydroxymethylpentanoic acid ethyl ester (450 mg, 1.1 mmol)

was dissolved in DCM (2 mL). Methanesulfonyl chloride (98 µL, 1.3 mmol) was added, followed by Et₃N (293 µL, 2.1 mmol). The mixture was stirred at room temperature for 30 minutes, then was purified by normal phase chromatography (0-100% EtOAc/hexanes) to yield Compound 1 (405 mg).

Preparation 23: (2R,4S)-4-t-butoxycarbonylamino-5-(3'-fluorobiphenyl-4-yl)-2-hydroxymethylpentanoic Acid Ethyl Ester (compound 23a) and (2S, 4S)-4-t-butoxycarbonylamino-5-(3'-fluorobiphenyl-4-yl)-2-hydroxymethylpentanoic Acid Ethyl Ester (compound 23-b)

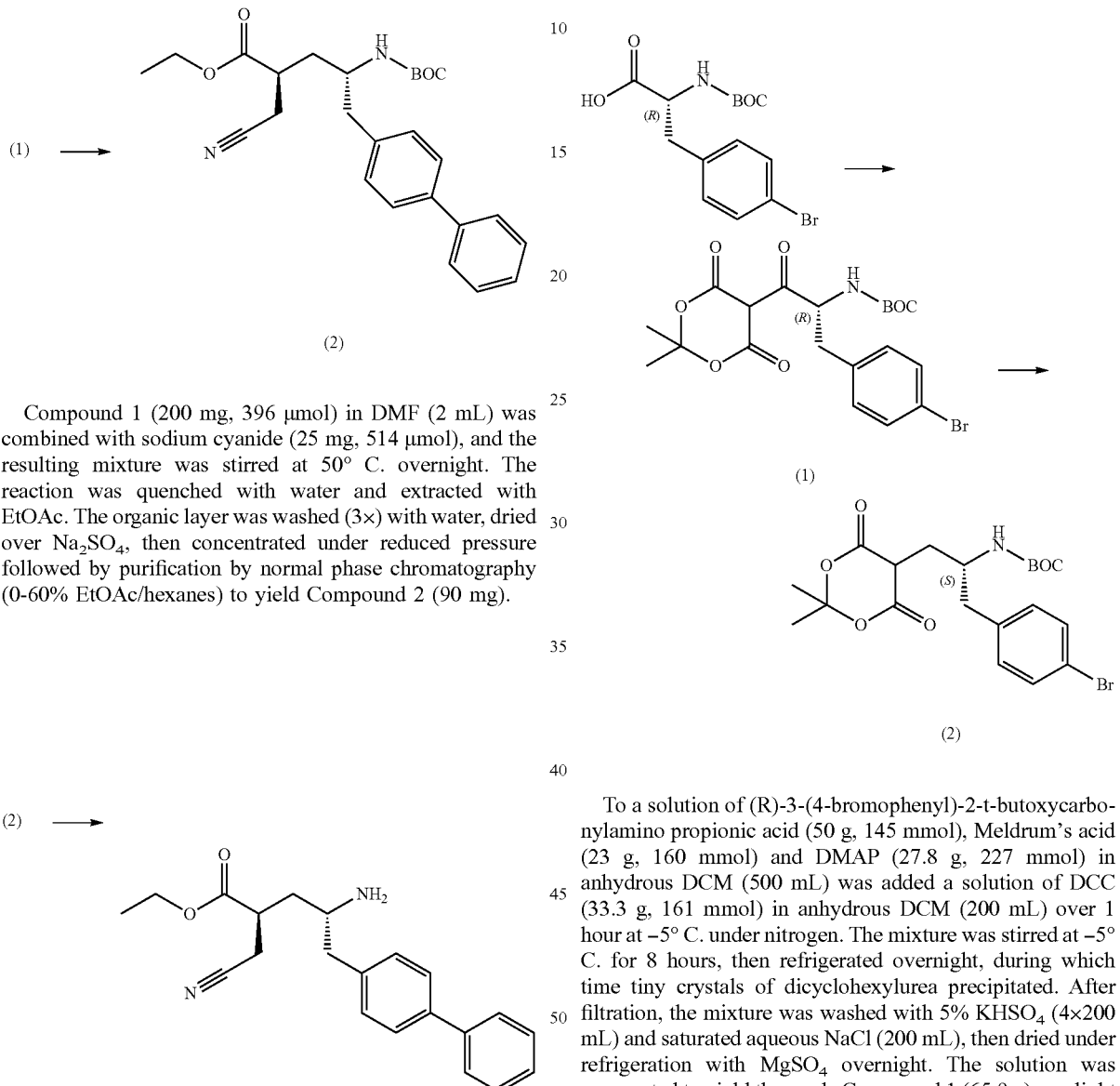

Compound 1 (200 mg, 396 µmol) in DMF (2 mL) was combined with sodium cyanide (25 mg, 514 µmol), and the resulting mixture was stirred at 50° C. overnight. The reaction was quenched with water and extracted with EtOAc. The organic layer was washed (3×) with water, dried over Na₂SO₄, then concentrated under reduced pressure followed by purification by normal phase chromatography (0-60% EtOAc/hexanes) to yield Compound 2 (90 mg).

To a solution of (R)-3-(4-bromophenyl)-2-t-butoxycarbonylamino propionic acid (50 g, 145 mmol), Meldrum's acid (23 g, 160 mmol) and DMAP (27.8 g, 227 mmol) in anhydrous DCM (500 mL) was added a solution of DCC (33.3 g, 161 mmol) in anhydrous DCM (200 mL) over 1 hour at −5° C. under nitrogen. The mixture was stirred at −5° C. for 8 hours, then refrigerated overnight, during which time tiny crystals of dicyclohexylurea precipitated. After filtration, the mixture was washed with 5% KHSO₄ (4×200 mL) and saturated aqueous NaCl (200 mL), then dried under refrigeration with MgSO₄ overnight. The solution was evaporated to yield the crude Compound 1 (65.9 g) as a light yellow solid. LC-MS: [M+Na]⁺:493, [2M+Na]⁺:963.

To a solution of crude Compound 1 (65.9 g, 140 mmol) in anhydrous DCM (1 L) was added AcOH (92.5 g, 1.5 mol) at −5° C. under nitrogen. The mixture was stirred at −5° C. for 0.5 hour, then NaBH₄ (13.2 g, 350 mmol) was added in small portions over 1 hour. After stirring for another 1 hour at −5° C., saturated aqueous NaCl (300 mL) was added. The organic layer was washed with saturated aqueous NaCl (2×300 mL) and water (2×300 mL), dried over MgSO₄, filtered, and concentrated to yield the crude residue, which was further purified by chromatography (hexanes:EtOAc=6:1) to yield Compound 2 (33 g) as a light yellow solid. LC-MS: [M+Na]⁺:479, [2M+Na]⁺:935.

Compound 2 (90 mg, 206 µmol) was dissolved in MeCN and 4N HCl in dioxane, and the mixture was stirred at room temperature for 10 minutes. The mixture was concentrated under reduced pressure to yield the title compound as an HCl salt, which was used without further purification.

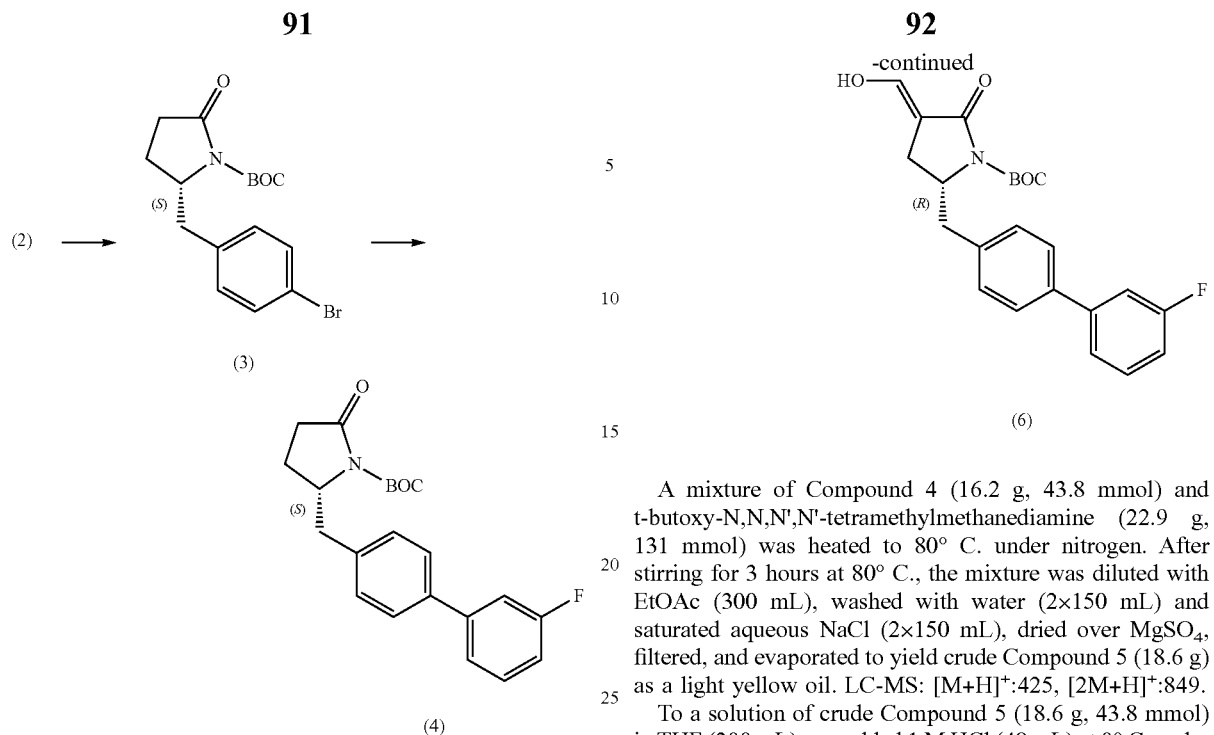

A solution of Compound 2 (33 g, 72.3 mmol) in anhydrous toluene (300 mL) was refluxed under nitrogen for 3 hours. After evaporation of the solvent, the residue was purified by chromatography (hexanes:EtOAc=10:1) to yield Compound 3 (21 g) as a light yellow oil. LC-MS: [M+Na]$^+$: 377, [2M+Na]$^+$:731.

To a solution of Compound 3 (21 g, 60 mmol) in 1,4-dioxane (250 mL) was added 3-fluorophenylboronic acid (8.8 g, 63 mmol) and Pd(dppf)$_2$Cl$_2$ (4.4 g, 6 mmol) at room temperature under nitrogen. After stirring for 10 minutes, a solution of K$_2$CO$_3$ (16.6 g, 120 mmol) in water (250 mL) was added. The mixture was heated to 100° C. and stirred overnight. After evaporation of the solvent, water (200 mL) was added and the material was extracted with EtOAc (3×200 mL). The combined organic layers were washed with saturated aqueous NaCl (250 mL), dried over Na$_2$SO$_4$, and concentrated to yield the crude residue, which was further purified by column chromatography (hexanes:EtOAc=4:1) to yield Compound 4 (16.2 g) as a light yellow oil. LC-MS: [M+Na]$^+$:392, [2M+Na]$^+$:761.

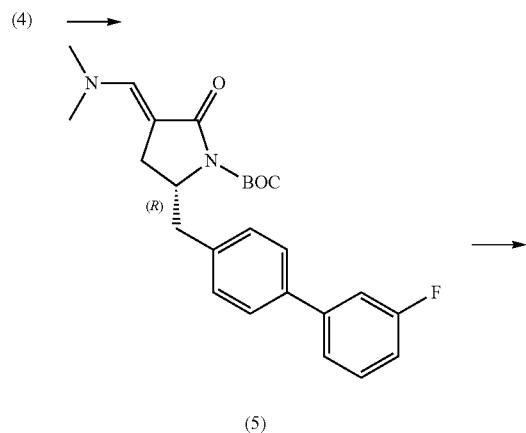

A mixture of Compound 4 (16.2 g, 43.8 mmol) and t-butoxy-N,N,N',N'-tetramethylmethanediamine (22.9 g, 131 mmol) was heated to 80° C. under nitrogen. After stirring for 3 hours at 80° C., the mixture was diluted with EtOAc (300 mL), washed with water (2×150 mL) and saturated aqueous NaCl (2×150 mL), dried over MgSO$_4$, filtered, and evaporated to yield crude Compound 5 (18.6 g) as a light yellow oil. LC-MS: [M+H]$^+$:425, [2M+H]$^+$:849.

To a solution of crude Compound 5 (18.6 g, 43.8 mmol) in THF (200 mL) was added 1 M HCl (48 mL) at 0° C. under nitrogen. After stirring for 1 hour at room temperature, the mixture was diluted with EtOAc (100 mL) and adjusted with saturated aqueous NaHCO$_3$ to pH 7. The aqueous layer was extracted with EtOAc (2×150 mL) and the combined organic layers were washed with water (2×150 mL) and saturated aqueous NaCl (150 mL), dried over MgSO$_4$, filtered, and evaporated to yield crude Compound 6 (17.4 g) as a yellow oil. LC-MS: [M+Na]$^+$:420, [2M+Na]$^+$:817.

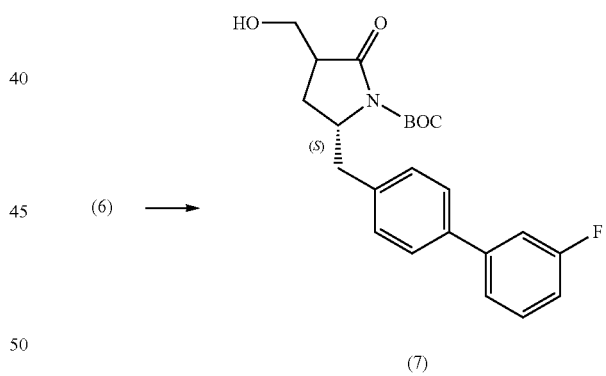

To a solution of Compound 6 (17.4 g, 43.8 mmol) in anhydrous THF (300 mL) was added anhydrous EtOH (30 mL) and AcOH (52.6 g, 867 mmol) at −5° C. under nitrogen. The mixture was stirred at −5° C. for 0.5 hour, then NaBH$_3$CN (6.9 g, 110 mmol) was added in small portions over 1 hour. After stirring for one additional hour at −5° C., the mixture was adjusted with saturated aqueous NaHCO$_3$ to pH 7. The aqueous layer was extracted with EtOAc (2×200 mL) and the combined organic layers were washed with water (2×150 mL) and saturated aqueous NaCl (150 mL), dried over MgSO$_4$, filtered, and concentrated to yield the crude residue, which was further purified by chromatography (hexanes:EtOAc=6:1) to yield Compound 7 (6.7 g) as a light yellow solid. LC-MS: [M+Na]$^+$:422, [2M+Na]$^+$:821.

(7) →

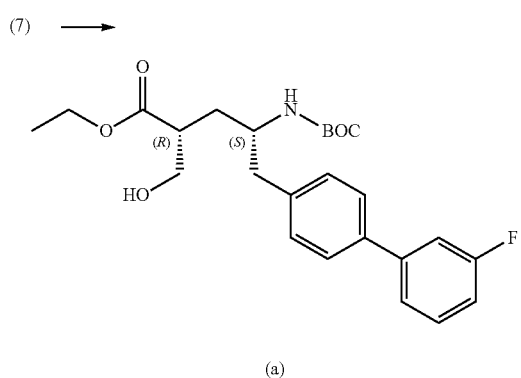

(a)

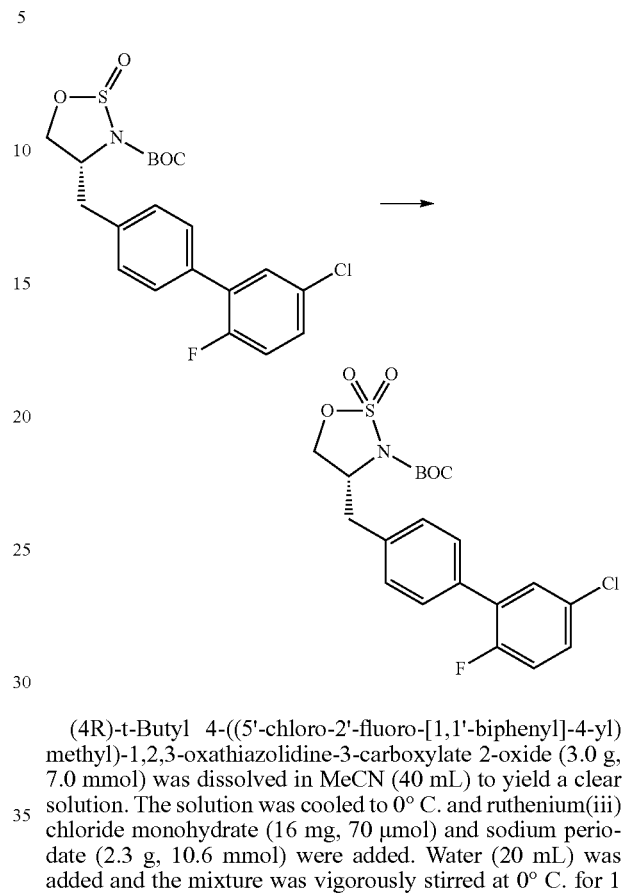

(b)

To a solution of Compound 7 (6.7 g, 16.7 mmol) in anhydrous EtOH (500 mL) was added anhydrous K₂CO₃ (4.6 g, 33.3 mmol) at 0° C. under nitrogen. After stirring for 1 hour at 0° C., the mixture was warmed to room temperature and stirred for 16 hours. After filtration, the filtrate was concentrated and the residue was diluted with water (150 mL), DCM (200 mL) and saturated aqueous NaCl (50 mL). The layers were separated and the aqueous layer was extracted with DCM (2×150 mL). The combined organic layers were washed with saturated aqueous NaCl (2×200 mL), dried over MgSO₄, and concentrated to yield the crude residue which was further purified by column chromatography (hexanes:EtOAc=5:1) to yield title compounds a and b (5.2 g) as light yellow solids.

Compound a: LC-MS: [M+Na]⁺=468, [2M+Na]⁺=913; ¹H NMR (300 MHz, CDCl₃): δ7.50-7.48 (m, 2H), 7.39-7.34 (m, 3H), 7.27-7.23 (m, 2H), 7.01 (m, 1H), 4.42 (s, 1H), 4.20-4.13 (m, 2H), 3.90 (s, 1H), 3.78-3.74 (m, 2H), 2.84-2.82 (m, 2H), 2.70 (s, 1H), 2.22 (s, 1H), 2.02-1.95 (m, 1H), 1.59-1.50 (m, 1H), 1.39 (s, 9H), 1.27-1.23 (m, 3H).

Compound b: LC-MS: [M+Na]⁺=468, [2M+Na]⁺=913; ¹H NMR (300 MHz, CDCl₃): δ7.50-7.48 (m, 2H), 7.39-7.34 (m, 3H), 7.25-7.23 (m, 2H), 7.01 (m, 1H), 4.42 (s, 1H), 4.19-4.13 (m, 2H), 3.90 (s, 1H), 3.79-3.75 (m, 2H), 2.83-2.81 (m, 2H), 2.70 (m, 1H), 2.21 (s, 1H), 1.79-1.74 (m, 2H), 1.37 (s, 9H), 1.29-1.23 (m, 3H).

Preparation 24: (R)-t-Butyl 4-((5'-chloro-2'-fluoro-[1,1'-biphenyl]-4-yl)methyl)-1,2,3-oxathiazolidine-3-carboxylate 2,2-dioxide (4R)-t-Butyl 4-((5'-chloro-2'-fluoro-[1,1'-biphenyl]-4-yl)methyl)-1,2,3-oxathiazolidine-3-carboxylate 2-oxide (3.0 g, 7.0 mmol) was dissolved in MeCN (40 mL) to yield a clear solution. The solution was cooled to 0° C. and ruthenium(iii) chloride monohydrate (16 mg, 70 µmol) and sodium periodate (2.3 g, 10.6 mmol) were added. Water (20 mL) was added and the mixture was vigorously stirred at 0° C. for 1 hour, yielding a thick slurry (analysis showed 10% conversion). The mixture was then stirred at 5° C. overnight (almost complete conversion was observed). Additional water (20 mL) was added and the mixture was stirred at room temperature for 1 hour. The mixture was filtered and dried to yield the crude residue (3 g; purity 95%). The crude material was stirred in DCM (50 mL) for 2 hours. The mixture was filtered and the filtrate was concentrated to dryness to yield the title compound (2 g) as an off-white solid.

Preparation 25: (2S,4S)-4-t-Butoxycarbonylamino-5-(5'-chloro-2'-fluorobiphenyl-4-yl)-2-methanesulfonyloxymethylpentanoic Acid Ethyl Ester

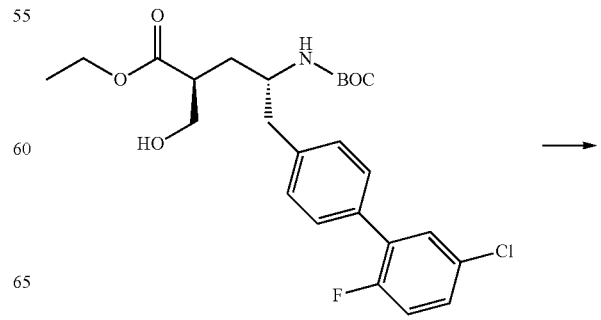

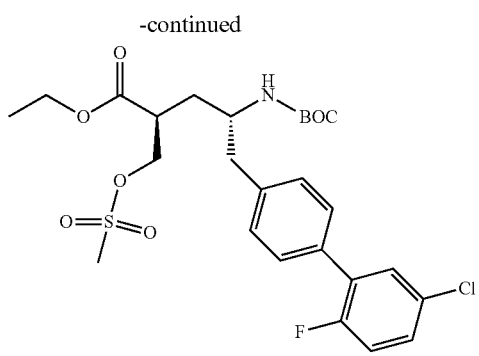

(2S,4S)-4-t-Butoxycarbonylamino-5-(5'-chloro-2'-fluoro-biphenyl-4-yl)-2-hydroxymethylpentanoic acid ethyl ester (250 mg, 521 μmol) was combined with DCM (2 mL), mesyl chloride (48.7 μL, 625 μmol), and Et₃N (145 μL, 1.0 mmol) slowly. The mixture was stirred for 10 minutes and purified by normal phase column chromatography (0-100% EtOAc/hexanes) to yield the title compound (240 mg).

Preparation 26: (2S,4S)-4-t-Butoxycarbonylamino-5-(5'-chloro-2'-fluorobiphenyl-4-yl)-2-(toluene-4-sulfonyloxymethyl)pentanoic Acid Ethyl Ester

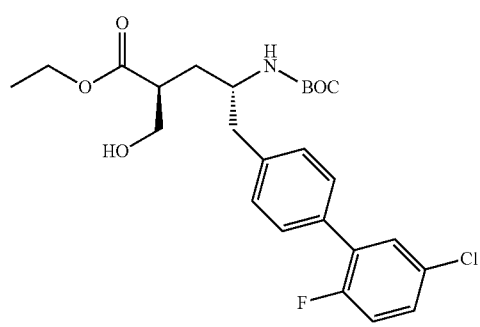

(2S,4S)-4-t-Butoxycarbonylamino-5-(5'-chloro-2'-fluoro-biphenyl-4-yl)-2-hydroxymethylpentanoic acid ethyl ester (250 mg, 521 μmol) was combined with DCM (2 mL), p-toluenesulfonyl chloride (109 mg, 573 μmol), and Et₃N (145 μL, 1.0 mmol) slowly. The mixture was stirred for 10 minutes and purified by normal phase column chromatography (0-100% EtOAc/hexanes) to yield the title compound (267 mg).

Preparation 27: (2S,4S)-2-(4-Bromobenzenesulfony-loxymethyl)-4-t-butoxycarbonylamino-5-(5'-chloro-2'-fluorobiphenyl-4-yl)pentanoic Acid Ethyl Ester

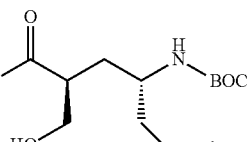

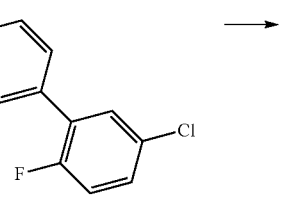

(1)

(2S,4S)-4-t-Butoxycarbonylamino-5-(5'-chloro-2'-fluoro-biphenyl-4-yl)-2-hydroxymethylpentanoic acid ethyl ester (2.0 g, 4.2 mmol) was dissolved in dry DCM (10 mL) and 4-bromobenzenesulfonyl chloride (1.4 g, 5.4 mmol), and Et₃N (1.2 L, 8.3 mmol) was slowly added. The mixture was stirred for 90 minutes at room temperature, at which time LCMS indicated the mass of the desired compound. The crude solution was purified by normal phase column chromatography (0-100% EtOAc/hexanes) to yield the title compound (2.2 g).

Preparation 28: (2R,4R)-4-Amino-5-(5'-chloro-2'-fluorobiphenyl-4-yl)-2-(1-isobutyryloxy-ethoxycar-bonylamino)pentanoic Acid Benzyl Ester

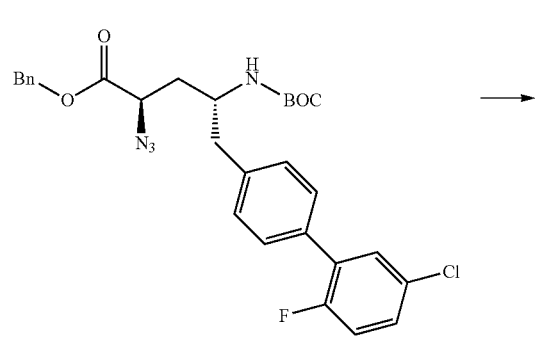

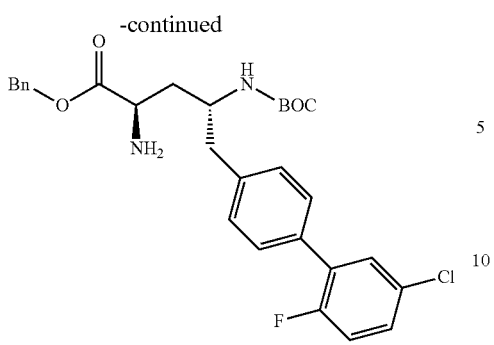

(1)

A mixture of (2R,4R)-2-azido-4-t-butoxycarbonylamino-5-(5'-chloro-2'-fluorobiphenyl-4-yl)pentanoic acid benzyl ester (2.6 g, 4.7 mmol), PPh₃ (1.5 g, 5.6 mmol) and THF/H₂O (50 mL/10 mL) was stirred at room temperature for two days. The solvent was concentrated in vacuo and purified by flash chromatography (DCM:MeOH=40:1) to yield compound 1 (1.3 g) as a colorless oil. LC-MS: m/z=527[(M⁺+1)].

(1) ⟶

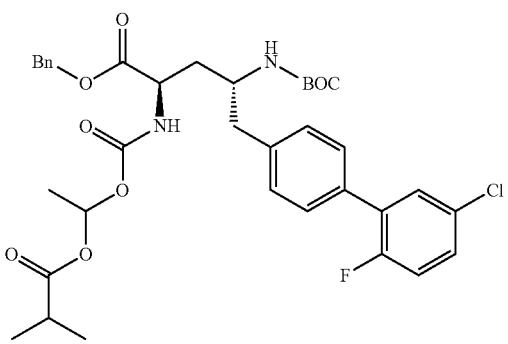

(2)

To a mixture of Compound 1 (763 mg, 1.5 mmol), DIPEA (374 mg, 2.9 mmol), DMAP (177 mg, 1.5 mmol) and THF (6 mL) was added a solution of 1-((4-nitrophenoxy) carbonyloxy)ethyl isobutyrate (645 mg, 2.2 mmol) in THF (2 mL) at 25° C. The resulting mixture was stirred at room temperature overnight. The solvent was removed under reduced pressure and purified by flash chromatography (PE:EtOAc=4:1) to yield Compound 2 (555 mg) as a white solid. LC-MS: m/z=707[(M⁺+Na)].

(2) ⟶

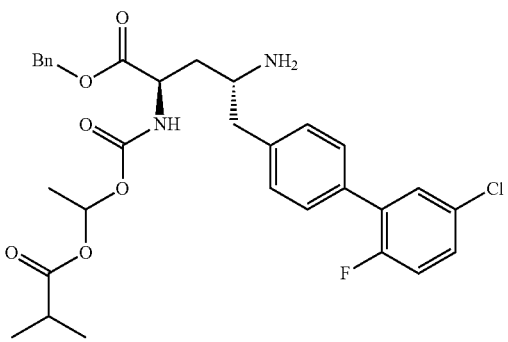

(2)

A suspension of Compound 2 (160 mg, 234 µmol) and ZnBr₂ (263 mg, 1.2 mmol) in DCM (1.2 mL) was stirred at 25° C. for 12 hours, then concentrated and purified by preparative HPLC (50-70% MeCN in water with 0.1% TFA) to yield the title compound (102 mg) as a white solid. LC-MS: m/z=585[(M⁺+1)]. ¹H NMR (300 MHz, CD₃OD) δ7.32-7.49 (m, 11H), 7.17-7.23 (m, 1H), 6.76-6.79 (m, 1H), 5.10-5.24 (m, 2H), 4.39-4.53 (m, 1H), 3.59-3.64 (m, 1H), 2.91-3.20 (m, 2H), 2.45-2.57 (m, 1H), 2.18-2.28 (m, 1H), 1.99-2.13 (m, 1H), 1.45-1.47 (m, 3H), 1.10-1.15 (m, 6H).

Preparation 29: (2S,4S)-4-Amino-2-(1-amino-1-methylethyl)-5-(5'-chloro-2'-fluorobiphenyl-4-yl) pentanoic Acid Ethyl Ester

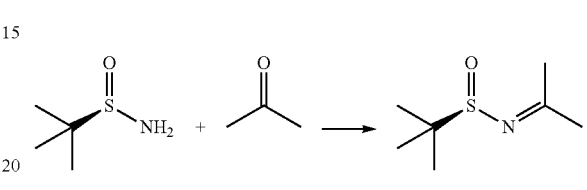

(1)

To a solution of 2-methylpropane-2-sulfinic acid amide (6.6 g, 54 mmol) in THF (400 mL) was added acetone (15.8 g, 273 mmol) and titanium ethoxide (62 g, 273 mmol) at room temperature. The mixture was refluxed for 24 hours and cooled to room temperature. Saturated aqueous NaHCO₃ was added and the resulting solution was stirred for 5 minutes before being filtered. The solids were washed with EtOAc (50 mL), and the combined filtrates were transferred to a separatory funnel, where the aqueous portion was separated and extracted with EtOAc (2×50 mL). The combined organic phases were dried, filtered, and concentrated to yield Compound 1 (8 g) as a colorless oil. ¹H NMR (300 MHz, CDCl₃) δ 2.31 (s, 3H), 2.16 (s, 3H), 1.20 (s, 9H).

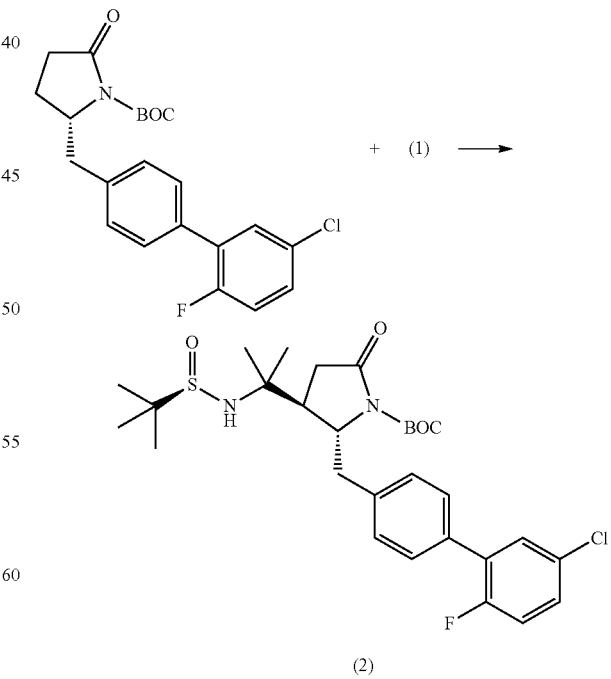

(2)

To a solution of (S)-2-(5'-chloro-2'-fluorobiphenyl-4-yl-methyl)-5-oxopyrrolidine-1-carboxylic acid t-butyl ester (1.1 g, 2.7 mmol) in anhydrous THF (20 mL) was added dropwise NaHMDS (1.8 mL, 3.5 mmol) at −78° C. under nitrogen. After stirring at −78° C. for 1.5 hours, Compound 1 (570 mg, 3.5 mmol) was added dropwise. After stirring at this temperature for 2 hours, the reaction was quenched with saturated aqueous NH₄Cl (20 mL), warmed to room temperature, and extracted with EtOAc (2×50 mL). The combined organic layers were washed with saturated aqueous NaCl (100 mL), dried over Na₂SO₄, filtered and concentrated to give the crude product which was purified by chromatography (PE:EtOAc=2:1) to yield Compound 2 (500 mg) as a colorless oil. LC-MS: [M+Na]⁺: 587.

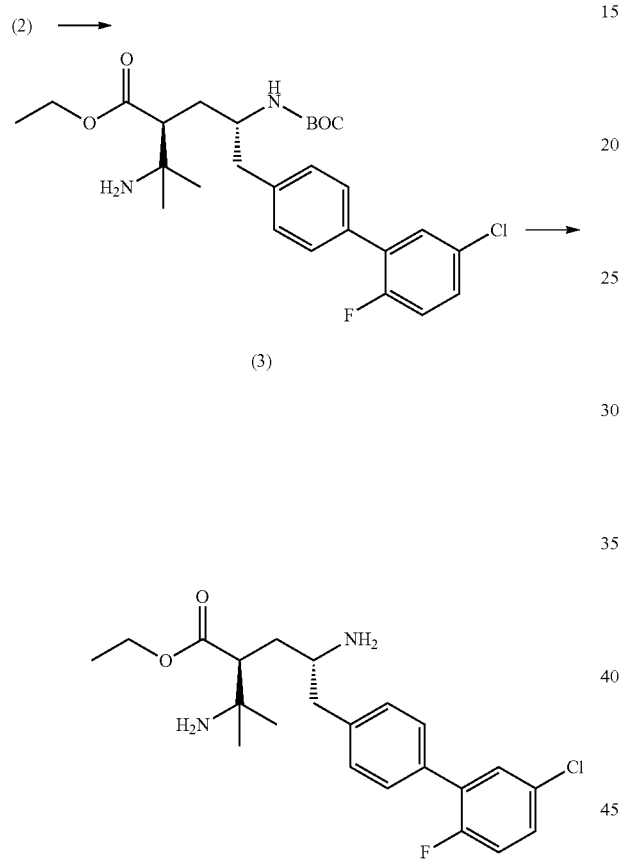

A mixture of Compound 2 (500 mg, 890 μmol) and K₂CO₃ (366 mg, 2.6 mmol) in EtOH (5 mL) was stirred at room temperature for 2 hours. The mixture was filtered, the filtrated was acidified with HCl (1N) to pH 5 and extracted with EtOAc (3×20 mL). The organic phase was dried over Na₂SO₄, filtered, and concentrated to afford a residue, which was purified by column chromatography (PE:EtOAc=2:1) to yield Compound 3 (450 mg) as a colorless oil. LC-MS: [M+H]⁺: 611.

A solution of Compound 3 (450 mg, 74 μmol) in 3.0 M HCl in dioxane (6 mL) was stirred at room temperature for 3 hours. The mixture was concentrated, and the residue was purified by washing with Et₂O (7 mL) to yield the title compound (0.2 g) as a white solid. LC-MS: [M+H]⁺: 407. ¹H NMR (300 MHz, CD₃OD) δ 7.57~7.37 (m, 6H), 7.25~7.18 (m, 1H), 4.20 (m, 2H), 3.48 (m, 1H), 3.10~2.98 (m, 3H), 2.14~2.02 (m, 2H), 1.45~1.40 (m, 6H), 1.24~1.18 (m, 3H).

Example 1

(2S,4S)-5-(5'-Chloro-2'-fluorobiphenyl-4-yl)-4-[(3-ethylisoxazole-5-carbonyl)amino]-2-methoxymethylpentanoic Acid

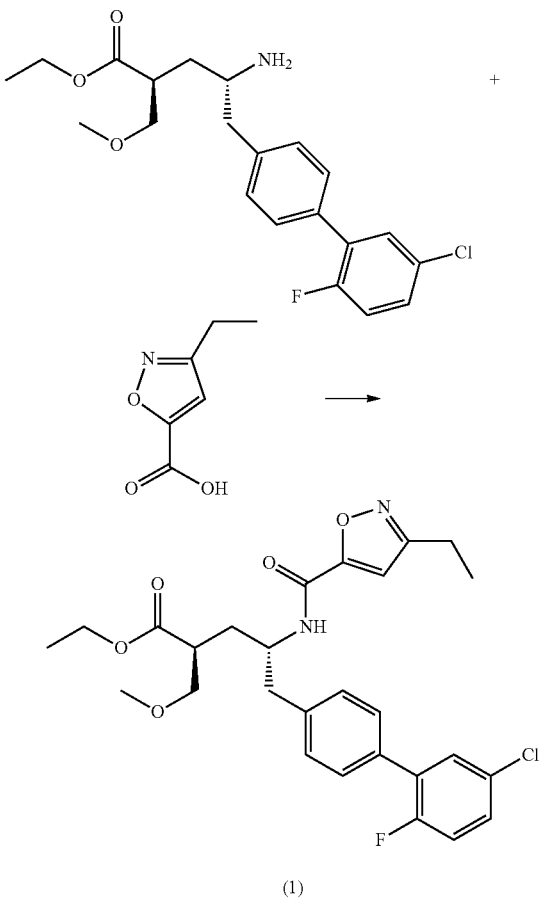

To a stirred solution of 3-ethylisoxazole-5-carboxylic acid (17 mg, 50 μmol) in HATU (23 mg, 60 μmol) and DMF, was added (2S,4S)-4-amino-5-(5'-chloro-2'-fluorobiphenyl-4-yl)-2-methoxymethylpentanoic acid ethyl ester (384 mg, 60 μmol), followed by DIPEA (19 mg, 150 μmol). The mixture was stirred overnight to yield Compound 1, which was used directly in the next step.

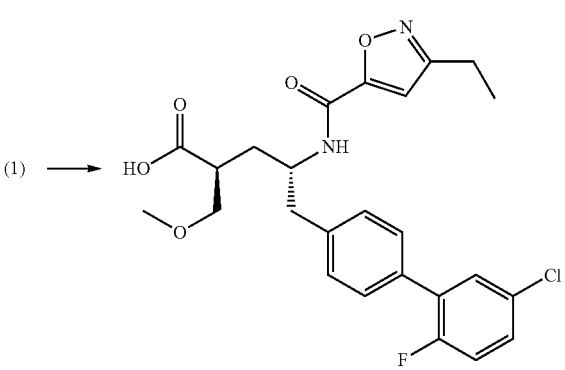 [SMILES: CCc1cc(C(=O)N[C@H](Cc2ccc(-c3cc(Cl)ccc3F)cc2)C[C@@H](COC)C(=O)O)on1]

Crude Compound 1 was dissolved in THF and 10N NaOH (65 μL, 650 μmol) and stirred at 50° C. overnight. The reaction was quenched with AcOH and the solution was purified by preparative HPLC to yield the title compound (6.6 mg; purity 100%). MS m/z [M+H]+ calc'd for $C_{25}H_{26}ClFN_2O_5$, 489.15. found 489.2.

Example 2

Following the procedures described herein, and substituting the appropriate starting materials and reagents, these compounds were prepared, either as the parent compound or as a TFA salt:

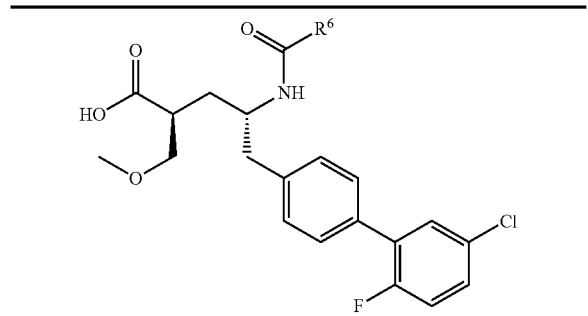

| Ex. | R⁶ | Formula | MS m/z: [M + H]⁺ calcd | found |
|---|---|---|---|---|
| 1 | | $C_{22}H_{22}ClFN_4O_4$ | 461.13 | 461.2 |
| 2 | | $C_{23}H_{21}ClF_4N_4O_4$ | 529.12 | 529.2 |
| 3 | | $C_{26}H_{26}ClF_2N_3O_4$ | 518.16 | 519.2 |
| 4 | | $C_{25}H_{25}ClFN_3O_5$ | 502.15 | 502.2 |
| 5 | | $C_{23}H_{22}ClFN_2O_6$ | 477.12 | 476 |
| 6 | | $C_{24}H_{24}ClFN_2O_6$ | 491.13 | 491.2 |

-continued

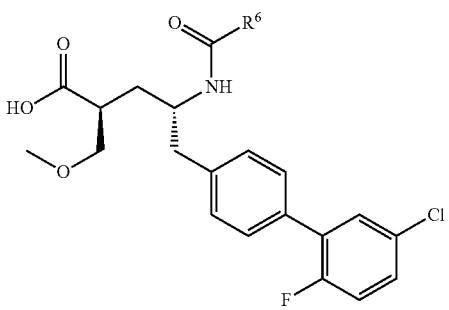

| Ex. | R⁶ | Formula | MS m/z: [M + H]⁺ calcd | found |
|---|---|---|---|---|
| 7 | | $C_{23}H_{22}ClFN_2O_5$ | 461.12 | 461.2 |
| 8 | | $C_{23}H_{22}ClFN_2O_5$ | 461.12 | 461.2 |
| 9 | | $C_{26}H_{26}ClFN_2O_5$ | 501.15 | 501.2 |
| 10 | | $C_{23}H_{22}ClFN_2O_6$ | 477.12 | 476 |
| 11 | | $C_{22}H_{21}ClFN_3O_6$ | 478.11 | 477 |
| 12 | | $C_{25}H_{23}Cl_2FN_2O_4$ | 505.10 | 506.2 |
| 13 | | $C_{24}H_{23}ClFN_3O_4$ | 472.14 | 472.2 |
| 14 | | $C_{26}H_{23}ClF_4N_2O_4$ | 539.13 | 537 |
| 15 | | $C_{24}H_{24}ClFN_2O_5$ | 475.14 | 475 |

103

-continued

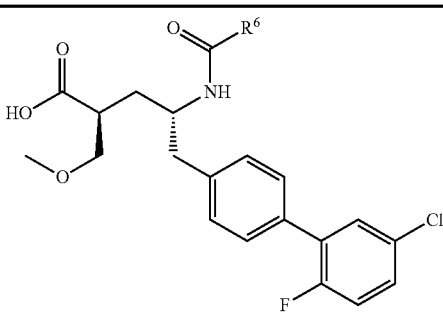

| Ex. | R⁶ | Formula | MS m/z: [M + H]⁺ calcd | found |
|---|---|---|---|---|
| 16 | (pyrazole with ethoxy) | $C_{25}H_{27}ClFN_3O_5$ | 504.16 | 504 |

1. (2S,4S)-5-(5'-Chloro-2'-fluorobiphenyl-4-yl)-2-methoxymethyl-4-[(1H-[1,2,3]triazole-4-carbonyl)amino]pentanoic acid
2. (2S,4S)-5-(5'-Chloro-2'-fluorobiphenyl-4-yl)-2-methoxymethyl-4-[(5-trifluoromethyl-1H-[1,2,4]triazole-3-carbonyl)amino]pentanoic acid
3. (2S,4S)-5-(5'-Chloro-2'-fluorobiphenyl-4-yl)-4-[(5-cyclopropyl-4-fluoro-2H-pyrazole-3-carbonyl)amino]-2-methoxymethylpentanoic acid
4. (2S,4S)-4-[(5-Acetyl-2H-pyrazole-3-carbonyl)-amino]-5-(5'-chloro-2'-fluorobiphenyl-4-yl)-2-methoxymethylpentanoic acid
5. (2S,4S)-5-(5'-Chloro-2'-fluorobiphenyl-4-yl)-4-[(3-hydroxyisoxazole-5-carbonyl)-amino]-2-methoxymethylpentanoic acid
6. (2S,4S)-5-(5'-Chloro-2'-fluorobiphenyl-4-yl)-4-[(3-methoxyisoxazole-5-carbonyl)-amino]-2-methoxymethylpentanoic acid
7. (2S,4S)-5-(5'-Chloro-2'-fluorobiphenyl-4-yl)-2-methoxymethyl-4-[(oxazole-2-carbonyl)amino]pentanoic acid
8. (2S,4S)-5-(5'-Chloro-2'-fluorobiphenyl-4-yl)-2-methoxymethyl-4-[(oxazole-4-carbonyl)amino]pentanoic acid
9. (2S,4S)-5-(5'-Chloro-2'-fluorobiphenyl-4-yl)-4-[(2-cyclopropyloxazole-4-carbonyl)amino]-2-methoxymethylpentanoic acid
10. (2S,4S)-5-(5'-Chloro-2'-fluorobiphenyl-4-yl)-2-methoxymethyl-4-[(2-oxo-2,3-dihydro-oxazole-5-carbonyl)amino]pentanoic acid
11. (2S,4S)-5-(5'-Chloro-2'-fluorobiphenyl-4-yl)-2-methoxymethyl-4-[(5-oxo-4,5-dihydro-[1,2,4]oxadiazole-3-carbonyl)amino]pentanoic acid
12. (2S,4S)-5-(5'-Chloro-2'-fluorobiphenyl-4-yl)-4-[(5-chloro-pyridine-2-carbonyl)-amino]-2-methoxymethylpentanoic acid
13. (2S,4S)-5-(5'-Chloro-2'-fluorobiphenyl-4-yl)-2-methoxymethyl-4-[(pyrimidine-2-carbonyl)amino]pentanoic acid
14. (2S,4S)-5-(5'-Chloro-2'-fluorobiphenyl-4-yl)-2-methoxymethyl-4-[(5-trifluoromethylpyridine-2-carbonyl)amino]pentanoic acid
15. (2S,4S)-5-(5'-Chloro-2'-fluorobiphenyl-4-yl)-2-methoxymethyl-4-[(5-methyloxazole-2-carbonyl)amino]pentanoic acid
16. (2S,4S)-5-(5'-Chloro-2'-fluorobiphenyl-4-yl)-4-[(5-ethoxy-1H-pyrazole-3-carbonyl)amino]-2-methoxymethylpentanoic acid Example 3

(2S,4S)-5-(3'-Chlorobiphenyl-4-yl)-2-methoxymethyl-4-[(3H-[1,2,3]triazole-4-carbonyl)amino]pentanoic Acid

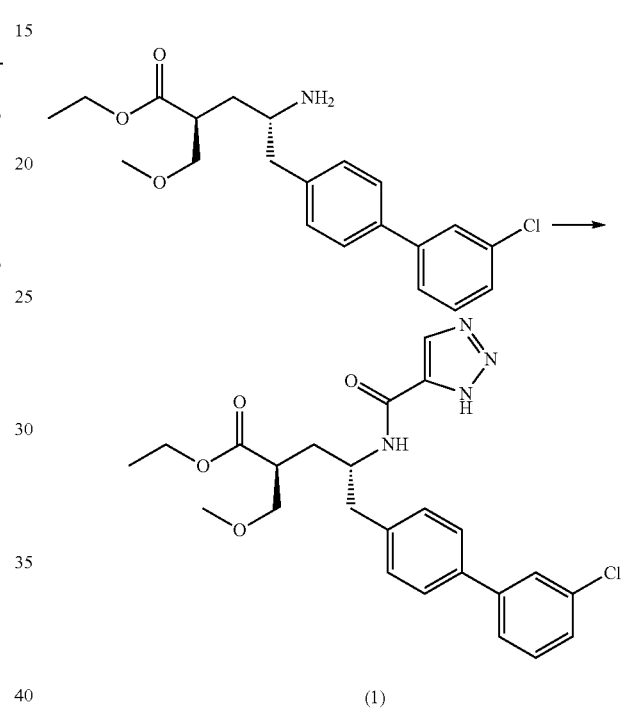

(1)

To a stirred solution of 3H-[1,2,3]triazole-4-carboxylic acid (20 mg, 50 μmol) in HATU (23 mg, 60 μmol) and DMF (1 mL), was added (2S,4S)-4-amino-5-(3'-chlorobiphenyl-4-yl)-2-methoxymethyl-pentanoic acid ethyl ester (75 mg, 60 μmol), followed by DIPEA (19 mg, 150 μmol). The resulting mixture was stirred for 15 minutes to yield Compound 1, which was used directly in the next step.

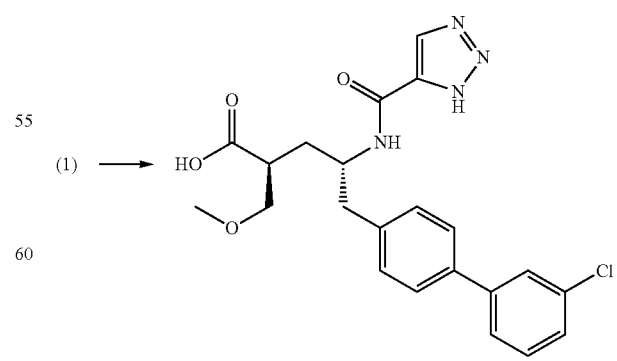

Compound 1 was dissolved in THF and 10N NaOH (50 μL, 0.5 mmol) and stirred overnight at 50° C. The reaction was quenched with AcOH and the material was purified by preparative HPLC to yield the title compound (3.8 mg; purity 98%) as a TFA salt. MS m/z [M+H]+ calc'd for $C_{22}H_{23}ClN_4O_4$, 443.14; found 443.2.

Example 4

Following the procedures described herein, and substituting the appropriate starting materials and reagents, these compounds were prepared, either as the parent compound or as a TFA salt:

| Ex. | R[6] | Formula | MS m/z: [M + H]+ calcd | found |
|---|---|---|---|---|
| 1 | (5-tert-butyl-1H-[1,2,4]triazol-3-yl, CF3) | $C_{23}H_{22}ClF_3N_4O_4$ | 511.13 | 511.2 |
| 2 | (5-tert-butyl-isoxazol-3-ol) | $C_{23}H_{23}ClN_2O_6$ | 459.12 | 458 |
| 3 | (5-oxo-4,5-dihydro-[1,2,4]oxadiazol-3-yl) | $C_{22}H_{22}ClN_3O_6$ | 460.12 | 459 |

1. (2S,4S)-5-(3'-Chlorobiphenyl-4-yl)-2-methoxymethyl-4-[(5-trifluoromethyl-1H-[1,2,4]triazole-3-carbonyl)amino]pentanoic acid
2. (2S,4S)-5-(3'-Chlorobiphenyl-4-yl)-4-[(3-hydroxy-isoxazole-5-carbonyl)amino]-2-methoxymethylpentanoic acid
3. (2S,4S)-5-(3'-Chlorobiphenyl-4-yl)-2-methoxymethyl-4-[(5-oxo-4,5-dihydro-[1,2,4]oxadiazole-3-carbonyl)amino]pentanoic acid Example 5

(2S,4S)-5-Biphenyl-4-yl-2-methoxymethyl-4-[(1H-[1,2,3]-triazole-4-carbonyl)amino]pentanoic Acid

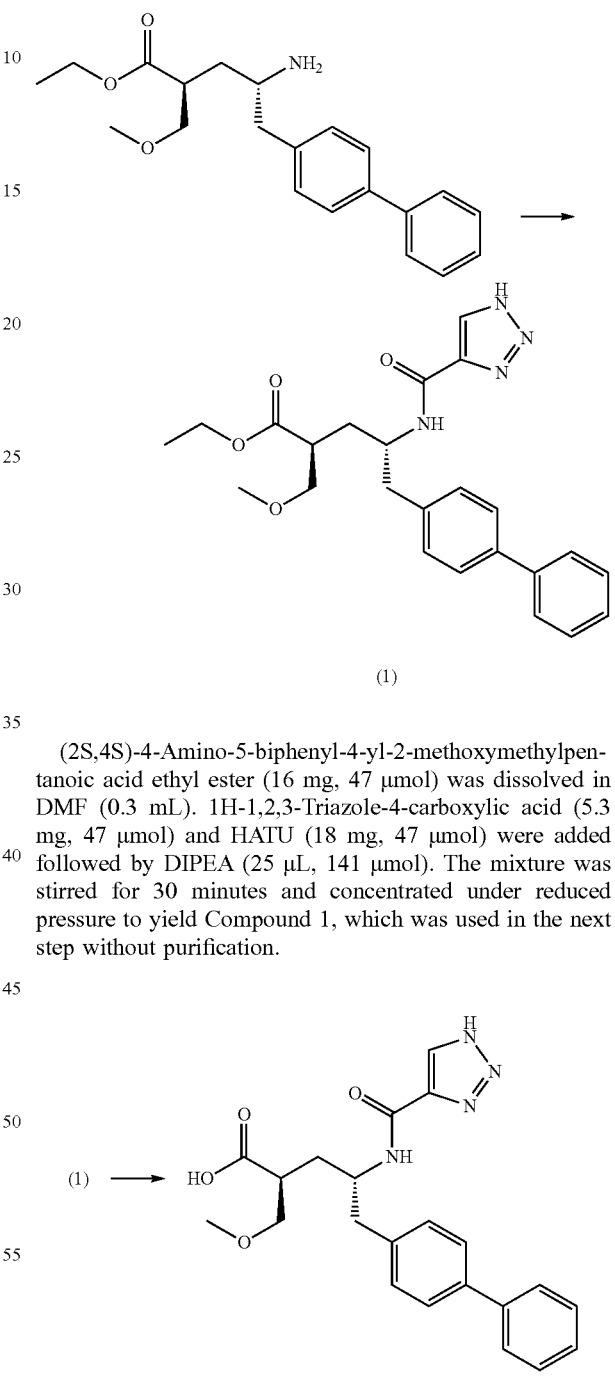

(2S,4S)-4-Amino-5-biphenyl-4-yl-2-methoxymethylpentanoic acid ethyl ester (16 mg, 47 μmol) was dissolved in DMF (0.3 mL). 1H-1,2,3-Triazole-4-carboxylic acid (5.3 mg, 47 μmol) and HATU (18 mg, 47 μmol) were added followed by DIPEA (25 μL, 141 μmol). The mixture was stirred for 30 minutes and concentrated under reduced pressure to yield Compound 1, which was used in the next step without purification.

Compound 1 (21 mg, 47 μmol) was dissolved in THF and NaOH (188 μL, 188 μmol) and stirred for 2 hours at room temperature. AcOH was added to quench the reaction and the solution was purified by preparative HPLC to yield the title compound (6.5 mg; purity 95%) as a TFA salt. MS m/z [M+H]+ calc'd for $C_{22}H_{24}N_4O_4$, 409.18; found 409.2.

Example 6

(2S,4S)-5-(5'-Chloro-2'-fluorobiphenyl-4-yl)-2-ethoxymethyl-4-[(5-trifluoromethyl-1H-[1,2,4]triazole-3-carbonyl)amino]pentanoic Acid

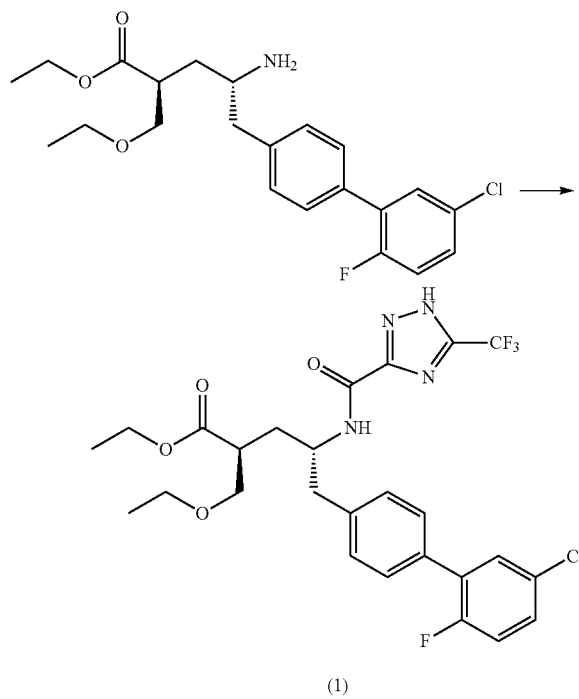

(1)

To a stirred solution of (2S,4S)-4-amino-5-(5'-chloro-2'-fluorobiphenyl-4-yl)-2-ethoxymethylpentanoic acid ethyl ester (398 mg, 65 µmol) in DMF (2 mL) and HATU (23 mg, 60 µmol), was added 5-methyl-1H-[1,2,4]triazole-3-carboxylic acid (22 mg, 60 µmol), followed by DIPEA (19 µL, 150 µmol). The mixture was stirred at room temperature overnight to yield Compound 1, which was used in the next step without purification.

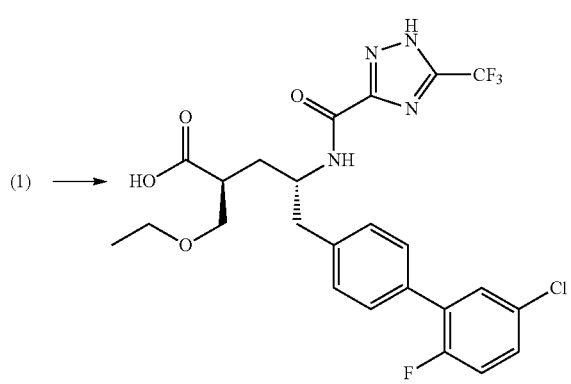 [SMILES: CCOC[C@H](C[C@@H](Cc1ccc(-c2cc(Cl)ccc2F)cc1)NC(=O)c1n[nH]c(C(F)(F)F)n1)C(=O)O]

To Compound 1 (65 µmol, 1 eq.) was added THF (0.4 mL) and 1N NaOH (65 µL, 65 µmol, 10 eq.). The mixture was stirred at 50° C. overnight. AcOH was added and the solution was purified by preparative HPLC to yield the title compound (4.7 mg; purity 99%) as a TFA salt. MS m/z [M+H]+ calc'd for $C_{24}H_{23}ClF_4N_4O_4$, 543.13; found 543.2.

Example 7

Following the procedures described herein, and substituting the appropriate starting materials and reagents, these compounds were prepared, either as the parent compound or as a TFA salt:

| Ex. | R⁶ | Formula | MS m/z: [M + H]+ calcd | found |
|---|---|---|---|---|
| 1 | | $C_{23}H_{24}ClFN_4O_4$ | 475.15 | 475.2 |
| 2 | | $C_{27}H_{28}ClF_2N_3O_4$ | 532.17 | 533.2 |
| 3 | | $C_{26}H_{27}ClFN_3O_5$ | 516.16 | 517.2 |
| 4 | | $C_{24}H_{24}ClFN_2O_6$ | 491.13 | 490 |
| 5 | | $C_{26}H_{28}ClFN_2O_5$ | 503.17 | 503.2 |
| 6 | | $C_{24}H_{24}ClFN_2O_5$ | 475.14 | 475.2 |
| 7 | | $C_{24}H_{24}ClFN_2O_5$ | 475.14 | 475.2 |
| 8 | | $C_{27}H_{28}ClFN_2O_5$ | 515.17 | 515.2 |

-continued

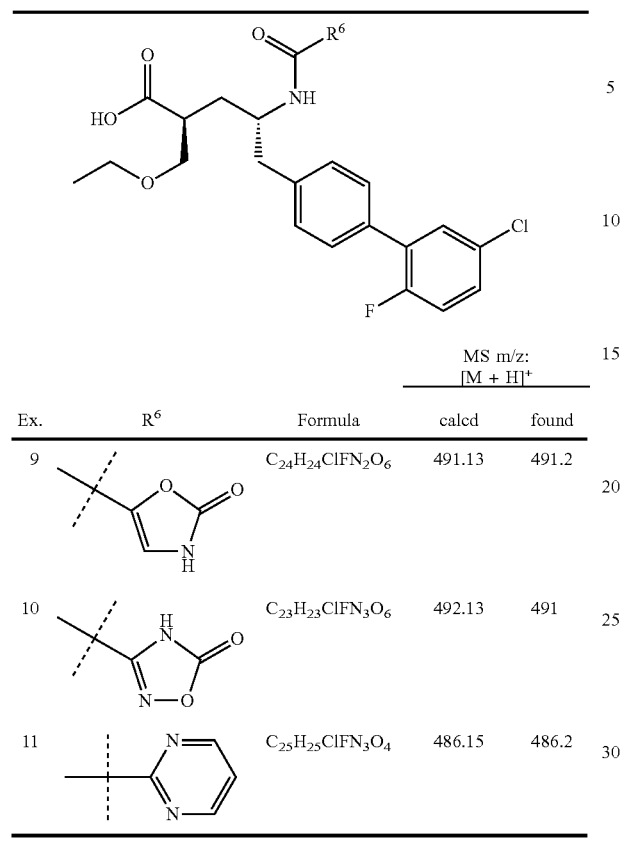

| Ex. | R⁶ | Formula | MS m/z: [M + H]⁺ calcd | found |
|---|---|---|---|---|
| 9 | | $C_{24}H_{24}ClFN_2O_6$ | 491.13 | 491.2 |
| 10 | | $C_{23}H_{23}ClFN_3O_6$ | 492.13 | 491 |
| 11 | | $C_{25}H_{25}ClFN_3O_4$ | 486.15 | 486.2 |

1. (2S,4S)-5-(5'-Chloro-2'-fluorobiphenyl-4-yl)-2-ethoxymethyl-4-[(1H-[1,2,3]triazole-4-carbonyl)amino]pentanoic acid
2. (2S,4S)-5-(5'-Chloro-2'-fluorobiphenyl-4-yl)-4-[(5-cyclopropyl-4-fluoro-2H-pyrazole-3-carbonyl)amino]-2-ethoxymethylpentanoic acid
3. (2S,4S)-4-[(5-Acetyl-2H-pyrazole-3-carbonyl)-amino]-5-(5'-chloro-2'-fluorobiphenyl-4-yl)-2-ethoxymethylpentanoic acid
4. (2S,4S)-5-(5'-Chloro-2'-fluoro-biphenyl-4-yl)-2-ethoxymethyl-4-[(3-hydroxy-isoxazole-5-carbonyl)amino]pentanoic acid
5. (2S,4S)-5-(5'-Chloro-2'-fluorobiphenyl-4-yl)-2-ethoxymethyl-4-[(3-ethylisoxazole-5-carbonyl)amino]pentanoic acid
6. (2S,4S)-5-(5'-Chloro-2'-fluorobiphenyl-4-yl)-2-ethoxymethyl-4-[(oxazole-2-carbonyl)amino]pentanoic acid
7. (2S,4S)-5-(5'-Chloro-2'-fluorobiphenyl-4-yl)-2-ethoxymethyl-4-[(oxazole-4-carbonyl)amino]pentanoic acid
8. (2S,4S)-5-(5'-Chloro-2'-fluorobiphenyl-4-yl)-4-[(2-cyclopropyloxazole-4-carbonyl)amino]-2-ethoxymethylpentanoic acid
9. (2S,4S)-5-(5'-Chloro-2'-fluorobiphenyl-4-yl)-2-ethoxymethyl-4-[(2-oxo-2,3-dihydro-oxazole-5-carbonyl)amino]pentanoic acid
10. (2S,4S)-5-(5'-Chloro-2'-fluorobiphenyl-4-yl)-2-ethoxymethyl-4-[(5-oxo-4,5-dihydro-[1,2,4]oxadiazole-3-carbonyl)amino]pentanoic acid
11. (2S,4S)-5-(5'-Chloro-2'-fluorobiphenyl-4-yl)-2-ethoxymethyl-4-[(pyrimidine-2-carbonyl)amino]pentanoic acid Example 8

(2S,4S)-5-(3'-Chlorobiphenyl-4-yl)-2-ethoxymethyl-4-[(3-hydroxyisoxazole-5-carbonyl)amino]pentanoic Acid

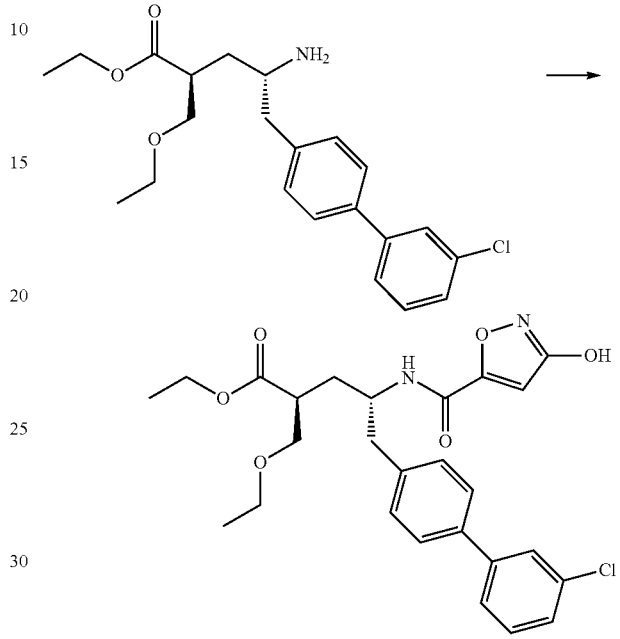

To a stirred solution of (2S,4S)-4-amino-5-(3'-chlorobiphenyl-4-yl)-2-ethoxymethylpentanoic acid ethyl ester (40 mg, 103 μmol) in HATU (46.8 mg, 123 μmol), 3-hydroxyisoxazole-5-carboxylic acid (13.2 mg, 133 μmol), and DMF (0.5 mL), was added DIPEA (53.8 μL, 308 μmol). The mixture was stirred for 1 hour, then concentrated under reduced pressure to yield crude Compound 1, which was used in the next step without purification.

(1) → 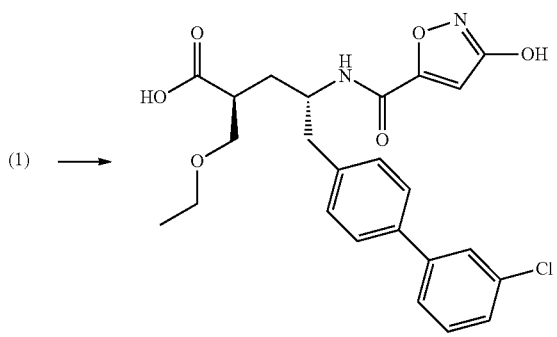 [SMILES: CCOC[C@H](C[C@@H](Cc1ccc(-c2cccc(Cl)c2)cc1)NC(=O)c1cc(O)no1)C(=O)O]

To Compound 1 (57 mg, 103 μmol) was added THF (0.8 mL) and 1N NaOH (412 μL, 412 μmol). A few drops of EtOH were added to the solution and it was stirred for 3 hours. The mixture was concentrated under reduced pressure. The residue was purified by reverse phase to yield the title compound (1 mg; purity 95%). MS m/z [M+H]⁺ calc'd for $C_{24}H_{25}ClN_2O_6$, 473.14; found 472.

Example 9

Following the procedures described herein, and substituting the appropriate starting materials and reagents, these compounds were prepared, either as the parent compound or as a TFA salt:

| Ex. | R⁶ | Formula | MS m/z: [M + H]⁺ calcd | found |
|---|---|---|---|---|
| 1 | (1H-1,2,3-triazol-4-yl) | $C_{23}H_{25}ClN_4O_4$ | 457.16 | 456 |
| 2 | (5-acetyl-1H-pyrazol-3-yl) | $C_{26}H_{28}ClN_3O_5$ | 498.17 | 497 |
| 3 | (5-trifluoromethyl-1H-[1,2,4]triazol-3-yl) | $C_{24}H_{24}ClF_3N_4O_4$ | 525.14 | 524 |
| 4 | (3-methoxy-isoxazol-5-yl) | $C_{25}H_{27}ClN_2O_6$ | 487.16 | 486 |
| 5 | (5-oxo-4,5-dihydro-[1,2,4]oxadiazol-3-yl) | $C_{23}H_{24}ClN_3O_6$ | 474.14 | 473 |

1. (2S,4S)-5-(3'-Chlorobiphenyl-4-yl)-2-ethoxymethyl-4-[(1H-[1,2,3]triazole-4-carbonyl)amino]pentanoic acid
2. (2S,4S)-4-[(5-Acetyl-1H-pyrazole-3-carbonyl)-amino]-5-(3'-chlorobiphenyl-4-yl)-2-ethoxymethylpentanoic acid
3. (2S,4S)-5-(3'-Chlorobiphenyl-4-yl)-2-ethoxymethyl-4-[(5-trifluoromethyl-1H-[1,2,4]triazole-3-carbonyl)amino]pentanoic acid
4. (2S,4S)-5-(3'-Chlorobiphenyl-4-yl)-2-ethoxymethyl-4-[(3-methoxy-isoxazole-5-carbonyl)amino]pentanoic acid
5. (2S,4S)-5-(3'-Chlorobiphenyl-4-yl)-2-ethoxymethyl-4-[(5-oxo-4,5-dihydro-[1,2,4]oxadiazole-3-carbonyl)amino]pentanoic acid

Example 10

(2S,4S)-5-Biphenyl-4-yl-2-ethoxymethyl-4-[(1H-[1,2,3]triazole-4-carbonyl)amino]pentanoic Acid

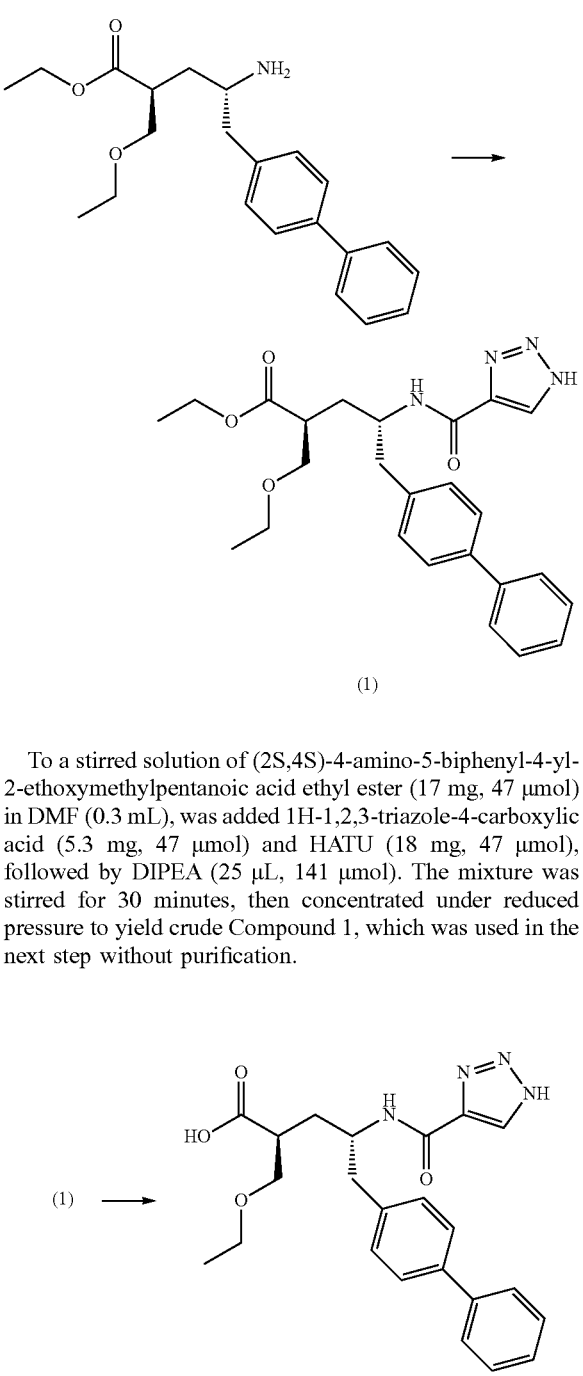

To a stirred solution of (2S,4S)-4-amino-5-biphenyl-4-yl-2-ethoxymethylpentanoic acid ethyl ester (17 mg, 47 µmol) in DMF (0.3 mL), was added 1H-1,2,3-triazole-4-carboxylic acid (5.3 mg, 47 µmol) and HATU (18 mg, 47 µmol), followed by DIPEA (25 µL, 141 µmol). The mixture was stirred for 30 minutes, then concentrated under reduced pressure to yield crude Compound 1, which was used in the next step without purification.

To Compound 1 (21 mg, 47 µmol) was added THF (0.5 mL) and 1N NaOH (188 µL, 188 µmol) was added and stirred for 2 hours at room temperature. AcOH was added and the solution was purified by preparative HPLC to yield the title compound (4.5 mg; purity 94%) as a TFA salt. MS m/z [M+H]⁺ calc'd for $C_{23}H_{26}N_4O_4$, 423.20; found 423.2.

Example 11

(2S,4S)-5-Biphenyl-4-yl-2-(2-hydroxyethoxymethyl)-4-[(1H-[1,2,3]triazole-4-carbonyl)amino]pentanoic Acid

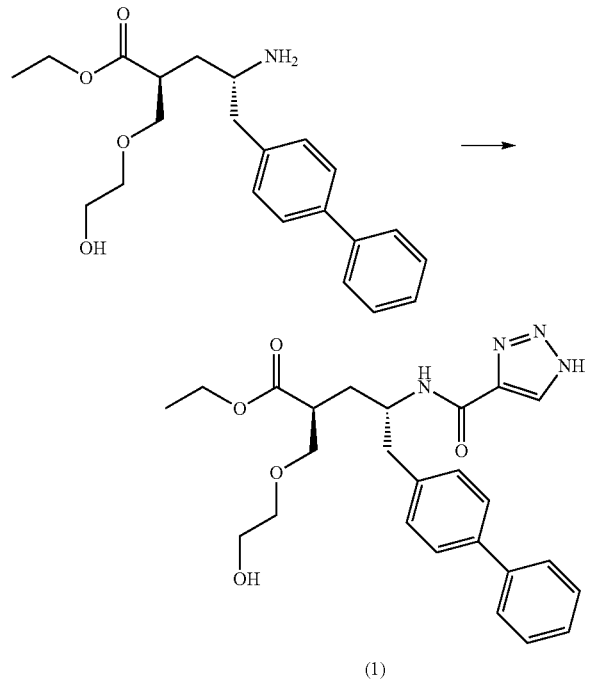

(1)

To a stirred solution of (2S,4S)-4-amino-5-biphenyl-4-yl-2-(2-hydroxyethoxymethyl)pentanoic acid ethyl ester (17 mg, 47 μmol) in DMF (0.3 mL), was added 1H-1,2,3-triazole-4-carboxylic acid (5.3 mg, 47 μmol) and HATU (18 mg, 47 μmol), followed by DIPEA (25 μL, 141 μmol). The mixture was stirred for 30 minutes, then concentrated under reduced pressure to yield crude Compound 1, which was used in the next step without purification.

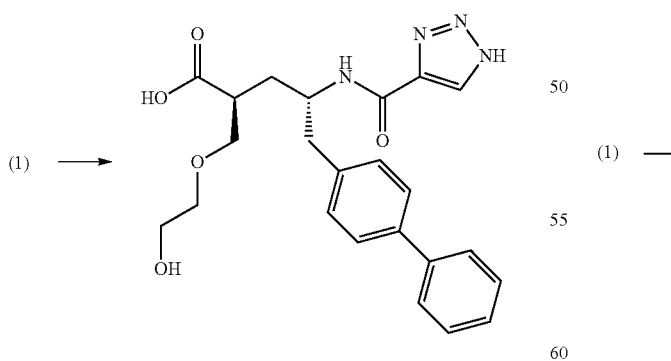

(1) →

To Compound 1 (22 mg, 47 μmol) was added THF (0.5 mL) and 1N NaOH (188 μL, 188 μmol) was added and stirred for 2 hours at room temperature. AcOH was added and the solution was purified by preparative HPLC to yield the title compound (3.8 mg; purity 98%) as a TFA salt. MS m/z [M+H]$^+$ calc'd for $C_{23}H_{26}N_4O_5$, 439.19; found 439.2.

Example 12

(2S,4S)-5-Biphenyl-4-yl-2-(3-hydroxypropoxymethyl)-4-[(1H-[1,2,3]triazole-4-carbonyl)amino]pentanoic Acid

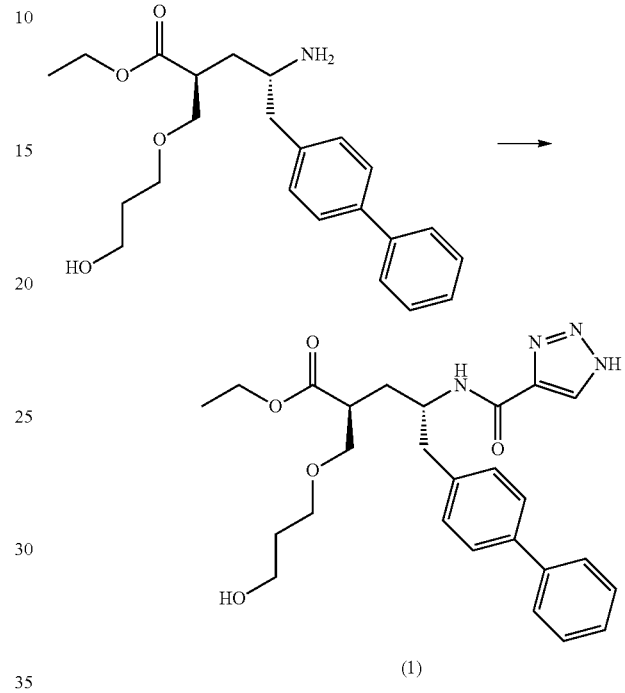

(1)

To a stirred solution of (2S,4S)-4-amino-5-biphenyl-4-yl-2-(3-hydroxypropoxymethyl)pentanoic acid ethyl ester (18 mg, 47 μmol) in DMF (0.3 mL), was added 1H-1,2,3-triazole-4-carboxylic acid (5.3 mg, 47 μmol) and HATU (18 mg, 47 μmol), followed by DIPEA (25 μL, 141 μmol). The mixture was stirred for 30 minutes, then concentrated under reduced pressure to yield crude Compound 1, which was used in the next step without purification.

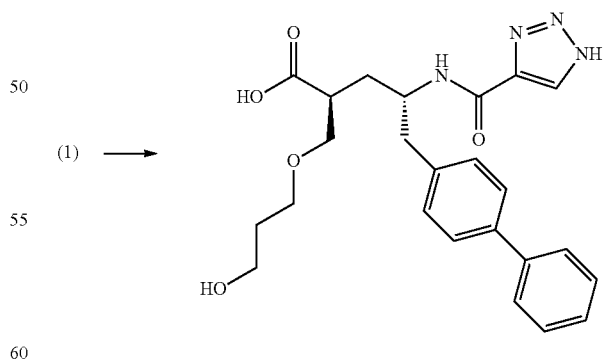

(1) →

To Compound 1 (23 mg, 47 μmol) was added THF (0.5 mL) and 1N NaOH (188 μL, 188 μmol) was added and stirred for 2 hours at room temperature. AcOH was added and the solution was purified by preparative HPLC to yield the title compound (1.3 mg; purity 100%) as a TFA salt. MS m/z [M+H]$^+$ calc'd for $C_{24}H_{28}N_4O_5$, 453.21; found 453.2.

Example 13

(2R,4R)-2-Amino-5-(5'-chloro-2'-fluorobiphenyl-4-yl)-4-[(1H-[1,2,3]triazole-4-carbonyl)amino]pentanoic Acid

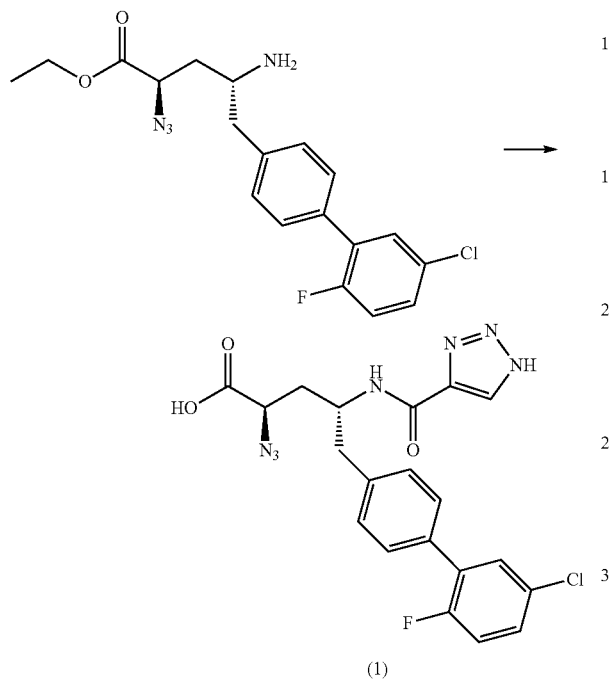

1H-1,2,3-triazole-4-carboxylic acid (15.9 mg, 141 μmol) and HATU (53.5 mg, 141 μmol) were dissolved in DMF (2 mL) and stirred for 15 minutes at room temperature. (2R,4R)-4-Amino-2-azido-5-(5'-chloro-2'-fluorobiphenyl-4-yl)pentanoic acid ethyl ester (50 mg, 128 μmol) and DIPEA (67 μL, 384 μmol) were added, and the mixture was stirred at room temperature for 15 minutes then concentrated in vacuo and the residue was dissolved in EtOH (2 mL). An aqueous solution of 1N NaOH (1.3 mL, 1.3 mmol) was added, and the mixture was stirred at room temperature for 30 minutes then concentrated in vacuo and the residue was purified by reverse phase chromatography to yield Compound 1 (45 mg).

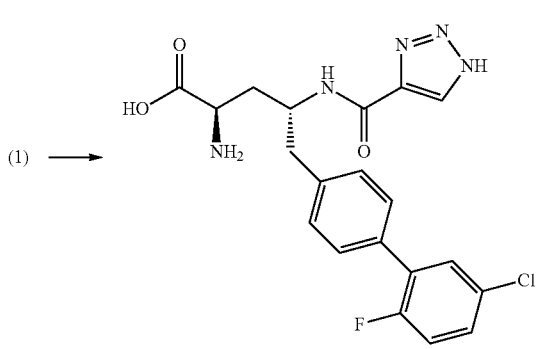 [SMILES: N[C@H](C[C@@H](Cc1ccc(-c2cc(Cl)ccc2F)cc1)NC(=O)c1c[nH]nn1)C(=O)O]

Compound 1 (45 mg, 98 μmol) and palladium hydroxide (2.1 mg, 15 μmol) were stirred at room temperature in dry MeOH (2 mL) and AcOH (2 mL). The reaction flask was placed under hydrogen and stirred at room temperature for 30 minutes. The hydrogen was removed in vacuo and the flask was purged with nitrogen. The mixture was filtered and the solution was concentrated in vacuo. The residue was purified by reverse phase chromatography in the absence of TFA to yield the title compound (27 mg; purity 96%). MS m/z $[M+H]^+$ calc'd for $C_{20}H_{19}ClFN_5O_3$, 432.12; found 432.2.

Example 14a (2R,4R)-2-Amino-5-(5'-chloro-2'-fluorobiphenyl-4-yl)-4-[(3H-[1,2,3]triazole-4-carbonyl)amino]pentanoic Acid Ethyl Ester

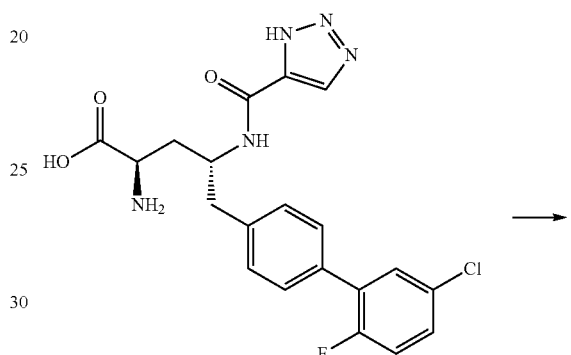

(2R,4R)-2-Amino-5-(5'-chloro-2'-fluorobiphenyl-4-yl)-4-[(3H-[1,2,3]triazole-4-carbonyl)amino]pentanoic acid (17 mg, 39 μmol) was dissolved in EtOH (5 mL). A solution of 4N HCl in dioxane (148 μL, 0.6 mmol) was added. The resulting mixture was stirred at room temperature for 2 days, at which time LCMS indicated the mass of the desired compound. The mixture was concentrated in vacuo and the residue was purified by reverse phase chromatography to yield the title compound (10 mg; purity 99%) as a white powder TFA salt. MS m/z $[M+H]^+$ calc'd for $C_{22}H_{23}ClFN_5O_3$, 460.15; found 460.

Example 14b (2R,4R)-2-Amino-5-(5'-chloro-2'-fluorobiphenyl-4-yl)-4-[(3H-[1,2,3]triazole-4-carbonyl)amino]pentanoic Acid Hexyl Ester

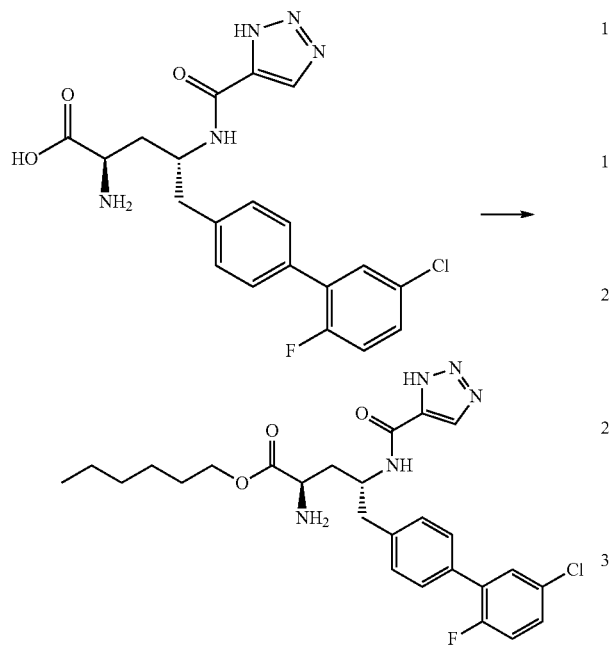

(2R,4R)-2-Amino-5-(5'-chloro-2'-fluorobiphenyl-4-yl)-4-[(3H-[1,2,3]triazole-4-carbonyl)amino]pentanoic acid (10 mg, 23 μmol) was dissolved in 1-hexanol (500 mL; 237 mg, 2.3 mol). A solution of 4N HCl in dioxane (174 μL, 0.7 mmol) was added. The resulting mixture was stirred overnight at 50° C. then concentrated in vacuo and the residue was purified by reverse phase chromatography to yield the title compound (4.1 mg; purity 95%) as a TFA salt. MS m/z [M+H]+ calc'd for $C_{26}H_{31}ClFN_5O_3$, 516.21; found 516.

Example 15

(2R,4R)-2-Amino-5-(5'-chloro-2'-fluorobiphenyl-4-yl)-4-[(4-isopropyloxazole-2-carbonyl)amino]pentanoic Acid

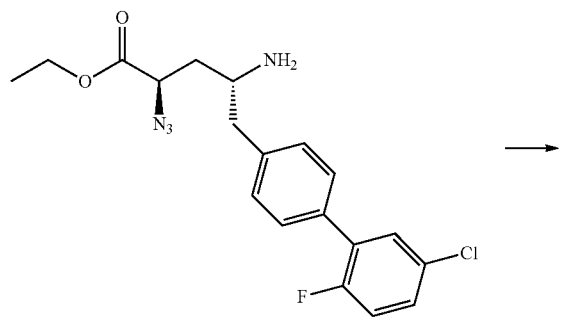

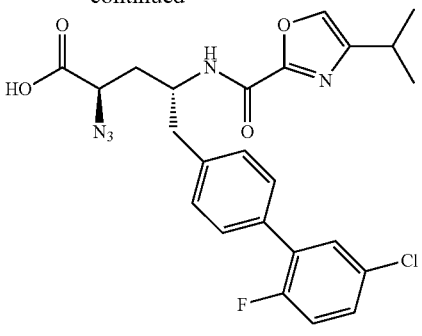

4-Isopropyloxazole-2-carboxylic acid (21.8 mg, 141 μmol) and HATU (53.5 mg, 141 μmol) were dissolved in DMF (3.5 mL) and stirred for 15 minutes at room temperature. (2R,4R)-4-Amino-2-azido-5-(5'-chloro-2'-fluorobiphenyl-4-yl)pentanoic acid ethyl ester (50 mg, 128 μmol) and DIPEA (67 μL, 384 μmol) were added, and the mixture was stirred at room temperature for 15 minutes, at which time LCMS indicated the mass of the desired compound. The mixture was concentrated in vacuo and the residue was dissolved in EtOH (3 mL). An aqueous solution of 1N NaOH (1.3 mL, 1.3 mmol) was added, and the mixture was stirred at room temperature for 1 hour, at which time LCMS indicated the mass of the desired compound. The mixture was concentrated in vacuo. An aqueous solution of 1N HCl was added, and the crude residue was extracted with EtOAc. The organic layers were combined, dried over MgSO4, filtered and evaporated to yield Compound 1, which was used in the next step without purification.

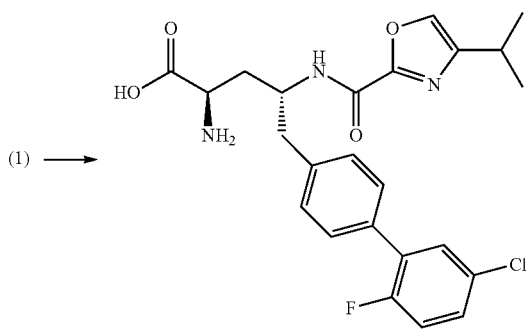 [SMILES: CC(C)c1coc(C(=O)N[C@H](Cc2ccc(-c3cc(Cl)ccc3F)cc2)C[C@@H](N)C(=O)O)n1]

Compound 1 (65 mg, 130 μmol) and palladium (10 wt % on carbon, wet, 50 g, 65 μmol) were mixed in dry EtOAc (3 mL) and AcOH (3 mL). The reaction flask was placed under hydrogen and stirred at room temperature for 3 hours. The hydrogen was removed in vacuo and the flask was purged with nitrogen. The mixture was filtered and the solution was concentrated in vacuo. The residue was purified by preparative HPLC to yield the title compound (15 mg; purity 100%) as a TFA salt. MS m/z [M+H]+ calc'd for $C_{24}H_{25}ClFN_3O_4$, 474.15, found 474.2.

Example 16

Following the procedures described herein, and substituting the appropriate starting materials and reagents, these compounds were prepared, either as the parent compound or as a TFA salt:

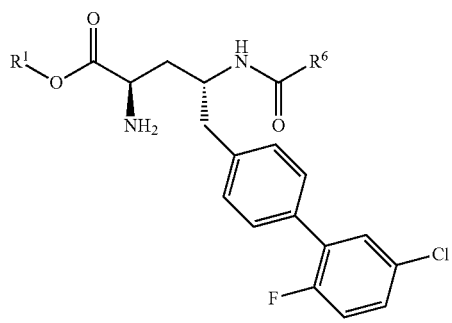
| Ex. | R¹ | R⁶ | Formula | MS m/z: [M + H]⁺ calcd | found |
|---|---|---|---|---|---|
| 1 | H | 5-ethyl-isoxazol-3-yl (t-Bu-substituted) | $C_{23}H_{23}ClFN_3O_4$ | 460.14 | 460.2 |
| 2 | H | 5-propyl-isoxazol-3-yl | $C_{24}H_{25}ClFN_3O_4$ | 474.15 | 474.2 |
| 3 | H | 5-methyl-oxazol-2-yl | $C_{22}H_{21}ClFN_3O_4$ | 446.12 | 446.2 |
| 4 | H | 2-cyclopropyl-oxazol-4-yl | $C_{24}H_{23}ClFN_3O_4$ | 472.14 | 472.2 |
| 5 | H | 2-ethoxy-oxazol-4-yl | $C_{23}H_{23}ClFN_3O_5$ | 476.13 | 476.2 |
| 6 | H | 2-propyl-oxazol-4-yl | $C_{24}H_{25}ClFN_3O_4$ | 474.15 | 474.2 |
| 7 | H | 5-chloro-pyridin-2-yl | $C_{23}H_{20}Cl_2FN_3O_3$ | 476.09 | 476.2 |
| 8 | H | isothiazol-5-yl | $C_{21}H_{19}ClFN_3O_3S$ | 448.08 | 448.2 |
| 9 | H | 3-acetyl-1H-pyrazol-5-yl | $C_{23}H_{22}ClFN_4O_4$ | 473.13 | 473.1 |

-continued

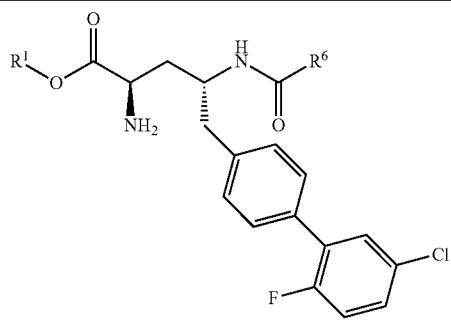

| Ex. | R¹ | R⁶ | Formula | MS m/z: [M + H]⁺ calcd | found |
|---|---|---|---|---|---|
| 10 | —CH₂CH₃ | (3-tert-butyl-1H-pyrazol-5-yl)carbonyl | $C_{25}H_{26}ClFN_4O_4$ | 501.16 | 501 |
| 11 | —CH₂CH₃ | (5-tert-butyl-3-hydroxyisoxazol-yl) | $C_{23}H_{23}ClFN_3O_5$ | 476.13 | 475 |
| 12 | —CH₂CH₃ | (5-tert-butyl-3-hydroxyisoxazol-yl) | $C_{23}H_{23}ClFN_3O_5$ | 476.13 | 475 |
| 13 | —CH—(CH₃)₂ | (5-tert-butyl-3-hydroxyisoxazol-yl) | $C_{24}H_{25}ClFN_3O_5$ | 490.15 | 490 |
| 14 | —(CH₂)₃—CH₃ | (5-tert-butyl-3-hydroxyisoxazol-yl) | $C_{25}H_{27}ClFN_3O_5$ | 504.16 | 504 |
| 15 | H | (3-tert-butyl-5-oxo-1,2,4-oxadiazol-yl) | $C_{20}H_{18}ClFN_4O_5$ | 449.10 | 449.2 |
| 16 | H | (3-tert-butyl-5-oxo-1,2,4-oxadiazol-yl) | $C_{20}H_{18}ClFN_4O_5$ | 449.10 | 449.1 |
| 17 | —CH₂CH₃ | (3-tert-butyl-5-oxo-1,2,4-oxadiazol-yl) | $C_{22}H_{22}ClFN_4O_5$ | 477.13 | 477 |
| 18 | H | (3-tert-butyl-N,N-dimethyl-1H-pyrazole-5-carboxamide) | $C_{24}H_{25}ClFN_5O_4$ | 502.16 | 502.2 |

-continued

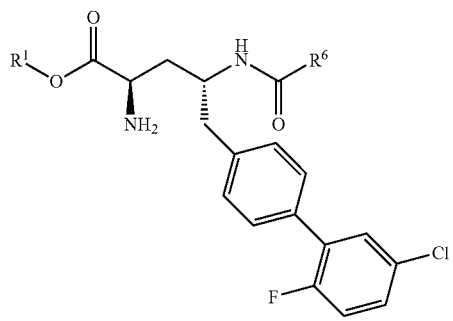

| | | | | MS m/z: [M + H]⁺ | |
|---|---|---|---|---|---|
| Ex. | R¹ | R⁶ | Formula | calcd | found |
| 19 | —CH₂CH₃ | [3-tert-butyl-1H-pyrazol-5-yl-C(O)N(CH₃)₂] | $C_{26}H_{29}ClFN_5O_4$ | 530.19 | 530.2 |
| 20 | H | [3-tert-butyl-4-fluoro-5-methyl-1H-pyrazole] | $C_{22}H_{21}ClF_2N_4O_3$ | 463.13 | 463.2 |
| 21 | H | [3-tert-butyl-1H-pyrazol-5-yl-C(O)NHCH₃] | $C_{23}H_{23}ClFN_5O_4$ | 488.14 | 488.2 |
| 22 | —CH₂CH₃ | [3-tert-butyl-1H-pyrazol-5-yl-C(O)NHCH₃] | $C_{25}H_{27}ClFN_5O_4$ | 516.17 | 516 |
| 23 | H | [3-tert-butyl-4-fluoro-5-(2-methylphenyl)-1H-pyrazole] | $C_{28}H_{25}ClFN_4O_3$ | 539.16 | 539.2 |
| 24 | H | [5-tert-butyl-3-(2-chlorophenyl)isoxazole] | $C_{27}H_{22}Cl_2FN_3O_4$ | 542.10 | 542.2 |
| 25 | H | [2-tert-butyl-6-chloro-[1,2,4]triazolo[1,5-a]pyridine] | $C_{24}H_{20}Cl_2FN_5O_3$ | 516.09 | 516.2 |

-continued

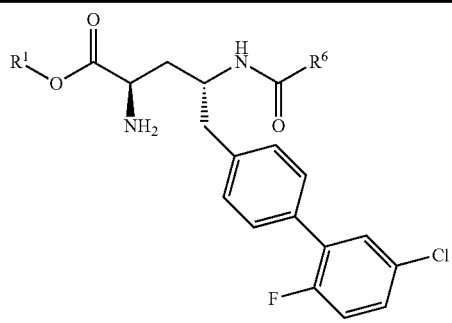

| Ex. | R¹ | R⁶ | Formula | MS m/z: [M + H]⁺ calcd | found |
|---|---|---|---|---|---|
| 26 | H | (2-tert-butyl-7-chloro-[1,2,4]triazolo[1,5-a]pyridine) | $C_{24}H_{20}Cl_2FN_5O_3$ | 516.09 | 516.2 |
| 27 | H | (5-tert-butyl-3-hydroxyisoxazole) | $C_{21}H_{19}ClFN_3O_5$ | 448.10 | 448.0 |
| 28 | H | (5-tert-butyl-3-hydroxyisoxazole) | $C_{21}H_{19}ClFN_3O_5$ | 448.10 | 448.0 |
| 29 | H | (2-tert-butylpyrimidine) | $C_{22}H_{20}ClFN_4O_3$ | 443.12 | 443.0 |
| 30 | —CH₂CH₃ | (2-tert-butylpyrimidine) | $C_{24}H_{24}ClFN_4O_3$ | 471.15 | 471.1 |
| 31 | H | (4-tert-butyl-oxazol-2(3H)-one) | $C_{21}H_{19}ClFN_3O_5$ | 448.10 | 448.0 |
| 32 | —CH₂CH₃ | (4-tert-butyl-oxazol-2(3H)-one) | $C_{23}H_{23}ClFN_3O_5$ | 476.13 | 476.1 |
| 33 | H | (5-tert-butyl-3-(pyrazin-2-yl)-1H-pyrazole) | $C_{25}H_{22}ClFN_6O_3$ | 509.14 | 509.1 |
| 34 | —CH₂CH₃ | (5-tert-butyl-3-(pyrazin-2-yl)-1H-pyrazole) | $C_{27}H_{26}ClFN_6O_3$ | 537.17 | 537.1 |

-continued

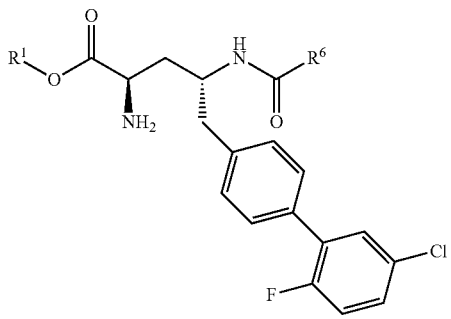

| Ex. | R¹ | R⁶ | Formula | MS m/z: [M + H]⁺ calcd | found |
|---|---|---|---|---|---|
| 35 | H | (3-tert-butyl-2-phenyl-5-oxo-2,5-dihydro-1H-1,2,4-triazol-yl) | $C_{26}H_{23}ClFN_5O_4$ | 524.14 | 524.1 |
| 36 | —CH₂CH₃ | (3-tert-butyl-2-phenyl-5-oxo-2,5-dihydro-1H-1,2,4-triazol-yl) | $C_{28}H_{27}ClFN_5O_4$ | 552.17 | 552.1 |

1. (2R,4R)-2-Amino-5-(5'-chloro-2'-fluorobiphenyl-4-yl)-4-[(3-ethylisoxazole-5-carbonyl)-amino]pentanoic acid
2. (2R,4R)-2-Amino-5-(5'-chloro-2'-fluorobiphenyl-4-yl)-4-[(5-propylisoxazole-3-carbonyl)-amino]pentanoic acid
3. (2R,4R)-2-Amino-5-(5'-chloro-2'-fluorobiphenyl-4-yl)-4-[(5-methyloxazole-2-carbonyl)-amino]pentanoic acid
4. (2R,4R)-2-Amino-5-(5'-chloro-2'-fluorobiphenyl-4-yl)-4-[(2-cyclopropyloxazole-4-carbonyl)amino]pentanoic acid
5. (2R,4R)-2-Amino-5-(5'-chloro-2'-fluorobiphenyl-4-yl)-4-[(2-ethoxyoxazole-4-carbonyl)-amino]pentanoic acid
6. (2R,4R)-2-Amino-5-(5'-chloro-2'-fluorobiphenyl-4-yl)-4-[(2-propyloxazole-4-carbonyl)-amino]pentanoic acid
7. (2R,4R)-2-Amino-5-(5'-chloro-2'-fluorobiphenyl-4-yl)-4-[(5-chloropyridine-2-carbonyl)-amino]pentanoic acid
8. (2R,4R)-2-Amino-5-(5'-chloro-2'-fluorobiphenyl-4-yl)-4-[(isothiazole-5-carbonyl)amino]-pentanoic acid
9. (2R,4R)-4-[(5-Acetyl-2H-pyrazole-3-carbonyl)amino]-2-amino-5-(5'-chloro-2'-fluoro-biphenyl-4-yl)pentanoic acid
10. (2R,4R)-4-[(5-Acetyl-2H-pyrazole-3-carbonyl)amino]-2-amino-5-(5'-chloro-2'-fluoro-biphenyl-4-yl)pentanoic acid ethyl ester
11. (2R,4R)-2-Amino-5-(5'-chloro-2'-fluorobiphenyl-4-yl)-4-[(3-hydroxyisoxazole-5-carbonyl)amino]pentanoic acid ethyl ester
12. (2S,4R)-2-Amino-5-(5'-chloro-2'-fluorobiphenyl-4-yl)-4-[(3-hydroxyisoxazole-5-carbonyl)amino]pentanoic acid ethyl ester
13. (2R,4R)-2-Amino-5-(5'-chloro-2'-fluorobiphenyl-4-yl)-4-[(3-hydroxyisoxazole-5-carbonyl)amino]pentanoic acid isopropyl ester
14. (2R,4R)-2-Amino-5-(5'-chloro-2'-fluorobiphenyl-4-yl)-4-[(3-hydroxyisoxazole-5-carbonyl)amino]pentanoic acid butyl ester
15. (2S,4R)-2-Amino-5-(5'-chloro-2'-fluorobiphenyl-4-yl)-4-[(5-oxo-4,5-dihydro-[1,2,4]oxadiazole-3-carbonyl)amino]pentanoic acid
16. (2R,4R)-2-Amino-5-(5'-chloro-2'-fluorobiphenyl-4-yl)-4-[(5-oxo-4,5-dihydro-[1,2,4]oxadiazole-3-carbonyl)amino]pentanoic acid
17. (2R,4R)-2-Amino-5-(5'-chloro-2'-fluorobiphenyl-4-yl)-4-[(5-oxo-4,5-dihydro-[1,2,4]oxadiazole-3-carbonyl)amino]pentanoic acid ethyl ester
18. (2R,4R)-2-Amino-5-(5'-chloro-2'-fluorobiphenyl-4-yl)-4-[(5-dimethylcarbamoyl-2H-pyrazole-3-carbonyl)amino]pentanoic acid
19. (2R,4R)-2-Amino-5-(5'-chloro-2'-fluorobiphenyl-4-yl)-4-[(5-dimethylcarbamoyl-2H-pyrazole-3-carbonyl)amino]pentanoic acid ethyl ester
20. (2R,4R)-2-Amino-5-(5'-chloro-2'-fluorobiphenyl-4-yl)-4-[(4-fluoro-5-methyl-2H-pyrazole-3-carbonyl)amino]pentanoic acid
21. (2R,4R)-2-Amino-5-(5'-chloro-2'-fluorobiphenyl-4-yl)-4-[(5-methylcarbamoyl-2H-pyrazole-3-carbonyl)amino]pentanoic acid
22. (2R,4R)-2-Amino-5-(5'-chloro-2'-fluorobiphenyl-4-yl)-4-[(5-methylcarbamoyl-2H-pyrazole-3-carbonyl)amino]pentanoic acid ethyl ester
23. (2R,4R)-2-Amino-5-(5'-chloro-2'-fluorobiphenyl-4-yl)-4-[(4-fluoro-5-o-tolyl-2H-pyrazole-3-carbonyl)amino]pentanoic acid
24. (2R,4R)-2-Amino-5-(5'-chloro-2'-fluorobiphenyl-4-yl)-4-{[3-(2-chlorophenyl)-isoxazole-5-carbonyl]amino}pentanoic acid
25. (2R,4R)-2-Amino-5-(5'-chloro-2'-fluorobiphenyl-4-yl)-4-[(7-chloro-[1,2,4]triazolo[1,5-a]pyridine-2-carbonyl)amino]pentanoic acid 26. (2S,4R)-2-Amino-5-(5'-chloro-2'-fluorobiphenyl-4-yl)-4-[(7-chloro-[1,2,4]triazolo[1,5-a]pyridine-2-carbonyl)amino]pentanoic acid 27. (2S,4R)-2-Amino-5-(5'-chloro-2'-fluorobiphenyl-4-yl)-4-[(3-hydroxyisoxazole-5-carbonyl)amino]pentanoic acid 28. (2R,4R)-2-Amino-5-(5'-chloro-2'-fluorobiphenyl-4-yl)-4-[(3-hydroxyisoxazole-5-carbonyl)amino]pentanoic acid 29. (2R,4R)-2-Amino-5-(5'-chloro-2'-fluorobiphenyl-4-yl)-4-[(pyrimidine-2-carbonyl)-amino]pentanoic acid 30. (2R,4R)-2-Amino-5-(5'-chloro-2'-fluorobiphenyl-4-yl)-4-[(pyrimidine-2-carbonyl)-amino]pentanoic acid ethyl ester 31. (2R,4R)-2-Amino-5-(5'-chloro-2'-fluorobiphenyl-4-yl)-4-[(2-oxo-2,3-dihydro-oxazole-4-carbonyl)amino]pentanoic acid 32. (2R,4R)-2-Amino-5-(5'-chloro-2'-fluorobiphenyl-4-yl)-4-[(2-oxo-2,3-dihydro-oxazole-4-carbonyl)amino]pentanoic acid ethyl ester 33. (2R,4R)-2-Amino-5-(5'-chloro-2'-fluorobiphenyl-4-yl)-4-[(5-pyrazin-2-yl-2H-pyrazole-3-carbonyl)amino]pentanoic acid 34. (2R,4R)-2-Amino-5-(5'-chloro-2'-fluorobiphenyl-4-yl)-4-[(5-pyrazin-2-yl-2H-pyrazole-3-carbonyl)amino]pentanoic acid ethyl ester 35. (2R,4R)-2-Amino-5-(5'-chloro-2'-fluorobiphenyl-4-yl)-4-[(5-oxo-1-phenyl-4,5-dihydro-1H-[1,2,4]triazole-3-carbonyl)amino]pentanoic acid 36. (2R,4R)-2-Amino-5-(5'-chloro-2'-fluorobiphenyl-4-yl)-4-[(5-oxo-1-phenyl-4,5-dihydro-1H-[1,2,4]triazole-3-carbonyl)amino]pentanoic acid ethyl ester Example 17

(2R,4R)-2-Amino-5-(3,5'-dichloro-2'-fluorobiphenyl-4-yl)-4-[(4-isopropyloxazole-2-carbonyl)amino]pentanoic Acid

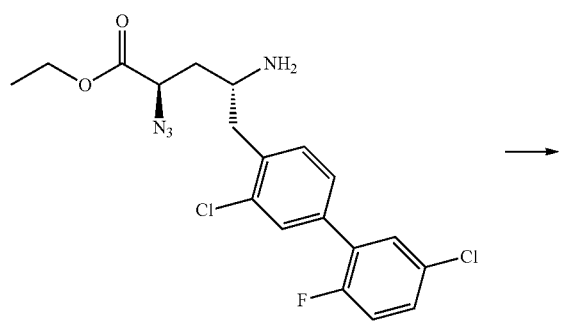

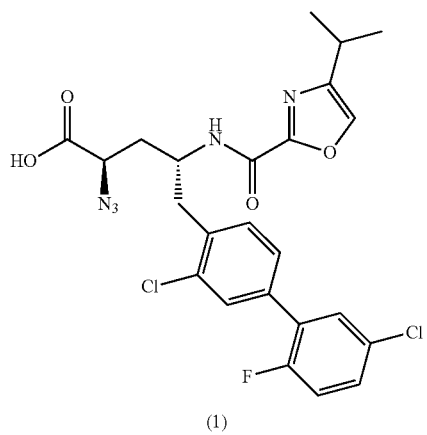

4-Isopropyloxazole-2-carboxylic acid (10.4 mg, 67 μmol) and HATU (25.6 mg, 67 lmo') were dissolved in DMF (2 mL) and stirred for 15 minutes at room temperature. (2R,4R)-4-Amino-2-azido-5-(3,5'-dichloro-2'-fluorobiphenyl-4-yl)pentanoic acid ethyl ester (26 mg, 61 μmol) and DIPEA (32 μL, 183 μmol) were added, and the mixture was stirred at room temperature for 15 minutes, at which time LCMS indicated the mass of the desired compound. The mixture was concentrated in vacuo and the residue was dissolved in EtOH (2 mL). An aqueous solution of 1N NaOH (611 μL, 611 μmol) was added, and the mixture was stirred at room temperature for 30 minutes, at which time LCMS indicated the mass of the desired compound. The mixture was concentrated in vacuo and the residue was diluted in an aqueous solution of 1N HCl and extracted twice with EtOAc. The organic layers were combined, dried over MgSO$_4$, filtered and evaporated, to yield crude Compound 1, which was directly in the next step.

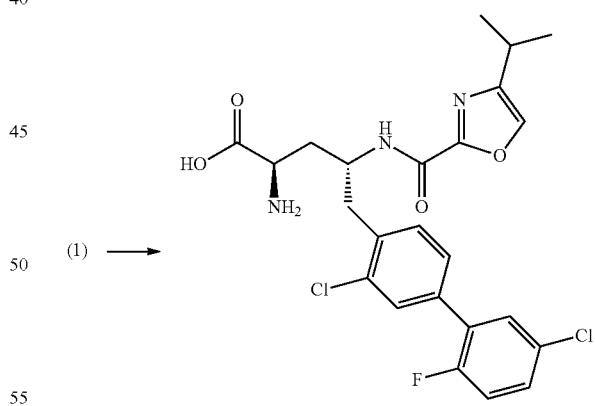

Compound 1 (30 mg, 56 μmol) and palladium (10 wt % on carbon, wet 50 g; 5 mg, 5.6 μmol) were stirred at room temperature in dry EtOAc (2 mL) and AcOH (2 mL). The reaction flask was placed under hydrogen and stirred at room temperature for 30 minutes. The hydrogen was removed in vacuo and the flask was purged with nitrogen. The mixture was filtered and the solution was concentrated in vacuo. The residue was purified by preparative HPLC to yield the title compound (1.4 mg; purity 80%) as a TFA salt. MS m/z [M+H]$^+$ calc'd for $C_{24}H_{24}Cl_2FN_3O_4$, 508.11; found 509.0.

Example 18

Following the procedures described herein, and substituting the appropriate starting materials and reagents, these compounds were prepared as a TFA salt:

| Ex. | R⁶ | Formula | MS m/z: [M + H]⁺ calcd | found |
|---|---|---|---|---|
| 1 | 4-isopropyloxazol-2-yl | $C_{24}H_{24}Cl_2FN_3O_4$ | 508.11 | 508.2 |
| 2 | 2-propyloxazol-4-yl | $C_{24}H_{24}Cl_2FN_3O_4$ | 508.11 | 508.2 |
| 3 | 5-methyloxazol-2-yl | $C_{22}H_{20}Cl_2FN_3O_4$ | 480.08 | 480.0 |
| 4 | 5-methyloxazol-2-yl | $C_{22}H_{20}Cl_2FN_3O_4$ | 480.08 | 480.0 |
| 5 | 3-ethylisoxazol-5-yl | $C_{23}H_{22}Cl_2FN_3O_4$ | 494.10 | 494.2 |
| 6 | 3-ethylisoxazol-5-yl | $C_{23}H_{22}Cl_2FN_3O_4$ | 494.10 | 494.2 |
| 7 | 5-methoxymethylisoxazol-3-yl | $C_{23}H_{22}Cl_2FN_3O_5$ | 510.09 | 510.2 |
| 8 | 5-methoxymethylisoxazol-3-yl | $C_{23}H_{22}Cl_2FN_3O_5$ | 510.09 | 510.2 |
| 9 | 5-cyclopropylisoxazol-3-yl | $C_{24}H_{22}Cl_2FN_3O_4$ | 506.10 | 506.2 |
| 10 | 5-cyclopropylisoxazol-3-yl | $C_{24}H_{22}Cl_2FN_3O_4$ | 506.10 | 506.2 |
| 11 | 5-methoxyoxazol-2-yl | $C_{22}H_{20}Cl_2FN_3O_5$ | 496.08 | 496.0 |
| 12 | 5-methoxyoxazol-2-yl | $C_{22}H_{20}Cl_2FN_3O_5$ | 496.08 | 496.0 |

1. (2S,4R)-2-Amino-5-(3,5'-dichloro-2'-fluorobiphenyl-4-yl)-4-[(4-isopropyloxazole-2-carbonyl)amino]pentanoic acid
2. (2R,4R)-2-Amino-5-(3,5'-dichloro-2'-fluorobiphenyl-4-yl)-4-[(2-propyloxazole-4-carbonyl)amino]pentanoic acid
3. (2R,4R)-2-Amino-5-(3,5'-dichloro-2'-fluorobiphenyl-4-yl)-4-[(5-methyloxazole-2-carbonyl)amino]pentanoic acid
4. (2S,4R)-2-Amino-5-(3,5'-dichloro-2'-fluorobiphenyl-4-yl)-4-[(5-methyloxazole-2-carbonyl)amino]pentanoic acid
5. (2R,4R)-2-Amino-5-(3,5'-dichloro-2'-fluorobiphenyl-4-yl)-4-[(3-ethylisoxazole-5-carbonyl)amino]pentanoic acid
6. (2S,4R)-2-Amino-5-(3,5'-dichloro-2'-fluorobiphenyl-4-yl)-4-[(3-ethylisoxazole-5-carbonyl)amino]pentanoic acid
7. (2R,4R)-2-Amino-5-(3,5'-dichloro-2'-fluorobiphenyl-4-yl)-4-[(5-methoxymethylisoxazole-3-carbonyl)amino]pentanoic acid
8. (2S,4R)-2-Amino-5-(3,5'-dichloro-2'-fluorobiphenyl-4-yl)-4-[(5-methoxymethylisoxazole-3-carbonyl)amino]pentanoic acid
9. (2R,4R)-2-Amino-4-[(5-cyclopropyl-isoxazole-3-carbonyl)-amino]-5-(3,5'-dichloro-2'-fluorobiphenyl-4-yl)pentanoic acid 10. (2S,4R)-2-Amino-4-[(5-cyclopropyl-isoxazole-3-carbonyl)-amino]-5-(3,5'-dichloro-2'-fluorobiphenyl-4-yl)pentanoic acid
11. (2R,4R)-2-Amino-5-(3,5'-dichloro-2'-fluoro-biphenyl-4-yl)-4-[(5-methoxyoxazole-2-carbonyl)amino]pentanoic acid
12. (2S,4R)-2-Amino-5-(3,5'-dichloro-2'-fluoro-biphenyl-4-yl)-4-[(5-methoxyoxazole-2-carbonyl)amino]pentanoic acid Example 19

(2S,4S)-2-Aminomethyl-5-(5'-chloro-2'-fluorobiphenyl-4-yl)-4-[(1H-[1,2,3]triazole-4-carbonyl)amino]pentanoic Acid Ethyl Ester

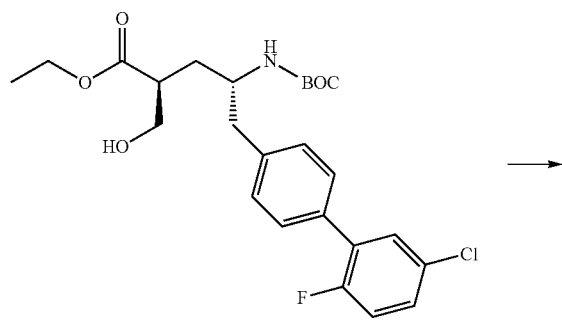

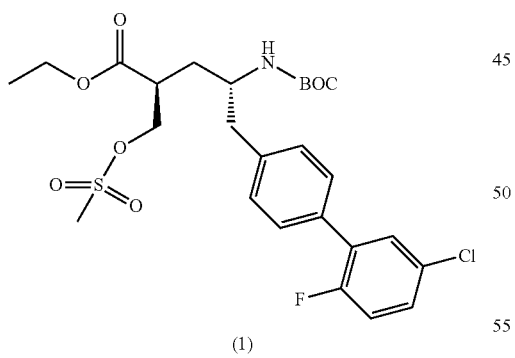

(1)

To a stirred solution of (2S,4S)-4-t-butoxycarbonylamino-5-(5'-chloro-2'-fluorobiphenyl-4-yl)-2-hydroxymethylpentanoic acid ethyl ester (525 mg, 1.1 mmol) in DCM (2 mL), was added methanesulfonyl chloride (102 µL, 1.3 mmol), followed by the slow addition of Et₃N (305 µL, 2.2 mmol). The mixture was stirred at room temperature for 30 minutes and was then purified by normal phase chromatography (0-100% EtOAc/hexanes) to yield Compound 1 (405 mg).

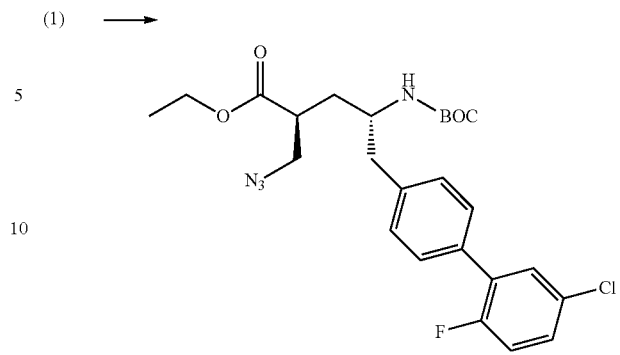

(2)

Compound 1 (325 mg, 582 µmol) was dissolved in DMF (2 mL) and combined with sodium azide (41.6 mg, 641 µmol), and the resulting mixture was stirred at room temperature for 3 hours. The reaction was quenched with water and extracted with EtOAc. The organic layer was washed (3×) with water, dried over Na₂SO₄, then concentrated under reduced pressure, and the residue purified by normal phase column chromatography (0-100% EtOAc/hexanes) to yield Compound 2 (290 mg).

(2) →

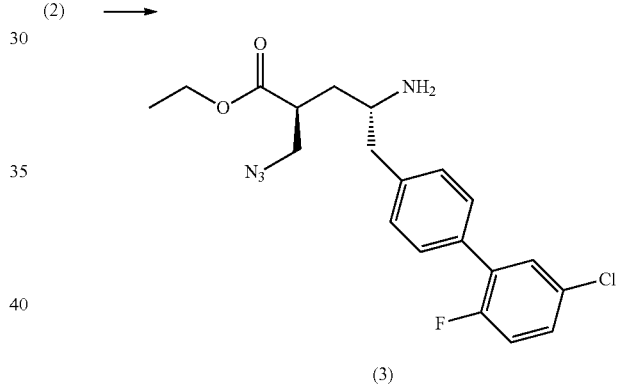

(3)

Compound 2 (290 mg, 574 µmol) was dissolved in MeCN (3 mL) and 4N HCl in dioxane (1 mL), and the mixture was stirred at room temperature for 10 minutes. The mixture was concentrated under reduced pressure to yield crude Compound 3 as an HCl salt.

(3) →

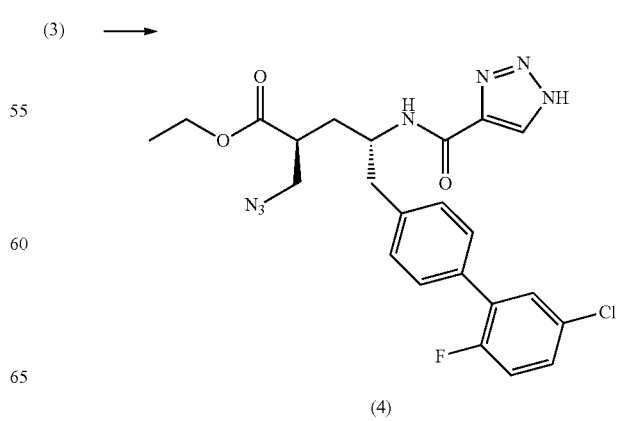

(4)

1H-1,2,3-triazole-5-carboxylic acid (55.9 mg, 494 μmol) was combined with HATU (188 mg, 494 μmol) in DMF (0.5 mL) and stirred for 10 minutes; DIPEA (1.5 eq.) was added and the mixture was stirred for 1 minute. Compound 3 (200 mg, 494 μmol) was dissolved in DMF (1 mL) and DIPEA (259 μL, 1.5 mmol) was added, followed by addition of the activated acid solution. The mixture was stirred for 30 minutes and the solvent was evaporated. The mixture was purified by normal phase chromatography (0-100% EtOAc/hexanes) to yield Compound 4 (100 mg).

(4) →

Compound 4 (100 mg, 0.2 mmol) was combined with PdOH$_2$/C (21.3 mg, 40 μmol) and EtOAc (1 mL) with 12N HCl (50 μL). Oxygen was removed in vacuo and the flask placed under hydrogen (1 atm), then stirred at room temperature for 6 hours. The hydrogen was removed in vacuo and the flask was purged with nitrogen. The reaction was quenched with AcOH and purified by reverse phase chromatography to yield the title compound (50 mg) as a TFA salt. MS m/z [M+H]$^+$ calc'd for C$_{23}$H$_{25}$ClFN$_5$O$_3$, 474.16; found 474.

Example 20

(2S,4S)-2-Aminomethyl-5-(5'-chloro-2'-fluorobiphenyl-4-yl)-4-[(1H-[1,2,3]triazole-4-carbonyl)amino]pentanoic Acid

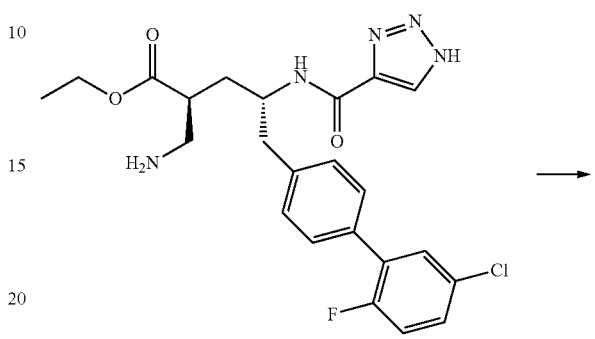

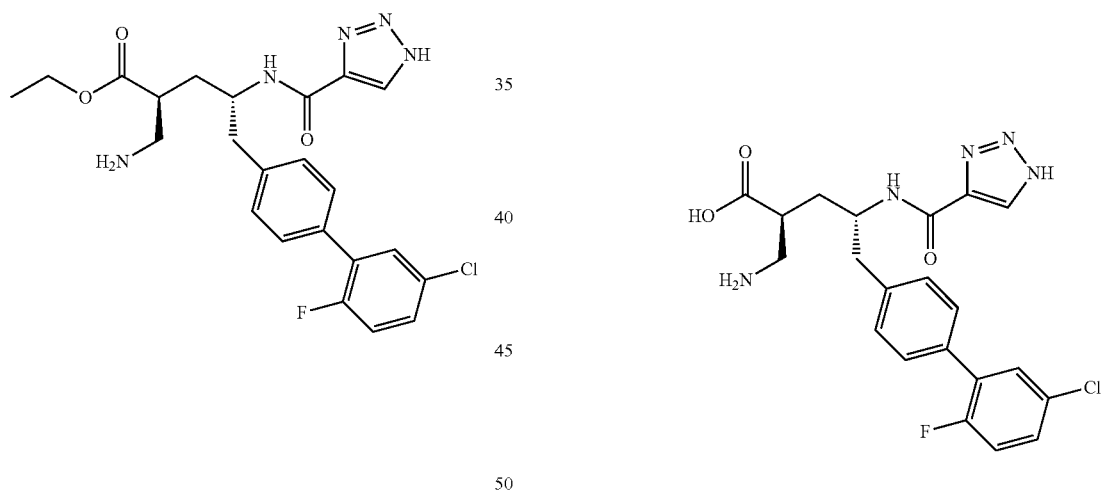

(2S,4S)-2-Aminomethyl-5-(5'-chloro-2'-fluorobiphenyl-4-yl)-4-[(1H-[1,2,3]triazole-4-carbonyl)amino]pentanoic acid ethyl ester (40 mg, 84 μmol) was dissolved in THF (1 mL), 1N LiOH (253 μL, 253 μmol) and 3 drops of MeOH and stirred at room temperature. The reaction was determined to be complete after 30 minutes and AcOH was added. The crude residue was purified (reverse phase chromatography) to yield the title compound (20 mg; purity 98%) as a TFA salt. MS m/z [M+H]$^+$ calc'd for C$_{21}$H$_{21}$ClFN$_5$O$_3$, 446.13; found 446.

Example 21

Following the procedures described herein, and substituting the appropriate starting materials and reagents, these compounds were prepared as TFA salts:

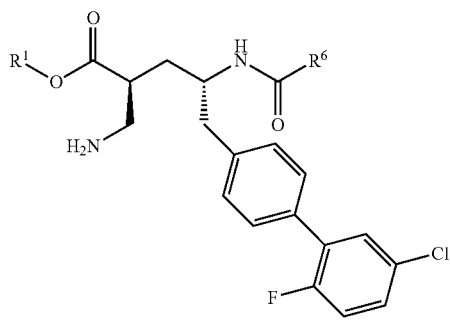
|  |  |  | MS m/z: [M + H]+ | |
|---|---|---|---|---|
| Ex. | R¹ | R⁶ | Formula | calcd | found |
| 1 | H | 5-ethyl-isoxazol-3-yl | $C_{24}H_{25}ClFN_3O_4$ | 474.15 | 473 |
| 2 | H | 2-cyclopropyl-oxazol-4-yl | $C_{25}H_{25}ClFN_3O_4$ | 486.15 | 485 |
| 3 | H | 5-methyl-oxazol-2-yl | $C_{23}H_{23}ClFN_3O_4$ | 460.14 | 459 |
| 4 | H | 2-ethoxy-oxazol-4-yl | $C_{24}H_{25}ClFN_3O_5$ | 490.15 | 489 |
| 5 | H | 2-methyl-oxazol-4-yl | $C_{23}H_{23}ClFN_3O_4$ | 460.14 | 459 |
| 6 | H | 3-methyl-isothiazol-5-yl | $C_{23}H_{23}ClFN_3O_3S$ | 476.11 | 475 |
| 7 | H | isothiazol-4-yl | $C_{22}H_{21}ClFN_3O_3S$ | 462.10 | 462 |
| 8 | —CH(CH₃)₂ | 1H-1,2,3-triazol-4-yl | $C_{24}H_{27}ClFN_5O_3$ | 488.18 | 489 |

-continued

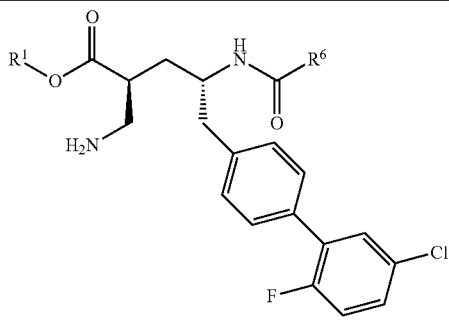

| Ex. | R¹ | R⁶ | Formula | MS m/z: [M + H]⁺ calcd | found |
|---|---|---|---|---|---|
| 9 | —(CH₂)₃—CH₃ | (N=N, NH triazole with t-Bu) | $C_{25}H_{29}ClFN_5O_3$ | 502.19 | 503 |
| 10 | —(CH₂)₅—CH₃ | (N=N, NH triazole with t-Bu) | $C_{27}H_{33}ClFN_5O_3$ | 530.23 | 531 |

1. (2S,4S)-2-Aminomethyl-5-(5'-chloro-2'-fluorobiphenyl-4-yl)-4-[(3-ethylisoxazole-5-carbonyl)amino]pentanoic acid
2. (2S,4S)-2-Aminomethyl-5-(5'-chloro-2'-fluorobiphenyl-4-yl)-4-[(2-cyclopropyl-oxazole-4-carbonyl)amino]pentanoic acid
3. (2S,4S)-2-Aminomethyl-5-(5'-chloro-2'-fluorobiphenyl-4-yl)-4-[(5-methyl-oxazole-2-carbonyl)amino]pentanoic acid
4. (2S,4S)-2-Aminomethyl-5-(5'-chloro-2'-fluorobiphenyl-4-yl)-4-[(2-ethoxy-oxazole-4-carbonyl)amino]pentanoic acid
5. (2S,4S)-2-Aminomethyl-5-(5'-chloro-2'-fluorobiphenyl-4-yl)-4-[(2-methyloxazole-4-carbonyl)amino]pentanoic acid
6. (2S,4S)-2-Aminomethyl-5-(5'-chloro-2'-fluorobiphenyl-4-yl)-4-[(3-methylisothiazole-5-carbonyl)amino]pentanoic acid
7. (2S,4S)-2-Aminomethyl-5-(5'-chloro-2'-fluorobiphenyl-4-yl)-4-[(isothiazole-4-carbonyl)amino]pentanoic acid
8. (2S,4S)-2-Aminomethyl-5-(5'-chloro-2'-fluorobiphenyl-4-yl)-4-[(1H-[1,2,3]triazole-4-carbonyl)amino]pentanoic acid isopropyl ester
9. (2S,4S)-2-Aminomethyl-5-(5'-chloro-2'-fluorobiphenyl-4-yl)-4-[(1H-[1,2,3]triazole-4-carbonyl)amino]pentanoic acid butyl ester
10. (2S,4S)-2-Aminomethyl-5-(5'-chloro-2'-fluorobiphenyl-4-yl)-4-[(1H-

Example 22

(2S,4S)-2-Aminomethyl-5-biphenyl-4-yl-4-[(1H-[1,2,3]triazole-4-carbonyl)amino]pentanoic Acid

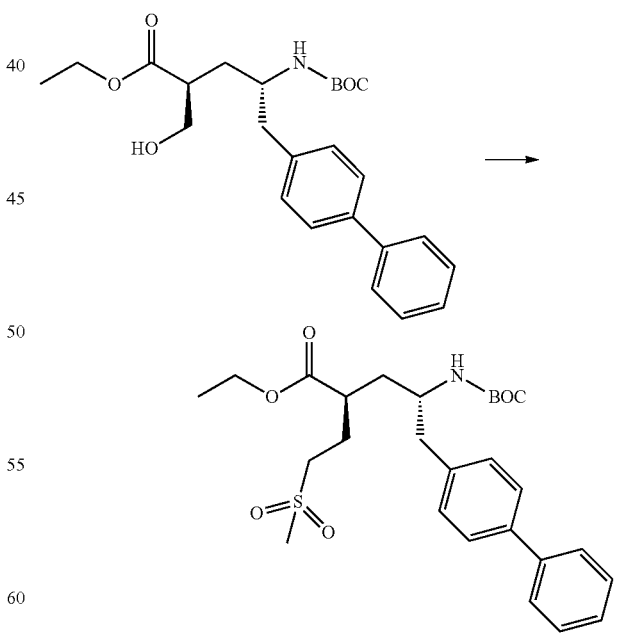

(1)

(2S,4S)-5-Biphenyl-4-yl-4-t-butoxycarbonylamino-2-hydroxymethylpentanoic acid ethyl ester (450 mg, 1.1 mmol) was dissolved in DCM (2 mL) and methanesulfonyl chloride (98 μL, 1.3 mmol) was added, followed by Et₃N (293 μL, 2.1 mmol). The mixture was stirred at room temperature for 30 minutes, and the solution was purified by normal phase chromatography (0-100% EtOAc/hexanes) to yield Compound 1 (405 mg).

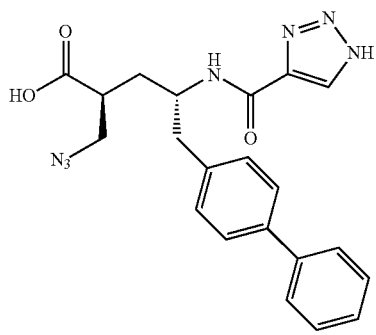

Compound 3 (30 mg, 199 μmol) was combined with 3H-[1,2,3]triazole-4-carboxylic acid (22 mg, 199 μmol), HATU (76 mg, 199 μmol) and DIPEA (104 μL, 596 μmol) in DMF (1 mL) and stirred at room temperature for 20 minutes then concentrated in vacuo and the crude residue was purified by normal phase chromatography (0-100% EtOAc/hexanes). The intermediate (30 mg, 67 μmol) was dissolved in THF (1 mL) and 10N NaOH (268 μL, 268 μmol) and stirred at room temperature for 1 hour. The mixture was acidified with AcOH and purified by preparative HPLC to yield Compound 4 (10 mg).

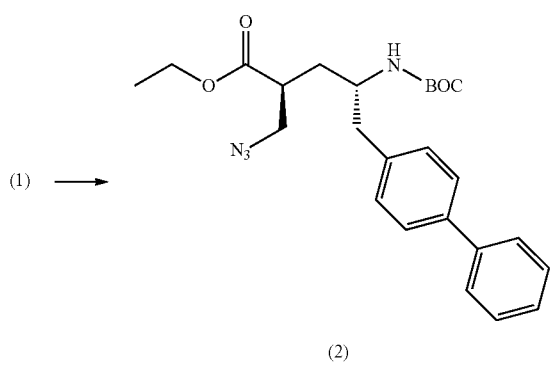 [SMILES: CCOC(=O)[C@H](CN=[N+]=[N-])C[C@@H](Cc1ccc(-c2ccccc2)cc1)NC(=O)OC(C)(C)C]

Compound 1 (200 mg, 396 μmol) in DMF (2 mL) was combined with sodium azide (33 mg, 514 μmol), and the resulting mixture was stirred at 50° C. overnight. The reaction was quenched with water and extracted with EtOAc. The organic layer was washed (3×) with water, dried over Na₂SO₄, then concentrated under reduced pressure and purified by normal phase chromatography (0-60% EtOAc/hexanes) to yield Compound 2 (115 mg).

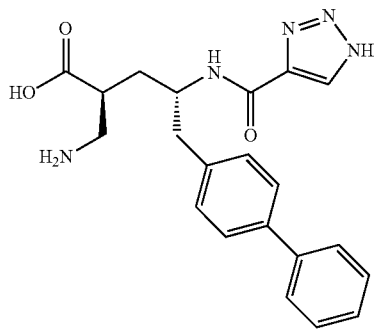

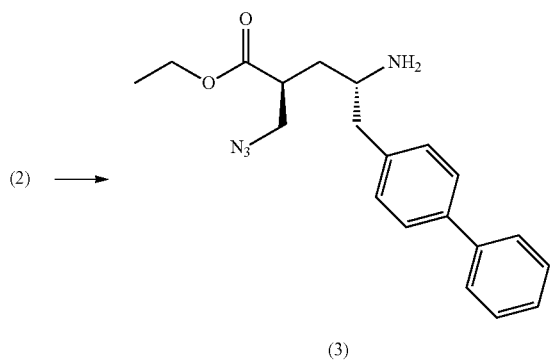 [SMILES: CCOC(=O)[C@H](CN=[N+]=[N-])C[C@H](N)Cc1ccc(-c2ccccc2)cc1]

Compound 2 (93 mg, 206 μmol) was dissolved in MeCN and 4N HCl in dioxane, and the mixture was stirred at room temperature for 10 minutes. The mixture was concentrated under reduced pressure to yield crude Compound 3 as an HCl salt, which was used directly in the next step.

Compound 4 (50 mg, 119 μmol) was combined with PdOH₂/C (17 mg, 119 μmol) in MeOH. Oxygen was removed in vacuo and the solution was placed under hydrogen (1 atm), then stirred for 2 hours. The flask was purged with nitrogen. The reaction was quenched with AcOH, filtered, and purified by reverse phase chromatography to yield the title compound (10 mg; purity 95%) as a TFA salt. MS m/z [M+H]⁺ calc'd for $C_{21}H_{23}N_5O_3$, 394.18; found 394.

Example 23

(2R,4S)-2-(2-Aminoethyl)-5-(5'-chloro-2'-fluorobiphenyl-4-yl)-4-[(5-methyloxazole-2-carbonyl)amino]pentanoic Acid

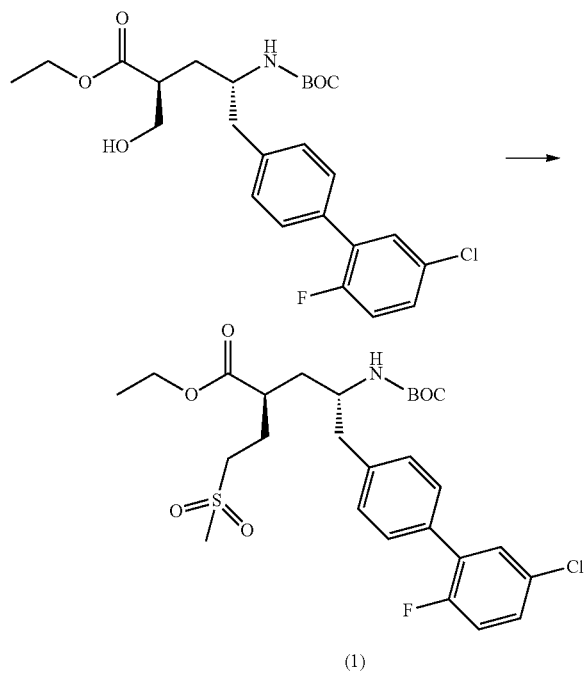

(1)

To a solution of (2S,4S)-4-t-Butoxycarbonylamino-5-(5'-chloro-2'-fluorobiphenyl-4-yl)-2-hydroxymethylpentanoic acid ethyl ester (530 mg, 1.1 mmol) in DCM (5.5 mL) was added Et₃N (308 μL, 2.2 mmol). The solution was cooled to 0° C. and methanesulfonyl chloride (95 μL, 1.2 mmol) was added slowly over a period of 5 minutes. After 20 minutes of stirring at this temperature, LCMS indicated that the desired product had been formed. The solution was washed with ice-cold water (5 mL), ice-cold 1N HCl (5 mL), NaHCO₃ (5 mL), and saturated aqueous NaCl (5 mL). The organic layer was dried over Na₂SO₄, filtered and concentrated in vacuo to yield Compound 1 (602 mg).

(1) →

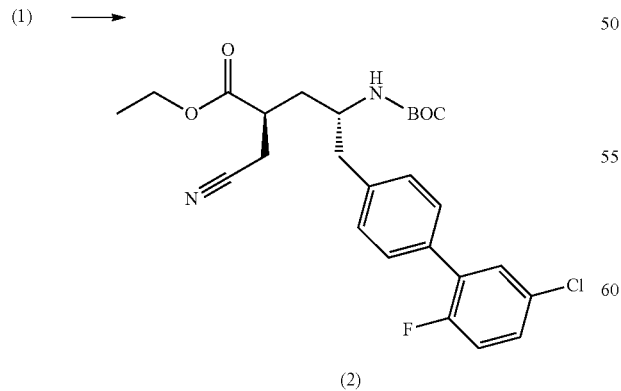

(2)

To a solution of Compound 1 (602 mg, 1.1 mmol) in DMF (6 mL) was added sodium cyanide (116 mg, 2.4 mmol) and 4-(dimethylamino)pyridine (13 mg, 0.1 mmol), and the resulting mixture was heated to 50° C. and stirred overnight. EtOAc (20 mL) and water (20 mL) were added, and the layers were separated. The organic layer was washed with water (3×20 mL), dried over Na₂SO₄, filtered, and concentrated in vacuo. The residue was purified by column chromatography (0-60% EtOAc/hexanes) to yield Compound 2 (421 mg).

(2) →

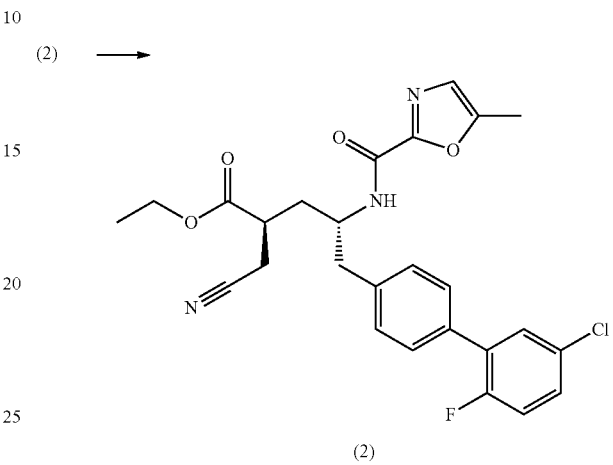

(2)

To a solution of Compound 2 (84 mg, 0.2 mmol) in dioxane (4.3 mL) was added HCl (861 μL, 3.4 mmol). The resulting mixture was stirred at room temperature for 3 hours, after which time LCMS indicated that the BOC group had been removed. The solution was concentrated in vacuo. The residue was dissolved in DMF (2 mL) and DIPEA (90 μL, 0.5 mmol) and added to a solution of 5-methyloxazole-2-carboxylic acid (26 mg, 0.2 mmol), HATU (79 mg, 0.2 mmol) in DMF (4.3 mL), that had been stirred at room temperature for 15 minutes. The resulting solution was stirred at room temperature for 1 hour, until the reaction was complete. The solution was concentrated in vacuo and the residue purified by column chromatography (0-60% EtOAc/hexanes) to yield Compound 3 (554 mg).

(3) →

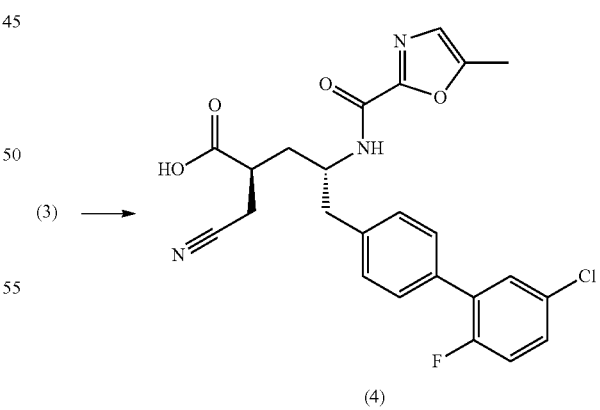

(4)

To a solution of Compound 3 (55 mg, 0.111 mmol) in EtOH (1.1 mL) was added NaOH (890 μl, 890 μmol). The solution was stirred at room temperature for 1 hour, then concentrated in vacuo and purified by reverse phase column chromatography. The desired fractions were combined and lyophilized to yield Compound 4 (31 mg).

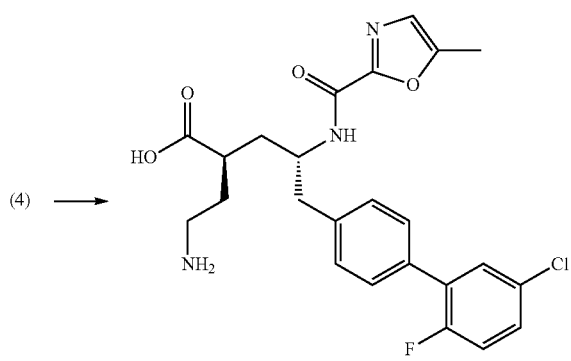 [SMILES: Cc1cnc(C(=O)N[C@H](Cc2ccc(-c3cc(Cl)ccc3F)cc2)C[C@@H](CCN)C(=O)O)o1]

(4) →

To a solution of Compound 4 (31 mg, 66 μmol) in EtOAc (1.5 mL) and AcOH (38 μL, 660 μmol) was added PdOH$_2$/C (4.6 mg, 33 μmol) and (BOC)$_2$O (15 pt, 66 μmol). The resulting solution was sparged with hydrogen and the then stirred at room temperature for 2 hours. The solution was concentrated in vacuo and the residue was purified by reverse phase column chromatography to yield the title compound (1.7 mg; purity 100%) as a TFA salt. MS m/z [M+H]$^+$ calc'd for $C_{24}H_{25}ClFN_3O_4$, 474.15; found 474.2.

Example 24

Following the procedures described herein, and substituting the appropriate starting materials and reagents, these compounds were prepared as a TFA salt:

| Ex. | R$^6$ | Formula | MS m/z: [M + H]$^+$ calcd | found |
|---|---|---|---|---|
| 1 | 4-isopropyloxazol-2-yl | $C_{26}H_{29}ClFN_3O_4$ | 502.18 | 502.2 |
| 2 | 1H-[1,2,3]triazol-4-yl | $C_{22}H_{23}ClFN_5O_3$ | 460.15 | 460.2 |

1. (2R,4S)-2-(2-Aminoethyl)-5-(5'-chloro-2'-fluorobiphenyl-4-yl)-4-[(4-isopropyloxazole-2-carbonyl)amino]pentanoic acid
2. (2R,4S)-2-(2-Aminoethyl)-5-(5'-chloro-2'-fluorobiphenyl-4-yl)-4-[(3H-[1,2,3]triazole-4-carbonyl)amino]pentanoic acid Example 25

(2R,4R)-2-Acetylamino-5-(2'-fluorobiphenyl-4-yl)-4-[(1H-[1,2,3]triazole-4-carbonyl)amino]pentanoic Acid

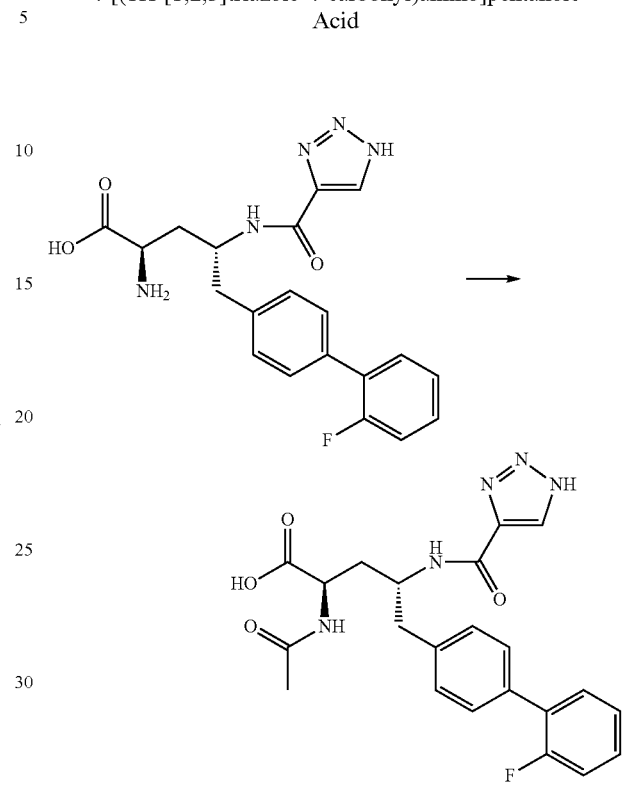

(2R,4R)-2-Amino-5-(2'-fluorobiphenyl-4-yl)-4-[(1H-[1,2,3]triazole-4-carbonyl)amino]pentanoic acid (9 mg, 23 μmol) was dissolved in DCM (2 mL). Acetyl chloride (1.8 μL, 25 μmol) and DIPEA (12 μL, 68 μmol) were added and the resulting mixture was stirred at room temperature for 15 minutes then concentrated in vacuo and the residue was dissolved in EtOH (2 mL). An aqueous solution of 1N NaOH (227 μL, 227 μmol) was added and the mixture was stirred at room temperature for 30 minutes then concentrated in vacuo and the residue was purified by reverse phase column chromatography to yield the title compound (5 mg; purity 98%). MS m/z [M+H]$^+$ calc'd for $C_{22}H_{22}FN_5O_4$, 440.17; found 440.1.

Example 26

(2R,4R)-2-Acetylamino-5-biphenyl-4-yl-4-[(1H-[1,2,3]triazole-4-carbonyl)amino]pentanoic Acid

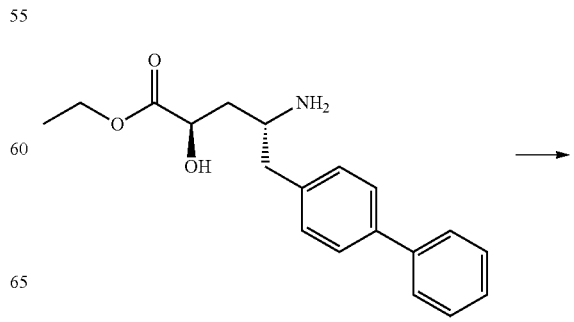

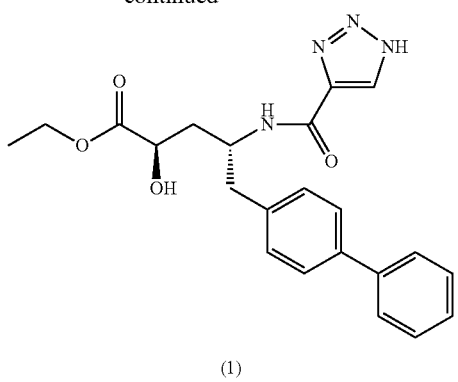

(1)

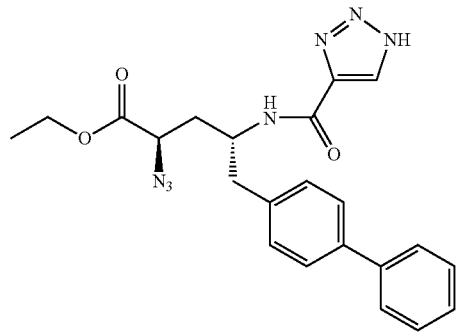

(3)

To a stirred solution of (2R,4R)-4-Amino-5-biphenyl-4-yl-2-hydroxypentanoic acid ethyl ester (200 mg, 638 μmol), HATU (291 mg, 766 μmol), 3H-[1,2,3]triazole-4-carboxylic acid (87 mg, 766 μmol), and DMF (3 mL), was added DIPEA (357 μL, 2.0 mmol), and the mixture was stirred at room temperature for 30 minutes. A saturated aqueous NH₄Cl was added and the mixture was extracted with EtOAc. The organics were combined, dried over Na₂SO₄, and the solvent was evaporated. The crude residue was purified by normal phase chromatography (0-100% EtOAc/hexanes) to yield Compound 1 (76 mg).

Compound 2 (60 mg, 123 μmol) in DMF (2 mL) was combined with sodium azide (17.6 mg, 271 μmol), and the resulting mixture was stirred overnight. The solution was purified by normal phase chromatography (0-100% EtOAc/hexanes) to yield Compound 3 (54 mg).

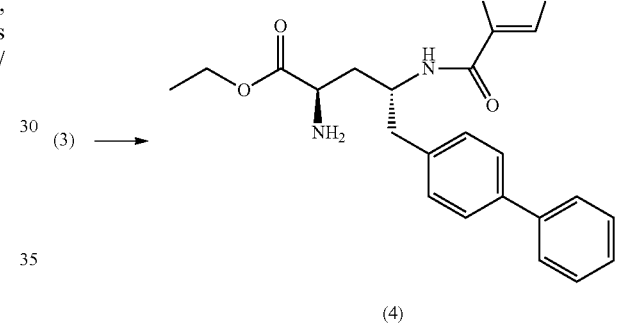

(4)

(1) →

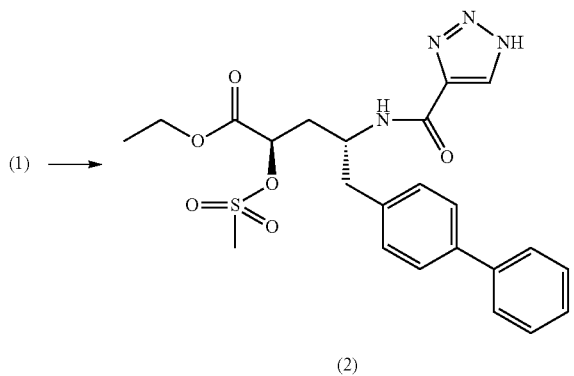 [SMILES: CCOC(=O)[C@@H](C[C@@H](Cc1ccc(-c2ccccc2)cc1)NC(=O)c1c[nH]nn1)OS(C)(=O)=O]

(2)

Compound 3 (54 mg, 125 μmol) was combined with PdOH₂/C (17.5 mg, 25 μmol) in MeOH. The flask was purged in vacuo (3×), then purged with nitrogen, then placed under hydrogen (1 atm) and stirred at room temperature for 30 minutes. The reaction was quenched with AcOH. The mixture was stirred for 10 minutes, filtered and concentrated in vacuo to yield Compound 4.

(4) →

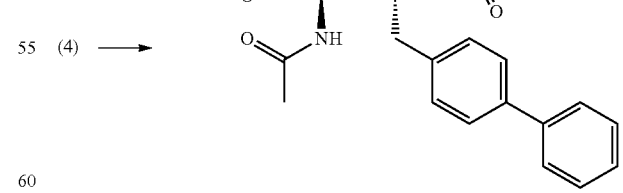

(5)

Compound 1 (111 mg, 272 μmol) was dissolved in DCM (3 mL). Methanesulfonyl chloride (46.4 μL, 599 μmol) was added at 0° C., followed by Et₃N (114 μL, 817 μmol). The mixture was stirred for 10 minutes, and then concentrated and was purified by normal phase chromatography (0-100% EtOAc/hexanes) to yield Compound 2 (60 mg).

Compound 4 (10 mg, 25 μmol) was combined with DCM (2 mL), methyl chloroformate (2.3 mg, 25 μmol) and Et₃N (3.4 μL, 25 μmol 1). The mixture was stirred for 10 minutes and the solvent evaporated to yield Compound 5.

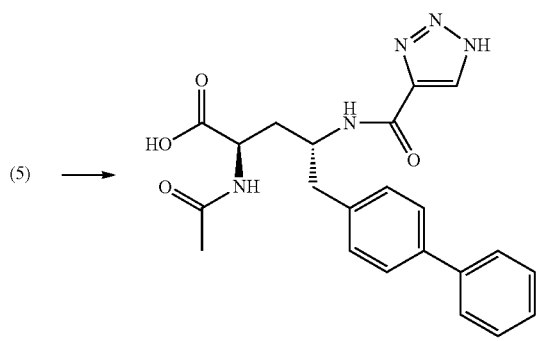 [SMILES: CC(=O)N[C@H](C[C@@H](Cc1ccc(-c2ccccc2)cc1)NC(=O)c1c[nH]nn1)C(=O)O]

Compound 5 (11 mg, 24 μmol) was dissolved in THF (1 mL) and 1N NaOH (119 μL, 119 μmol) and stirred at room temperature for 3 hours. To the mixture was added AcOH and the solution was purified by reverse phase chromatography to yield the title compound (2 mg; purity 98%) as a TFA salt. MS m/z [M+H]+ calc'd for $C_{22}H_{23}N_5O_4$, 422.18; found 422.

Example 27

(2R,4R)-5-Biphenyl-4-yl-2-propionylamino-4-[(1H-[1,2,3]triazole-4-carbonyl)amino]pentanoic Acid Compound 4 was prepared as described herein.

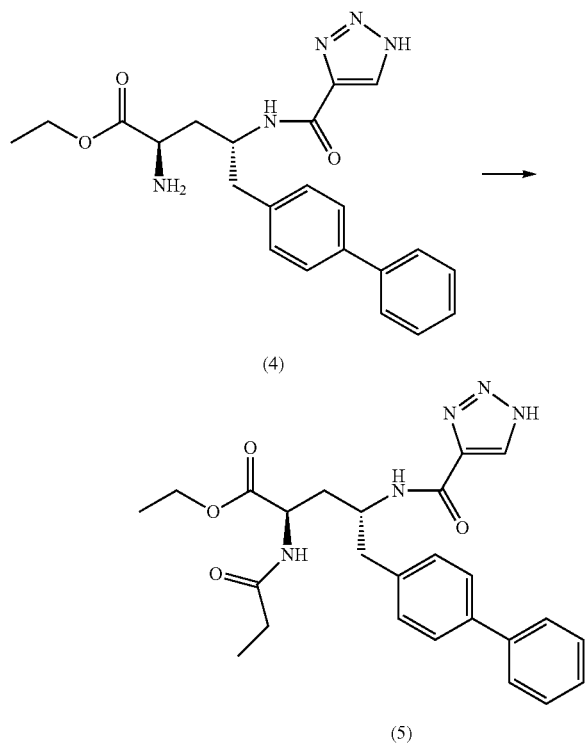

Compound 4 (10 mg, 25 μmol) was combined with DCM (2 mL), propionyl chloride (2.3 mg, 25 μmol) and Et₃N (3.4 μL, 25 μmol). The mixture was stirred for 10 minutes and the solvent evaporated to yield Compound 5.

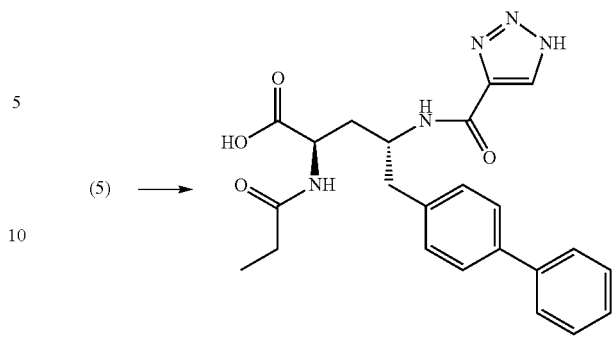

Compound 5 (11 mg, 24 μmol) was dissolved in THF (1 mL) and 10N NaOH (119 μL, 119 μmol) and stirred for 3 hours. To the mixture was added AcOH and the solution was purified by reverse phase chromatography to yield the title compound (2 mg; purity 95%) as a TFA salt. MS m/z [M+H]+ calc'd for $C_{23}H_{25}N_5O_4$, 436.19; found 436.

Example 28

(2S,4S)-2-(Acetylaminomethyl)-5-(5'-chloro-2'-fluoro-biphenyl-4-yl)-4-[(1H-[1,2,3]triazole-4-carbonyl)amino]pentanoic Acid

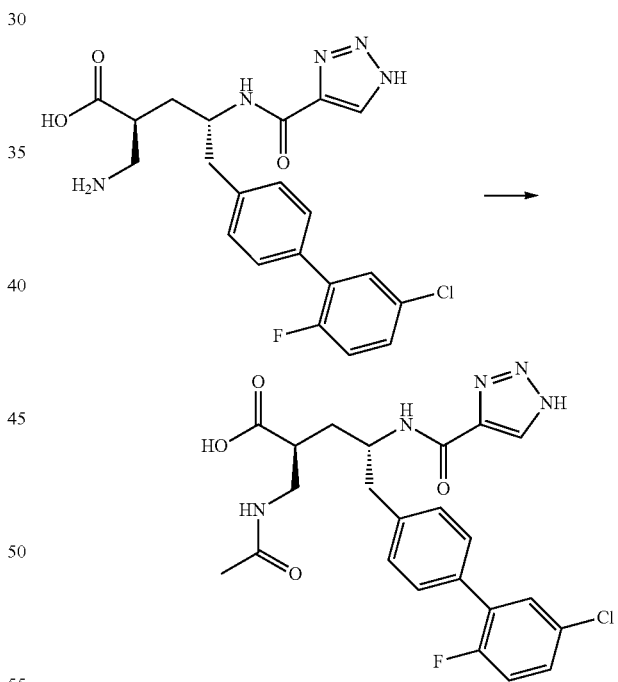

To a stirred solution of (2S,4S)-2-aminomethyl-5-(5'-chloro-2'-fluorobiphenyl-4-yl)-4-[(1H-[1,2,3]triazole-4-carbonyl)amino]pentanoic acid (5 mg, 11 μmol), DCM (0.3 mL), and acetyl chloride (3.5 mg, 45 μmol), was added Et₃N (9.4 μL, 67 μmol), and the mixture was stirred for 5 minutes. The reaction was quenched with 1N NaOH (0.1 mL) and THF (0.5 mL) and the mixture stirred for 10 minutes. The solvent was evaporated and the residue was purified by reverse phase chromatography to yield the title compound (2 mg; purity 95%) as a TFA salt. MS m/z [M+H]+ calc'd for $C_{23}H_{23}ClFN_5O_4$, 488.14; found 488.

Example 29

(2R,4R)-5-(5'-Chloro-2'-fluorobiphenyl-4-yl)-4-[(3-ethylisoxazole-5-carbonyl)amino]-2-methoxycarbonylaminopentanoic Acid

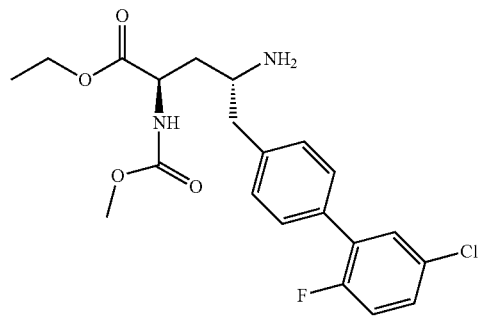

→

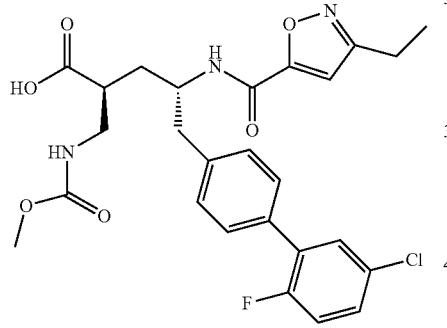

3-Ethylisoxazole-5-carboxylic acid (5.5 mg, 39 μmol) and HATU (14.8 mg, 39 μmol) were dissolved in DMF (3 mL) and stirred at room temperature for 15 minutes. (2R,4R)-4-Amino-5-(5'-chloro-2'-fluorobiphenyl-4-yl)-2-methoxycarbonylamino-pentanoic acid ethyl ester (15 mg, 35 μmol) and DIPEA (19 μL, 106 μmol) were added, and the resulting mixture was stirred at room temperature for 15 minutes (LC/MS showed reaction completion) then concentrated in vacuo and the residue was dissolved in EtOH (3 mL). An aqueous 1N NaOH solution (355 μL, 355 μmol) was added, and the resulting mixture was stirred at room temperature for 1 hour (LC/MS showed reaction completion) then concentrated in vacuo and the residue purified by preparative HPLC to yield the title compound (3.7 mg; purity 100%). MS m/z [M+H]+ calc'd for $C_{25}H_{25}ClFN_3O_6$, 518.14; found 518.2.

Example 30

Following the procedures described herein, and substituting the appropriate starting materials and reagents, these compounds were prepared, either as the parent compound or as a TFA salt:

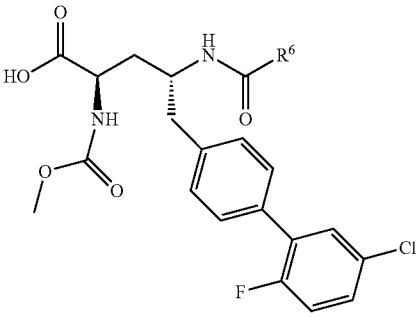

| Ex. | R⁶ | Formula | MS m/z: [M + H]+ calcd | found |
|---|---|---|---|---|
| 1 | 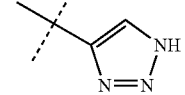 | $C_{22}H_{21}ClFN_5O_5$ | 490.12 | 490.0 |
| 2 | 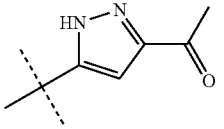 | $C_{25}H_{24}ClFN_4O_6$ | 531.14 | 531.2 |
| 3 | 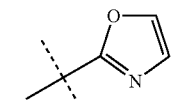 | $C_{23}H_{21}ClFN_3O_6$ | 490.11 | 490.2 |
| 4 | 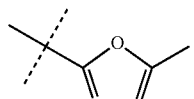 | $C_{24}H_{23}ClFN_3O_6$ | 504.13 | 504 |
| 5 | 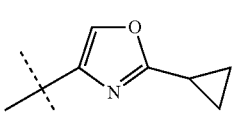 | $C_{24}H_{23}ClFN_3O_6$ | 530.14 | 530.2 |
| 6 | 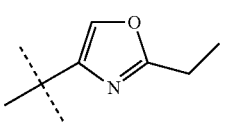 | $C_{25}H_{25}ClFN_3O_6$ | 518.14 | 518.2 |
| 7 | 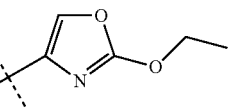 | $C_{25}H_{25}ClFN_3O_7$ | 534.14 | 534.2 |
| 8 | 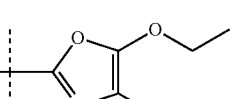 | $C_{26}H_{27}ClFN_3O_7$ | 548.15 | 548.2 |
| 9 | 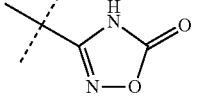 | $C_{22}H_{20}ClFN_4O_7$ | 507.10 | 507.2 |

12. (2R,4R)-5-(5'-Chloro-2'-fluorobiphenyl-4-yl)-4-[(5-chloro-pyridine-2-carbonyl)-amino]-2-methoxycarbonylaminopentanoic acid

Example 31

(2R,4R)-5-Biphenyl-4-yl-2-methoxycarbonylamino-4-[(1H-[1,2,3]triazole-4-carbonyl)amino]pentanoic Acid Compound 4 was prepared as described herein.

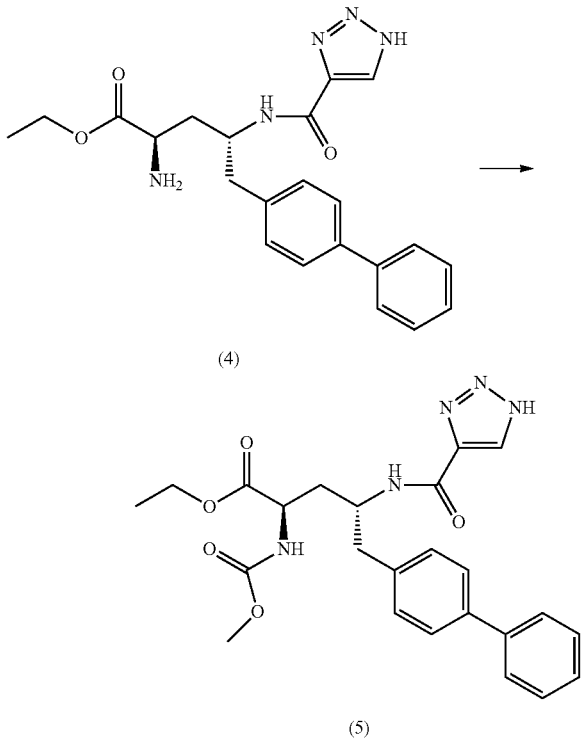

To a stirred solution of Compound 4 (10 mg, 25 µmol) in DCM (2 mL), was added methyl chloroformate (2.3 mg, 25 µmol) and Et₃N (3.4 µL, 25 µmol). The mixture was stirred for 10 minutes and the solvent evaporated to yield Compound 5.

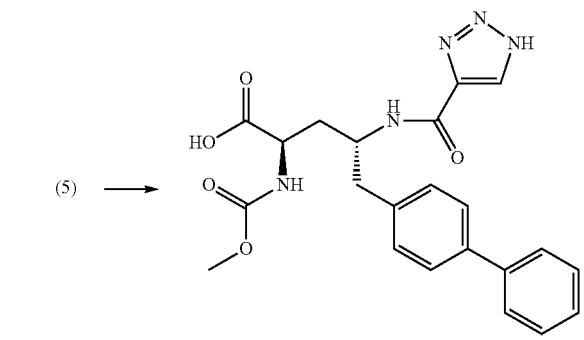 [SMILES: COC(=O)N[C@H](C[C@@H](Cc1ccc(-c2ccccc2)cc1)NC(=O)c1c[nH]nn1)C(=O)O]

A solution of Compound 5 (11 mg, 24 µmol) in THF (1 mL) and 1N NaOH (119 µL, 119 µmol) was stirred for 3 hours. To the mixture was added AcOH and the solution was purified by reverse phase chromatography to yield the title

| Ex. | R⁶ | Formula | MS m/z: [M + H]⁺ calcd | found |
|---|---|---|---|---|
| 10 |  | C₂₃H₂₁ClFN₃O₇ | 506.11 | 506.2 |
| 11 |  | C₂₃H₂₁ClFN₃O₇ | 506.11 | 506.2 |
| 12 |  | C₂₅H₂₂Cl₂FN₃O₅ | 534.09 | 534.2 |

1. (2R,4R)-5-(5'-Chloro-2'-fluoro-biphenyl-4-yl)-2-methoxycarbonylamino-4-[(1H-[1,2,3]triazole-4-carbonyl)amino]pentanoic acid
2. (2R,4R)-4-[(5-Acetyl-2H-pyrazole-3-carbonyl)-amino]-5-(5'-chloro-2'-fluoro-biphenyl-4-yl)-2-methoxycarbonylaminopentanoic acid
3. (2R,4R)-5-(5'-Chloro-2'-fluoro-biphenyl-4-yl)-2-methoxycarbonylamino-4-[(oxazole-2-carbonyl)amino]pentanoic acid
4. (2R,4R)-5-(5'-Chloro-2'-fluorobiphenyl-4-yl)-2-methoxycarbonylamino-4-[(5-methyloxazole-2-carbonyl)amino]pentanoic acid
5. (2R,4R)-5-(5'-Chloro-2'-fluorobiphenyl-4-yl)-4-[(2-cyclopropyl-oxazole-4-carbonyl)amino]-2-methoxycarbonylaminopentanoic acid
6. (2R,4R)-5-(5'-Chloro-2'-fluorobiphenyl-4-yl)-4-[(2-ethyl-oxazole-4-carbonyl)amino]-2-methoxycarbonylaminopentanoic acid
7. (2R,4R)-5-(5'-Chloro-2'-fluorobiphenyl-4-yl)-4-[(2-ethoxy-oxazole-4-carbonyl)amino]-2-methoxycarbonylaminopentanoic acid
8. (2R,4R)-5-(5'-Chloro-2'-fluorobiphenyl-4-yl)-4-[(5-ethoxy-4-methyl-oxazole-2-carbonyl)amino]-2-methoxycarbonylaminopentanoic acid
9. (2R,4R)-5-(5'-Chloro-2'-fluorobiphenyl-4-yl)-2-methoxycarbonylamino-4-[(5-oxo-4,5-dihydro-[1,2,4]oxadiazole-3-carbonyl)amino]pentanoic acid
10. (2R,4R)-5-(5'-Chloro-2'-fluorobiphenyl-4-yl)-2-methoxycarbonylamino-4-[(2-oxo-2,3-dihydro-oxazole-5-carbonyl)amino]pentanoic acid
11. (2R,4R)-5-(5'-Chloro-2'-fluorobiphenyl-4-yl)-2-methoxycarbonylamino-4-[(2-oxo-2,3-dihydro-oxazole-4-carbonyl)amino]pentanoic acid compound (2 mg; purity 95%) as a TFA salt. MS m/z [M+H]+ calc'd for $C_{22}H_{23}N_5O_5$, 438.17; found 438.

Example 32

(2R,4R)-2-(2-Amino acetylamino)-5-(2'-fluorobiphenyl-4-yl)-4-[(1H-[1,2,3]triazole-4-carbonyl)amino]pentanoic Acid

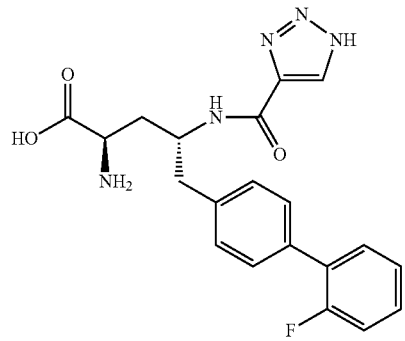

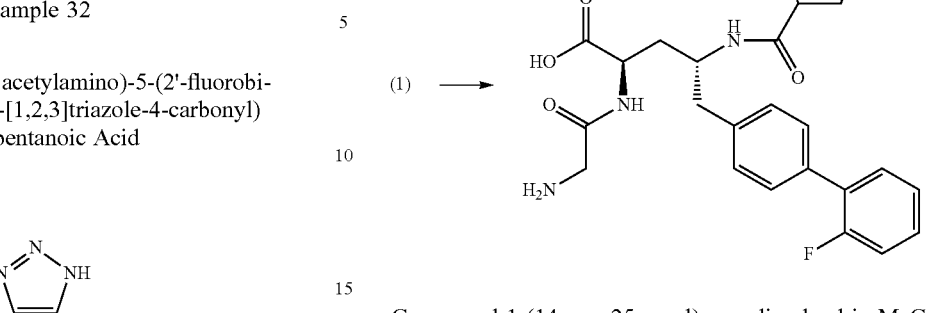

Compound 1 (14 mg, 25 µmol) was dissolved in MeCN (2 mL). A solution of 4N HCl in dioxane (63 µL, 252 µmol) was added and the mixture was stirred at room temperature for 10 minutes, at which time LCMS indicated the mass of the desired compound. The mixture was concentrated in vacuo and the residue was purified by reverse phase column chromatography to yield the title compound (3 mg; purity 96%) as a TFA salt. MS m/z [M+H]+ calc'd for $C_{22}H_{23}FN_6O_4$, 455.18; found 455.

Example 33

(2R,4R)-2-(2-Aminoacetylamino)-5-(5'-chloro-2'-fluoro-biphenyl-4-yl)-4-[(1H-[1,2,3]triazole-4-carbonyl)amino]pentanoic Acid

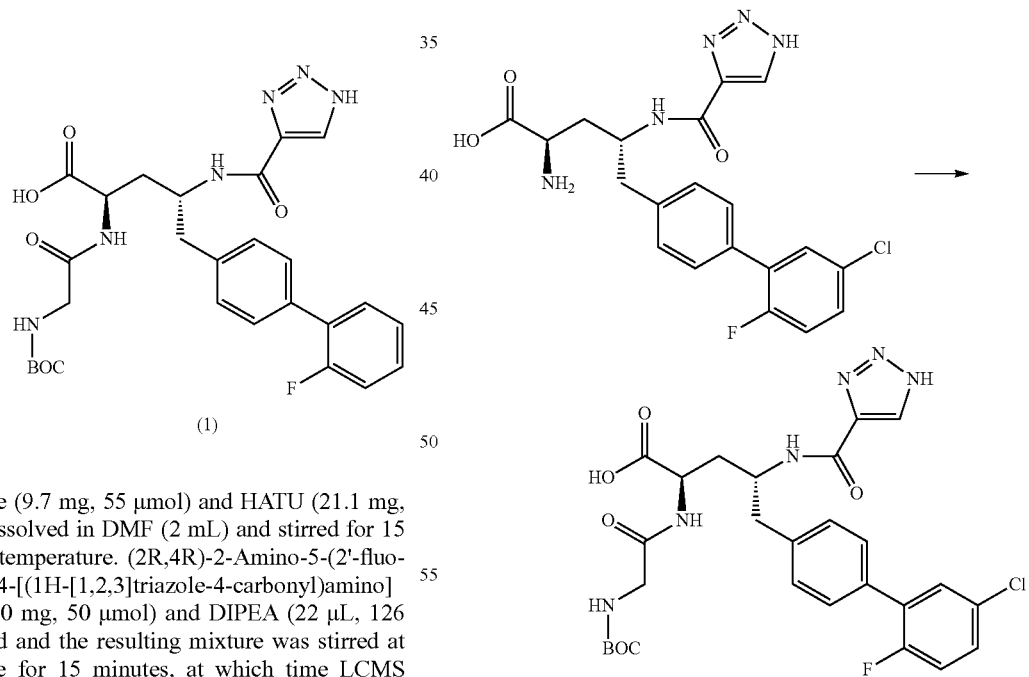

n-BOC-Glycine (9.7 mg, 55 µmol) and HATU (21.1 mg, 55 µmol) were dissolved in DMF (2 mL) and stirred for 15 minutes at room temperature. (2R,4R)-2-Amino-5-(2'-fluorobiphenyl-4-yl)-4-[(1H-[1,2,3]triazole-4-carbonyl)amino] pentanoic acid (20 mg, 50 µmol) and DIPEA (22 µL, 126 µmol) were added and the resulting mixture was stirred at room temperature for 15 minutes, at which time LCMS indicated the mass of the desired compound. The mixture was concentrated in vacuo and the residue was dissolved in EtOH (2 mL). An aqueous solution of 1N NaOH (503 µl, 503 µmol) was added and the resulting mixture was stirred at room temperature for 30 minutes (LC/MS showed the mass of the desired product) then concentrated in vacuo to yield Compound 1, which was used in the next step without purification.

n-BOC-Glycine (3.3 mg, 19 µmol) and HATU (7.1 mg, 19 µmol) were dissolved in DMF (2 mL) and stirred for 15 minutes at room temperature. (2R,4R)-2-Amino-5-(5'-chloro-2'-fluorobiphenyl-4-yl)-4-[(1H-[1,2,3]triazole-4-carbonyl)amino]pentanoic acid (7.3 mg, 17 µmol) and DIPEA (8.9 µL, 51 µmol) were added and the resulting mixture was stirred at room temperature for 15 minutes, at which time LCMS indicated the mass of the desired compound. The mixture was concentrated in vacuo to yield Compound 1, which was used in the next step without purification.

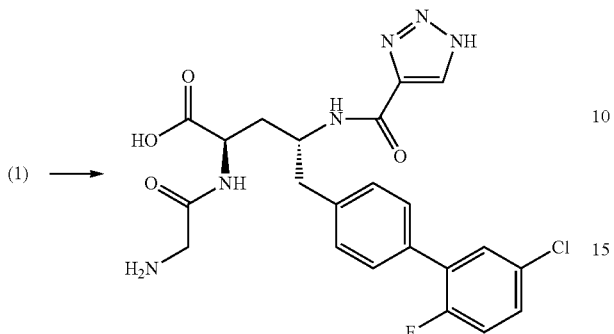

(1) →

Compound 1 (10 mg, 17 μmol) was dissolved in MeCN (2 mL). A solution of 4N HCl in dioxane (4.2 μL, 17 μmol) was added and the mixture was stirred at room temperature for 15 minutes, at which time LCMS indicated the mass of the desired compound. The mixture was concentrated in vacuo and the residue was purified by reverse phase column chromatography to yield the title compound (2.5 mg; purity 98%) as a TFA salt. MS m/z [M+H]$^+$ calc'd for $C_{22}H_{22}ClFN_6O_4$, 489.14; found 489.

Example 34

Following the procedures described herein, and substituting the appropriate starting materials and reagents, this compound was prepared as a TFA salt:

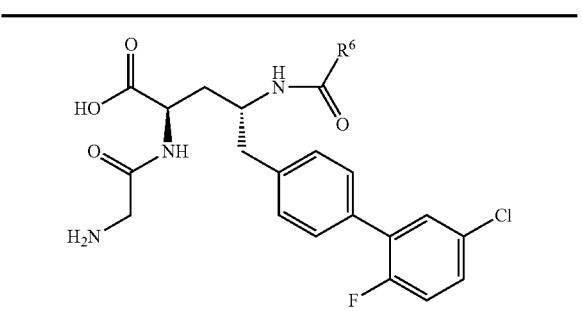

| Ex. | R$^6$ | Formula | MS m/z: [M + H]$^+$ calcd | found |
|---|---|---|---|---|
| 1 | 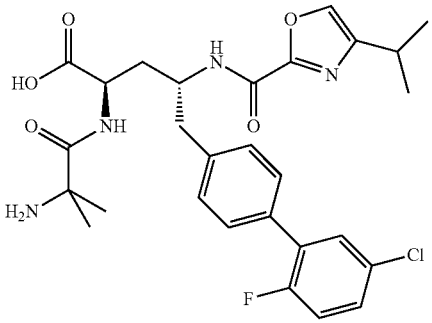 | $C_{26}H_{28}ClFN_4O_5$ | 531.17 | 531.2 |

1. (2R,4R)-2-(2-Aminoacetylamino)-5-(5'-chloro-2'-fluoro-biphenyl-4-yl)-4-[(4-isopropyloxazole-2-carbonyl)amino]pentanoic acid

Example 35

(2R,4R)-2-(2-Amino-2-methylpropionylamino)-5-(5'-chloro-2'-fluorobiphenyl-4-yl)-4-[(4-isopropyloxazole-2-carbonyl)amino]pentanoic Acid 2-t-Butoxycarbonylamino-2-methylpropionic acid (4.5 mg, 22 μmol) and HATU (8.4 mg, 22 μmol) were dissolved in DMF (2 mL) and stirred for 15 min at room temperature. (2R,4R)-2-Amino-5-(5'-chloro-2'-fluorobiphenyl-4-yl)-4-[(4-isopropyloxazole-2-carbonyl)amino]pentanoic acid (10 mg, 21 μmol) and DIPEA (11 μL, 63 μmol) were added, and the resulting mixture was stirred at room temperature for 15 minutes, at which time LCMS indicated the mass of the desired compound. The mixture was concentrated in vacuo and the residue was dissolved in MeCN (2 mL). An excess of a solution of 4N HCl in dioxane was added, and the resulting mixture was stirred at room temperature for 15 minutes, at which time LCMS indicated the mass of the desired compound. The mixture was concentrated in vacuo and the residue was purified by preparative HPLC to yield the title compound (2.1 mg; purity 96%) as a TFA salt. MS m/z [M+H]$^+$ calc'd for $C_{28}H_{32}ClFN_4O_5$, 559.20; found 559.2.

Example 36

(2R,4R)-2-((S)-2-Aminopropionylamino)-5-(5'-chloro-2'-fluorobiphenyl-4-yl)-4-[(4-isopropyloxazole-2-carbonyl)amino]pentanoic Acid (compound 36-1) and (2R,4R)-2-((R)-2-Aminopropionylamino)-5-(5'-chloro-2'-fluorobiphenyl-4-yl)-4-[(4-isopropy-oxazole-2-carbonyl)-amino]pentanoic Acid (compound 36-2)

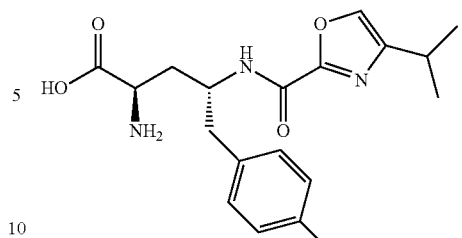

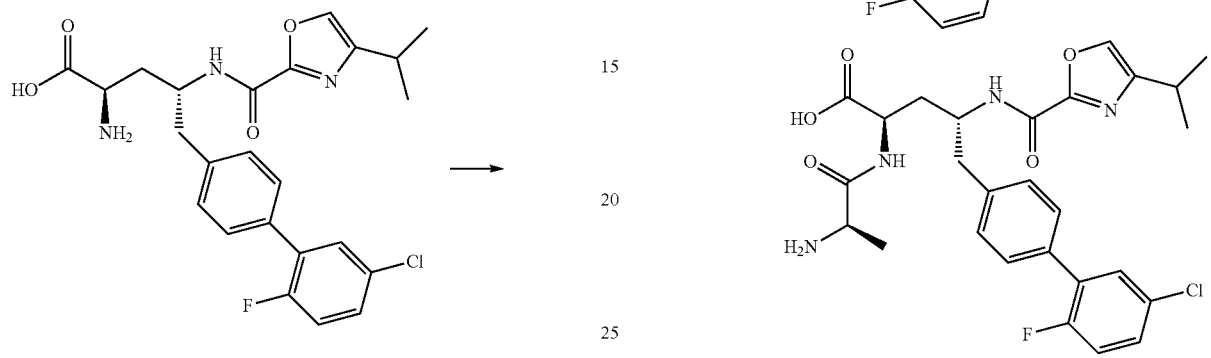

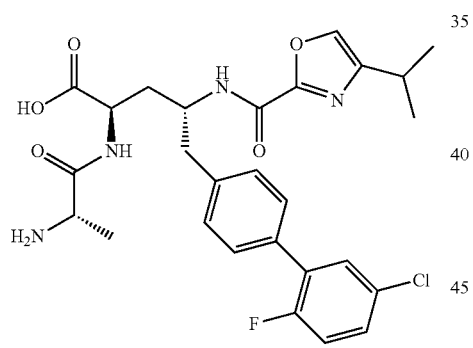

(S)-2-t-Butoxycarbonylaminopropionic acid (4.2 mg, 22 µmol) and HATU (8.4 mg, 22 µmol) were dissolved in DMF (2 mL) and stirred for 15 min at room temperature. (2R,4R)-2-Amino-5-(5'-chloro-2'-fluorobiphenyl-4-yl)-4-[(4-isopropyloxazole-2-carbonyl)amino]pentanoic acid (10 mg, 21 µmol) and DIPEA (11 µL, 63 µmol) were added, and the resulting mixture was stirred at room temperature for 15 minutes, at which time LCMS indicated the mass of the desired compound. The mixture was concentrated in vacuo and the residue was dissolved in MeCN (2 mL). An excess of a solution of 4N HCl in dioxane was added, and the resulting mixture was stirred at room temperature for 15 minutes, at which time LCMS indicated the mass of the desired compound. The mixture was concentrated in vacuo and the residue was purified by preparative HPLC to yield the title Compound 36-1 (2.4 mg; purity 100%) as a TFA salt. MS m/z [M+H]$^+$ calc'd for $C_{27}H_{30}ClFN_4O_5$, 545.19; found 545.2.

This procedure was repeated using (R)-2-t-butoxycarbonylaminopropionic acid (4.5 mg, 22 µmol) to yield the title Compound 36-2 (2.2 mg; purity 100%) as a TFA salt. MS m/z [M+H]$^+$ calc'd for $C_{27}H_{30}ClFN_4O_5$, 545.19; found 545.2.

Example 37

Following the procedures described herein, and substituting the appropriate starting materials and reagents, this compound was prepared as a TFA salt:

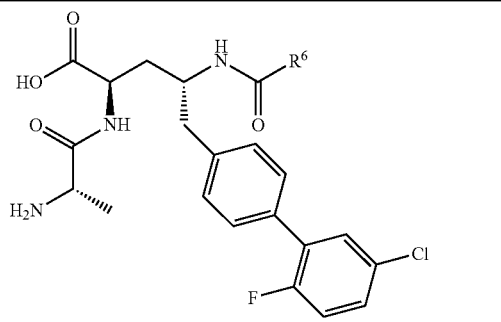

| Ex. | R$^6$ | Formula | MS m/z: [M + H]$^+$ calcd | found |
|---|---|---|---|---|
| 1 | 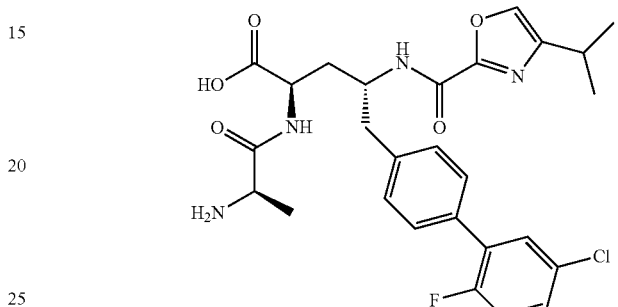 | $C_{23}H_{24}ClFN_6O_4$ | 503.15 | 503.2 |

1. (2R,4R)-2-((S)-2-Aminopropionylamino)-5-(5'-chloro-2'-fluorobiphenyl-4-yl)-4-[(3H-[1,2,3]triazole-4-carbonyl)amino]pentanoic acid

Example 38

(2R,4R)-2-((R)-2-Amino-3-methylbutyrylamino)-5-(5'-chloro-2'-fluorobiphenyl-4-yl)-4-[(4-isopropyloxazole-2-carbonyl)amino]pentanoic Acid (compound 38-1) and (2R,4R)-2-((S)-2-Amino-3-methylbutyrylamino)-5-(5'-chloro-2'-fluorobiphenyl-4-yl)-4-[(4-isopropyloxazole-2-carbonyl)-amino]pentanoic Acid (compound 38-2)

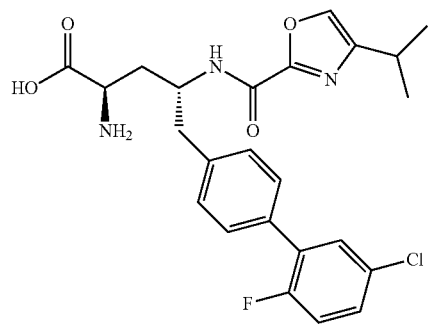

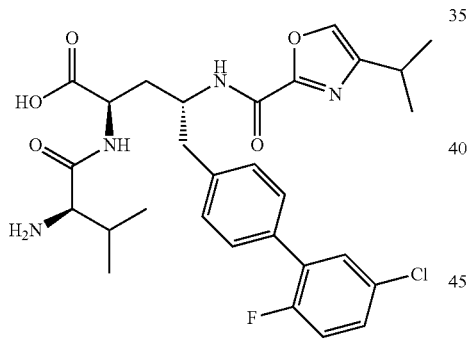

(R)-2-t-Butoxycarbonylamino-3-methylbutyric acid (4.8 mg, 22 µmol) and HATU (8.4 mg, 22 µmol) were dissolved in DMF (2 mL) and stirred for 15 min at room temperature. (2R,4R)-2-Amino-5-(5'-chloro-2'-fluorobiphenyl-4-yl)-4-[(4-isopropyloxazole-2-carbonyl)amino]pentanoic acid (10 mg, 21 µmol) and DIPEA (11 µL, 63 µmol) were added, and the resulting mixture was stirred at room temperature for 15 minutes, at which time LCMS indicated the mass of the desired compound. The mixture was concentrated in vacuo and the residue was dissolved in MeCN (2 mL). An excess of a solution of 4N HCl in dioxane was added, and the resulting mixture was stirred at room temperature for 15 minutes, at which time LCMS indicated the mass of the desired compound. The mixture was concentrated in vacuo and the residue was purified by preparative HPLC to yield the title Compound 38-1 (1.7 mg; purity 92%) as a TFA salt. MS m/z [M+H]$^+$ calc'd for $C_{29}H_{34}ClFN_4O_5$, 573.22; found 573.2.

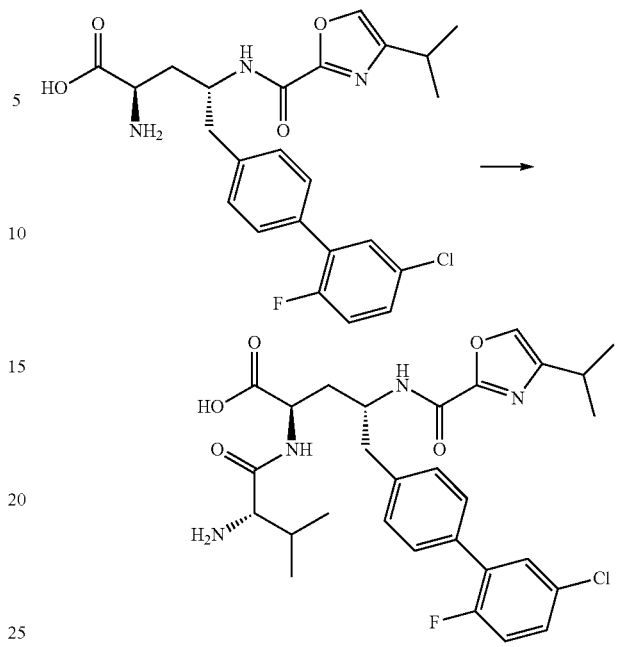

This procedure was repeated using (S)-2-t-butoxycarbonylamino-3-methylbutyric acid (4.8 mg, 22 µmol) to yield the title Compound 38-2 (1.1 mg; purity 81%) as a TFA salt. MS m/z [M+H]$^+$ calc'd for $C_{29}H_{34}ClFN_4O_5$, 573.22; found 573.2. MS m/z [M+H]$^+$ calc'd for $C_{27}H_{30}ClFN_4O_5$, 545.19; found 545.2.

Example 39

Following the procedures described herein, and substituting the appropriate starting materials and reagents, this compound was prepared as a TFA salt:

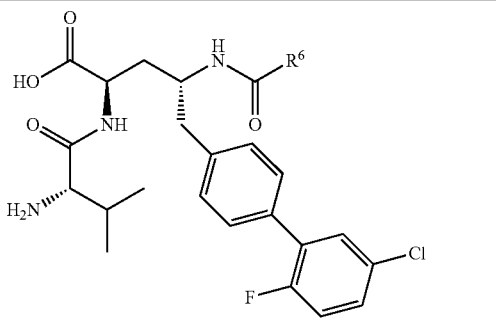

| Ex. | R$^6$ | Formula | MS m/z: [M + H]$^+$ calcd | found |
|---|---|---|---|---|
| 1 | ![triazole] | $C_{25}H_{28}ClFN_6O_4$ | 531.18 | 531.2 |

1. (2R,4R)-2-((S)-2-Amino-3-methylbutyrylamino)-5-(5'-chloro-2'-fluorobiphenyl-4-yl)-4-[(3H-[1,2,3]triazole-4-carbonyl)amino]pentanoic acid

Example 40

(2R,4R)-2-(4-Aminobutyrylamino)-5-(5'-chloro-2'-fluorobiphenyl-4-yl)-4-[(3H-[1,2,3]triazole-4-carbonyl)amino]pentanoic Acid

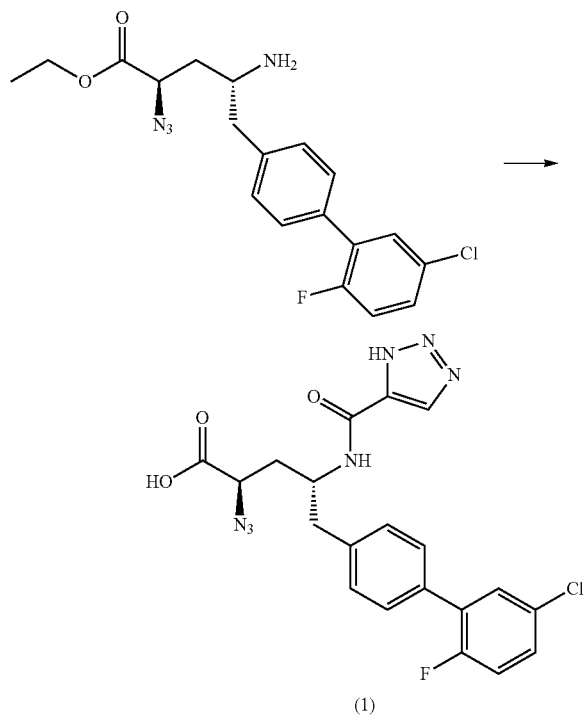

1H-1,2,3-triazole-4-carboxylic acid (135 mg, 1.2 mmol) and HATU (453 mg, 1.2 mmol) were dissolved in DMF (4 mL) and stirred for 15 minutes at room temperature. (2R,4R)-4-Amino-2-azido-5-(5'-chloro-2'-fluorobiphenyl-4-yl)pentanoic acid ethyl ester (423 mg, 1.2 mmol) and DIPEA (567 µL, 3.3 mmol) were added, and the mixture was stirred at room temperature for 15 minutes, at which time LCMS indicated the mass of the desired compound. The mixture was concentrated in vacuo and the crude residue was purified by normal phase column chromatography (20-100% EtOAc/hexanes) to yield Compound 1 (324 mg).

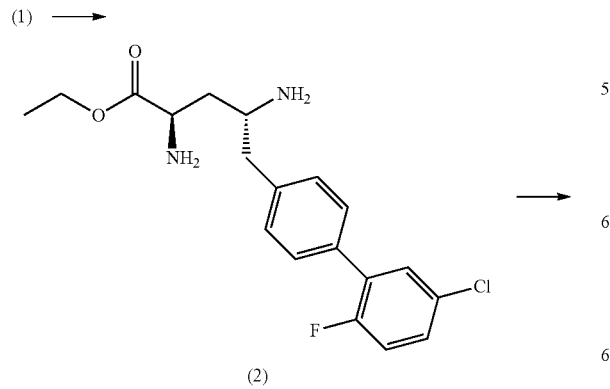

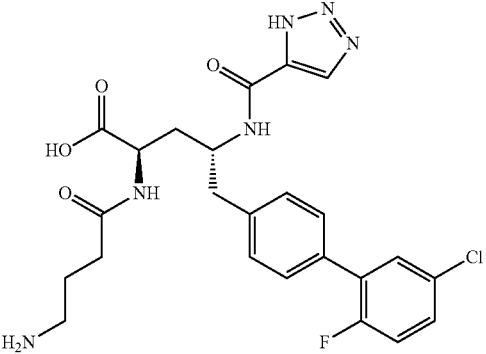

Compound 1 (203 mg, 443 µmol) and palladium hydroxide (12.5 mg, 89 µmol) were stirred in dry MeOH (3 mL) and AcOH (3 mL). The hydrogen was removed in vacuo and the flask was purged with nitrogen and the mixture stirred at room temperature for 1 hour. LC/MS showed the desired mass. The mixture was filtered and the solution was purified by preparative HPLC to yield Compound 2 (105 mg).

4-t-Butoxycarbonylaminobutyric acid (6.4 mg, 31 µmol) and HATU (10.8 mg, 28 µmol) were dissolved in DMF (3 mL) and stirred for 15 minutes at room temperature. Compound 2 (12.3 mg, 28 µmol) and DIPEA (15 µL, 85 µmol) were added, and the mixture was stirred at room temperature for 15 minutes (LC/MS showed the desired product) then concentrated in vacuo and the residue was dissolved in MeCN (2 mL). A solution of 4N HCl in dioxane (107 mL, 427 µmol) was added, and the mixture was stirred for 15 minutes at room temperature. LC/MS showed the desired mass. The solvent was removed in vacuo and the residue was purified by preparative HPLC to yield the title compound (8 mg; purity 100%) as a TFA salt. MS m/z [M+H]$^+$ calc'd for $C_{24}H_{26}ClFN_6O_4$, 517.17; found 517.2.

Example 41

(2R,4R)-2-(3-Aminopropionylamino)-5-(5'-chloro-2'-fluoro-biphenyl-4-yl)-4-[(3H-[1,2,3]triazole-4-carbonyl)amino]pentanoic Acid Compound 2 was prepared as described herein.

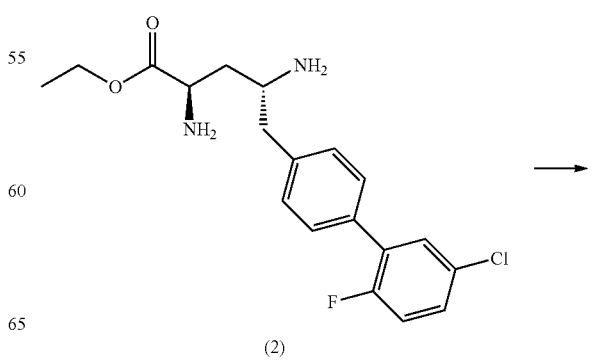

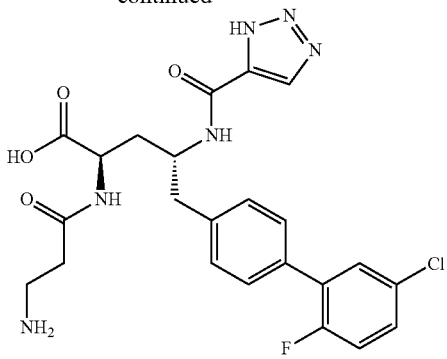

3-t-Butoxycarbonylaminopropionic acid (5.9 mg, 31 μmol) and HATU (10.8 mg, 28 μmol) were dissolved in DMF (3 mL) and stirred for 15 minutes at room temperature. Compound 2 (12.3 mg, 28 μmol) and DIPEA (15 μL, 85 μmol) were added, and the mixture was stirred at room temperature for 15 minutes (LC/MS showed the desired product) then concentrated in vacuo and the residue was dissolved in MeCN (2 mL). A solution of 4N HCl in dioxane (107 mL, 427 μmol) was added, and the mixture was stirred for 15 minutes at room temperature. LC/MS showed the desired mass. The solvent was removed in vacuo and the residue was purified by preparative HPLC to yield the title compound (8.2 mg; purity 100%) as a TFA salt. MS m/z [M+H]$^+$ calc'd for $C_{23}H_{24}ClFN_6O_4$, 503.15; found 503.2.

Example 42

(2R,4R)-2-((R)-2-Amino-3-hydroxypropionylamino)-5-(5'-chloro-2'-fluorobiphenyl-4-yl)-4-[(4-isopropyloxazole-2-carbonyl)-amino]pentanoic Acid (compound 42-1) and (2R,4R)-2-((S)-2-Amino-3-hydroxypropionylamino)-5-(5'-chloro-2'-fluorobiphenyl-4-yl)-4-[(4-isopropyloxazole-2-carbonyl)amino]pentanoic Acid (compound 42-2)

(R)-2-t-Butoxycarbonylamino-3-hydroxypropionic acid (4.5 mg, 22 μmol) and HATU (8.4 mg, 22 μmol) were dissolved in DMF (2 mL) and stirred at room temperature for 15 minutes. (2R,4R)-2-Amino-5-(5'-chloro-2'-fluorobiphenyl-4-yl)-4-[(4-isopropyloxazole-2-carbonyl)amino]pentanoic acid (10 mg, 21 μmol) and DIPEA (11 μL, 63 μmol) were added, and the resulting mixture was stirred at room temperature for 15 minutes, at which time LCMS indicated the mass of the desired compound. The mixture was concentrated in vacuo and the residue was dissolved in MeCN (2 mL). An excess of a solution of 4N HCl in dioxane was added, and the resulting mixture was stirred at room temperature for 15 minutes, at which time LCMS indicated the mass of the desired compound. The mixture was concentrated in vacuo and the residue was purified by preparative HPLC to yield the title Compound 42-1 (1 mg; purity 100%) as a TFA salt. MS m/z [M+H]$^+$ calc'd for $C_{27}H_{30}ClFN_4O_6$, 561.18; found 561.2.

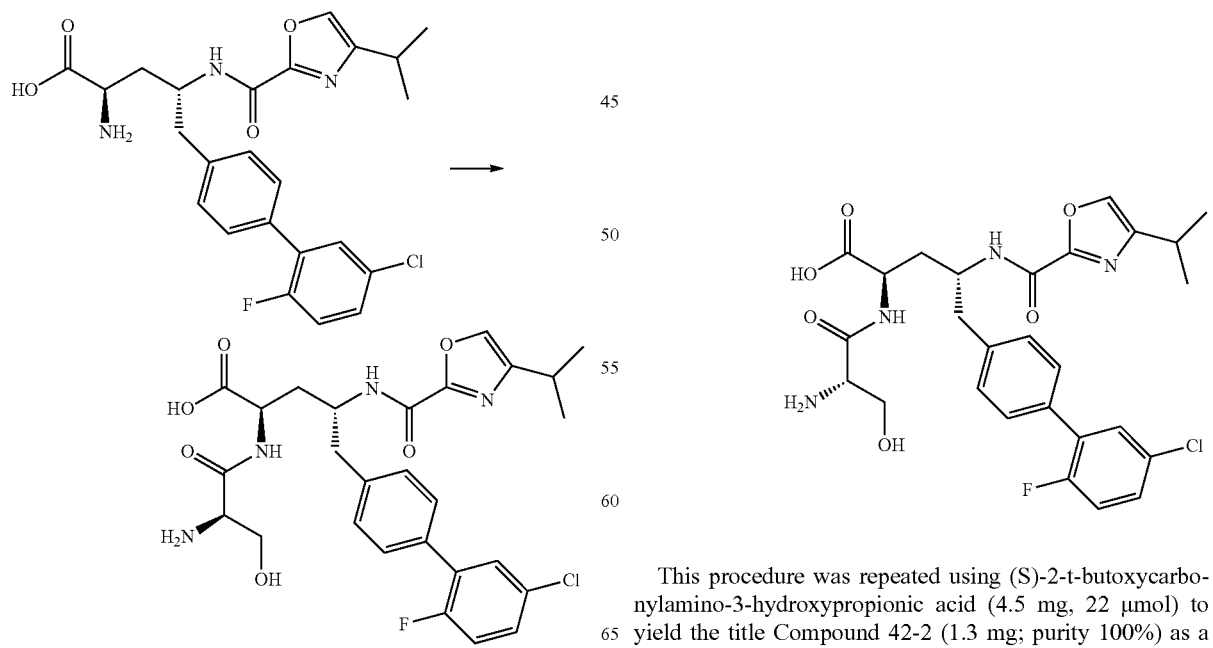

This procedure was repeated using (S)-2-t-butoxycarbonylamino-3-hydroxypropionic acid (4.5 mg, 22 μmol) to yield the title Compound 42-2 (1.3 mg; purity 100%) as a TFA salt. MS m/z [M+H]$^+$ calc'd for $C_{27}H_{30}ClFN_4O_6$, 561.18; found 561.2.

Example 43

(2S,4S)-2-[(2-Aminoacetylamino)methyl]-5-(5'-chloro-2'-fluorobiphenyl-4-yl)-4-[(5-methyloxazole-2-carbonyl)amino]pentanoic Acid

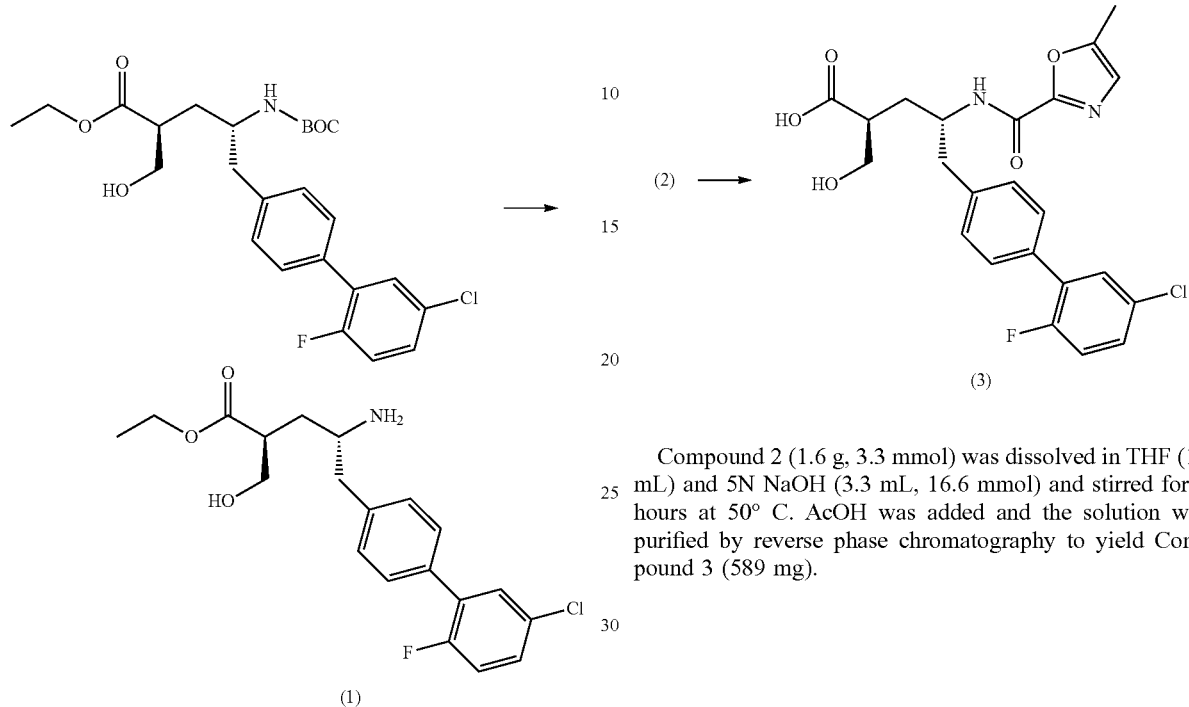

(2S,4S)-4-t-Butoxycarbonylamino-5-(5'-chloro-2'-fluoro-biphenyl-4-yl)-2-hydroxymethylpentanoic acid ethyl ester (1.65 g, 3.4 mmol) was dissolved in MeCN (6 mL) and 4N HCl in dioxane (3 mL), and stirred for 10 minutes. The mixture was concentrated under reduced pressure to yield Compound 1 (1.26 g) as and HCl salt, which was used without further purification.

5-methyloxazole-2-carboxylic acid (422 mg, 3.3 mmol) was combined with HATU (1261 mg, 3.3 mmol) in DMF (3 mL) and stirred for 10 minutes. DIPEA (869 µL) was added and the mixture was stirred for 1 minute. Compound 1 (1.26 g, 3.3 mmol) was dissolved in DMF (1 mL) and DIPEA (869 µL) was added, followed by addition of the activated 5-methyloxazole-2-carboxylic acid solution. The resulting mixture was stirred for 30 minutes and concentrated in vacuo to yield Compound 2, which was used without further purification.

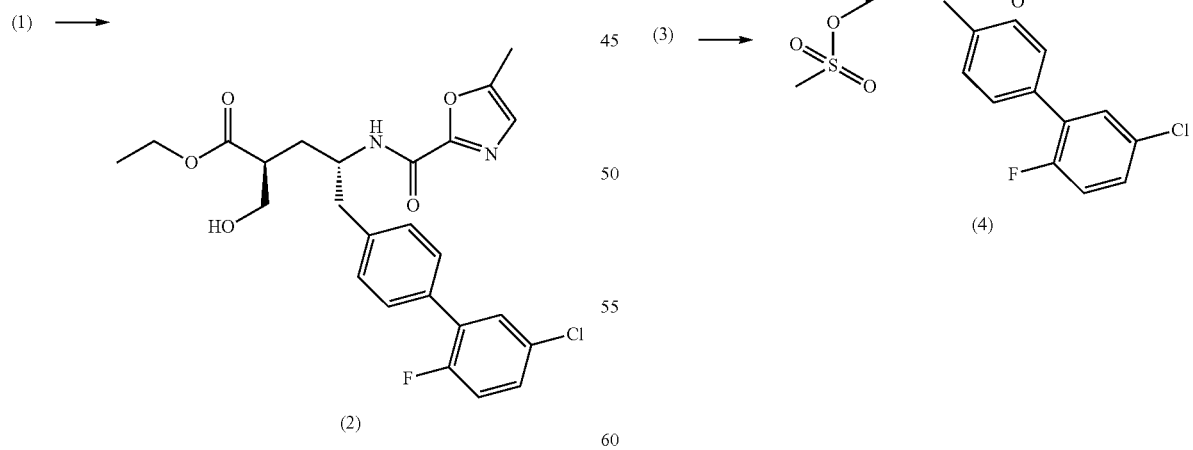

Compound 2 (1.6 g, 3.3 mmol) was dissolved in THF (10 mL) and 5N NaOH (3.3 mL, 16.6 mmol) and stirred for 2 hours at 50° C. AcOH was added and the solution was purified by reverse phase chromatography to yield Compound 3 (589 mg).

To a stirred solution of Compound 3 (390 mg, 846 µmol) in DCM (10 mL), was added methanesulfonyl chloride (79 µL, 1.0 mmol) and Et₃N (259 µL, 1.9 mmol). The resulting mixture was stirred for 5 minutes and concentrated in vacuo to yield Compound 4, which was used without further purification.

(4) ⟶

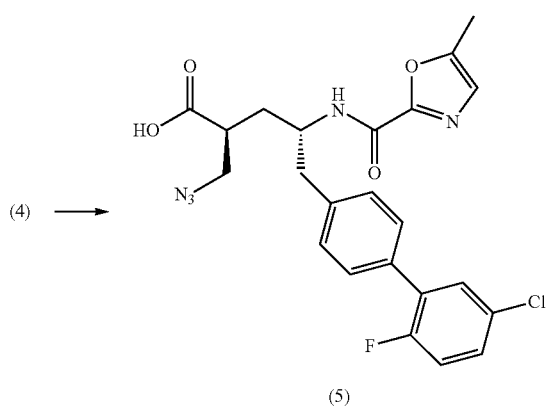 [SMILES: Cc1cnc(C(=O)N[C@H](Cc2ccc(-c3cc(Cl)ccc3F)cc2)C[C@@H](CN=[N+]=[N-])C(=O)O)o1]

(5)

Compound 4 (200 mg, 371 µmol) in DMF (1 mL) was combined with sodium azide (72.4 mg, 1.1 mmol) and the mixture was stirred at 50° C. for 2 hours. The reaction was quenched with water and extracted with EtOAc. The organic layer was washed with water (3×) and then concentrated in vacuo. The residue was then purified by normal phase chromatography (0-100% EtOAc/hexanes) to yield Compound 5.

(5) ⟶

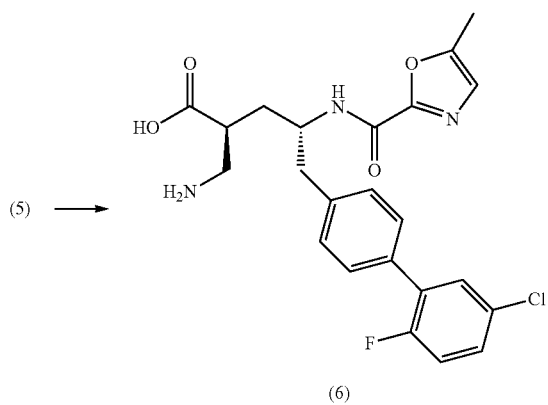 [SMILES: Cc1cnc(C(=O)N[C@H](Cc2ccc(-c3cc(Cl)ccc3F)cc2)C[C@@H](CN)C(=O)O)o1]

(6)

Compound 5 (100 mg, 206 µmol) was combined with palladium on carbon (11 mg, 21 µmol), AcOH (0.3 mL) and EtOAc (1 mL). The reaction flask was purged with nitrogen and hydrogen (1 atm) added. The mixture was stirred for 2 hours. Hydrogen was removed in vacuo and nitrogen added. To the mixture was added AcOH (2 mL), the mixture was filtered and the solution was purified by reverse phase chromatography to yield Compound 6 (40 mg).

(6) ⟶

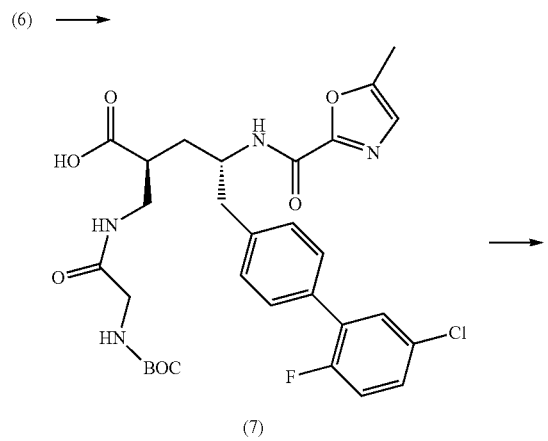

(7)

-continued

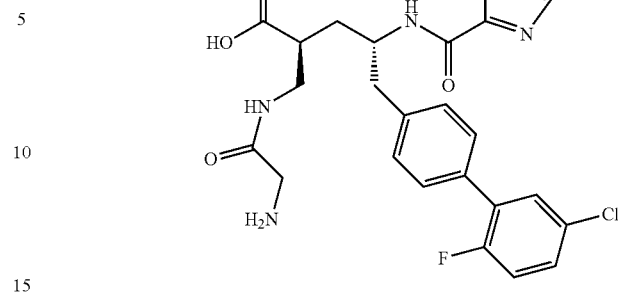

t-Butoxycarbonylamino acetic acid (3.1 mg, 17 µmol) was combined with HATU (6.6 mg, 17 µmol), DMF (0.5 mL) and DIPEA (9.1 µL, 52 µmol), and stirred for 5 minutes. This was then added to a solution of Compound 6 (8.0 mg, 17 µmol) in DMF (0.5 mL) and DIPEA (3 eq.). The mixture was stirred for 10 minutes and the reaction was quenched with a saturated NaHCO₃ solution (1 mL) and EtOAc (3 mL). The organic layer was extracted and dried over MgSO₄, filtered and concentrated under pressure to yield Compound 7.

Compound 7 (8 mg, 13 µmol) was dissolved in MeCN (0.5 mL) and dry 4N HCl in dioxane (0.5 mL). The mixture was stirred for 10 minutes and the solvent removed under reduced pressure. The residue was then purified by reverse phase chromatography to yield the title compound (2.5 mg; purity 95%) as a TFA salt. MS m/z [M+H]⁺ calc'd for $C_{25}H_{26}ClFN_4O_5$, 517.16; found 517.

Example 44

Following the procedures described herein, and substituting the appropriate starting materials and reagents, these compounds were prepared as a TFA salt:

| Ex. | R¹ | R⁶ | Formula | MS m/z: [M + H]⁺ calcd | found |
|---|---|---|---|---|---|
| 1 | H | triazole | $C_{23}H_{24}ClFN_6O_4$ | 503.15 | 502 |
| 2 | —CH₂CH₃ | triazole | $C_{25}H_{28}ClFN_6O_4$ | 531.18 | 531 |

1. (2S,4S)-2-[(2-Aminoacetylamino)methyl]-5-(5'-chloro-2'-fluorobiphenyl-4-yl)-4-[(3H-[1,2,3]triazole-4-carbonyl)amino]pentanoic acid
2. (2S,4S)-2-[(2-Aminoacetylamino)methyl]-5-(5'-chloro-2'-fluorobiphenyl-4-yl)-4-[(3H-[1,2,3]triazole-4-carbonyl)amino]pentanoic acid ethyl ester Example 45

(2S,4S)-2-[(2-Amino-2-methylpropionylamino)methyl]-5-(5'-chloro-2'-fluorobiphenyl-4-yl)-4-[(5-methyloxazole-2-carbonyl)-amino]pentanoic Acid Compound 6 was prepared as described herein

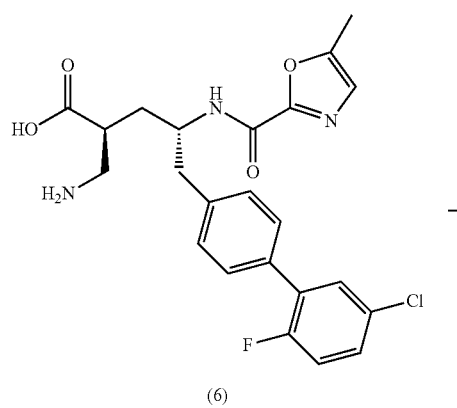

(6)

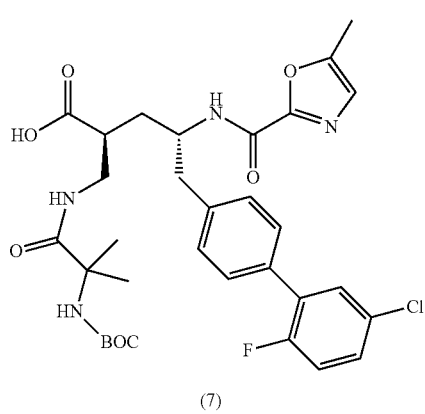

(7)

2-t-Butoxycarbonylamino-2-methylpropionic acid (3.5 mg, 17 µmol) was combined with HATU (6.6 mg, 17 µmol), DMF (0.5 mL) and DIPEA (9.1 µL, 52 µmol), and stirred for 5 minutes. This was then added to a solution of Compound 6 (8.0 mg, 17 µmol) in DMF (0.5 mL) and DIPEA (3 eq.). The mixture was stirred for 10 minutes and the reaction was quenched with a saturated aqueous NaHCO₃ solution (1 mL) and EtOAc (3 mL). The organic layer was separated and dried over MgSO₄ followed by evaporation under pressure to yield Compound 7.

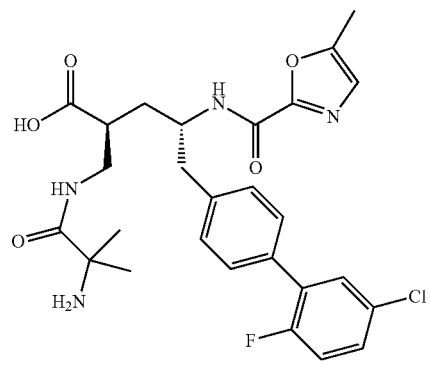

(7) →

Compound 7 (8.4 mg, 13 µmol) was dissolved in MeCN (0.5 mL) and dry 4N HCl in dioxane (0.5 mL). The mixture was stirred for 10 minutes and the solvent removed under reduced pressure. The residue was then purified (reverse phase chromatography) to yield the title compound (2 mg; purity 95%) as a TFA salt. MS m/z [M+H]⁺ calc'd for $C_{27}H_{30}ClFN_4O_5$, 545.19; found 545.

Example 46

(2R,4R)-5-(5'-Chloro-2'-fluorobiphenyl-4-yl)-2-((S)-2-methoxycarbonylamino-3-methylbutyrylamino)-4-[(1H-[1,2,3]triazole-4-carbonyl)amino]pentanoic Acid

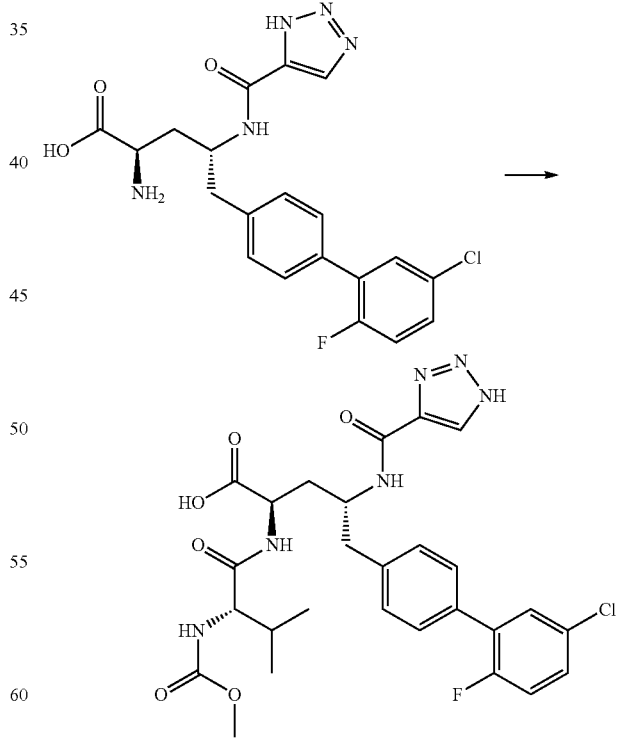

(2S)-2-[(methoxycarbonyl)amino]-3-methylbutanoic acid (6.7 mg, 38 µmol) and HATU (13.9 mg, 36 µmol) were dissolved in DMF (4 mL) and stirred at room temperature for 15 minutes. (2R,4R)-2-Amino-5-(5'-chloro-2'-fluorobiphenyl-4-yl)-4-[(3H-[1,2,3]triazole-4-carbonyl)amino]pentanoic acid (15 mg, 35 μmol) and DIPEA (15 μL, 87 μmol) were then added, and the resulting mixture was stirred at room temperature for 15 minutes. LC/MS showed reaction completion (2 isomers were observed). The solution was concentrated in vacuo and the residue was purified by preparative HPLC to yield the title compound (6 mg; purity 100%) as a white powder TFA salt. The 1:1 ratio of isomers were not isolated. MS m/z [M+H]+ calc'd for $C_{27}H_{30}ClFN_6O_6$, 589.19; found 589.19.

Example 47

(2R,4R)-5-Biphenyl-4-yl-2-methanesulfonylamino-4-[(1H-[1,2,3]triazole-4-carbonyl)amino]pentanoic Acid Compound 4 was prepared as described herein.

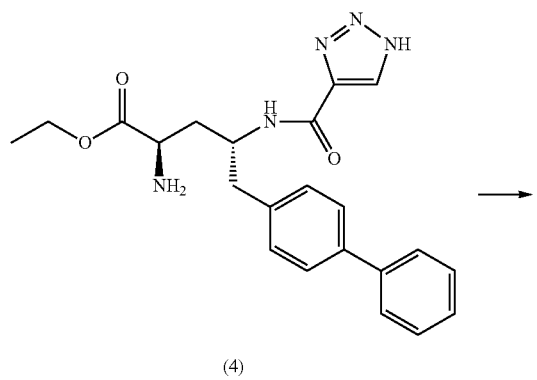

(4)

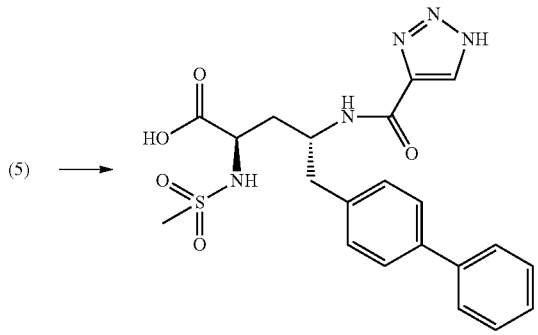 [SMILES: CS(=O)(=O)N[C@H](C[C@@H](Cc1ccc(-c2ccccc2)cc1)NC(=O)c1c[nH]nn1)C(=O)O]

(5)

Compound 5 (11.5 mg, 24 μmol) was dissolved in THF (1 mL) and 1N NaOH (119 μL, 119 μmol) and stirred for 3 hours. The reaction was quenched with AcOH and the solution was purified by reverse phase chromatography to yield the title compound (2 mg; purity 95%) as a TFA salt. MS m/z [M+H]$^+$ calc'd for $C_{21}H_{23}N_5O_5S$, 458.14; found 458.

Example 48

(2S,4S)-5-(5'-Chloro-2'-fluorobiphenyl-4-yl)-2-[(2-hydroxyethylamino)methyl]-4-[(3H-[1,2,3]triazole-4-carbonyl)amino]pentanoic Acid (isomer a) and (isomer b) and (2S,4S)-5-(5'-Chloro-2'-fluorobiphenyl-4-yl)-2-[(2-hydroxyethylamino)methyl]-4-[(3H-[1,2,3]triazole-4-carbonyl)-amino]pentanoic Acid Ethyl Ester (compound c)

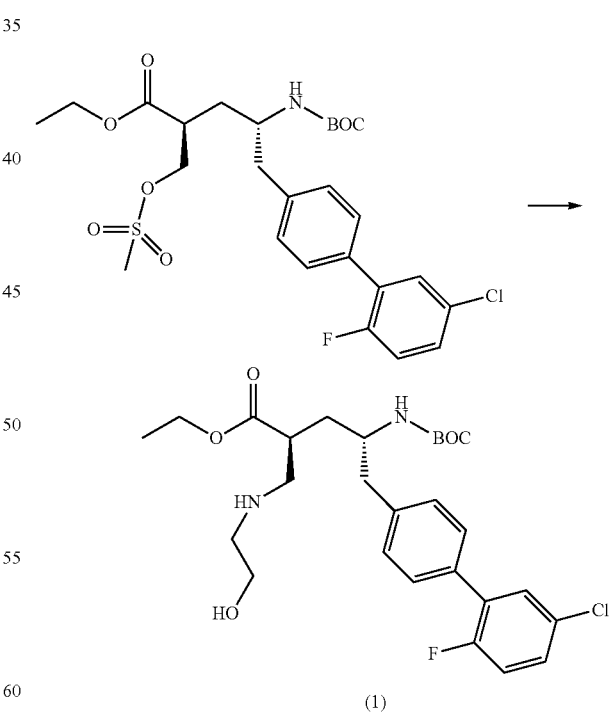

(1)

Compound 4 (10 mg, 25 μmol) was combined with DCM (2 mL), methanesulfonyl chloride (2.8 mg, 25 μmol) and Et$_3$N (3.4 μL, 25 μmol). The mixture was stirred for 10 minutes and the solvent evaporated to yield Compound 5.

(2S,4S)-4-t-Butoxycarbonylamino-5-(5'-chloro-2'-fluorobiphenyl-4-yl)-2-methanesulfonyloxymethylpentanoic acid ethyl ester (28 mg, 50 μmol) was combined with EtOH (2 mL), followed by Na$_2$CO$_3$ (16.0 mg, 151 μmol) and 2-aminoethanol (9.2 mg, 151 μmol) and stirred at 70° C. overnight.

EtOAc and water were added, the organic layer was separated and concentrated under reduced pressure to yield Compound 1.

(1) ⟶

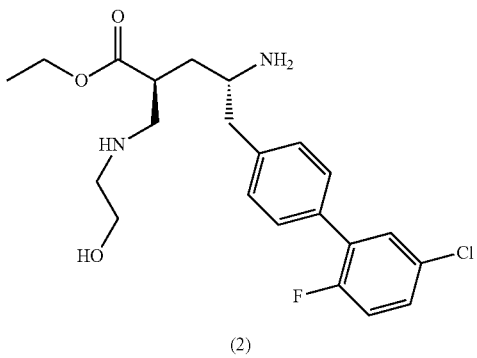

(2)

Compound 1 (25.7 mg, 49 μmol) was dissolved in MeCN (0.5 mL) and dry 4N HCl in dioxane (0.1 mL). The mixture was stirred for 10 minutes and was then concentrated under reduced pressure. The residue was purified by reverse phase chromatography to yield Compound 2 (8 mg).

(2) ⟶

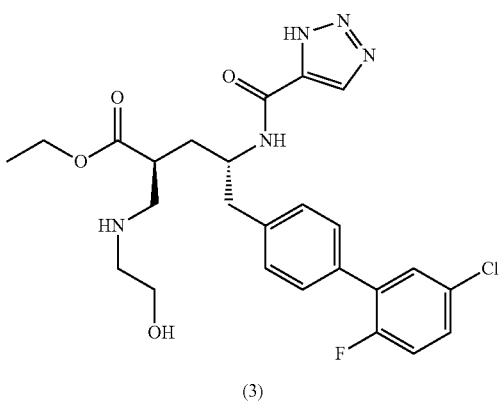

(3)

3H-1,2,3-triazole-5-carboxylic acid (1.1 mg, 10.0 μmol) was combined with HATU (3.0 mg, 7.8 μmol) in DMF (0.5 mL) and stirred for 10 minutes; DIPEA (1.0 eq.) was added and the mixture was stirred for 1 minute. Compound 2 (4.7 mg, 11 μmol) was dissolved in DMF (1 mL) and DIPEA (5.8 μL, 33 mmol) was added, followed by addition of the activated acid solution. The mixture was stirred for 30 minutes to yield crude Compound 3.

(3) ⟶

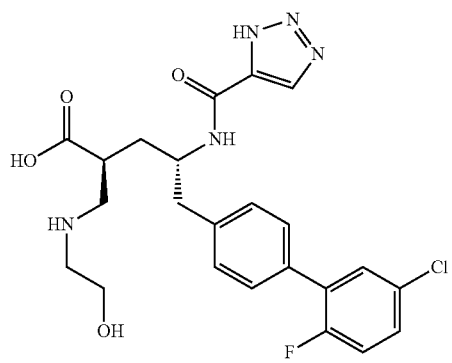

To the crude solution of Compound 3 (5.7 mg, 11 μmol) was added 1N LiOH (55.1 μL, 55 μmol) and THF (0.5 mL). The mixture was stirred for 40 minutes and AcOH (1 mL) was added. The solution was purified by reverse phase chromatography to yield isomer a (MS m/z [M+H]$^+$ calc'd for $C_{23}H_{25}ClFN_5O_4$, 490.16; found 490) and isomer b (MS m/z [M+H]$^+$ calc'd for $C_{23}H_{25}ClFN_5O_4$, 490.16; found 490).

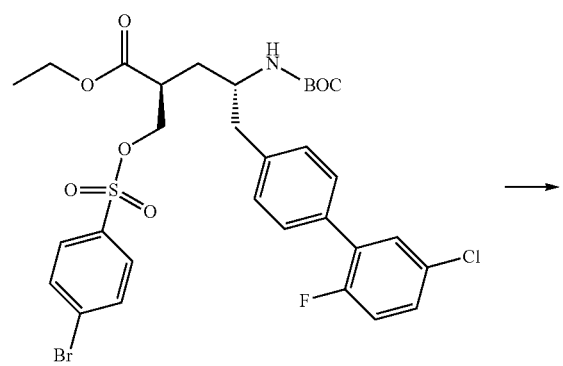

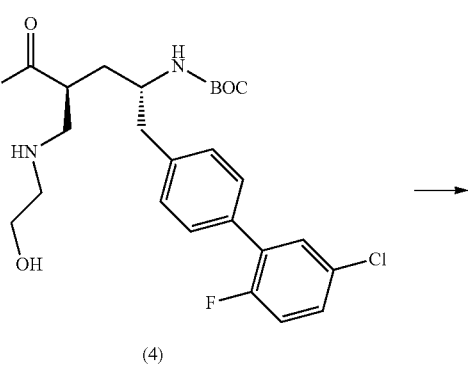

(4)

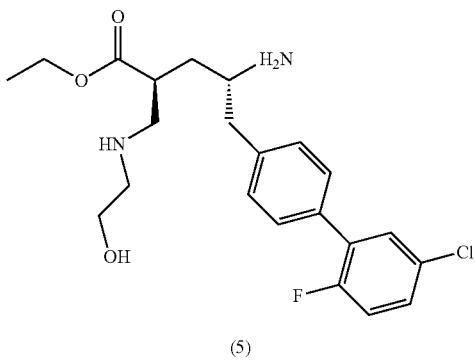

(5)

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (100 mg, 143 μmol) was dissolved in EtOH (3 mL), followed by addition of Na₂CO₃ (152 mg, 1.4 mmol) and 2-aminoethanol (44 mg, 715 μmol). The resulting mixture was stirred for 2 days at 70° C., at which time LCMS indicated the mass of the desired compound. The mixture was concentrated under reduced pressure and the crude residue was dissolved in AcOH (4 mL) and H₂O (1 mL) and purified by reverse phase chromatography (10-80% MeCN/H₂O gradient) to yield Compound 4 (20 mg).

Compound 4 (26 mg, 50 μmol) was dissolved in MeCN (1 mL) and dry 4N HCl in dioxane (0.5 mL). The mixture was stirred for 10 minutes and then concentrated under reduced pressure to yield Compound 5 as an HCl salt, which was used in the next step without purification.

(5) ⟶

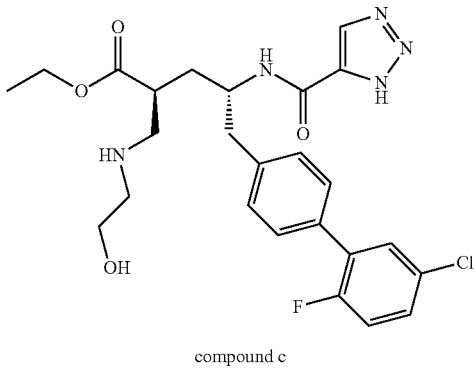

compound c 1H-1,2,3-triazole-5-carboxylic acid (3.4 mg, 30 μmol) was combined with HATU (11 mg, 30 μmol) in DMF (0.3 mL) and stirred at room temperature for 10 minutes; DIPEA (1 eq.) was added and the mixture was stirred for 1 minute. Compound 5 (9 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield the title compound c as a TFA salt (1 mg). MS m/z [M+H]⁺ calc'd for C₂₅H₂₉ClFN₅O₄, 518.19; found 518.

Example 49

(2S,4S)-5-(5'-Chloro-2'-fluorobiphenyl-4-yl)-2-[(2-methoxyethylamino)-methyl]-4-[(3H-[1,2,3]triazole-4-carbonyl)aminol]pentanoic Acid (isomer a) and (isomer b) and (2S,4S)-5-(5'-Chloro-2'-fluorobiphenyl-4-yl)-2-[(2-methoxyethylamino)methyl]-4-[(3H-[1,2,3]triazole-4-carbonyl)-amino]pentanoic Acid Ethyl Ester (compound c)

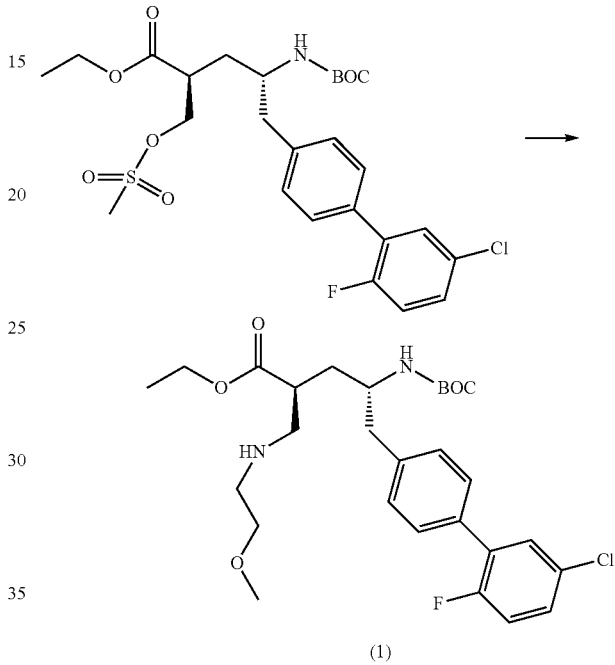

(1)

(2S,4S)-4-t-Butoxycarbonylamino-5-(5'-chloro-2'-fluorobiphenyl-4-yl)-2-methanesulfonyloxymethylpentanoic acid ethyl ester (28 mg, 50 μmol) was combined with EtOH (2 mL), followed by Na₂CO₃ (16.0 mg, 151 μmol) and 2-methoxyethylamine (11.3 mg, 151 μmol) and stirred at room temperature overnight. EtOAc and water was added, the organic layer was separated and concentrated under reduced pressure to yield Compound 1.

(1) ⟶

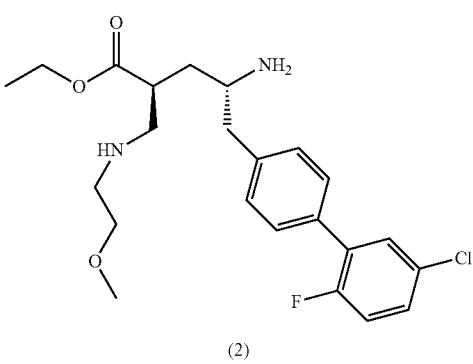

(2)

Compound 1 (26.4 mg, 49 μmol) was dissolved in MeCN (0.5 mL) and dry 4N HCl in dioxane (0.1 mL). The mixture was stirred for 10 minutes and was then concentrated under reduced pressure. The residue was purified by reverse phase chromatography to yield Compound 2 (10 mg).

(2) ⟶

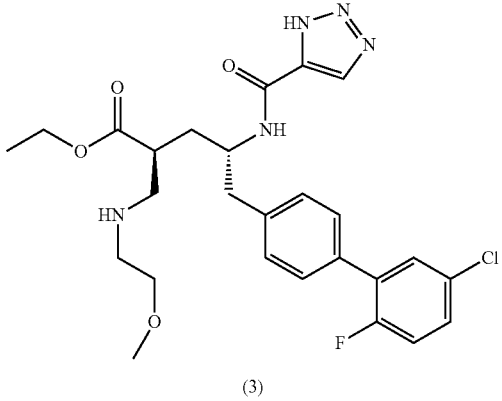

(3)

3H-1,2,3-triazole-5-carboxylic acid (1.1 mg, 10.0 μmol) was combined with HATU (3.0 mg, 7.8 μmol) in DMF (0.5 mL) and stirred for 10 minutes; DIPEA (1.0 eq.) was added and the mixture was stirred for 1 minute. Compound 2 (4.9 mg, 11 μmol) was dissolved in DMF (1 mL) and DIPEA (5.8 μL, 33 mmol) was added, followed by addition of the activate acid solution. The mixture was stirred for 30 minutes to yield Compound 3.

(3) ⟶

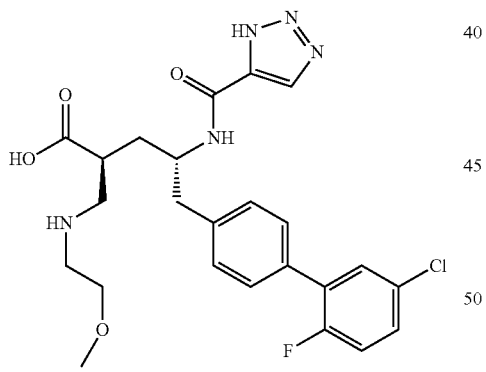

To a solution of crude Compound 3 (5.9 mg, 11 μmol) was added 1N LiOH (55.1 μL, 55 μmol) and THF (0.5 mL). The mixture was stirred for 40 minutes and AcOH (1.0 mL) was added. The solution was purified by reverse phase chromatography to yield isomer a (MS m/z [M+H]$^+$ calc'd for $C_{24}H_{27}ClFN_5O_4$, 504.17; found 504) and isomer b (MS m/z [M+H]$^+$ calc'd for $C_{24}H_{27}ClFN_5O_4$, 504.17; found 504).

compound c 1H-1,2,3-triazole-4-carboxylic acid (2.6 mg, 23 μmol) and HATU (9.6 mg, 25 μmol) were combined in DMF (3.0 mL) and stirred at room temperature for 15 minutes. (2S, 4S)-4-Amino-5-(5'-chloro-2'-fluorobiphenyl-4-yl)-2-[(2-methoxyethylamino)methyl]-pentanoic acid ethyl ester (10 mg, 23 μmol) and DIPEA (12 μL, 69 μmol) were added and the resulting solution was stirred at room temperature for 15 minutes, after which time LCMS indicated desired product formation. The solvent was removed in vacuo and the crude residue was purified by reverse phase chromatography to yield the title compound c as a TFA salt (1.2 mg). MS m/z [M+H]$^+$ calc'd for $C_{26}H_{31}ClFN_5O_4$, 532.21; found 532.

Example 50

(2S,4S)-5-Biphenyl-4-yl-2-cyanomethyl-4-[(3H-[1,2,3]triazole-4-carbonyl)amino]pentanoic Acid

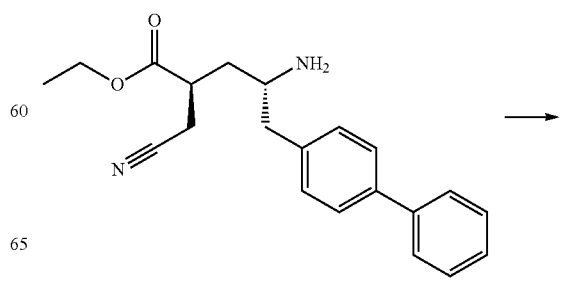

-continued

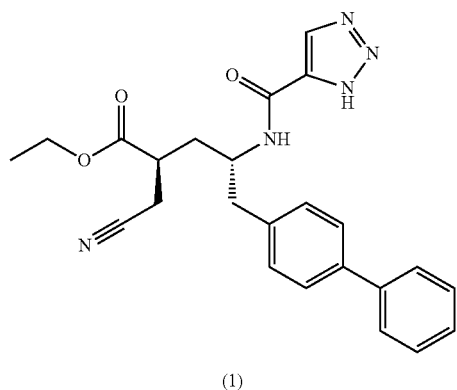

(1)

(2S,4S)-4-Amino-5-biphenyl-4-yl-2-cyanomethylpentanoic acid ethyl ester (70 mg, 199 µmol) was combined with DMF (1 mL), HATU (76 mg, 199 µmol), DIPEA (104 µL, 596 µmol), and 3H-[1,2,3]triazole-4-carboxylic acid (22 mg, 199 µmol) and the mixture was stirred at room temperature for 20 minutes. The solvent was evaporated and the crude mixture was purified by normal phase chromatography (0-100% EtOAc/hexanes) to yield Compound 1 (60 mg).

(1) → 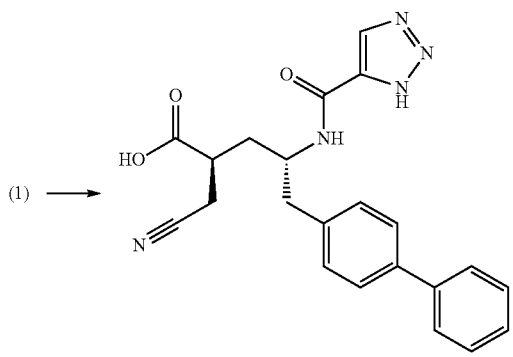 [SMILES: N#CC[C@H](C[C@@H](Cc1ccc(-c2ccccc2)cc1)NC(=O)c1cnn[nH]1)C(=O)O]

Compound 1 (28.9 mg, 67 µmol) was dissolved in THF (1 mL) and 1N NaOH (268 µL, 268 µmol) and stirred at room temperature for 1 hour. The mixture was acidified with AcOH (1 mL) and purified by preparative HPLC to yield the title compound (19 mg; purity 90%) as a TFA salt. MS m/z [M+H]$^+$ calc'd for $C_{22}H_{21}N_5O_3$, 404.16; found 404.

Example 51

(2S,4S)-5-(5'-Chloro-2'-fluorobiphenyl-4-yl)-2-cyanomethyl-4-[(1H-[1,2,3]triazole-4-carbonyl)amino]pentanoic Acid

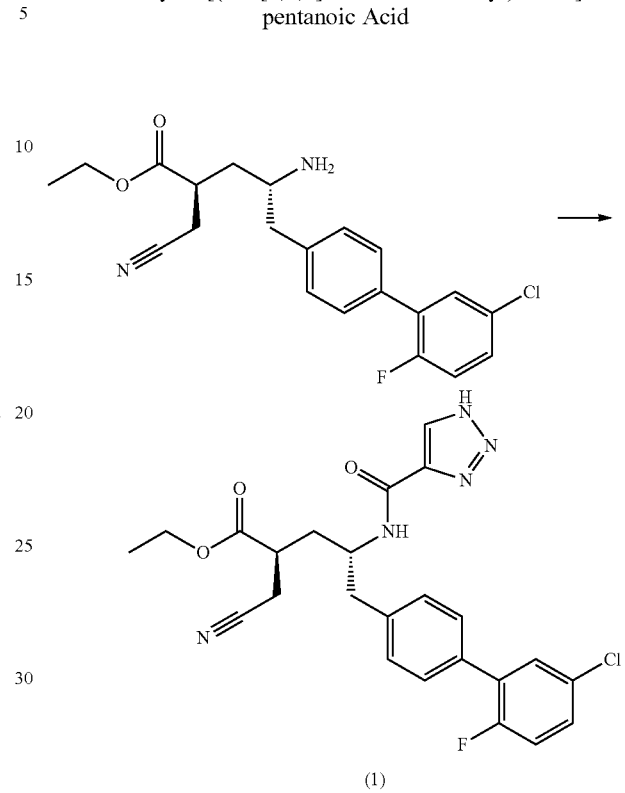

(1)

(2S,4S)-4-Amino-5-(5'-chloro-2'-fluorobiphenyl-4-yl)-2-cyanomethylpentanoic acid ethyl ester (55 mg, 141 µmol) was combined with 3H-[1,2,3]triazole-4-carboxylic acid (19.2 mg, 170 µmol), HATU (64.5 mg, 170 µmol) and DIPEA (79 µL, 453 µmol) in DMF (2 mL) and was stirred at room temperature for 30 minutes then concentrated in vacuo and the crude residue was purified by normal phase chromatography (0-100% EtOAc/hexanes) to yield Compound 1 55 mg).

(1) → 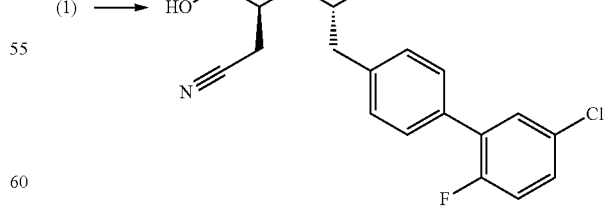

Compound 1 (48.4 mg, 0.1 mmol) was dissolved in THF (2 mL) and 2N NaOH (250 µL, 0.5 mmol) and stirred for 1 hour, then concentrated under reduced pressure. The crude residue was dissolved in AcOH (2 mL) was purified by reverse phase chromatography to yield the title compound (15 mg; purity 95%) as a TFA salt. MS m/z [M+H]+ calc'd for $C_{22}H_{19}ClFN_5O_3$, 456.12; found 455.

Example 52

Following the procedures described herein, and substituting the appropriate starting materials and reagents, these compounds were prepared as the parent compound:

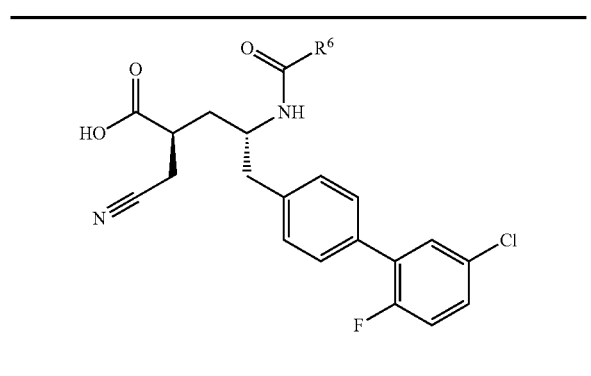

| Ex. | R⁶ | Formula | MS m/z: [M + H]+ calcd | found |
|---|---|---|---|---|
| 1 | (5-tert-butyl-3-methylisothiazol-4-yl) | $C_{24}H_{21}ClFN_3O_3S$ | 486.1 | 486.2 |
| 2 | (5-tert-butyl-3-methylisothiazol-4-yl) | $C_{24}H_{21}ClFN_3O_3S$ | 486.1 | 486.2 |
| 3 | (tert-butylisothiazol-4-yl) | $C_{23}H_{19}ClFN_3O_3S$ | 472.08 | 472.2 |

1. (S)-5-(5'-Chloro-2'-fluorobiphenyl-4-yl)-2-cyanomethyl-4-[(3-methylisothiazole-5-carbonyl)amino]pentanoic acid (diastereomer 1)
2. (S)-5-(5'-Chloro-2'-fluorobiphenyl-4-yl)-2-cyanomethyl-4-[(3-methylisothiazole-5-carbonyl)amino]pentanoic acid (diastereomer 2)
3. (2S,4S)-5-(5'-Chloro-2'-fluorobiphenyl-4-yl)-2-cyanomethyl-4-[(isothiazole-4-carbonyl)amino]pentanoic acid

Example 53

(2S,4S)-5-Biphenyl-4-yl-2-carbamoylmethyl-4-[(3H-[1,2,3]triazole-4-carbonyl)amino]pentanoic Acid

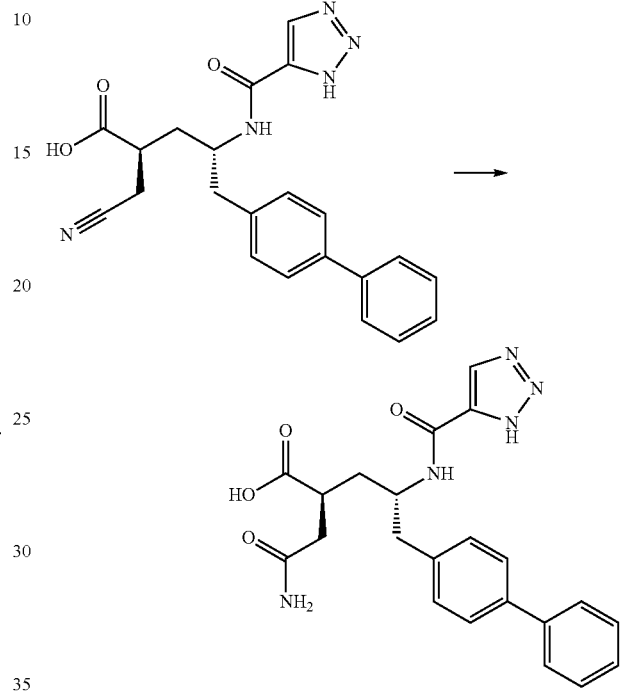

(2S,4S)-5-Biphenyl-4-yl-2-cyanomethyl-4-[(3H-[1,2,3] triazole-4-carbonyl)amino]pentanoic acid (5 mg, 12 μmol) was combined with DMSO (0.5 mL), $H_2O_2$ (54.4 μL, 533 μmol) and $K_2CO_3$ (15.4 mg, 112 μmol), and stirred overnight. The reaction was quenched with 1 drop of concentrated HCl. AcOH was added and the mixture was purified by reverse phase chromatography to yield the title compound (2 mg; purity 95%) as a TFA salt. MS m/z [M+H]+ calc'd for $C_{22}H_{23}N_5O_4$, 422.18; found 422.

Example 54

(2R,4S)-2-Carbamoylmethyl-5-(3'-fluorobiphenyl-4-yl)-4-[(3H-[1,2,3]triazole-4-carbonyl)amino]pentanoic Acid

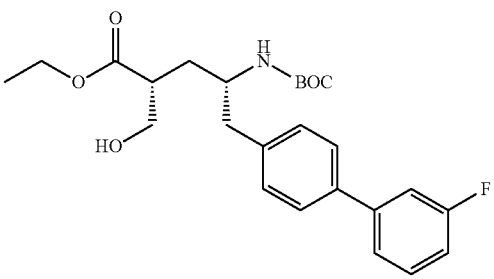

-continued

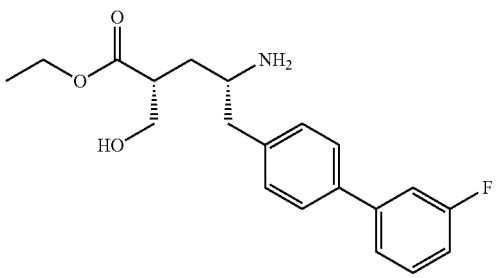

(1)

(2R,4S)-4-t-butoxycarbonylamino-5-(3'-fluorobiphenyl-4-yl)-2-hydroxymethylpentanoic acid ethyl ester (985 mg, 2.2 mmol) was dissolved in MeCN (10 mL) and 4N HCl in dioxane (5 mL) and stirred for 15 minutes, then concentrated under reduced pressure to yield Compound 1.

(1) →

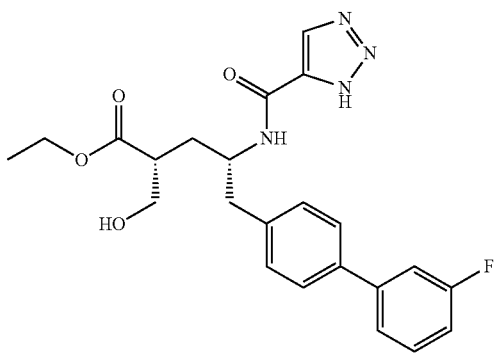

(2)

Compound 1 (500 mg, 1.4 mmol) was combined with HATU (656 mg, 1.7 mmol), 3H-[1,2,3]triazole-4-carboxylic acid (195 mg, 1.7 mmol) and DMF (3 mL). DIPEA (803 μL, 4.6 mmol) was added and the mixture was stirred for 30 minutes. Saturated aqueous NH₄Cl (10 mL) and EtOAc (40 mL) were added. The organic layer was separated and dried over MgSO₄. The solvent was evaporated and the residue purified by normal phase chromatography (0-100% EtOAc/hexanes) to yield Compound 2 (650 mg).

(2) →

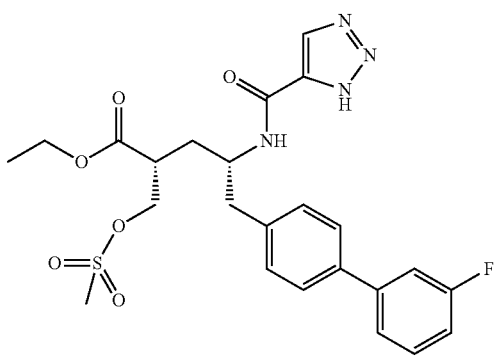

(3)

Compound 2 (650 mg, 1.5 mmol) was dissolved in DCM (3 mL). Methanesulfonyl chloride (173 μL, 2.2 mmol) was added at 0° C., followed by the slow addition of Et₃N (425 μL, 3.0 mmol). The mixture was stirred for 10 minutes and the solution was purified by normal phase chromatography (0-100% EtOAc/hexanes) to yield Compound 3 (690 mg).

(3) →

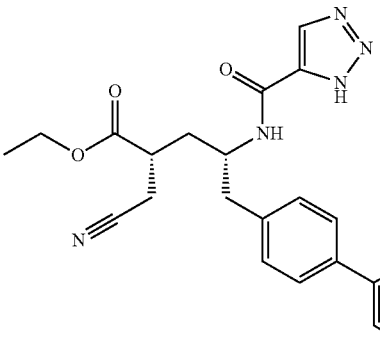

(4)

Compound 3 (390 mg, 752 μmol) was dissolved in DMF (2 mL). Sodium cyanide (47.9 mg, 978 μmol) and DMAP (3 mg) was added and the mixture was stirred at 50° C. overnight. EtOAc (5 mL) and water (2 mL) were added, the organics were separated and washed (3×) with water, then concentrated under reduced pressure. The crude residue was purified by normal phase chromatography (0-100% EtOAc/hexanes) to yield Compound 4 (90 mg).

(4) →

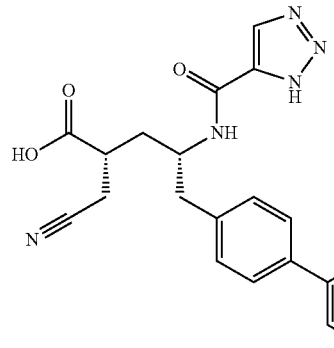

(5)

Compound 4 (90 mg, 0.2 mmol) was dissolved in THF (1 mL) and 2N NaOH (160 μL, 0.8 mmol). The mixture was stirred for 2 hours. AcOH (2 mL0 was added and the solution was purified by reverse phase chromatography to yield Compound 5 (35 mg).

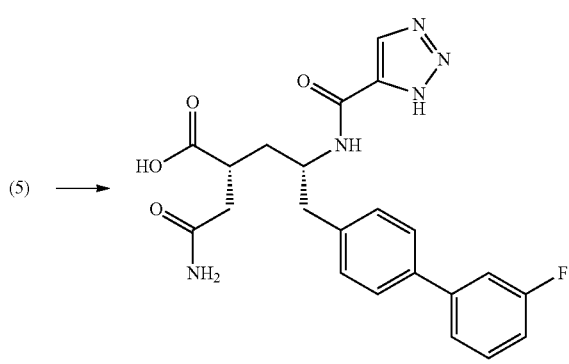 [SMILES: NC(=O)C[C@@H](C[C@@H](Cc1ccc(-c2cccc(F)c2)cc1)NC(=O)c1cnn[nH]1)C(=O)O]

(5) →

Compound 5 (8 mg, 19 μmol) was combined with DMSO (0.5 mL), H$_2$O$_2$ (83 μL, 816 μmol) and K$_2$CO$_3$ (23.6 mg, 171 μmol), and stirred overnight. The reaction was quenched with 1 drop of concentrated HCl. AcOH was added and the mixture was purified by reverse phase chromatography to yield the title compound (2 mg; purity 95%) as a TFA salt. MS m/z [M+H]$^P$ calc'd for C$_{22}$H$_{22}$FN$_5$O$_4$, 440.17; found 441.

Example 55

(2R,4R)-5-(5'-Chloro-2'-fluorobiphenyl-4-yl)-2-[((S)-pyrrolidine-2-carbonyl)amino]-4-[(3H-[1,2,3]triazole-4-carbonyl)amino]pentanoic Acid Compound 2 was prepared as described herein.

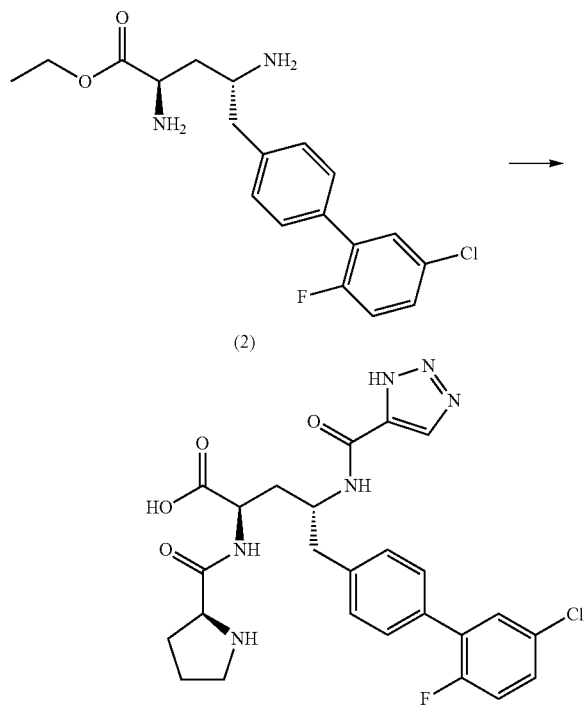

(S)-Pyrrolidine-2-carboxylic acid (3.6 mg, 31 μmol) and HATU (11.4 mg, 30 μmol) were dissolved in DMF (3 mL) and stirred for 15 minutes at room temperature. Compound 2 (12.3 mg, 28 μmol) and DIPEA (15 μL, 85 μmol) were added, and the mixture was stirred at room temperature for 15 minutes (LC/MS showed the desired product) then concentrated in vacuo and the residue was purified by preparative HPLC to yield the title compound (4 mg; purity 100%) as a TFA salt. MS m/z [M+H]$^+$ calc'd for C$_{25}$H$_{26}$ClFN$_6$O$_4$, 529.17; found 530.0.

Example 56

(2R,4R)-5-(5'-Chloro-2'-fluorobiphenyl-4-yl)-2-((S)-2,6-diaminohexanoylamino)-4-[(3H-[1,2,3]triazole-4-carbonyl)amino]pentanoic Acid Compound 2 was prepared as described herein.

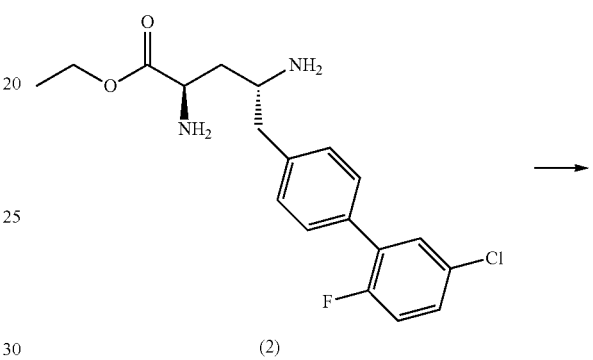

(2)

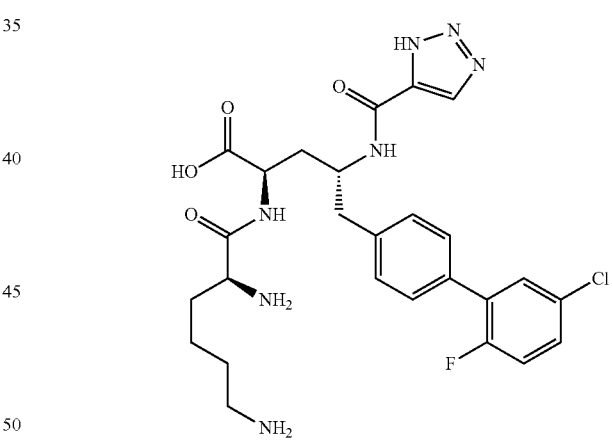

(S)-2,6-Bis-t-butoxycarbonylaminohexanoic acid (10.9 mg, 31 μmol) and HATU (11.4 mg, 30 μmol) were dissolved in DMF (3 mL) and stirred for 15 minutes at room temperature. Compound 2 (12.3 mg, 28 μmol) and DIPEA (15 μL, 85 μmol) were added, and the mixture was stirred at room temperature for 15 minutes (LC/MS showed the desired product) then concentrated in vacuo and the residue was dissolved in MeCN (3 mL). A solution of 4N HCl in dioxane (107 mL, 427 μmol) was added, and the mixture was stirred for 15 minutes at room temperature. LC/MS showed the desired mass. The solvent was removed in vacuo and the residue was purified by preparative HPLC to yield the title compound (7.8 mg; purity 100%) as a TFA salt. MS m/z [M+H]$^+$ calc'd for C$_{26}$H$_{31}$ClFN$_7$O$_4$, 560.21; found 560.2.

Example 57

(2R,4R)-2-((S)-2-Amino-3-phenylpropionylamino)-5-(5'-chloro-2'-fluorobiphenyl-4-yl)-4-[(3H-[1,2,3]triazole-4-carbonyl)amino]pentanoic Acid Compound 2 was prepared as described herein.

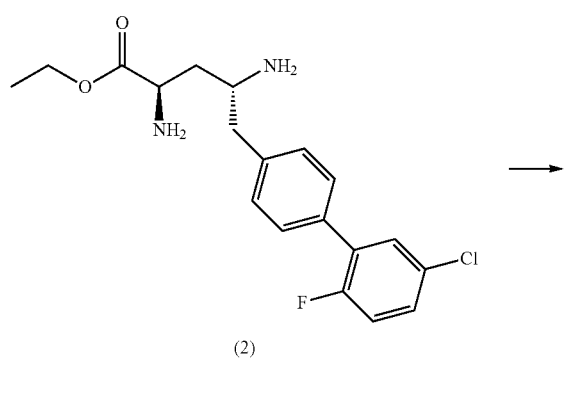

(2)

(S)-2-t-Butoxycarbonylamino-3-phenylpropionic acid (8.3 mg, 31 µmol) and HATU (11.4 mg, 30 µmol) were dissolved in DMF (3 mL) and stirred for 15 minutes at room temperature. Compound 2 (12.3 mg, 28 µmol) and DIPEA (15 µL, 85 µmol) were added, and the mixture was stirred at room temperature for 15 minutes (LC/MS showed the desired product) then concentrated in vacuo and the residue was dissolved in MeCN (3 mL). A solution of 4N HCl in dioxane (107 mL, 427 µmol) was added, and the mixture was stirred for 15 minutes at room temperature. LC/MS showed the desired mass. The solvent was removed in vacuo and the residue was purified by preparative HPLC to yield the title compound (5.5 mg; purity 100%) as a TFA salt. MS m/z [M+H]$^+$ calc'd for $C_{29}H_{28}ClFN_6O_4$, 579.18; found 579.2.

Example 58

(S)-5-Biphenyl-4-yl-2-(tetrahydropyran-4-yl)-4-[(3H-[1,2,3]triazole-4-carbonyl)amino]pentanoic Acid Compound 3 was prepared as described herein.

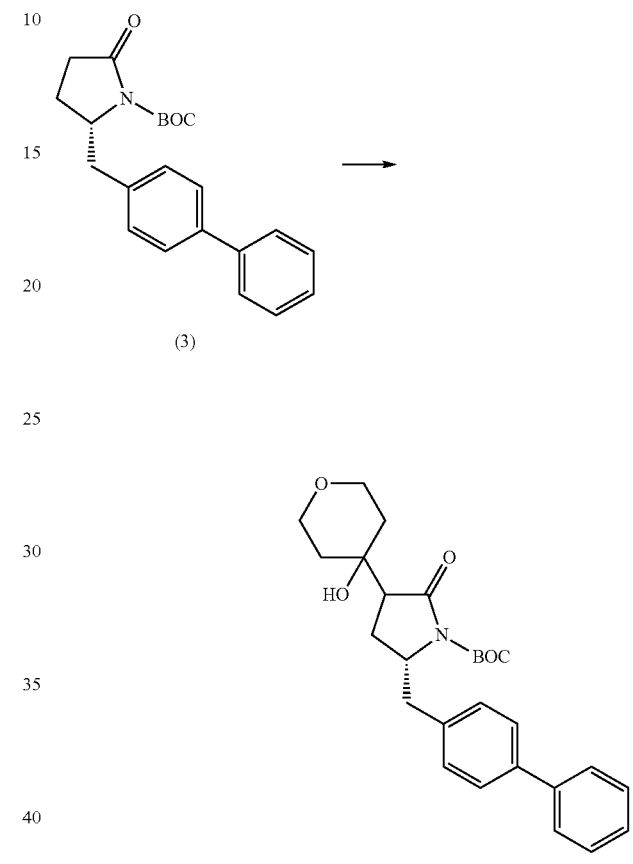

(3)

(4)

Compound 3 (80 mg, 230 µmol, 1.0 eq.) was dissolved in dry THF (1.5 mL). The resulting solution was cooled to −78° C., then LDA (1.8 M, 157 µL, 290 µmol, 1.3 eq.) was added dropwise and the resulting solution was stirred at −78° C. for 20 minutes. A solution of tetrahydropyran-4-one (25 mg, 280 µmol, 1.2 eq.) in THF (100 µL) was added dropwise, and the resulting mixture was stirred at −78° C. for 30 minutes. LC/MS analysis revealed a mixture of starting material and desired product. LDA (1.8M, 100 µL, 180 lmo¹, 0.8 eq.) was added and the mixture was stirred for 20 minutes at −78° C., then tetrahydropyran-4-one (20 mg, 220 µmol, 1.0 eq.) was added and the mixture was stirred for an additional 20 minutes at −78° C. and when the reaction was complete (as determined by LC/MS analysis), the mixture was warmed to −40° C. and the reaction was quenched with 10% citric acid (10 mL), then extracted with EtOAc (2×10 mL). The aqueous phase was discarded and the combined organics were dried over $Na_2SO_4$, filtered and concentrated in vacuo, then purified by flash chromatography (0-60% EtOAc/hexanes, 40 minutes) to yield Compound 4 (100 mg). LCMS (ESI): calc. $C_{27}H_{33}NO_5$=451; obs. M+H$^+$= 452.2. Retention time: 6.05 min.

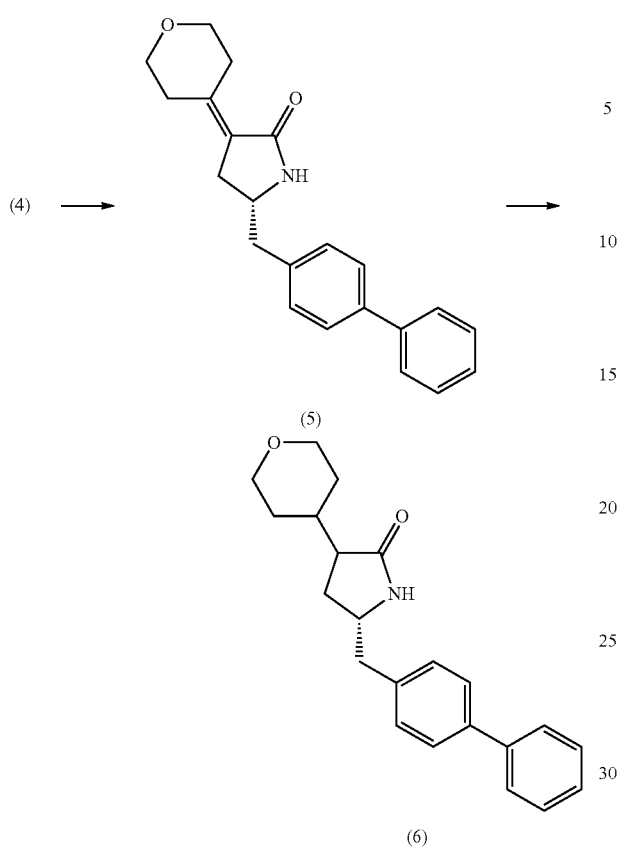

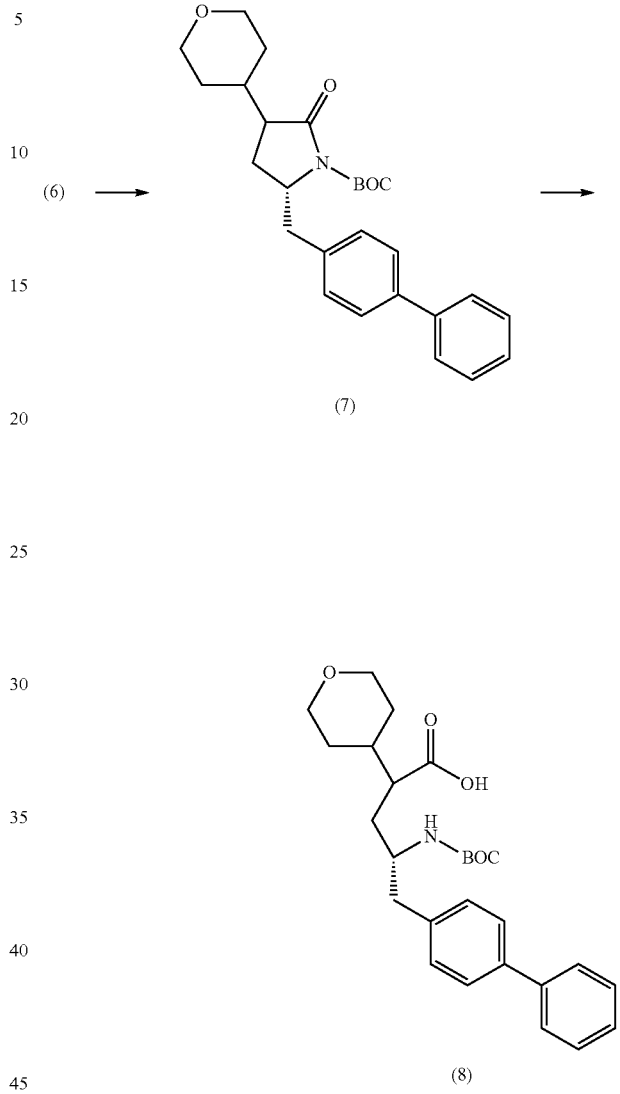

Compound 4 (100 mg, 220 μmol, 1.0 eq.) was dissolved in 50% (v/v) sulfuric acid/H$_2$O (10 mL) and heated to 105° C. for 30 minutes. LC/MS analysis after 30 minutes revealed ~50% of the desired product. The mixture was heated at 105° C. for 1.5 hours, cooled to room temperature, and poured onto ice. The pH was adjusted to ~6 with 4M NaOH and the resulting mixture was extracted with DCM (3×75 mL). The aqueous phase was discarded and the combined organics were washed with saturated aqueous NaCl (50 mL). The aqueous phase was discarded and the organic phase was dried over Na$_2$SO$_4$, filtered, and concentrated in vacuo, then purified by flash chromatography 0-60% EtOAc/hexanes, 40 minutes) to yield Compound 5 (100 mg; quantitative). LCMS (ESI): calc. C$_{22}$H$_{23}$NO$_2$=333; obs. M+H$^+$=334.3. Retention time: 5.23 min.

Compound 5 (100 mg, 220 μmol, 1.0 eq.) was dissolved in MeOH (10 mL). Palladium on carbon (20 mg, 10% w/w) and AcOH (100 μL) were added and the mixture was stirred under 1 atm. of hydrogen overnight. LC/MS analysis revealed a mixture of starting material and desired product. The mixture was filtered through Celite®. The Celite® was then washed with MeOH (2×20 mL) and the combined solutions were concentrated and re-dissolved in MeOH (10 mL). Palladium on carbon (10 mg, 10% w/w) was added and the mixture was hydrogenated on a Parr apparatus at 40 psi hydrogen. LC/MS analysis revealed a mixture of starting material and desired product. AcOH (300 μL) was added and the hydrogen pressure was increased to 60 psi and when the reaction was complete (as determined by LC/MS analysis), the mixture was filtered through Celite®, and the Celite® was then washed with MeOH (2×20 mL). The combined organics were concentrated in vacuo to yield Compound 6 (40 mg). LCMS (ESI): calc. C$_{22}$H$_{25}$NO$_2$=335; obs. M+H$^+$=336.2. Retention time: 5.23 min.

Compound 6 (40 mg, 120 mmol, 1 eq.) and (BOC)$_2$O (57 mg, 280 μmol, 2.3 eq.) were dissolved in dry THF (2 mL) and cooled to −40° C. for ten minutes. NaHMDS (1.0 M, 260 μL, 2.2 eq.) was added and the mixture was stirred for 20 minutes at −40° C. and when the reaction was complete (as determined by LC/MS analysis), the mixture was warmed to room temperature and the reaction was quenched with a few drops of water, then concentrated in vacuo to yield Compound 7, which was used directly in the next step. LCMS (ESI): calc. C$_{27}$H$_{33}$NO$_4$=435; obs. M+H=436.1. Retention time: 6.87 min.

Compound 7 was dissolved in a mixture of THF (2 mL) and 4N NaOH (0.5 mL) and stirred at room temperature for three days and when the reaction was complete (as determined by LC/MS analysis), the mixture was acidified with 5% HCl (5 mL) and extracted with EtOAc (2×10 mL). The aqueous phase was discarded and the combined organics were dried over Na$_2$SO$_4$ and purified by preparative HPLC to yield Compound 8 (17 mg). LCMS (ESI): calc. C$_{27}$H$_{35}$NO$_5$=453; obs. M+H$^+$=454.3. Retention time: 5.36 min.

193

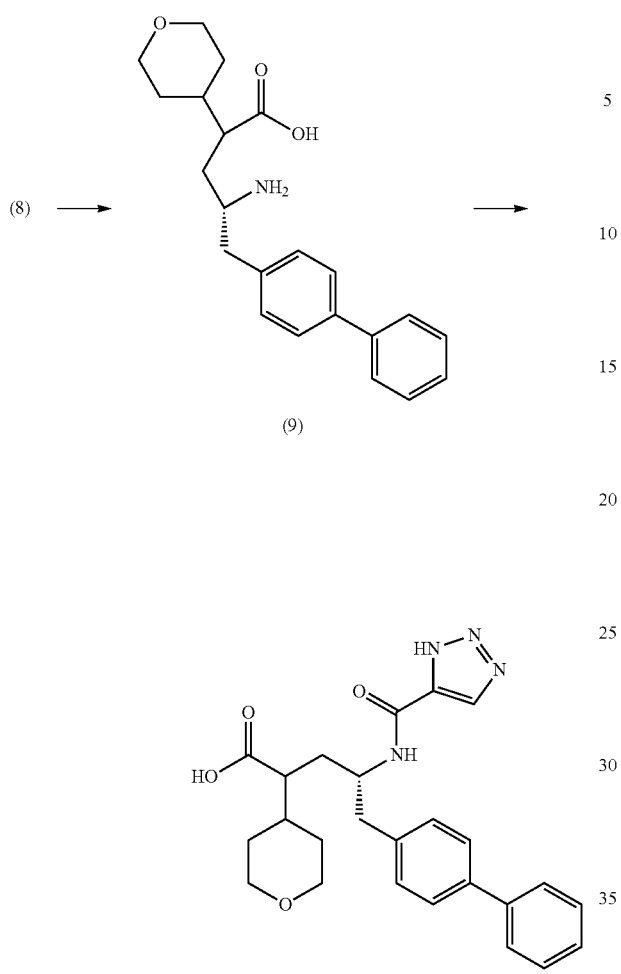

194

Example 59

(S)-5-(5'-Chloro-2'-fluorobiphenyl-4-yl)-2-piperidin-4-yl-4-[(3H-[1,2,3]triazole-4-carbonyl)amino]pentanoic Acid Compound 3 was prepared as described herein.

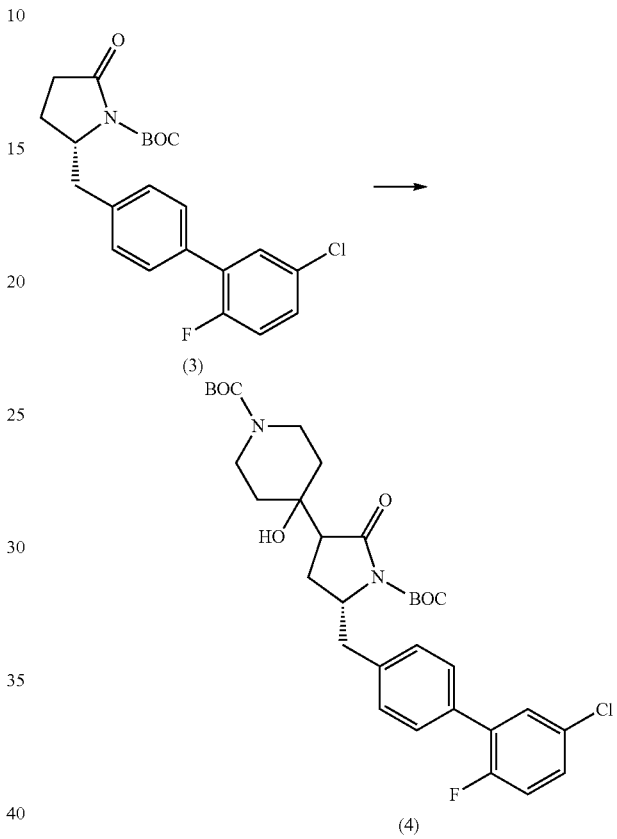

Compound 8 (17 mg, 46 μmol, 1.0 eq.) was dissolved in 4M HCl/p-dioxane (2 mL) and stirred at room temperature for one hour and when the reaction was complete (as determined by LC/MS analysis), the mixture was concentrated to dryness to yield Compound 9 (17 mg; quantitative) as a TFA salt. LCMS (ESI): calc. $C_{22}H_{27}NO_3$=353; obs. M+H$^+$=354.4. Retention time: 3.79 min.

Compound 9 (17 mg, 46 μmol, 1.0 eq.) was dissolved in a solution of DIPEA (29 μL, 170 μmol, 4.0 eq.) in DMF (350 μL). A solution of 1H-1,2,3-triazole-4-carboxylic acid (15 mg, 130 μmol, 3.0 eq.), HATU (25 mg, 65 μmol, 1.5 eq.), and DIPEA (29 μL, 170 μmol, 4.0 eq.) in DMF (350 μL) was stirred at room temperature for 20 minutes then added to the Compound 9 solution and stirred at room temperature for 30 minutes and when complete (as determined by LC/MS analysis), the reaction was quenched with water (1 mL), diluted with 10% citric acid (10 mL), and extracted with EtOAc (2×20 mL). The aqueous phase was discarded and the organic phase concentrated to dryness and purified by preparative HPLC to yield the title compound (9.6 mg; purity 99.9%). LCMS (ESI): calc. $C_{25}H_{28}N_4O_4$=448; obs. M+H$^+$=449.1. Retention time: 4.49 min.

LC/MS Method: flow rate: 1.5 mL/min; Buffer A: 0.1% TFA/H$_2$O; Buffer B 0.1% TFA/MeCN; gradient elution from 5% B to 100% B over 9.6 min, then 100% B for 1.0 minute, detection at 254 nm.

A solution of Compound 3 (210 mg, 552 μmol) in THF (1.8 mL) under a stream of nitrogen was cooled to −78° C., followed by the dropwise addition of a 1.8 M THF solution of LDA (348 μL, 626 μmol). The mixture was stirred at −78° C. for 20 minutes and a solution of 4-oxo-piperidine-1-carboxylic acid t-butyl ester (114 mg, 572 μmol) in dry THF (1 mL) was added dropwise. The mixture was stirred at −78° C. for an additional 20 minutes and a solution of LDA (250 μL, 450 μmol) was added dropwise, followed by the dropwise addition of a solution of 4-oxo-piperidine-1-carboxylic acid t-butyl ester (85 mg, 427 μmol) in dry THF (0.5 mL). After stirring at −78° C. for 20 minutes, the temperature of the mixture was raised to −30° C. and the reaction was quenched with 10% citric acid (10 mL). The mixture was extracted with EtOAc (3×25 mL), washed with saturated aqueous NaCl (20 mL) and dried over MgSO$_4$. The mixture was filtered and the filtrate was evaporated. The residue was purified by flash chromatography (0-50% hexanes/EtOAc gradient over 55 minutes). The fractions containing the desired product were combined and evaporated. The residue was dried in vacuo at room temperature overnight to yield Compound 4 (250 mg). LC-MS (ESI): calc. $C_{32}H_{40}ClFN_2O_6$=603.1; obs. m/z 603.2 [M+H]$^+$. Retention time 7.39 min.

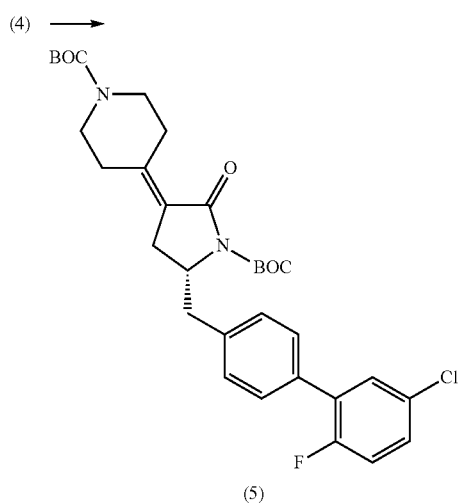

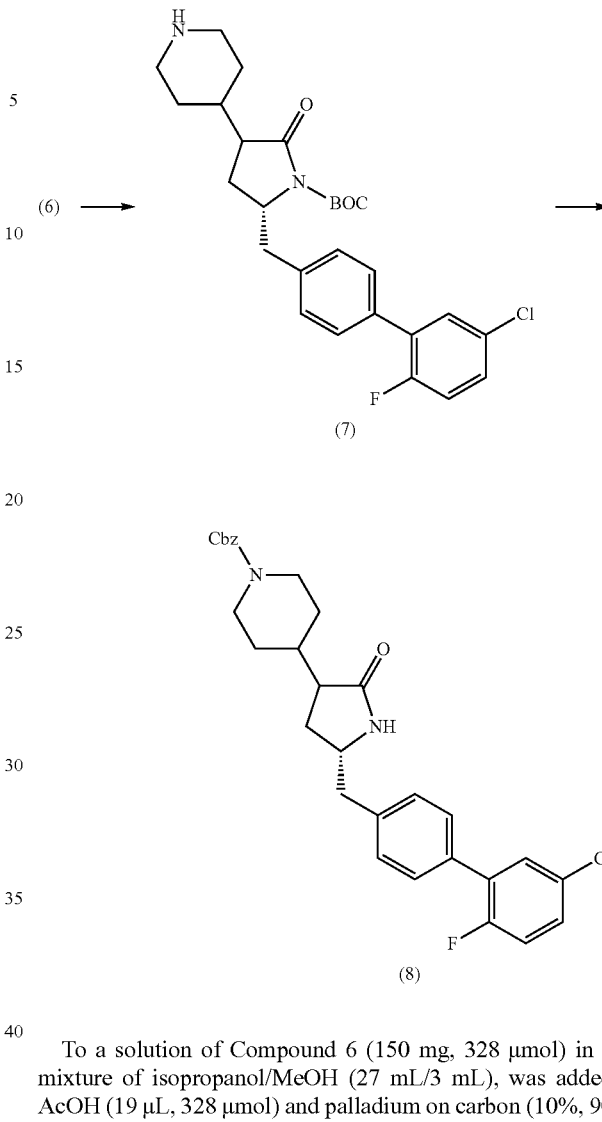

To a solution of Compound 4 (260 mg, 215 μmol) and Et₃N (338 μL, 2.3 mmol) in DCM (710 μL) was added methylsilyl chloride (193 μL, 2.3 mmol) dropwise at room temperature under a stream of nitrogen. The mixture was stirred at room temperature for 5 minutes, then the reaction was quenched with 2% aqueous HCl and extracted with EtOAc (3×30 mL), washed with saturated aqueous NaCl (20 mL), and dried over MgSO₄. The mixture was filtered and the filtrate was evaporated. The residue was purified by flash chromatography (0-30% hexanes/EtOAc gradient over 55 minutes). The fractions containing the desired product were combined and evaporated. The residue was dried in vacuo at room temperature overnight to yield Compound 5 (210 mg). LC-MS (ESI): calc. $C_{32}H_{38}ClFN_2O_5$=585.1; obs. m/z 585.2 [M+H]⁺. Retention time 7.86 min.

Compound 5 (210 mg, 360 μmol) was dissolved in 4N HCl/dioxane (8 mL, 32 mmol) and stirred for 20 minutes at room temperature. The solvent was evaporated and the residue was dried in vacuo at room temperature overnight to yield Compound 6 as the HCl salt (150 mg). LC-MS (ESI): calc. $C_{22}H_{22}ClFN_2O$=384.9; obs. m/z 385.2 [M+H]⁺. Retention time 2.71 min.

To a solution of Compound 6 (150 mg, 328 μmol) in a mixture of isopropanol/MeOH (27 mL/3 mL), was added AcOH (19 μL, 328 μmol) and palladium on carbon (10%, 90 mg). The mixture was subjected to hydrogenation (H₂, Parr apparatus, 60 psi) at room temperature for 2 hours. The mixture was filtered through Celite® and evaporated. The residue was dried in vacuo at room temperature for 4 hours to yield Compound 7 (146 mg). LC-MS (ESI): calc. $C_{22}H_{24}ClFN_2O$=386.9; obs. m/z 387.1 [M+H]⁺. Retention time 4.34 min.

A solution of Compound 7 (146 mg, 318 μmol) and Et₃N (90 μL, 637 μmol) in DCM (1.5 mL) was cooled to 4° C., followed by the dropwise addition of benzyl chloroformate (45 μL, 318 μmol). The mixture was stirred at 4° C. for 20 minutes, then the reaction was quenched with 5% aqueous NaHCO₃ (10 mL). The mixture was extracted with DCM (2×10 mL), and the organic layer was washed with saturated aqueous NaCl (20 mL) and dried over MgSO₄. The mixture was filtered and the filtrate was evaporated. The residue was purified by flash chromatography (0-50% hexanes/EtOAc gradient over 45 minutes). The fractions containing the desired product were combined and evaporated. The residue was dried in vacuo at room temperature overnight to yield Compound 8 (120 mg). LC-MS (ESI): calc. $C_{30}H_{30}ClFN_2O_3$=521.0; obs. m/z 521.1 [M+H]⁺. Retention time 6.70 min.

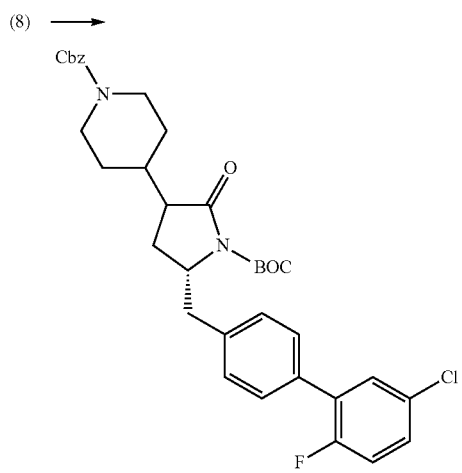

(9)

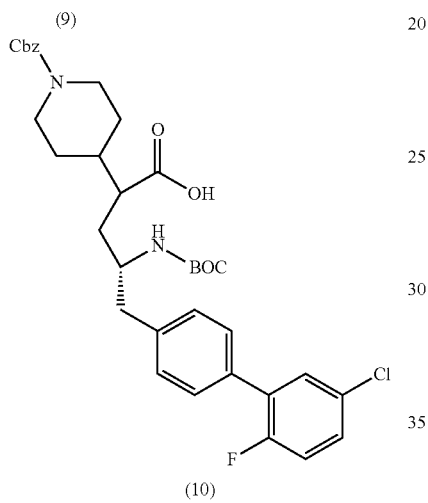

(10)

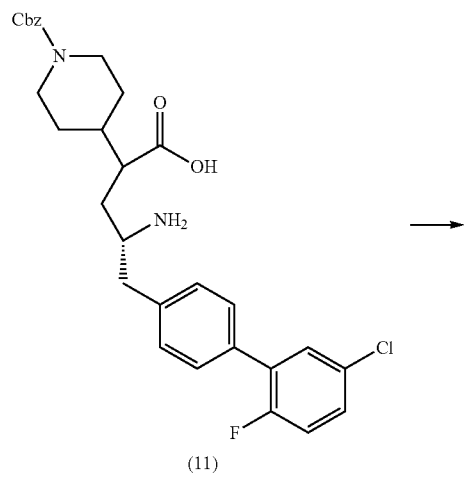

(11)

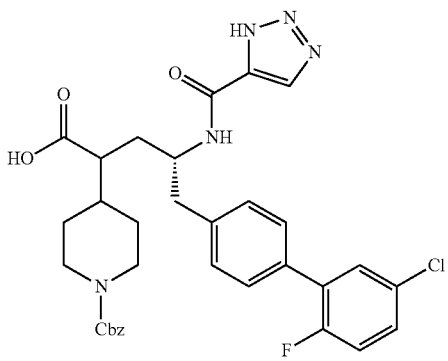

(12)

A solution of Compound 8 (120 mg, 230 µmol), Boc$_2$O (125 mg, 576 µmol) in THF (1.1 ml) was cooled to −40° C., followed by the dropwise addition of a 1M THF solution of NaHMDS (576 µL, 576 µmol). The mixture was stirred at −40° C. for 10 minutes, before being warmed to room temperature and the reaction was quenched with 5% aqueous NaHCO$_3$ (10 mL). The mixture was extracted with EtOAc (2×25 mL), washed with saturated aqueous NaCl (20 mL), and dried over MgSO$_4$. The mixture was filtered and the filtrate was evaporated. The residue was dried in vacuo at room temperature overnight to yield Compound 9 (156 mg). LC-MS (ESI): calc. C$_{35}$H$_{38}$ClFN$_2$O$_5$=621.1; obs. m/z 621.3 [M+H]$^+$. Retention time 7.93 min.

To a solution of Compound 9 (150 mg, 230 µmol) in a mixture of THF/water (2.5 mL/0.5 mL) was added NaOH (40 mg, 1 mmol) and H$_2$O$_2$ (60 µL, 530 µmol) at room temperature. The mixture was stirred at room temperature overnight, followed by the addition of 5% aqueous HCl to take the pH of the solution to 3. The mixture was extracted with EtOAc (2×20 mL), washed with saturated aqueous NaCl (10 mL), and dried over MgSO$_4$. The mixture was filtered and the filtrate was evaporated. The residue was dried in vacuo at room temperature overnight to yield Compound 10 (133 mg). LC-MS (ESI): calc. C$_{35}$H$_{40}$ClFN$_2$O$_6$=639.2; obs. m/z 639.3 [M+H]$^+$. Retention time 7.01 min.

Compound 10 (133 mg, 210 µmol) was dissolved in 4N HCl/dioxane (5 mL, 20 mmol) and stirred for 20 minutes at room temperature. The solvent was evaporated and the residue was dried in vacuo at room temperature overnight to yield Compound 11 as the hydrochloric salt (140 mg). LC-MS (ESI): calc. C$_{30}$H$_{32}$ClFN$_2$O$_4$=539.1; obs. m/z 539.2 [M+H]$^+$. Retention time 5.14 min.

To a solution of 3H-[1,2,3]triazole-4-carboxylic acid (77 mg, 688 µmol) and HATU (130 mg, 344 µmol) in DMF (1.5 mL) was added DIPEA (160 µL, 920 µmol). The mixture was stirred at room temperature for 20 minutes, followed by the addition of Compound 11 (140 mg, 210 µmol). The mixture was stirred at room temperature for 20 minutes, then the reaction was quenched with 10% aqueous citric acid (15 mL) to pH 4. The mixture was extracted with EtOAc (3×20 mL), washed with saturated aqueous NaCl (10 mL) and dried over MgSO$_4$. The mixture was filtered and the filtrate was evaporated. The residue was purified by flash chromatography (10-100% hexanes/EtOAc gradient over 45 minutes). The fractions containing the desired product were combined and evaporated. The residue was dried in vacuo at room temperature overnight to yield Compound 12 (70 mg). LC-MS (ESI): calc. C$_{33}$H$_{33}$ClFN$_5$O$_5$=634.1; obs. m/z 634.2 [M+H]$^+$. Retention time 5.96 min.

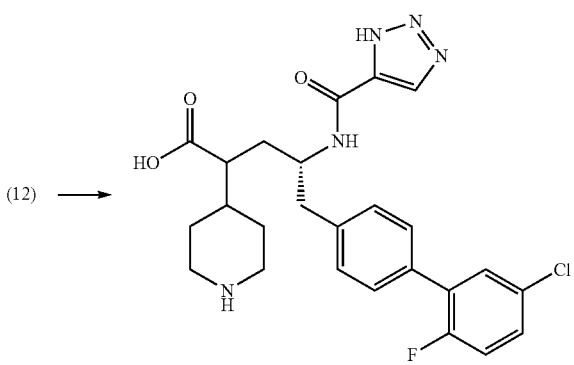

(12) →

To a solution of Compound 12 (70 mg, 110 μmol) in dioxane (1 mL) was added 6N aqueous HCl (2 mL, 12 mmol) under a stream of nitrogen. The mixture was stirred at 100° C. for 20 minutes, then cooled to room temperature. The solvent was evaporated and the residue was purified (preparative LCMS). The fractions containing desired compound were combined and lyophilized to yield the title compound (29 mg, 53%; purity by LC-MS 95.7%) as a TFA salt. LC-MS (ESI): calc. $C_{25}H_{27}ClFN_5O_3$=500.0; obs. m/z 500.2 $[M+H]^+$. Retention time 1.75 min.

Example 60

(S)-2-(1-Acetylpiperidin-4-yl)-5-biphenyl-4-yl-4-[(3H-[1,2,3]triazole-4-carbonyl)amino]pentanoic Acid Compound 3 was prepared as described herein.

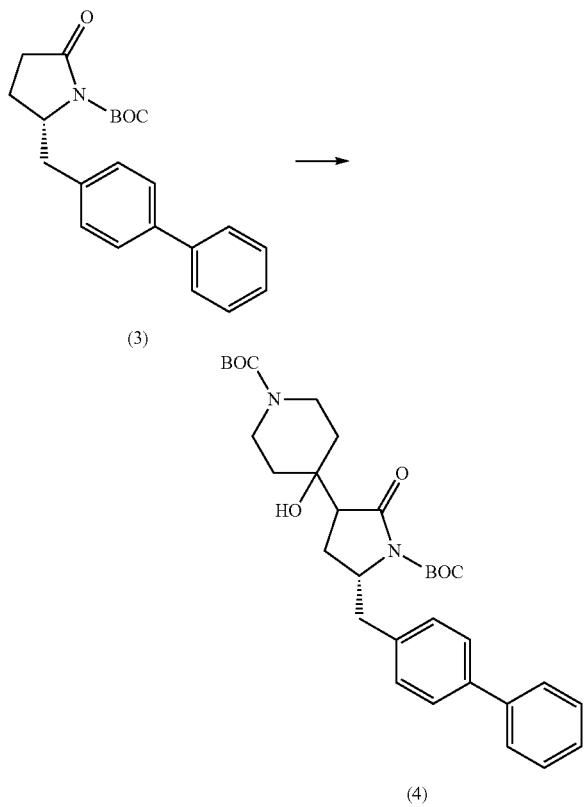 [SMILES: CC(C)(C)OC(=O)N1C(=O)CC[C@H]1Cc1ccc(-c2ccccc2)cc1 ; CC(C)(C)OC(=O)N1C(=O)C(C2(O)CCOCC2)C[C@H]1Cc1ccc(-c2ccccc2)cc1]

Compound 3 (450 mg, 1280 μmol, 1.0 eq.) was dissolved in dry THF (4.2 mL). The resulting solution was cooled to −78° C., then LDA (1.8 M, 990 μL, 1790 μmol, 1.4 eq.) was added dropwise and the resulting solution was stirred at −78° C. for 30 minutes. A solution of N-t-butoxycarbonyl-4-piperidone (356 mg, 1790 μmol, 1.4 eq.) in THF (500 μL) was added dropwise. The resulting mixture was stirred at −78° C. for 20 minutes. LC/MS analysis revealed a mixture of starting material and desired product. LDA (1.8 M, 400 μL, 720 μmol, 0.6 eq.) was added and the mixture was stirred for 20 minutes at −78° C., then a solution of N-t-butoxycarbonyl-4-piperidone (190 mg, 960 μmol, 0.7 eq.) in THF (200 μL) was added and the resulting mixture stirred at −78° C. for one hour and when the reaction was complete (as determined by LC/MS analysis), the mixture was then warmed to −50° C. and the reaction was quenched with 10% citric acid (10 mL) then extracted with EtOAc (2×25 mL). The aqueous phase was discarded and the combined organics were dried over $Na_2SO_4$, concentrated in vacuo, and purified by flash chromatography (0-80% EtOAc/hexanes) to yield Compound 4 (600 mg). LCMS (ESI): calc. $C_{32}H_{42}N_2O_6$=550; obs. $[M+H]^+$=551.2. Retention time: 7.06 min.

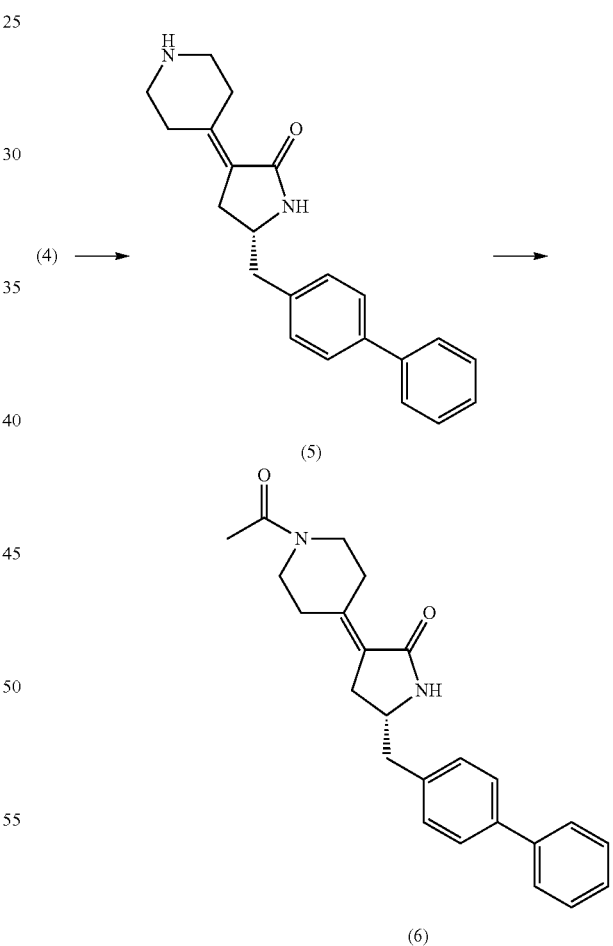

Compound 4 (300 mg, 544 μmol, 1.0 eq.) was dissolved in a mixture of MeCN (2 mL) and 50% (v/v) aqueous $H_2SO_4$ (16 mL) and heated to 130° C. for two hours and when the reaction was complete (as determined by LC/MS analysis), the mixture was cooled to room temperature, poured onto ice, and the pH was adjusted to ~7 with 4M NaOH and the resulting mixture was extracted with DCM (3×50 mL) and chloroform (3×50 mL). The aqueous phase was discarded and the combined organics were dried over Na$_2$SO$_4$, filtered, and concentrated in vacuo to yield Compound 5 (60 mg). LCMS (ESI): calc. C$_{22}$H$_{24}$N$_2$O=332; obs. [M+H]$^+$=333.3. Retention time: 3.98 min.

Compound 5 (60 mg, 180 µmol, 1 eq.) was dissolved in DCM (3 mL). Et$_3$N (50 µL, 360 µmol 2.0 eq.) was added, followed by acetic anhydride (28 µL, 270 µmol, 1.5 eq.). The mixture was stirred for 20 minutes at room temperature and when the reaction was complete (as determined by LC/MS analysis), the mixture was diluted with DCM (10 mL) and saturated aqueous NaHCO$_3$ (2 mL). The phases were separated and the aqueous phase was extracted with DCM (10 mL). The aqueous phase was then discarded and the combined organics were dried over Na$_2$SO$_4$, filtered, and concentrated in vacuo, and purified by preparative HPLC (30-60% H$_2$O/MeCN with 0.1% TFA, 30 mL/minute, 30 minutes) to yield Compound 6 (28 mg). LCMS (ESI): calc. C$_{24}$H$_{26}$N$_2$O$_2$=374; obs. [M+H]$^+$=375.2. Retention time: 4.85 min.

trated to yield crude Compound 7 (32 mg; quantitative). LCMS (ESI): calc. C$_{24}$H$_{28}$N$_2$O$_2$=376; obs. [M+H]$^+$=377.4. Retention time: 4.78 min.

Compound 7 (32 mg, 85 µmol, 1.0 eq.) was dissolved in dry THF (2 mL) at −40° C., followed by (BOC)$_2$O (37 mg, 170 µmol, 2.0 eq.). The mixture was stirred for ten minutes then NaHMDS (1.0M, 170 µL, 170 µmol, 2.0 eq.) was added and the mixture was stirred at −40° C. for 20 minutes and when the reaction was complete (as determined by LC/MS analysis), the mixture was warmed to room temperature, the reaction quenched with water (50 µL), and the mixture concentrated to dryness to yield crude Compound 8, which was used directly in the next step. LCMS (ESI): calc. C$_{29}$H$_{36}$N$_2$O$_4$=476; obs. [M+H]$^+$=477.3. Retention time: 6.15 min.

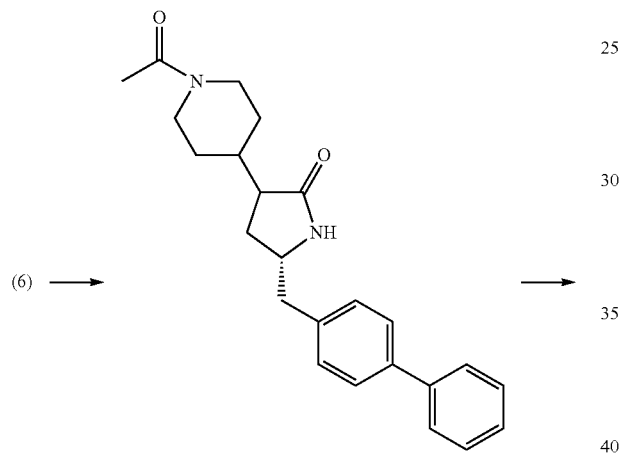

(6) →

(7)

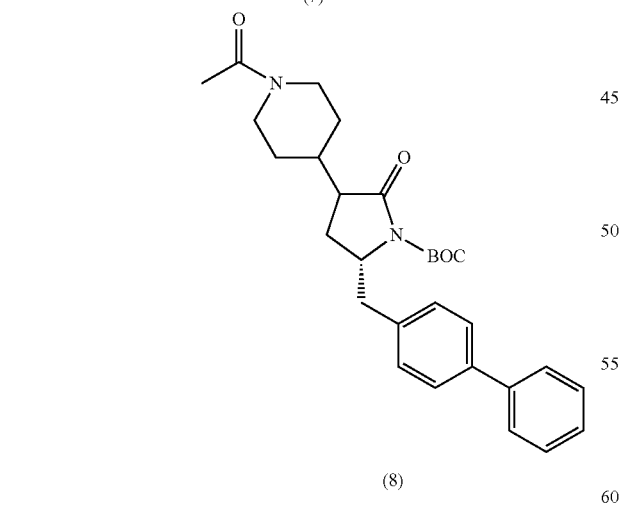

(8)

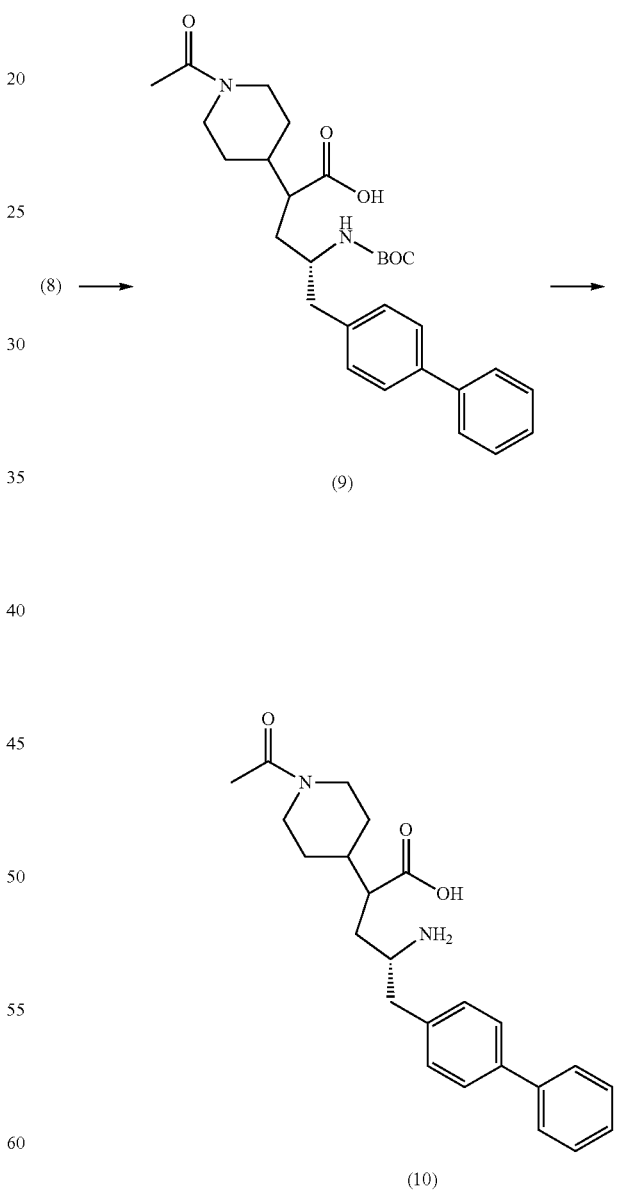

(8) →

(9)

(10)

Compound 6 (28 mg, 150 µmol, 1.0 eq.) was dissolved in MeOH (5 mL). Palladium on carbon (10 mg, 10% w/w) and AcOH (25 µL) were added and the mixture was stirred under 1 atm. of hydrogen overnight and when the reaction was complete (as determined by LC/MS analysis), the mixture filtered through Celite® with MeOH (20 mL) and concen- Compound 8 was dissolved in a mixture of THF (2 mL) and 4N NaOH (2 mL) and stirred at room temperature for two hours. Additional THF (1 mL) was added and the mixture was stirred at room temperature overnight and when the reaction was complete (as determined by LC/MS analysis), the pH was adjusted to 4 with 5% aqueous HCl and the mixture extracted with EtOAc (2×20 mL). The aqueous phase was discarded and the combined organics were extracted with saturated aqueous NaCl (5 mL). The aqueous phase was discarded and the organic phase was dried over $Na_2SO_4$, filtered, and concentrated to dryness to yield Compound 9 (32 mg), which was used without purification in the next step. LCMS (ESI): calc. $C_{29}H_{38}N_2O_5$=494; obs. [M+H]$^+$=495.1. Retention time: 5.39 min.

Compound 9 (32 mg, 85 µmol, 1.0 eq.) was dissolved in 4N HCl in p-dioxane (1.2 mL) and stirred at room temperature for 20 minutes and when the reaction was complete (as determined by LC/MS analysis), the solution was concentrated to dryness to yield Compound 10 as the hydrochloride salt (32 mg). LCMS (ESI): calc. $C_{24}H_{30}N_2O_3$=394; obs. M+H=395.2. Retention time: 3.64 min.

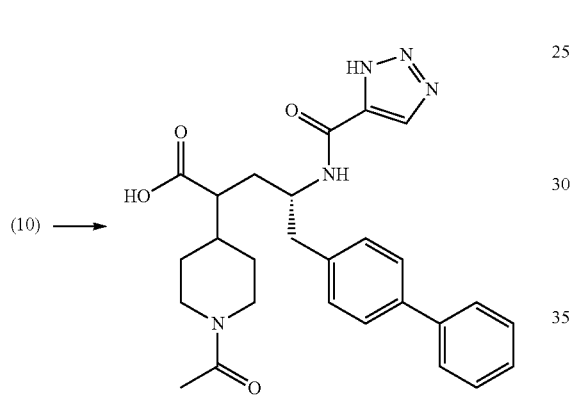

Compound 10 (32 mg, 75 µmol, 1.0 eq.) was dissolved in DMF (500 µL). 1H-1,2,3-triazole-4-carboxylic acid (25 mg, 221 µmol, 3.0 eq.) was dissolved in DMF (500 µL), followed by the addition of DIPEA (51 µL, 297 µmol, 4.0 eq.) and HATU (42 mg, 111 µmol, 1.5 eq.). The solutions were stirred at room temperature for 20 minutes, then combined and stirred at room temperature for an additional 20 minutes and when the reaction was complete (as determined by LC/MS analysis), the mixture was diluted with water (0.5 mL), the pH adjusted to 4 with 10% citric acid, then washed with EtOAc (2×20 mL). The aqueous phase was discarded and the combined organics were extracted with saturated aqueous NaCl (10 mL). The aqueous phase was discarded and the organic phase was dried over $Na_2SO_4$, filtered, and concentrated in vacuo, and purified by preparative HPLC to yield the title compound (11 mg; purity 99.6%). LCMS (ESI): calc. $C_{27}H_{31}N_5O_4$=489; obs. M+H=490.2. Retention time: 4.23 min.

LC/MS Method: flow rate: 1.5 mL/min; Buffer A: 0.1% TFA/H$_2$O; Buffer B 0.1% TFA/MeCN; gradient elution from 5%-100% B over 9.6 min, then 100% B for 1.0 minute, detection at 254 nm.

Example 61

(2S,4S)-5-(5'-Chloro-2'-fluorobiphenyl-4-yl)-4-[(3H-[1,2,3]triazole-4-carbonyl)amino]-2-[1,2,3]triazol-1-ylmethylpentanoic Acid (Compound a) and (2S, 4S)-5-(5'-Chloro-2'-fluorobiphenyl-4-yl)-4-[(3H-[1,2,3]triazole-4-carbonyl)amino]-2-[1,2,3]triazol-2-ylmethylpentanoic Acid (Compound b)

(2S,4S)-4-t-Butoxycarbonylamino-5-(5'-chloro-2'-fluorobiphenyl-4-yl)-2-hydroxymethylpentanoic acid ethyl ester (200 mg, 417 µmol) was dissolved in DCM (5 mL). Methanesulfonyl chloride (39 µL, 0.5 mmol) and Et$_3$N (116 µL, 833 µmol) were added. The mixture was stirred for 10 minutes and the solution was purified by normal phase chromatography (0-100% EtOAc/hexanes) to yield Compound 1 (198 mg).

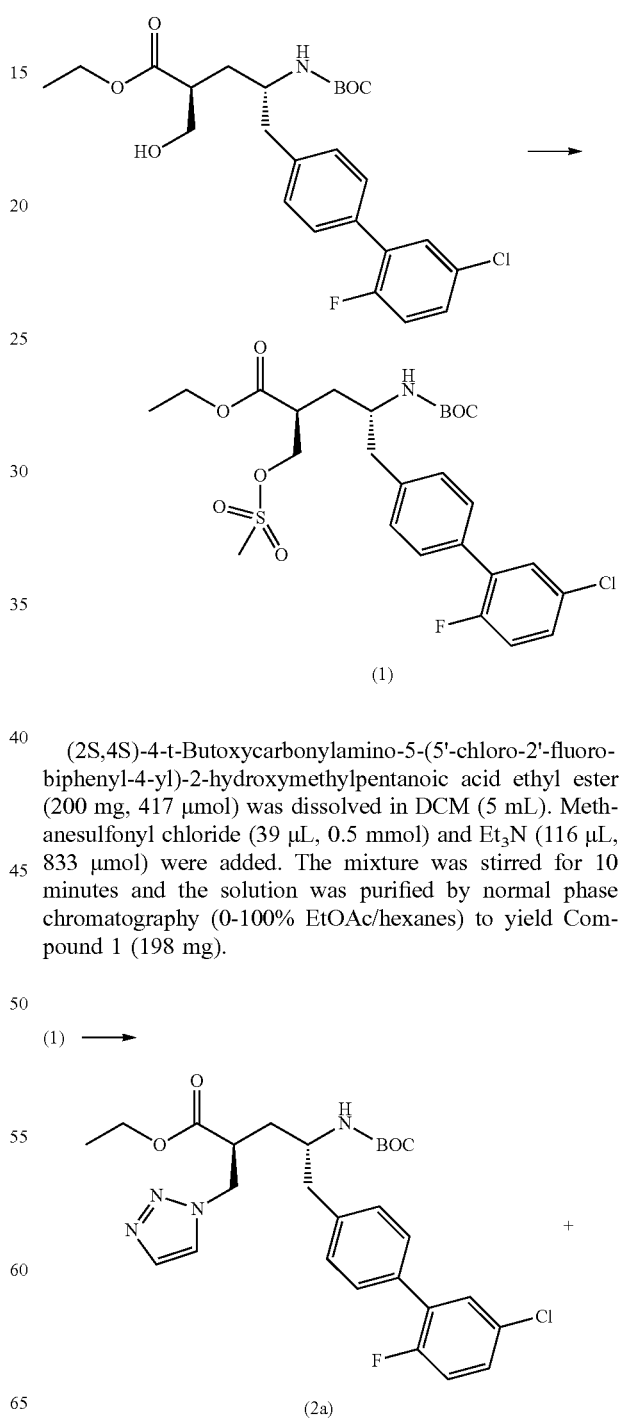

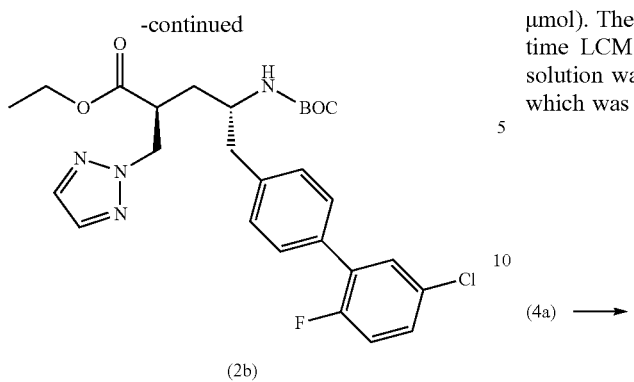

(2b)

Compound 1 (25 mg, 45 µmol) was combined with K₂CO₃ (12.4 mg, 90 µmol), 1,2,3-triazole (4.3 mg, 63 µmol), and DMF (0.5 mL), and the mixture was stirred overnight. The mixture was concentrated under reduced pressure and the residue was purified by normal phase chromatography (0-100% EtOAc/hexanes), to yield Compounds 2a (8 mg) and 2b (7 mg).

(2a) →

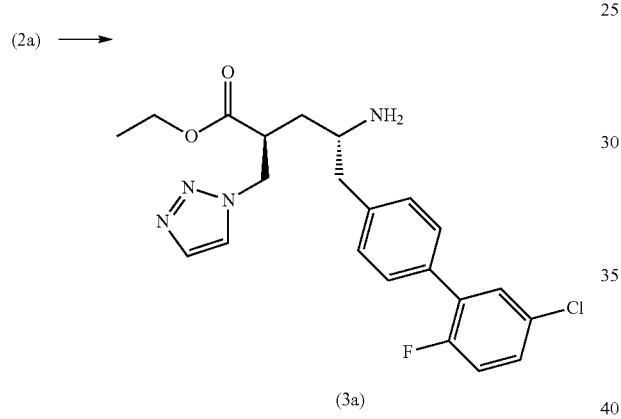

(3a)

Compound 2a (8 mg, 15 µmol) was dissolved in MeCN (0.3 mL) and 4N HCl in dioxane (0.3 mL). The mixture was stirred for 10 minutes and concentrated under reduced pressure to yield Compound 3a as an HCl salt.

(3a) →

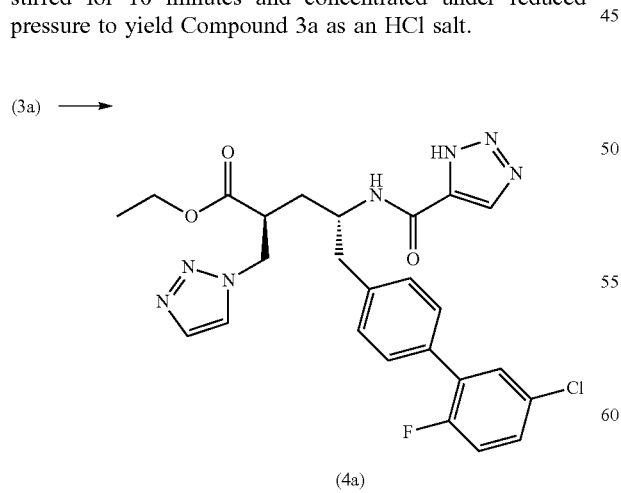

(4a)

Compound 3a (7.0 mg, 16 µmol) was combined with DMF (0.5 mL), 1H-1,2,3-triazole-5-carboxylic acid (2.0 mg, 18 µmol), HATU (6.8 mg, 18 µmol) and DIPEA (8.5 µL, 49 µmol). The mixture was stirred for 30 minutes after which time LCMS showed the desired product formation. The solution was concentrated in vacuo to yield Compound 4a which was used directly in the next step.

(4a) →

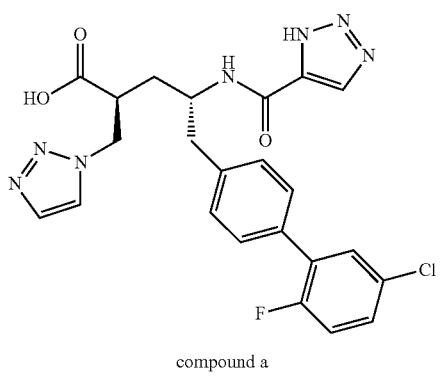

compound a

Compound 4a (8.0 mg, 15 µmol) was dissolved in THF (0.5 mL) and 1N NaOH (76 µL, 76 µmol) and stirred for 2 hours. AcOH (1 mL) was added and the mixture was purified by reverse phase chromatography to yield the title compound (Compound a; 2 mg; purity 95%) as a TFA salt. MS m/z [M+H]⁺ calc'd for $C_{23}H_{21}ClFN_7O_3$, 498.14; found 498.

(2b) →

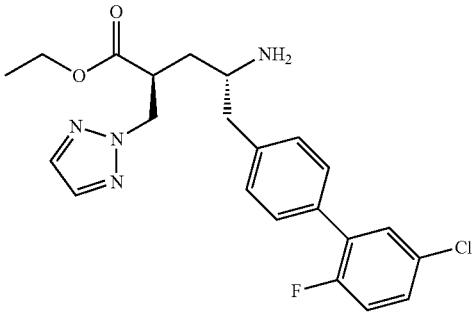

(3b)

Compound 2b (7 mg, 13 µmol) was dissolved in MeCN (0.3 mL) and 4N HCl in dioxane (0.3 mL). The mixture was stirred for 10 minutes and concentrated under reduced pressure to yield Compound 3b as an HCl salt.

(3b) ⟶

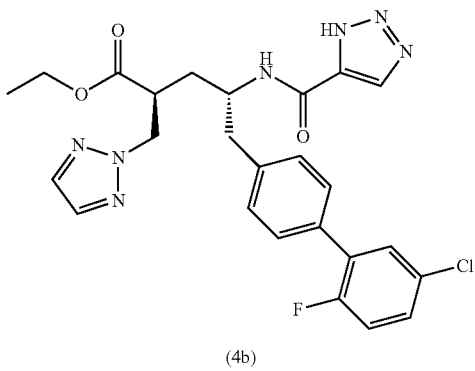

(4b)

Compound 3b (7.0 mg, 16 μmol) was combined with DMF (0.5 mL), 1H-1,2,3-triazole-5-carboxylic acid (2.0 mg, 18 μmol), HATU (6.8 mg, 18 μmol) and DIPEA (8.5 μL, 49 μmol). The mixture was stirred for 30 minutes after which time LCMS showed the desired product formation. The solution was concentrated in vacuo to yield Compound 4b which was used directly in the next step.

(4b) ⟶

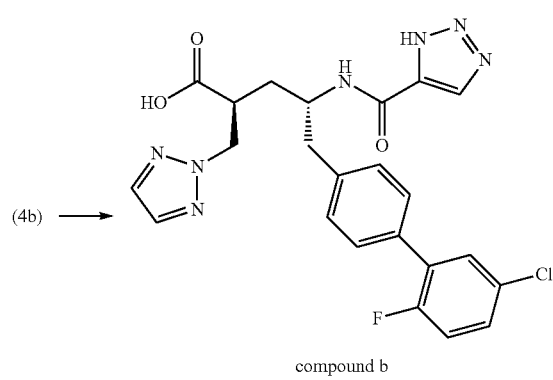 [SMILES: O=C(N[C@H](Cc1ccc(-c2cc(Cl)ccc2F)cc1)C[C@@H](Cn1nccn1)C(=O)O)c1cnn[nH]1]

compound b

Compound 4b (8.0 mg, 15 μmol) was dissolved in THF (0.5 mL) and 10N NaOH (76 μL, 76 μmol) and stirred for 2 hours. AcOH (1 mL) was added and the mixture was purified by reverse phase chromatography to yield the title compound (Compound b; 2 mg; purity 95%) as a TFA salt. MS m/z [M+H]$^+$ calc'd for $C_{23}H_{21}ClFN_2O_3$, 498.14; found 498.

Example 62

(2S,4S)-5-(5'-Chloro-2'-fluorobiphenyl-4-yl)-2-imidazol-1-ylmethyl-4-[(3H-[1,2,3]triazole-4-carbonyl)amino]pentanoic Acid Compound 1 was prepared as described herein.

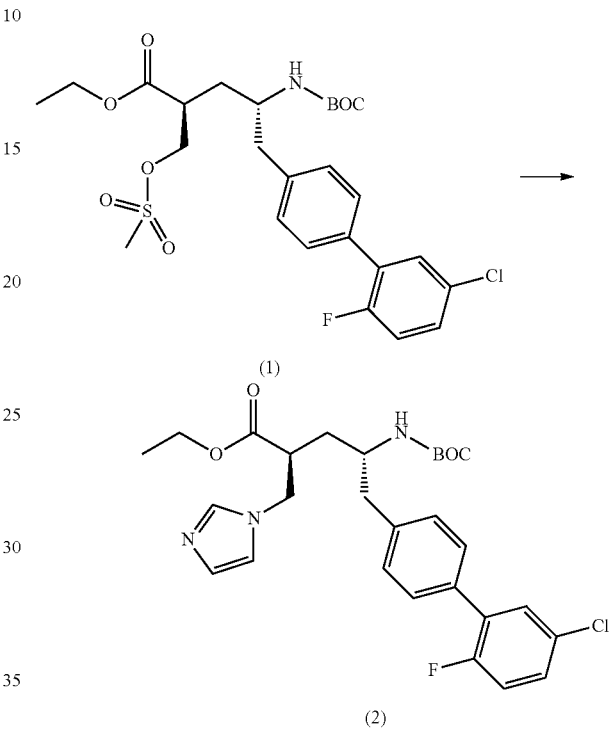

Compound 1 (25 mg, 45 μmol) was combined with K$_2$CO$_3$ (12.4 mg, 90 μmol), imidazole (4.0 mg, 58 μmol), and DMF (0.5 mL), and the mixture was stirred overnight. The solution was concentrated under reduced pressure and the residue was purified by normal phase chromatography (0-100% EtOAc/hexanes) to yield Compound 2 (15 mg).

(2) ⟶

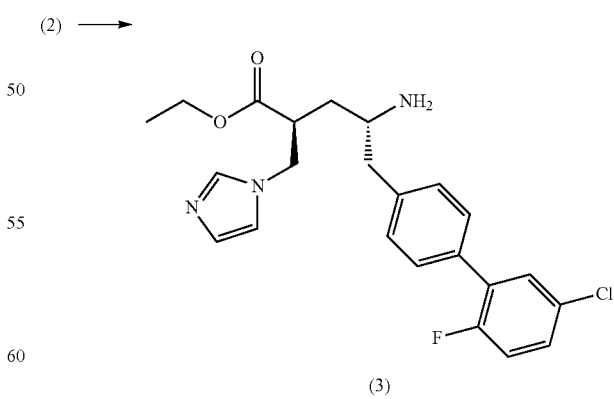

Compound 2 (15 mg, 28 μmol) was dissolved in MeCN (0.3 mL) and 4N HCl in dioxane (0.3 mL). The mixture was stirred for 10 minutes and concentrated under reduced pressure to yield Compound 3 as an HCl salt.

(3) →

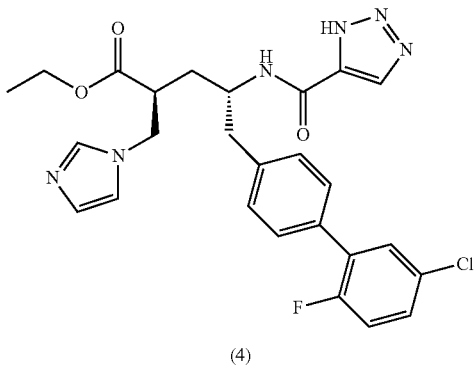

(4)

Compound 3 (7.0 mg, 16 µmol) was combined with DMF (0.5 mL), 1H-1,2,3-triazole-5-carboxylic acid (2.0 mg, 18 µmol), HATU (6.8 mg, 18 µmol) and DIPEA (8.5 µL, 49 µmol). The mixture was stirred for 30 minutes after which time LCMS showed the desired product formation, Compound 4, which was used directly in the next step.

(4) →

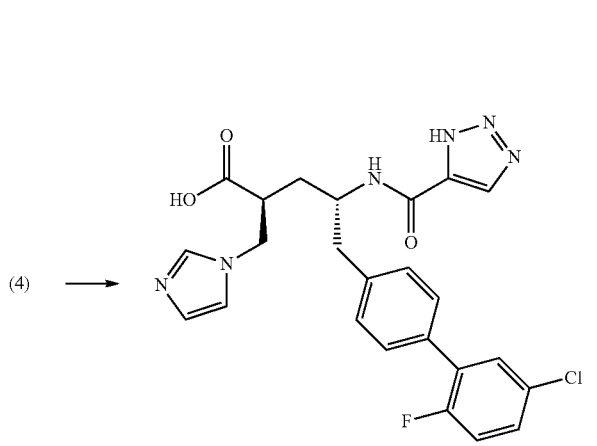 [SMILES: O=C(N[C@H](Cc1ccc(-c2cc(Cl)ccc2F)cc1)C[C@@H](Cn1ccnc1)C(=O)O)c1cnn[nH]1]

Compound 4 (8.0 mg, 15 µmol) was dissolved in THF (0.5 mL) and NaOH (76 µL, 76 µmol) and stirred for 2 hours. AcOH (1 mL) was added and the mixture was purified by reverse phase chromatography to yield the title compound (4 mg) as a TFA salt. MS m/z [M+H]$^+$ calc'd for $C_{24}H_{22}ClFN_6O_3$, 497.14; found 497.

Example 63

(2S,4S)-5-(5'-Chloro-2'-fluorobiphenyl-4-yl)-2-(1H-tetrazol-5-ylmethyl)-4-[(3H-[1,2,3]triazole-4-carbonyl)amino]pentanoic Acid

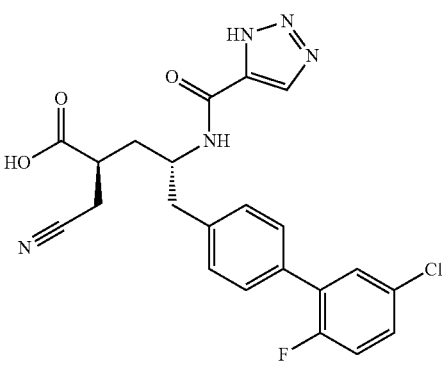

→

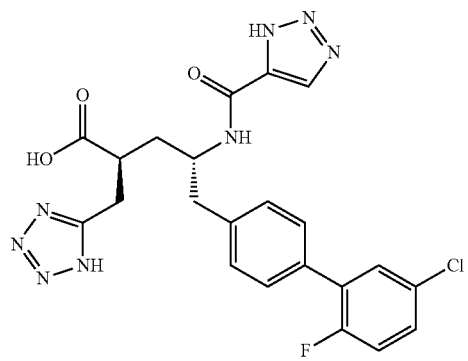

A solution of (2S,4S)-5-(5'-chloro-2'-fluorobiphenyl-4-yl)-2-cyanomethyl-4-[(3H-[1,2,3]triazole-4-carbonyl)amino]pentanoic acid (10.5 mg, 22 µmol), sodium azide (2.8 mg, 43 µmol) and zinc bromide (4.9 mg, 22 µmol) in water (0.2 Ml) and isopropanol (0.1 Ml) was heated at 100° C. overnight. The solution was cooled to room temperature and 3M HCl (60 µL) and EtOAc (1 mL) were added. The organic layer was isolated and the aqueous layer was extracted with EtOAc (2×1 mL). The combined organic layers were washed with saturated aqueous NaCl and concentrated in vacuo. The residue (12 mg, 22 µmol) was dissolved in EtOH (22 µL) and 10N NaOH (176 µL, 176 µmol) was added. The resulting solution was stirred for 2 hours, then concentrated in vacuo. The residue was purified by preparative HPLC to yield the title compound (2.2 mg). MS m/z [M+H]$^+$ calc'd for $C_{22}H_{20}ClFN_8O_3$, 499.13; found 499.2.

Example 64

(2R,4R)-5-(5'-Chloro-2'-fluorobiphenyl-4-yl)-2-(2-dimethylaminoacetylamino)-4-[(3H-[1,2,3]triazole-4-carbonyl)amino]pentanoic Acid

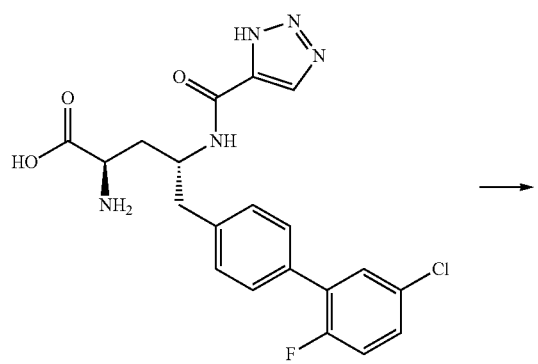

Example 65

(2R,4R)-5-(5'-Chloro-2'-fluorobiphenyl-4-yl)-2-(2-methylaminoacetylamino)-4-[(3H-[1,2,3]triazole-4-carbonyl)amino]pentanoic Acid

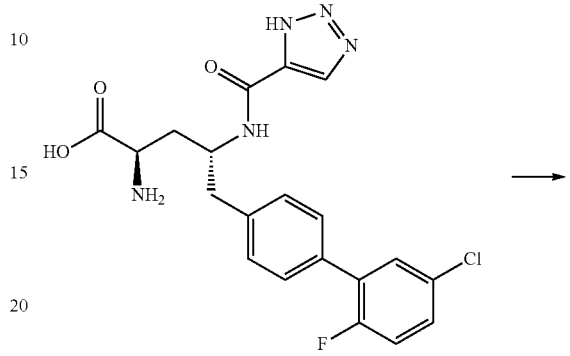

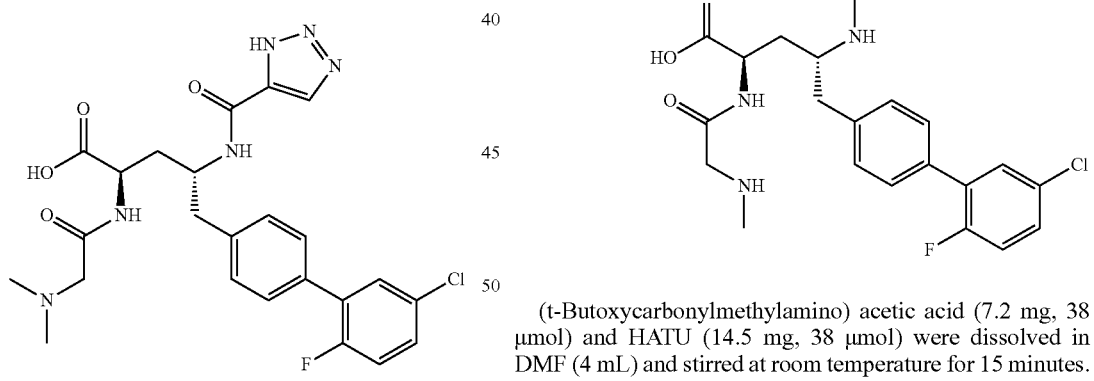

Dimethylamino acetic acid (3.9 mg, 38 μmol) and HATU (14.5 mg, 38 μmol) were dissolved in DMF (4 mL) and stirred at room temperature for 15 minutes. (2R,4R)-2-Amino-5-(5'-chloro-2'-fluorobiphenyl-4-yl)-4-[(3H-[1,2,3]triazole-4-carbonyl)amino]pentanoic acid (15 mg, 35 μmol) and DIPEA (18 μL, 104 μmol) were then added and the resulting mixture was stirred at room temperature for 15 minutes (LC/MS showed reaction completion) then concentrated in vacuo and the residue was purified by preparative HPLC to yield the title compound (14.5 mg; purity 100%) as a TFA salt. MS m/z [M+H]$^+$ calc'd for $C_{24}H_{26}ClFN_6O_4$, 517.17; found 517.2.

(t-Butoxycarbonylmethylamino) acetic acid (7.2 mg, 38 μmol) and HATU (14.5 mg, 38 μmol) were dissolved in DMF (4 mL) and stirred at room temperature for 15 minutes. (2R,4R)-2-Amino-5-(5'-chloro-2'-fluorobiphenyl-4-yl)-4-[(3H-[1,2,3]triazole-4-carbonyl)amino]pentanoic acid (15 mg, 35 μmol) and DIPEA (18 μL, 104 μmol) were then added and the resulting mixture was stirred at room temperature for 15 minutes (LC/MS showed reaction completion) then concentrated in vacuo and the residue was dissolved in MeCN (2 mL). A solution of 4N HCl in dioxane (130 μL, 521 μmol) was added, and the mixture was stirred at room temperature for 10 min. LC/MS showed the mass of the desired product. The solvent was removed in vacuo and the residue was purified by preparative HPLC to yield the title compound (10.4 mg; purity 100%) as a TFA salt. MS m/z [M+H]$^+$ calc'd for $C_{23}H_{24}ClFN_6O_4$, 503.15; found 503.2.

Example 66

(2S,4S)-5-(5'-Chloro-2'-fluorobiphenyl-4-yl)-2-(5-oxo-4,5-dihydro-[1,2,4]oxadiazol-3-ylmethyl)-4-[(3H-[1,2,3]triazole-4-carbonyl)amino]pentanoic Acid

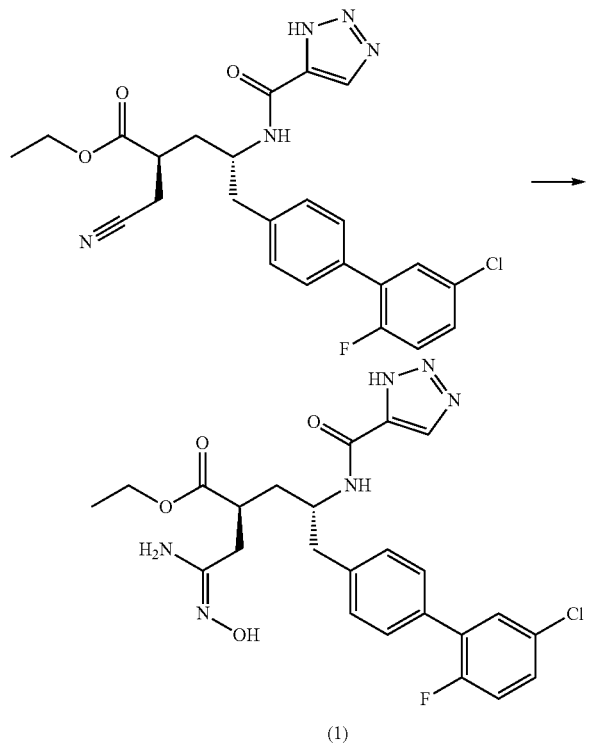

To a solution of (2S,4S)-5-(5'-chloro-2'-fluorobiphenyl-4-yl)-2-cyanomethyl-4-[(3H-[1,2,3]triazole-4-carbonyl)amino]pentanoic acid ethyl ester (11 mg, 22 µmol) in DMSO (25 µL) was added hydroxylamine (1.3 µL, 22 µmol) and NaHCO₃ (1.8 mg, 22 µmol), and the resulting suspension was heated at 70° C. to yield a yellow solution. The solution was removed from the heat and diluted with water (0.2 mL), and the resulting suspension was extracted with EtOAc. The organic layers were washed with saturated aqueous NaCl, dried over Na₂SO₄, filtered, and concentrated in vacuo to yield Compound 1, which was used without further purification.

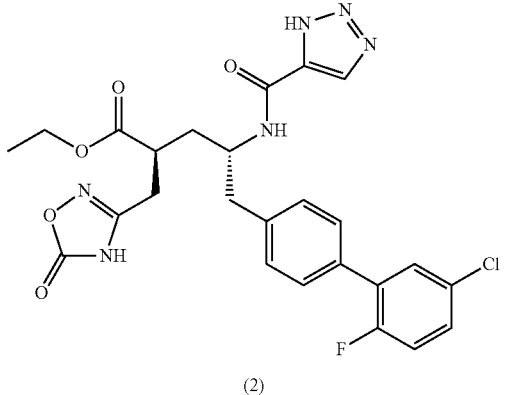

A solution of Compound 1 (11 mg, 22 µmol), DIPEA (9.6 µL, 55 µmol) and TFA (1.7 µL, 22 µmol) in chloroform (0.6 mL) was cooled to 0° C. A solution of diphosgene (3.2 µL, 26 µmol) in chloroform (0.3 mL) was added dropwise. The resulting solution was stirred at 0° C. for 1 h, and then at 110° C. for 30 min in a microwave. After this time, the solution was concentrated in vacuo to yield Compound 2, which was used without further purification.

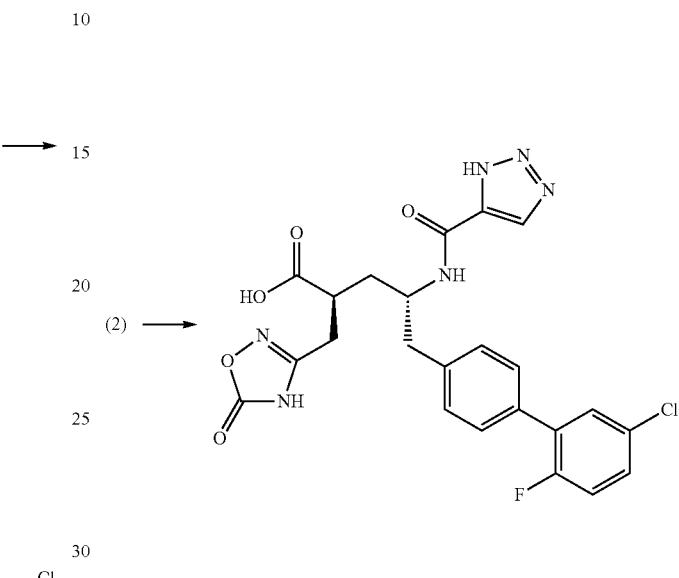

NaOH (176 µL, 176 µmol) was added to a solution of Compound 2 (12 mg, 22 µmol) in EtOH (220 µL), and the resulting mixture was stirred at room temperature overnight. The solution was then concentrated and the residue was purified by preparative HPLC to yield the title compound (0.5 mg; purity 100%). MS m/z [M+H]⁺ calc'd for $C_{23}H_{20}ClFN_6O_5$, 515.12; found 515.2.

Example 67

(2R,4R)-5-(5'-Chloro-2'-fluorobiphenyl-4-yl)-2-(2-methoxycarbonylaminoacetylamino)-4-[(1H-[1,2,3]triazole-4-carbonyl)amino]pentanoic Acid

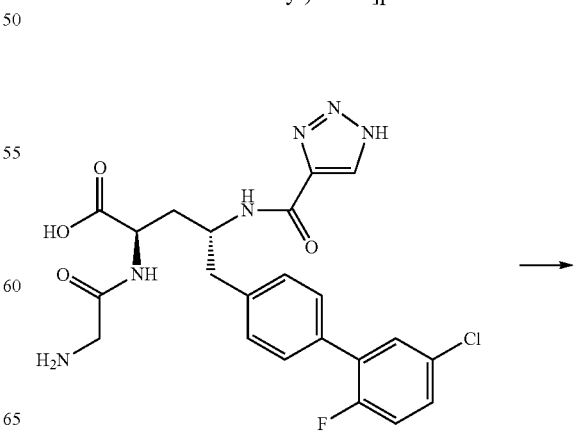

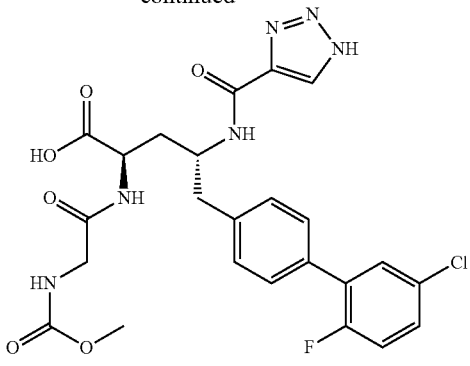

(2R,4R)-2-(2-Aminoacetylamino)-5-(5'-chloro-2'-fluorobiphenyl-4-yl)-4-[(1H-[1,2,3]triazole-4-carbonyl)amino]pentanoic acid (6.4 mg, 13 μmol) was dissolved in DCM (2 mL). Methyl chloroformate (1.1 μL, 14 μmol) was added, followed by DIPEA (6.9 μL, 39 μmol). The resulting mixture was stirred at room temperature for 10 minutes (LC/MS indicated no starting material) then concentrated in vacuo and the crude residue was purified by reverse phase chromatography to yield the title compound (0.6 mg; purity 99%) as a TFA salt. MS m/z [M+H]$^+$ calc'd for $C_{24}H_{24}ClFN_6O_6$, 547.14; found 547.

Example 68

(2S,4S)-2-[(4-Aminobutyrylamino)methyl]-5-(5'-chloro-2'-fluorobiphenyl-4-yl)-4-[(3H-[1,2,3]triazole-4-carbonyl)amino]pentanoic acid

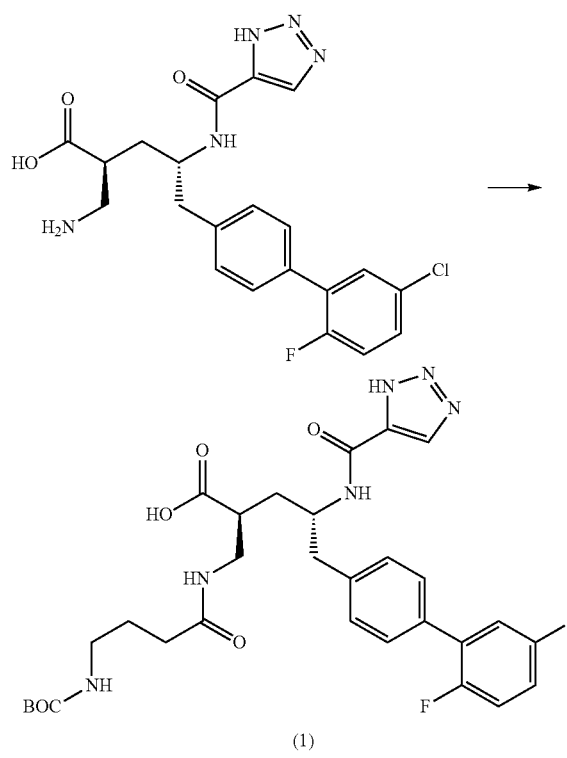

(1)

4-t-Butoxycarbonylaminobutyric acid (2.3 mg, 11 μmol) and HATU (4.3 mg, 11 μmol) were dissolved in DMF (0.5 mL) and stirred at room temperature for 10 minutes. DIPEA (1 eq.) was added and stirred for 1 minute. (2S,4S)-2-aminomethyl-5-(5'-chloro-2'-fluorobiphenyl-4-yl)-4-[(3H-[1,2,3]triazole-4-carbonyl)amino]pentanoic acid (5 mg, 11 μmol) was dissolved in DMF (1 mL) and DIPEA (5.9 μL, 34 μmol) was added, followed by addition of the activated acid solution. The resulting mixture was stirred for 30 minutes, followed by the addition of EtOAc (1 mL) and saturated aqueous NaHCO$_3$ (1 mL). The organic layer was separated and the solution was concentrated in vacuo to yield Compound 1.

(1) →

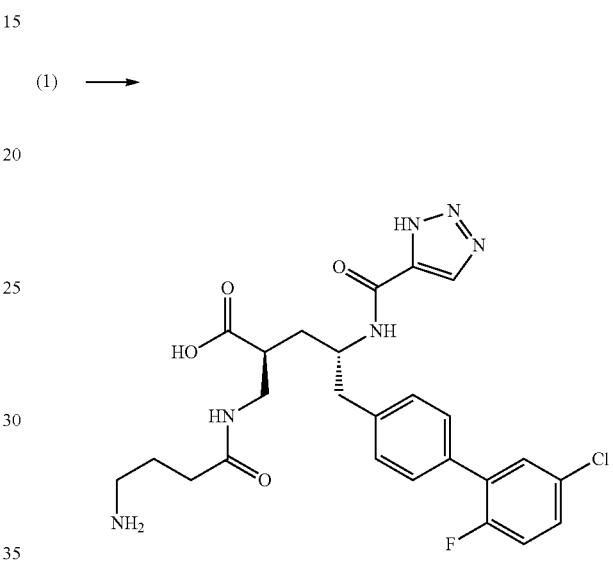

Compound 1 (7 mg, 11 μmol) was dissolved in MeCN (0.4 mL) and 4N HCl in dioxane (0.1 mL). The mixture was stirred for 30 minutes and the solvent was evaporated. AcOH (1 mL) was added and the solution was purified by reverse phase chromatography to yield the title compound as a TFA salt. MS m/z [M+H]$^+$ calc'd for $C_{25}H_{28}ClFN_6O_4$, 531.18; found 531.

Example 69a (2S,4S)-5-(5'-Chloro-2'-fluorobiphenyl-4-yl)-2-morpholin-4-ylmethyl-4-[(1H-[1,2,3]triazole-4-carbonyl)amino]pentanoic Acid

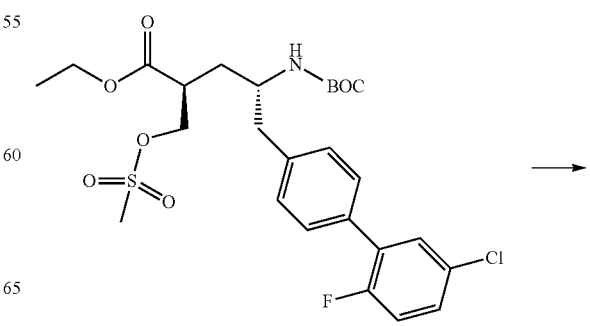

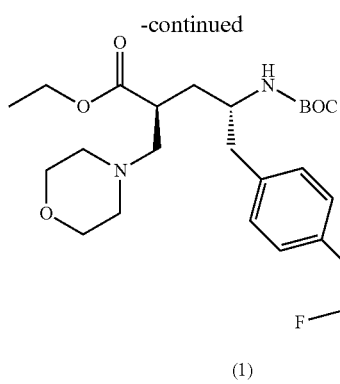

(1)

(2S,4S)-4-t-Butoxycarbonylamino-5-(5'-chloro-2'-fluorobiphenyl-4-yl)-2-methanesulfonyloxymethylpentanoic acid ethyl ester (2.8 mg, 50 µmol) was combined with EtOH (2 mL), followed by Na$_2$CO$_3$ (16.0 mg, 151 µmol) and morpholine (13.1 mg, 151 µmol) and stirred at room temperature overnight. EtOAc (1 mL) and water (1 mL) were added, the organic layer was separated and concentrated under reduced pressure to yield Compound 1.

(1) →

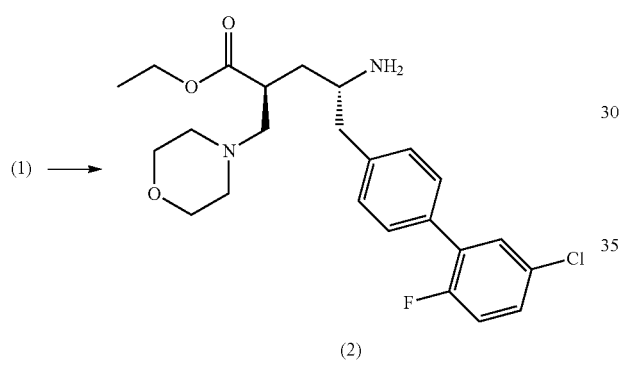

(2)

Compound 1 (27 mg, 49 µmol) was dissolved in MeCN (0.5 mL) and dry 4N HCl in dioxane (0.1 mL). The mixture was stirred for 10 minutes and was then concentrated under reduced pressure. The residue was dissolved in AcOH (1 mL) and purified by reverse phase chromatography to yield Compound 2 (5 mg).

(2) →

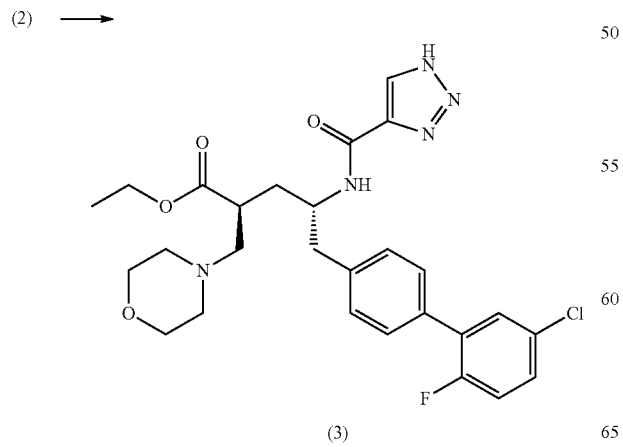

(3)

1H-1,2,3-triazole-5-carboxylic acid (1.1 mg, 10.0 µmol) was combined with HATU (3.0 mg, 7.8 µmol) in DMF (0.5 mL) and stirred for 10 minutes; DIPEA (1 eq.) was added and the mixture was stirred for 1 minute. Compound 2 (5.0 mg, 11 µmol) was dissolved in DMF (1 mL) and DIPEA (5.8 µL, 33 µmol) was added, followed by addition of the activated acid solution. The mixture was stirred for 30 minutes to yield Compound 3.

(3) →

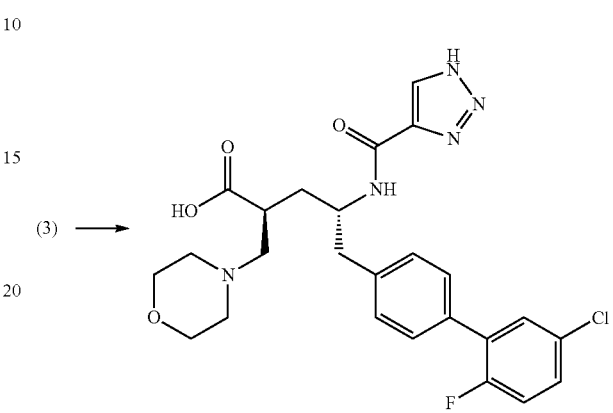

Compound 3 (6 mg, 11 µmol) was dissolved in 1N LiOH (55.1 µL, 55 µmol) in THF (0.5 mL). The mixture was stirred for 40 minutes and AcOH was added. The solution was purified by reverse phase chromatography to yield the title compound. MS m/z [M+H]$^+$ calc'd for C$_{25}$H$_{22}$ClFN$_5$O$_4$, 516.17; found 516.

Example 69b (2S,4S)-5-(5'-Chloro-2'-fluorobiphenyl-4-yl)-2-morpholin-4-ylmethyl-4-[(3H-[1,2,3]triazole-4-carbonyl)amino]pentanoic Acid Ethyl Ester

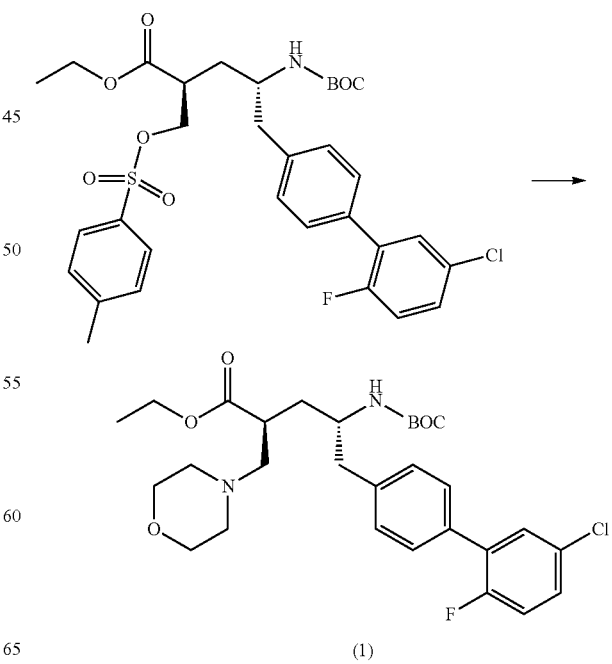

(1)

(2S,4S)-4-t-Butoxycarbonylamino-5-(5'-chloro-2'-fluoro-biphenyl-4-yl)-2-(toluene-4-sulfonyloxymethyl)pentanoic acid ethyl ester (35 mg, 55 μmol) was dissolved in EtOH (2 mL), followed by addition of $Na_2CO_3$ (10 eq.) and morpholine (24 mg, 276 μmol). The mixture was stirred at 70° C. for 2 days, at which time LCMS indicated the mass of the desired compound. The mixture was concentrated under reduced pressure and the crude residue was purified by reverse phase chromatography to yield Compound 1 (12 mg).

(1) →

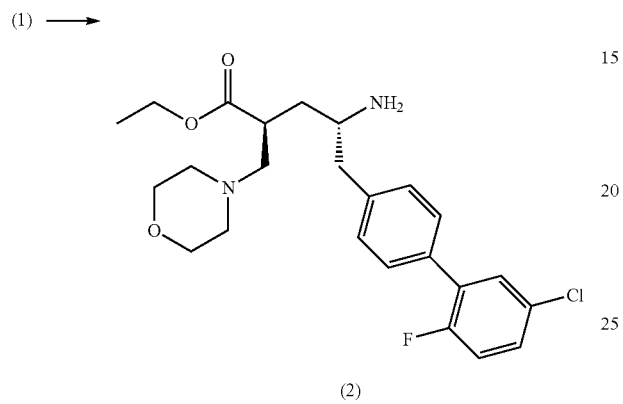

(2)

Compound 1 (12 mg, 50 μmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) →

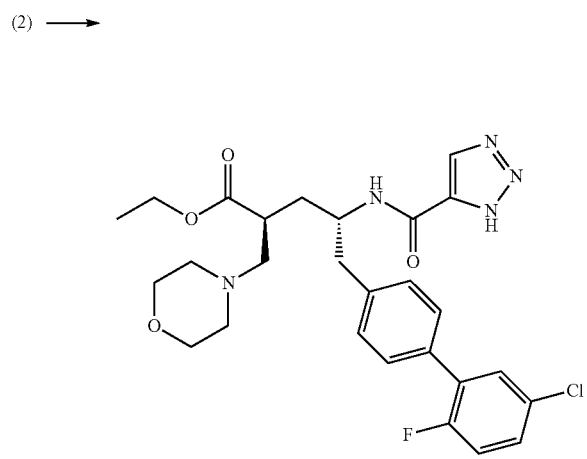

3H-1,2,3-triazole-5-carboxylic acid (2.5 mg, 22 μmol) was combined with HATU (8.4 mg, 22 μmol) in DMF (0.3 mL) and stirred for 10 minutes; $Et_3N$ (1 eq.) was added and the mixture was stirred for 1 minute. Compound 2 (22 μmol) was dissolved in DMF (0.5 mL) and $Et_3N$ (3.1 μL, 22 μmol) was added, followed by addition of the activated acid solution. The mixture was stirred for 30 minutes, concentrated, and purified by preparative HPLC to yield the title compound. MS m/z $[M+H]^+$ calc'd for $C_{27}H_{31}ClFN_5O_4$, 544.21; found 544.2.

Example 70

(2R,4R)-2-(6-Aminohexanoylamino)-5-(5'-chloro-2'-fluorobiphenyl-4-yl)-4-[(1H-[1,2,3]triazole-4-carbonyl)amino]pentanoic Acid

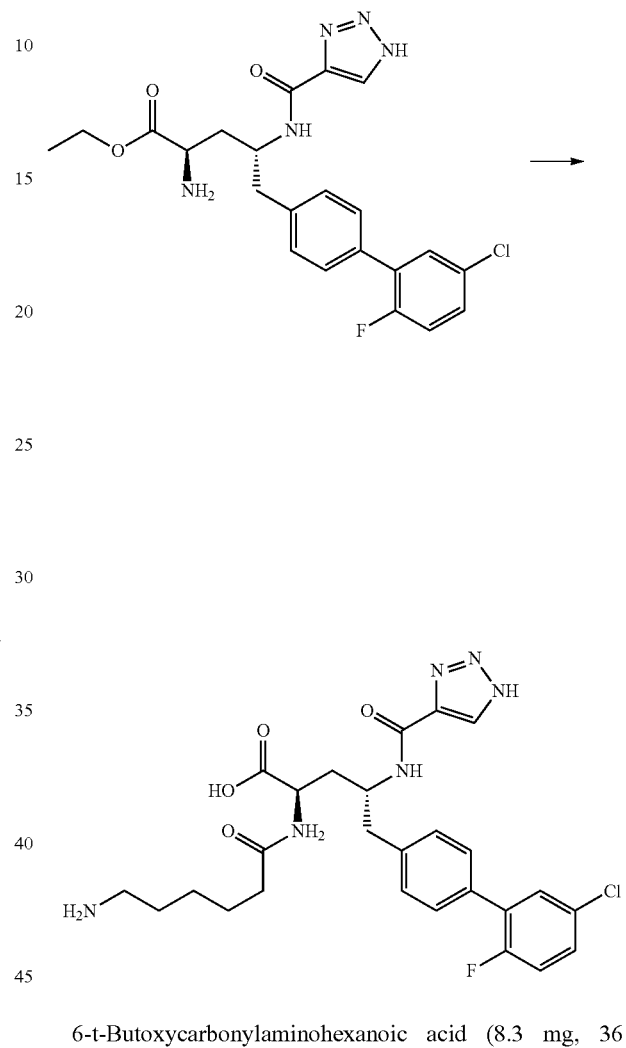

6-t-Butoxycarbonylaminohexanoic acid (8.3 mg, 36 μmol) and HATU (13.6 mg, 36 μmol) were dissolved in DMF (2 mL) and stirred at room temperature for 15 minutes. (2R,4R)-2-Amino-5-(5'-chloro-2'-fluorobiphenyl-4-yl)-4-[(1H-[1,2,3]triazole-4-carbonyl)amino]pentanoic acid ethyl ester (15 mg, 33 μmol) and DIPEA (17 μL, 98 μmol) were then added, and the mixture was stirred at room temperature for 15 minutes (LC/MS showed reaction completion) then concentrated in vacuo. The residue was dissolved in MeCN (2 mL) and a solution of 4N HCl in dioxane (122 μL, 489 μmol) was added. The mixture was stirred at room temperature for 20 minutes (LC/MS showed the mass of the desired product) then concentrated in vacuo and the residue was dissolved in EtOH (2 mL). A solution of 1N LiOH in water (261 μL, 261 μmol) was added and the mixture was stirred at room temperature for 30 minutes (LC/MS showed reaction completion) then concentrated in vacuo and the residue was purified by preparative HPLC to yield the title compound (21.3 mg; purity 100%) as a TFA salt. MS m/z $[M+H]^+$ calc'd for $C_{26}H_{30}ClFN_6O_4$, 545.20; found 545.2.

Example 71

(2R,4R)-5-(5'-Chloro-2'-fluorobiphenyl-4-yl)-2-(4-methylamino-butyrylamino)-4-[(1H-[1,2,3]triazole-4-carbonyl)amino]pentanoic Acid

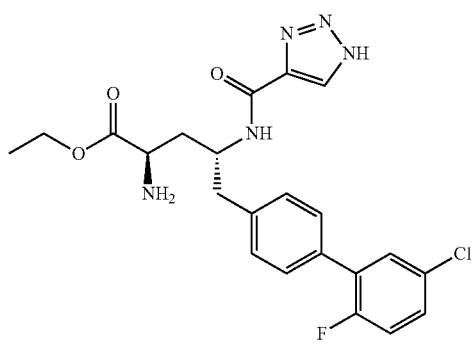

Example 72

(2R,4R)-2-(5-Amino-pentanoylamino)-5-(5'-chloro-2'-fluorobiphenyl-4-yl)-4-[(1H-[1,2,3]triazole-4-carbonyl)amino]pentanoic Acid

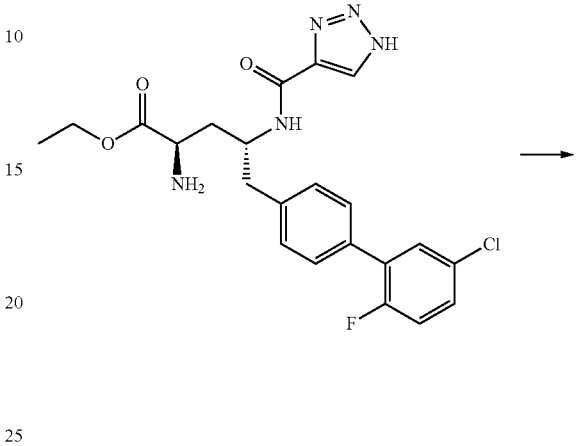

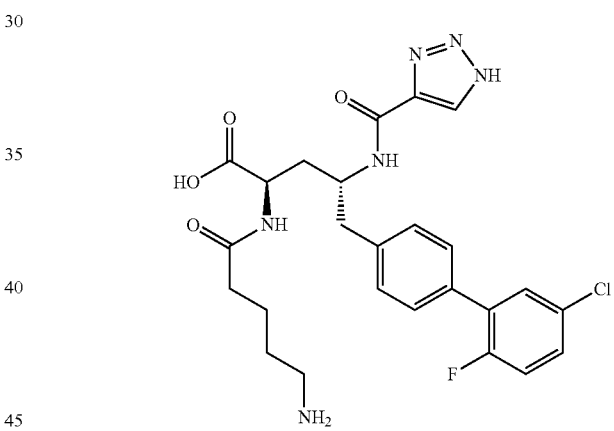

4-(t-Butoxycarbonylmethylamino)butyric acid (7.8 mg, 36 μmol) and HATU (13.6 mg, 36 μmol) were dissolved in DMF (2 mL) and stirred at room temperature for 15 minutes. (2R,4R)-2-Amino-5-(5'-chloro-2'-fluorobiphenyl-4-yl)-4-[(1H-[1,2,3]triazole-4-carbonyl)amino]pentanoic acid ethyl ester (15 mg, 33 μmol) and DIPEA (17 μL, 98 μmol) were then added, and the mixture was stirred at room temperature for 15 minutes (LC/MS showed reaction completion) then concentrated in vacuo. The residue was dissolved in MeCN (2 mL) and a solution of 4N HCl in dioxane (122 μL, 489 μmol) was added. The mixture was stirred at room temperature for 20 minutes (LC/MS showed the mass of the desired product) then concentrated in vacuo and the residue was dissolved in EtOH (2 mL). A solution of 1N LiOH in water (261 μL, 261 μmol) was added and the mixture was stirred at room temperature for 30 minutes (LC/MS showed reaction completion) then concentrated in vacuo and the residue was purified by preparative HPLC to yield the title compound (20.5 mg; purity 100%) as a TFA salt. MS m/z [M+H]+ calc'd for $C_{25}H_{28}ClFN_6O_4$, 531.18; found 531.2.

5-t-Butoxycarbonylaminopentanoic acid (7.8 mg, 36 μmol) and HATU (13.6 mg, 36 μmol) were dissolved in DMF (2 mL) and stirred at room temperature for 15 minutes. (2R,4R)-2-Amino-5-(5'-chloro-2'-fluorobiphenyl-4-yl)-4-[(1H-[1,2,3]triazole-4-carbonyl)amino]pentanoic acid ethyl ester (15 mg, 33 μmol) and DIPEA (17 μL, 98 μmol) were then added, and the mixture was stirred at room temperature for 15 minutes (LC/MS showed reaction completion) then concentrated in vacuo. The residue was dissolved in MeCN (2 mL) and a solution of 4N HCl in dioxane (122 μL, 489 μmol) was added. The mixture was stirred at room temperature for 20 minutes (LC/MS showed the mass of the desired product) then concentrated in vacuo and the residue was dissolved in EtOH (2 mL). A solution of 1N LiOH in water (261 μL, 261 μmol) was added and the mixture was stirred at room temperature for 30 minutes (LC/MS showed reaction completion) then concentrated in vacuo and the residue was purified by preparative HPLC to yield the title compound (20.7 mg; purity 100%) as a TFA salt. MS m/z [M+H]+ calc'd for $C_{25}H_{28}ClFN_6O_4$, 531.18; found 531.2.

Example 73

(2R,4R)-5-(5'-Chloro-2'-fluorobiphenyl-4-yl)-2-(4-dimethylaminobutyrylamino)-4-[(1H-[1,2,3]triazole-4-carbonyl)amino]pentanoic Acid

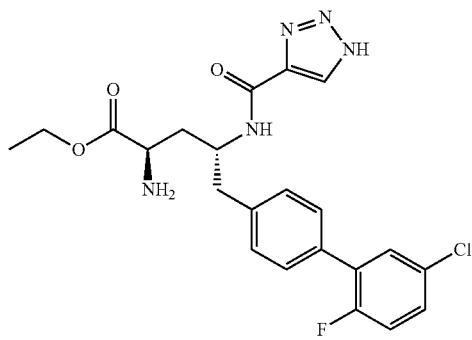

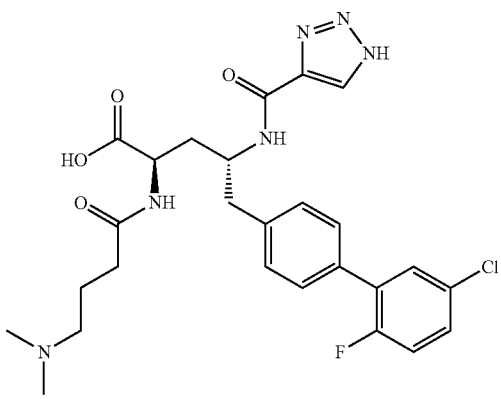

4-Dimethylaminobutyric acid hydrochloride (6.0 mg, 36 µmol) and HATU (13.6 mg, 36 µmol) were dissolved in DMF (2 mL) and stirred at room temperature for 15 minutes. (2R,4R)-2-Amino-5-(5'-chloro-2'-fluorobiphenyl-4-yl)-4-[(1H-[1,2,3]triazole-4-carbonyl)amino]pentanoic acid ethyl ester (15 mg, 33 µmol) and DIPEA (17 µL, 98 µmol) were then added, and the mixture was stirred at room temperature for 15 minutes (LC/MS showed reaction completion) then concentrated in vacuo. The residue was dissolved in EtOH (2 mL). A solution of 1N LiOH in water (261 µL, 261 µmol) was added and the mixture was stirred at room temperature for 30 minutes (LC/MS showed reaction completion) then concentrated in vacuo and the residue was purified by preparative HPLC to yield the title compound (24.3 mg; purity 100%) as a TFA salt. MS m/z [M+H]$^+$ calc'd for $C_{26}H_{30}ClFN_6O_4$, 545.20; found 545.2.

Example 74

(2S,4S)-5-(5'-Chloro-2'-fluorobiphenyl-4-yl)-2-[(3-methoxypropylamino)-methyl]-4-[(3H-[1,2,3]triazole-4-carbonyl)amino]pentanoic Acid

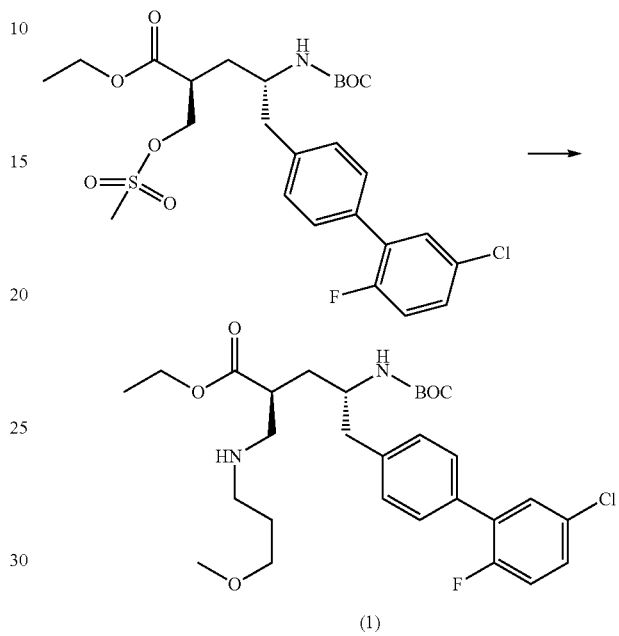

To a stirred solution of (2S,4S)-4-t-butoxycarbonylamino-5-(5'-chloro-2'-fluorobiphenyl-4-yl)-2-methanesulfonyloxymethylpentanoic acid ethyl ester (60 mg, 108 µmol) in EtOH (2 mL), was added 2-methoxypropylamine (19.2 mg, 215 µmol). The resulting mixture was stirred at 50° C. overnight. EtOAc (2 mL) and water (1 mL) were added, the organic layer was separated and washed with water (3×), dried over Na$_2$SO$_4$, then concentrated under reduced pressure and purified by normal phase chromatography (0-60% EtOAc:hexanes) to yield Compound 1 (15 mg).

(1) ⟶

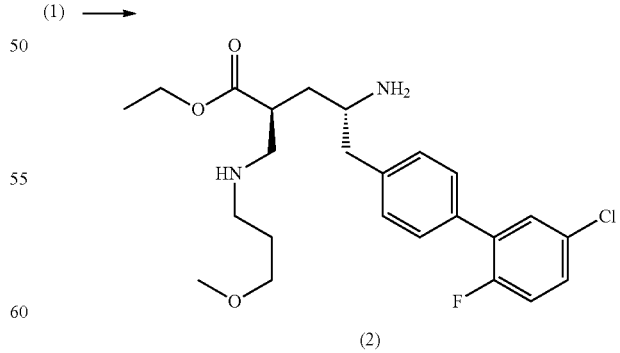

Compound 1 (10.0 mg, 18 µmol) was dissolved in MeCN (0.5 mL) and dry 4N HCl in dioxane (0.3 mL). The mixture was stirred for 10 minutes and was then concentrated under reduced pressure to yield Compound 2 as an HCl salt.

(2) →

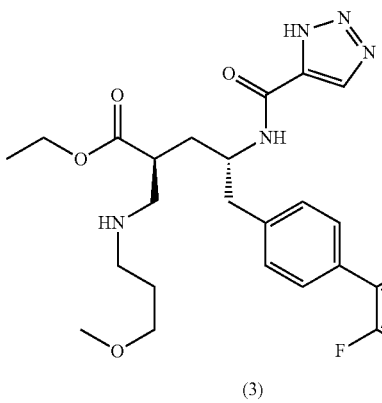

1H-1,2,3-triazole-5-carboxylic acid (2.3 mg, 20 μmol) was combined with HATU (5.9 mg, 15 μmol) in DMF (0.5 mL) and stirred for 10 minutes; DIPEA (1 eq.) was added and the mixture was stirred for 1 minute. Compound 2 (10.0 mg, 22 μmol) was dissolved in DMF (1 mL) and DIPEA (11.6 μL, 66 μmol) was added, followed by addition of the activated acid solution. The mixture was stirred for 30 minutes and then concentrated in vacuo to yield Compound 3.

(3) →

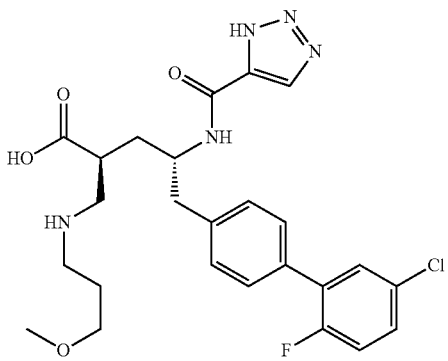

To the crude solution of Compound 3 (10.0 mg, 18 μmol) was added 1N LiOH (92 μL, 92 μmol) and THF (0.5 mL), followed by MeOH (0.1 mL). The mixture was stirred for 1 hour and AcOH (1 mL) was added. The solution was purified by reverse phase chromatography to yield the title compound (2 mg; purity 95%) as a TFA salt. MS m/z [M+H]+ calc'd for $C_{25}H_{29}ClFN_5O_4$, 518.19; found 518.

Example 75

(2S,4S)-5-(5'-Chloro-2'-fluorobiphenyl-4-yl)-2-dimethylaminomethyl-4-[(3H-[1,2,3]triazole-4-carbonyl)amino]pentanoic Acid

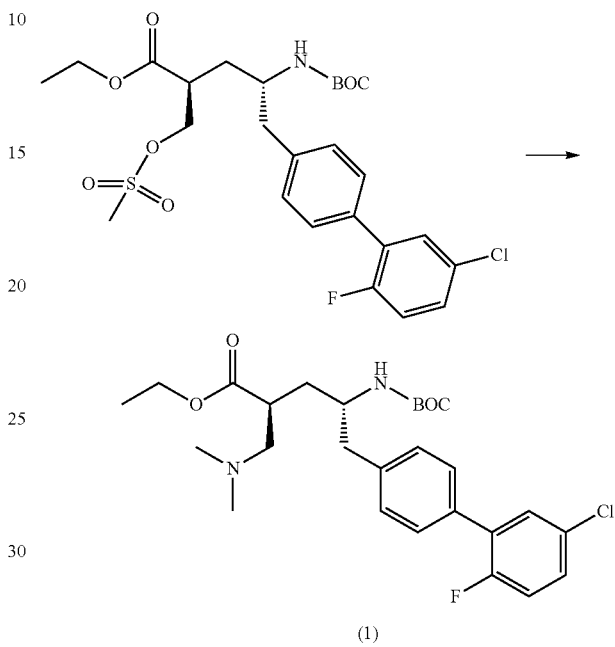

To a stirred solution of (2S,4S)-4-t-Butoxycarbonylamino-5-(5'-chloro-2'-fluorobiphenyl-4-yl)-2-methanesulfonyloxymethylpentanoic acid ethyl ester (60 mg, 108 μmol) in EtOH (2 mL), was added dimethylamine in THF (108 μL, 215 μmol). The resulting mixture was stirred at 50° C. overnight. EtOAc (2 mL) and water (2 mL) were added. The organic layer was separated and washed with water (3×), then concentrated under reduced pressure and purified by normal phase chromatography (0-60% EtOAc:hexanes) to yield Compound 1 (10 mg).

(1) →

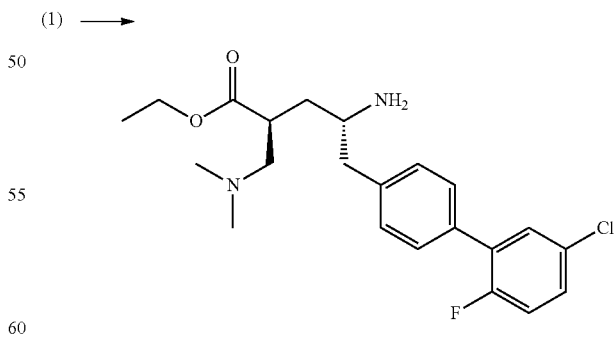

Compound 1 (9.2 mg, 18 μmol) was dissolved in MeCN (0.5 mL) and dry 4N HCl in dioxane (0.3 mL). The mixture was stirred for 10 minutes and then concentrated under reduced pressure to yield Compound 2 as an HCl salt.

(2) →

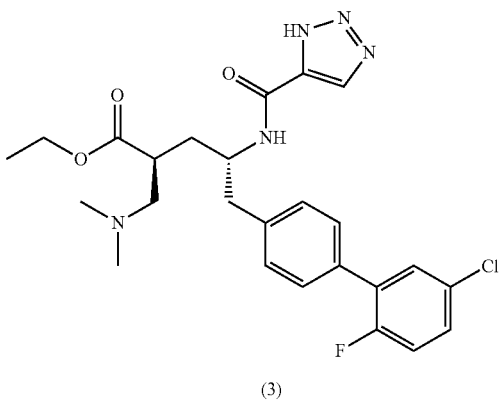

1H-1,2,3-triazole-5-carboxylic acid (2.3 mg, 20 µmol) was combined with HATU (5.9 mg, 15 µmol) in DMF (0.5 mL) and stirred for 10 minutes; DIPEA (1 eq.) was added and the mixture was stirred for 1 minute. Compound 2 (9.0 mg, 22 µmol) was dissolved in DMF (1 mL) and DIPEA (11.6 µL, 66 µmol) was added, followed by addition of the activated acid solution. The mixture was stirred for 30 minutes and the solution was concentrated in vacuo to yield Compound 3.

(3) →

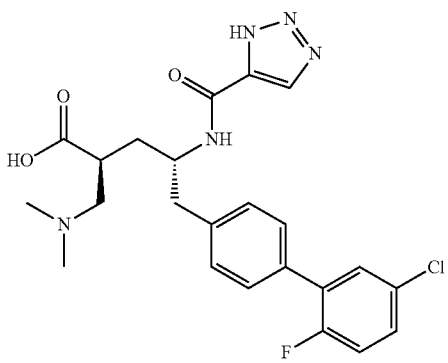

To a solution of crude Compound 3 (9.0 mg, 18 µmol) was added 1N LiOH (92 µL, 92 µmol) and THF (0.5 mL), followed by MeOH (0.1 mL). The mixture was stirred for 1 hour and AcOH was added. The solution was purified by reverse phase chromatography to yield the title compound (2 mg; purity 95%) as a TFA salt. MS m/z [M+H]+ calc'd for $C_{23}H_{25}ClFN_5O_3$, 474.16; found 474.

Example 76

(S)-5-(5'-Chloro-2'-fluorobiphenyl-4-yl)-2-pyridin-2-yl-4-[(3H-[1,2,3]triazole-4-carbonyl)amino]pentanoic Acid

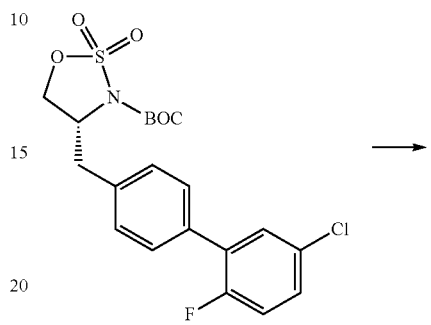

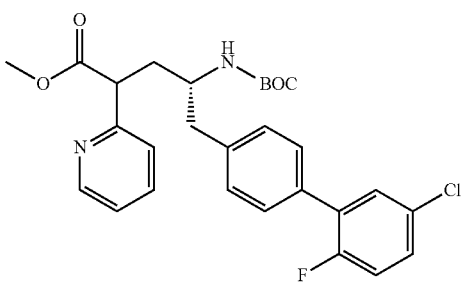

A 1M solution of lithium bis(trimethylsilyl)amide in hexanes (88 µL, 88 µmol) in THF (110 µL) was cooled to 0° C. and methyl 2-(pyridin-2-yl)acetate (12 µL, 88 µmol) was added. After stirring at this temperature for 30 minutes, a solution of (R)-t-butyl 4-((5'-chloro-2'-fluoro-[1,1'-biphenyl]-4-yl)methyl)-1,2,3-oxathiazolidine-3-carboxylate 2,2-dioxide (46 mg, 105 µmol) in THF (0.5 mL) was added. The resulting mixture was stirred at this temperature for 1 hour and then slowly warmed up to room temperature overnight. 1N HCl (0.5 mL) was added and the solution was stirred at room temperature for 10 minutes. DCM (1.5 mL) was added, the layers were separated and the aqueous layer was extracted with DCM (2×1.5 mL). The combined organic layers were dried over $Na_2SO_4$, filtered and concentrated. The crude product was purified by column chromatography (0-30% EtOAc in hexanes over 20 minutes) to yield Compound 1 (21.8 mg) as a clear oil.

229

(1) →

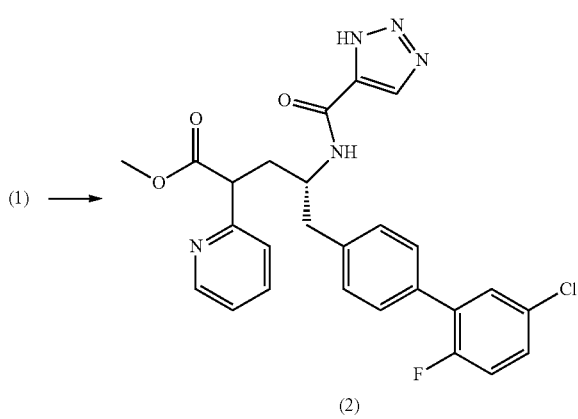 [SMILES: COC(=O)C(C[C@@H](Cc1ccc(-c2cc(Cl)ccc2F)cc1)NC(=O)c1cnn[nH]1)c1ccccn1]

(2)

A solution of Compound 1 (8.9 mg, 18 µmol) in HCl (88 µL, 351 µmol) was stirred at room temperature for 20 minutes. After this time, LCMS indicated that the BOC group had been cleaved so the solution was concentrated in vacuo. In a separate flask, a solution of 3H-[1,2,3]triazole-4-carboxylic acid (2.4 mg, 21 µmol) and HATU (8.0 mg, 21 µmol) in DMF (180 µL) was stirred at room temperature for 30 minutes. After this time, a solution of the crude amine in DMF (180 µL) was added, followed by DIPEA (9.2 µL, 53 µmol). The resulting solution was stirred overnight at room temperature. LCMS indicated that the reaction was complete and the solution was concentrated in vacuo to yield Compound 2 (8.9 mg), which was used without further purification.

(2) →

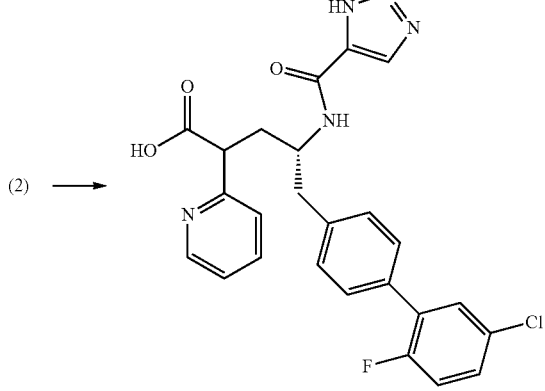

To a solution of Compound 2 (9.1 mg, 18 µmol) in MeOH (180 µL) was added 10N NaOH (144 µL, 144 µmol). The resulting solution was stirred at room temperature overnight. LCMS indicated that a large amount of starting material was present so additional 10N NaOH (144 µL, 144 µmol) was added. After stirring at room temperature for 2 hours, the reaction was complete and the solution was concentrated in vacuo. The residue was purified by preparative HPLC to yield the title compound (3.8 mg; purity 97%) as a mixture of diastereomers at the pyridine center. MS m/z [M+H]+ calc'd for $C_{25}H_{21}ClFN_5O_3$, 494.13; found 494.0.

230

Example 77

(S)-5-(5'-Chloro-2'-fluoro-biphenyl-4-yl)-2-pyridin-3-yl-4-[(3H-[1,2,3]triazole-4-carbonyl)amino]pentanoic Acid (diastereomers a and b)

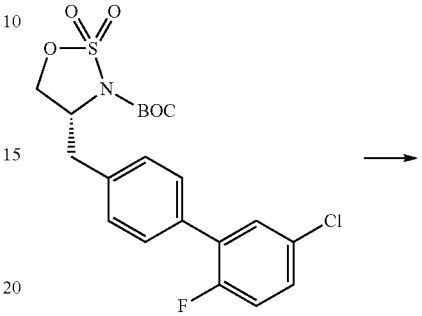

→

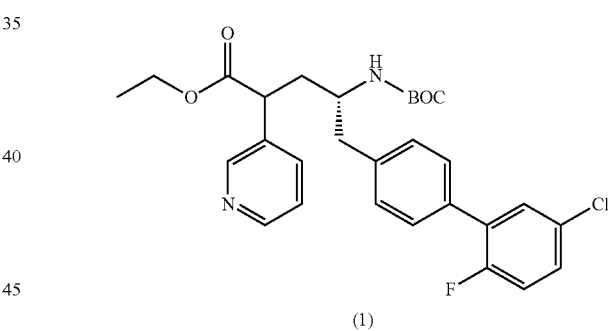

(1)

A 1M solution of lithium bis(trimethylsilyl)amide in hexanes (87 µL, 87 µmol) in THF (110 µL) was cooled to 0° C. and ethyl 2-(pyridin-3-yl)acetate (13 µL, 87 µmol) was added. After stirring at this temperature for 30 minutes, a solution of (R)-t-butyl 4-((5'-chloro-2'-fluoro-[1,1'-biphenyl]-4-yl)methyl)-1,2,3-oxathiazolidine-3-carboxylate 2,2-dioxide (46 mg, 104 µmol) in THF (0.5 mL) was added. The resulting mixture was stirred at this temperature for 1 hour and then slowly warmed up to room temperature overnight. 1N HCl (0.5 mL) was added and the solution was stirred at room temperature for 10 minutes. DCM (1.5 mL) was added, the layers were separated and the aqueous layer was extracted with DCM (2×1.5 mL). The combined organic layers were dried over $Na_2SO_4$, filtered and concentrated. The crude product was purified by column chromatography (0-30% EtOAc in hexanes over 20 minutes) to yield Compound 1 (9.7 mg) as a clear oil.

(1) ⟶

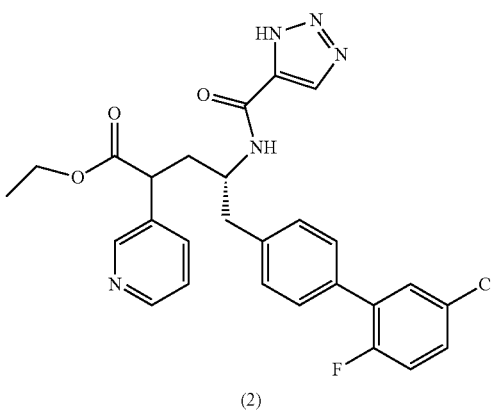

(2)

To a solution of Compound 1 (9.7 mg, 18 μmol) in dioxane (180 μL) was added HCl (92 μL, 368 μmol). The resulting solution was stirred at room temperature for 2 hours, and then concentrated in vacuo. In a separate flask, a solution of 3H-[1,2,3]triazole-4-carboxylic acid (2.5 mg, 22 μmol) and HATU (8.4 mg, 22 μmol) in DMF (180 μL) was stirred at room temperature for 30 minutes. After this time, a solution of the crude amine in DMF (180 μL) was added, followed by DIPEA (9.6 μL, 55 μmol). The resulting solution was stirred for 1 hour at room temperature then concentrated in vacuo when the reaction was deemed complete by LCMS to yield Compound 2 (9.6 mg), which was used without further purification.

(2) ⟶

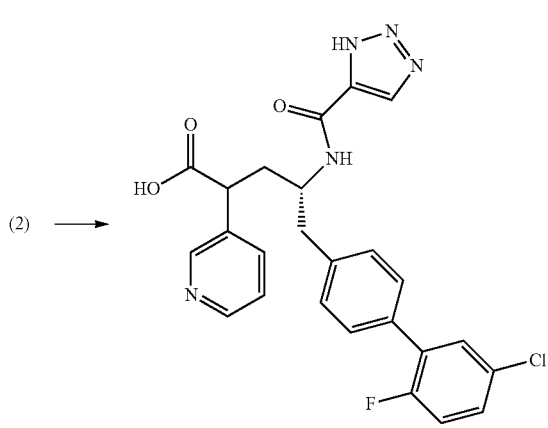 [SMILES: O=C(N[C@H](Cc1ccc(-c2cc(Cl)ccc2F)cc1)CC(C(=O)O)c1cccnc1)c1cnn[nH]1]

To a solution of Compound 2 (9.4 mg, 18 μmol) in EtOH (180 μL) was added 10N NaOH (288 μL, 288 μmol). The resulting solution was stirred at room temperature for 1 hour and then concentrated in vacuo. The residue was purified by preparative HPLC to yield the title compound (diastereomer a; 3.1 mg; purity 96% and diastereomer b; 1.3 mg; purity 100%). MS m/z [M+H]$^+$ calc'd for $C_{25}H_{21}ClFN_5O_3$, 494.13; found 494.2.

Example 78

(S)-5-(5'-Chloro-2'-fluorobiphenyl-4-yl)-2-thiophen-2-yl-4-[(3H-[1,2,3]triazole-4-carbonyl)amino]pentanoic Acid

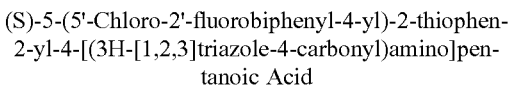

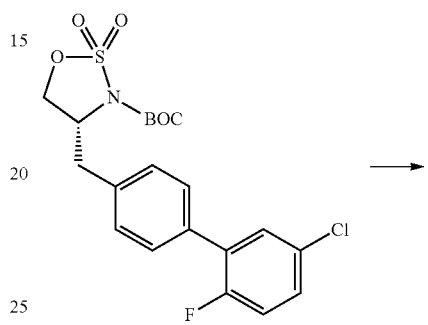

⟶

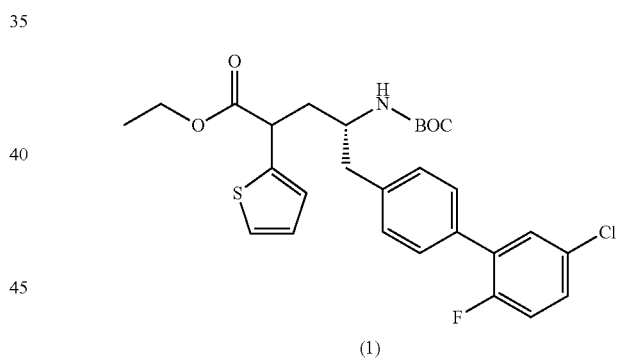

(1)

A 1M solution of lithium bis(trimethylsilyl)amide in hexanes (87 μL, 87 μmol) in THF (110 μL) was cooled to 0° C. and ethyl 2-(thiophen-2-yl)acetate (13 μL, 87 μmol) was added. After stirring at this temperature for 30 minutes, a solution of (R)-t-butyl 4-((5'-chloro-2'-fluoro-[1,1'-biphenyl]-4-yl)methyl)-1,2,3-oxathiazolidine-3-carboxylate 2,2-dioxide (46 mg, 104 μmol) in THF (0.5 mL) was added. The resulting mixture was stirred at this temperature for 1 hour and then slowly warmed up to room temperature overnight. 1N HCl (0.5 mL) was added and the solution was stirred at room temperature for 10 minutes. DCM (1.5 mL) was added, the layers were separated and the aqueous layer was extracted with DCM (2×1.5 mL). The combined organic layers were dried over Na$_2$SO$_4$, filtered and concentrated. The crude product was purified by column chromatography (0-30% EtOAc in hexanes over 20 minutes) to yield Compound 1 (15.9 mg) as a clear oil.

(1) →

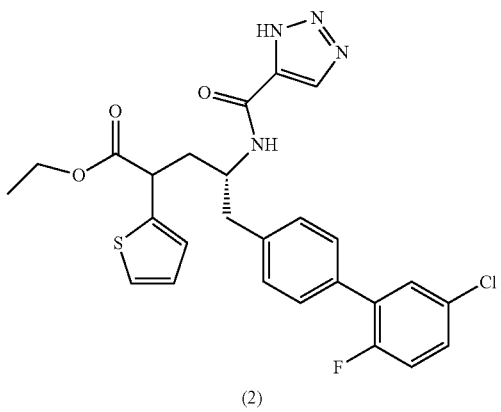

(2)

To a solution of Compound 1 (15.9 mg, 30 μmol) in dioxane (0.3 mL) was added HCl (149 μL, 598 μmol). The resulting solution was stirred at room temperature for 2 hours, and then concentrated in vacuo. In a separate flask, a solution of 3H-[1,2,3]triazole-4-carboxylic acid (4.1 mg, 36 μmol) and HATU (14 mg, 36 μmol) in DMF (0.3 mL) was stirred at room temperature for 30 minutes. After this time, a solution of the crude amine in DMF (0.3 mL) was added, followed by DIPEA (16 μL, 90 μmol). The resulting solution was stirred for 1 hour at room temperature then concentrated in vacuo when the reaction was deemed complete by LCMS to yield Compound 2 (16 mg), which was used without further purification.

(2) →

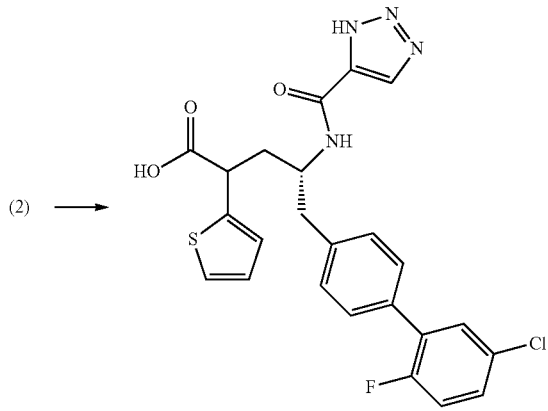 [SMILES: O=C(N[C@H](Cc1ccc(-c2cc(Cl)ccc2F)cc1)CC(C(=O)O)c1cccs1)c1cnn[nH]1]

To a solution of Compound 2 (15.8 mg, 30 μmol) in EtOH (0.3 mL) was added 10N NaOH (240 μL, 240 μmol). The resulting solution was stirred at room temperature for 1 hour and then concentrated in vacuo. The residue was purified by preparative HPLC to yield the title compound (2.6 mg; purity 99.5%) as a mixture of diastereomers at the point of attachment of the thiophene ring. MS m/z [M+H]$^+$ calc'd for $C_{24}H_{20}ClFN_4O_3S$, 499.09; found 499.0.

Example 79

(S)-5-(5'-Chloro-2'-fluorobiphenyl-4-yl)-2-thiophen-3-yl-4-[(3H-[1,2,3]triazole-4-carbonyl)amino]pentanoic Acid

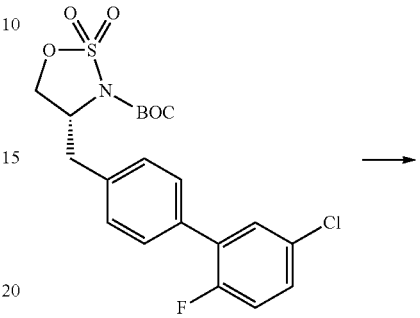

→

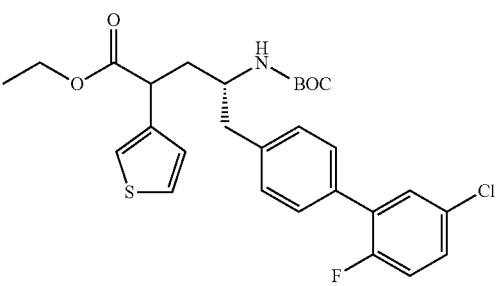

(1)

A 1M solution of lithium bis(trimethylsilyl)amide in hexanes (87 μL, 87 μmol) in THF (110 μL) was cooled to 0° C. and ethyl 2-(thiophen-3-yl)acetate (13 μL, 87 μmol) was added. After stirring at this temperature for 30 minutes, a solution of (R)-t-butyl 4-((5'-chloro-2'-fluoro-[1,1'-biphenyl]-4-yl)methyl)-1,2,3-oxathiazolidine-3-carboxylate 2,2-dioxide (46 mg, 104 μmol) in THF (0.5 mL) was added. The resulting mixture was stirred at this temperature for 1 hour and then slowly warmed up to room temperature overnight. 1N HCl (0.5 mL) was added and the solution was stirred at room temperature for 10 minutes. DCM (1.5 mL) was added, the layers were separated and the aqueous layer was extracted with DCM (2×1.5 mL). The combined organic layers were dried over $Na_2SO_4$, filtered and concentrated. The crude product was purified by column chromatography (0-30% EtOAc in hexanes over 20 minutes) to yield Compound 1 (51.3 mg) as a clear oil.

(1) →

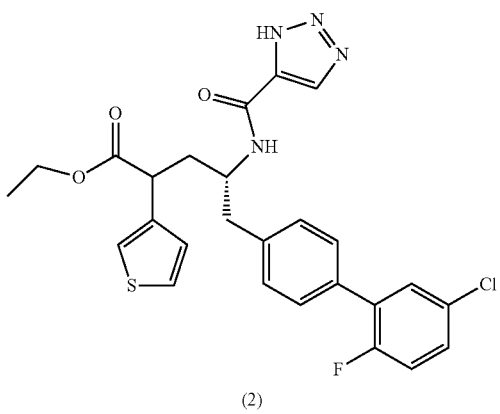

(2)

A solution of Compound 1 (51.3 mg, 96 µmol) in HCl (482 µL, 1.9 mmol) was stirred at room temperature for 2 hours, and then concentrated in vacuo. In a separate flask, a solution of 3H-[1,2,3]triazole-4-carboxylic acid (13 mg, 116 µmol) and HATU (44 mg, 116 µmol) in DMF was stirred at room temperature for 30 minutes. After this time, a solution of the crude amine in DMF was added, followed by DIPEA (51 µL, 289 µmol). The resulting solution was stirred for 1 hour at room temperature then concentrated in vacuo when the reaction was deemed complete by LCMS to yield Compound 2 (96 mg), which was used without further purification.

(2) →

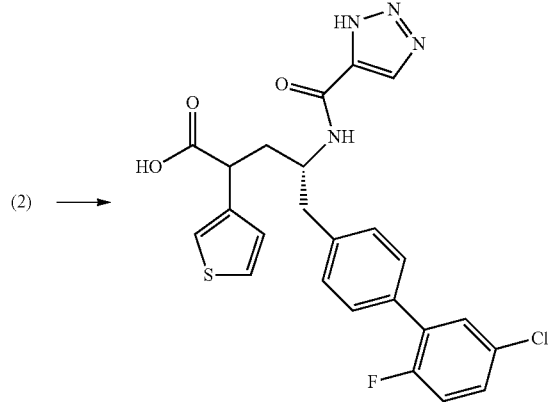 [SMILES: O=C(N[C@H](Cc1ccc(-c2cc(Cl)ccc2F)cc1)CC(C(=O)O)c1ccsc1)c1cnn[nH]1]

To a solution of Compound 2 (50.6 mg, 96 µmol) in EtOH (1.0 mL) was added 10N NaOH (768 µL, 768 µmol). The resulting solution was stirred at room temperature for 2 hours and then concentrated in vacuo. The residue was purified by preparative HPLC to yield the title compound (3.3 mg; purity 100%) as a mixture of diastereomers at the point of attachment of the thiophene ring. MS m/z [M+H]$^+$ calc'd for $C_{24}H_{20}ClFN_4O_3S$, 499.09; found 499.2.

Example 80

(2S,4S)-5-(3'-Bromobiphenyl-4-yl)-2-methoxymethyl-4-[(3H-[1,2,3]triazole-4-carbonyl)amino]pentanoic Acid

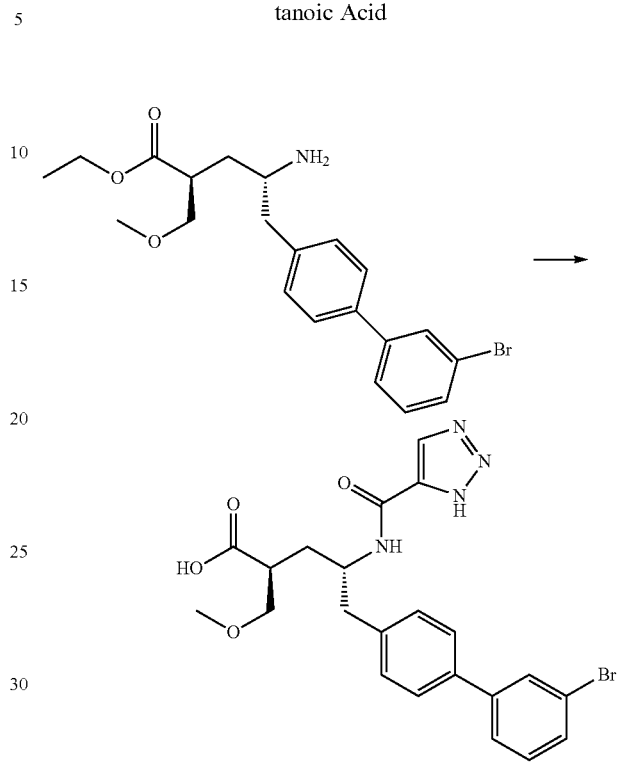

DIPEA (42 µL, 243 µmol) was added to a solution of (2S,4S)-4-amino-5-(3'-bromobiphenyl-4-yl)-2-methoxymethylpentanoic acid ethyl ester (34 mg, 81 µmol), 3H-[1,2,3]triazole-4-carboxylic acid (11.0 mg, 97 µmol) and HATU (46.2 mg, 122 µmol) in DMF (0.3 mL), and the resulting mixture was stirred at room temperature for 15 minutes. 5.0 M aqueous LiOH (130 µL, 649 µmol) was added dropwise and the mixture was stirred at room temperature for 15 hours then purified by preparative HPLC to yield the title compound (23.5 mg) as a TFA salt. MS m/z [M+H]$^+$ calc'd for $C_{22}H_{23}BrN_4O_4$, 487.09; found 487.2.

Example 81

(2S,4S)-5-(5'-Chloro-2'-fluorobiphenyl-4-yl)-2-[(2-fluoroethylamino)methyl]-4-[(3H-[1,2,3]triazole-4-carbonyl)amino]pentanoic Acid

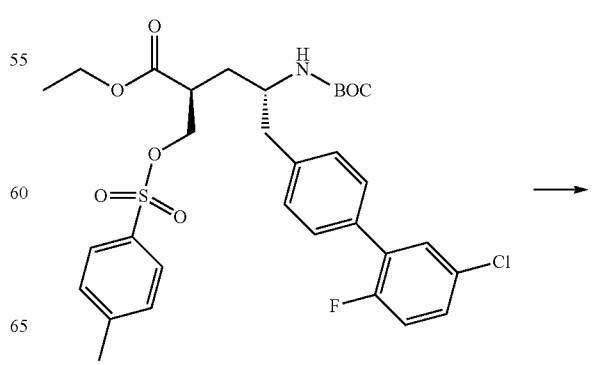

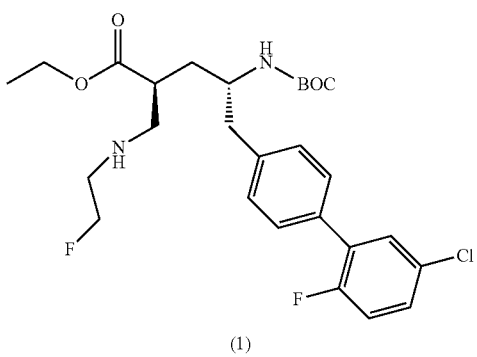

(1)

(2S,4S)-4-t-Butoxycarbonylamino-5-(5'-chloro-2'-fluoro-biphenyl-4-yl)-2-(toluene-4-sulfonyloxymethyl)pentanoic acid ethyl ester (35 mg, 55 µmol) was dissolved in EtOH (2 mL), followed by addition of Na$_2$CO$_3$ (10 eq.) and 2-fluoroethylamine (17 mg, 276 µmol). The mixture was stirred at 70° C. for 2 days, at which time LCMS indicated the mass of the desired compound. The mixture was concentrated under reduced pressure and the crude residue was purified by reverse phase chromatography to yield Compound 1 (4 mg).

(1) →

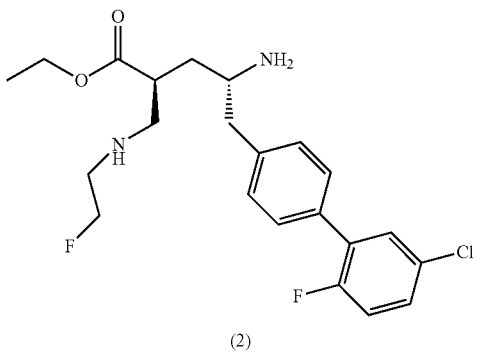

(2)

Compound 1 (4 mg, 50 µmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) →

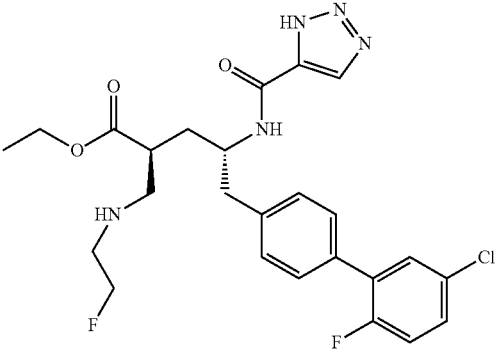

(3)

3H-1,2,3-triazole-5-carboxylic acid (2.5 mg, 22 µmol) was combined with HATU (8.4 mg, 22 µmol) in DMF (0.3 mL) and stirred for 10 minutes; Et$_3$N (1 eq.) was added and the mixture was stirred for 1 minute. Compound 2 (22 µmol) was dissolved in DMF (0.5 mL) and Et$_3$N (3.1 µL, 22 µmol) was added, followed by addition of the activated acid solution. The mixture was stirred for 30 minutes and concentrated to yield Compound 3, which was carried to the next step without purification.

(3) → 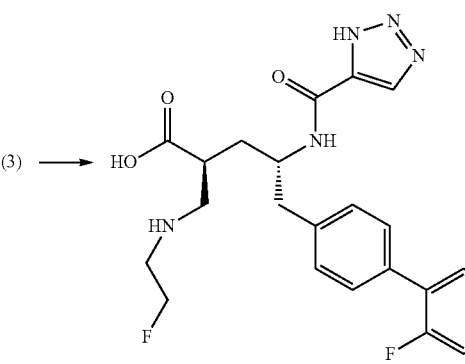

To crude Compound 3 (22 µmol) was added 1N LiOH (88 µL, 88 µmol), THF (0.3 mL), and 2 drops of MeOH. The mixture was stirred overnight and AcOH was added. The solution was purified by purified by reverse phase chromatography to yield the title compound (0.6 mg) as a TFA salt. MS m/z [M+H]$^+$ calc'd for C$_{23}$H$_{24}$ClF$_2$N$_5$O$_3$, 492.15; found 492.2.

Example 82

(2S,4S)-5-(5'-Chloro-2'-fluorobiphenyl-4-yl)-2-[(2,2-difluoroethylamino)methyl]-4-[(3H-[1,2,3]triazole-4-carbonyl)amino]pentanoic Acid (Compound a) and (2S,4S)-5-(5'-Chloro-2'-fluorobiphenyl-4-yl)-2-[(2,2-difluoroethylamino)methyl]-4-[(1H-[1,2,3]triazole-4-carbonyl)amino]pentanoic Acid Ethyl Ester (Compound b)

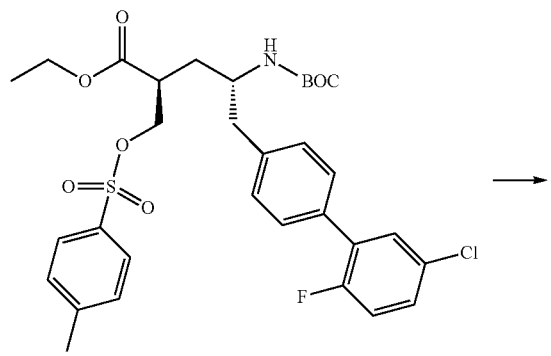

(1)

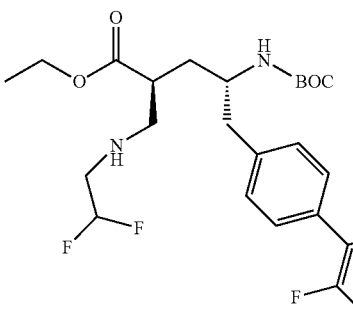

(2)

(2S,4S)-4-t-Butoxycarbonylamino-5-(5'-chloro-2'-fluorobiphenyl-4-yl)-2-(toluene-4-sulfonyloxymethyl)pentanoic acid ethyl ester (35 mg, 55 µmol) was dissolved in EtOH (2 mL), followed by addition of Na₂CO₃ (10 eq.) and 2,2-fifluoroethylamine (22 mg, 276 µmol). The mixture was stirred at 70° C. for 2 days, at which time LCMS indicated the mass of the desired compound. The mixture was concentrated under reduced pressure and the crude residue was purified by reverse phase chromatography to yield Compound 1 (6 mg).

Compound 1 (6 mg, 50 µmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) →

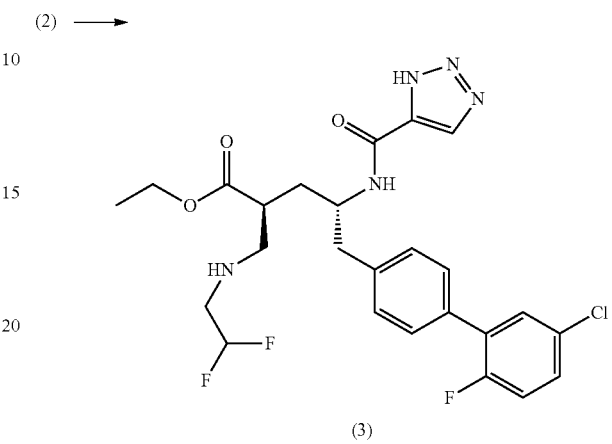

(3)

3H-1,2,3-triazole-5-carboxylic acid (2.5 mg, 22 µmol) was combined with HATU (8.4 mg, 22 µmol) in DMF (0.3 mL) and stirred for 10 minutes; Et₃N (1 eq.) was added and the mixture was stirred for 1 minute. Compound 2 (22 µmol) was dissolved in DMF (0.5 mL) and Et₃N (3.1 µL, 22 µmol) was added, followed by addition of the activated acid solution. The mixture was stirred for 30 minutes and concentrated to yield Compound 3, which was carried to the next step without purification.

(3) →

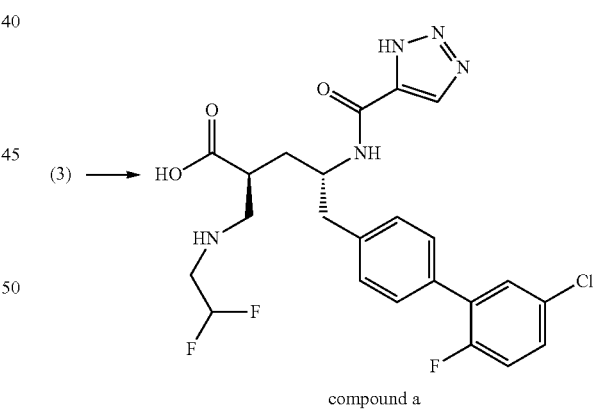

compound a

To the crude Compound 3 (22 µmol) was added 1N LiOH (88 µL, 88 µmol), THF (0.3 mL), and 2 drops of MeOH. The mixture was stirred overnight and AcOH was added. The solution was purified by purified by reverse phase chromatography to yield Compound a (1.1 mg) as a TFA salt. MS m/z [M+H]⁺ calc'd for $C_{23}H_{23}ClF_3N_5O_3$, 510.14; found 510.2.

(2) →

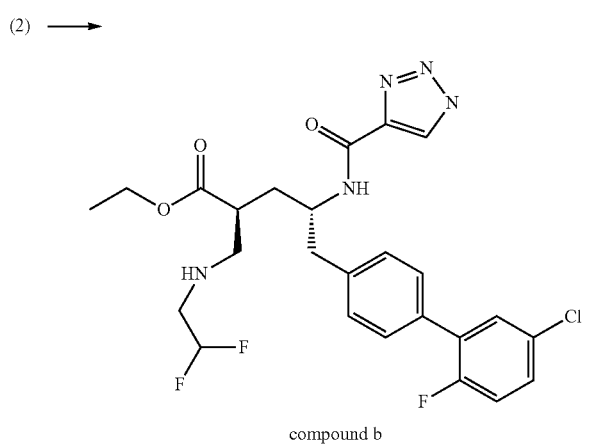

compound b 1H-1,2,3-triazole-4-carboxylic acid (2.6 mg, 23 μmol) was combined with HATU (9.6 mg, 25 μmol) in DMF (3.0 mL) and stirred at room temperature for 15 minutes. Compound 2 (13 mg, 29 μmol) was dissolved in DIPEA (12 μL, 69 μmol) and combined with the activated acid solution. The mixture was stirred at room temperature for 15 minutes, after which time LCMS indicated desired product formation. The solvent was removed in vacuo and the crude residue was purified by reverse phase chromatography to yield Compound b (0.8 mg) as a TFA salt. MS m/z [M+H]$^+$ calc'd for $C_{25}H_{27}ClF_3N_5O_3$, 538.18; found 538.

Example 83

(2S,4S)-5-(5'-Chloro-2'-fluorobiphenyl-4-yl)-2-(3-hydroxyazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-(3-hydroxyazetidin-1-ylmethyl)-4-[(3H-[1,2,3]triazole-4-carbonyl)amino]pentanoic Acid (Compound b)

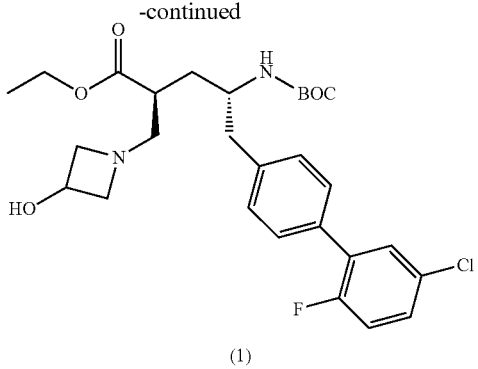

(1)

(2S,4S)-4-t-Butoxycarbonylamino-5-(5'-chloro-2'-fluorobiphenyl-4-yl)-2-(toluene-4-sulfonyloxymethyl)pentanoic acid ethyl ester (35 mg, 55 μmol) was dissolved in EtOH (2 mL), followed by addition of $Na_2CO_3$ (10 eq.) and azetidin-3-ol (20 mg, 276 μmol). The mixture was stirred at 70° C. for 2 days, at which time LCMS indicated the mass of the desired compound. The mixture was concentrated under reduced pressure and the crude residue was purified by reverse phase chromatography to yield Compound 1 (13 mg).

(1) →

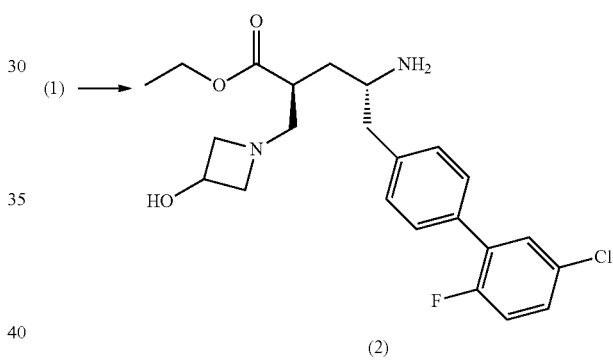

(2)

Compound 1 (13 mg, 50 μmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) →

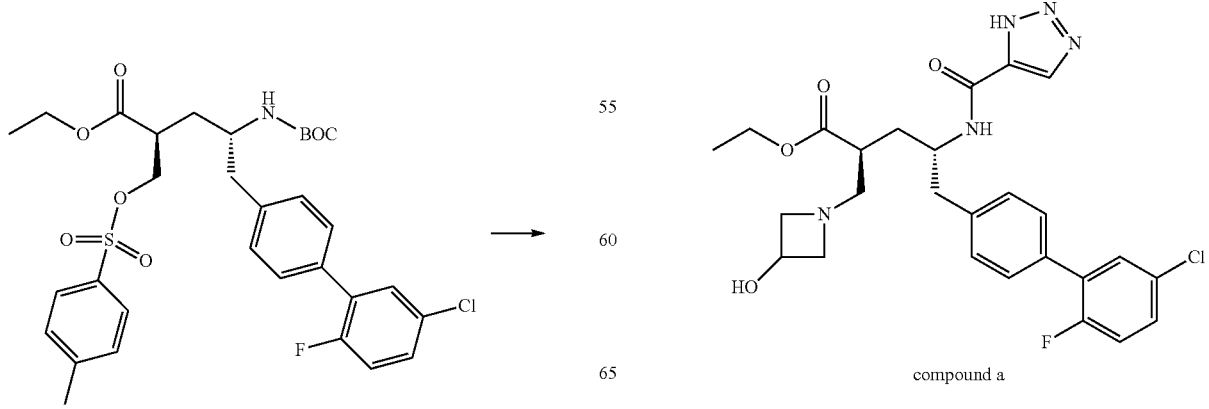

compound a 3H-1,2,3-triazole-5-carboxylic acid (2.5 mg, 22 μmol) was combined with HATU (8.4 mg, 22 μmol) in DMF (0.3 mL) and stirred for 10 minutes; Et₃N (1 eq.) was added and the mixture was stirred for 1 minute. Compound 2 (22 μmol) was dissolved in DMF (0.5 mL) and Et₃N (3.1 μL, 22 μmol) was added, followed by addition of the activated acid solution. The mixture was stirred for 30 minutes, concentrated, and purified by preparative HPLC to yield Compound a (7 mg) as a TFA salt. MS m/z [M+H]⁺ calc'd for $C_{26}H_{29}ClFN_5O_4$, 530.19. found 530.2.

compound a ⟶

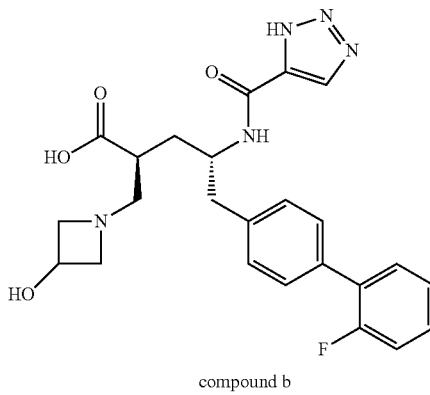

compound b

Compound a (22 μmol) was combined with 1N LiOH (88 μL, 88 μmol), THF (0.3 mL), and 2 drops of MeOH. The mixture was stirred overnight and AcOH was added. The solution was purified by purified by reverse phase chromatography to yield Compound b (3 mg) as a TFA salt. MS m/z [M+H]⁺ calc'd for $C_{24}H_{25}ClFN_5O_4$, 502.16. found 502.

Example 84

(2S,4S)-2-Azetidin-1-ylmethyl-5-(5'-chloro-2'-fluorobiphenyl-4-yl)-4-[(3H-[1,2,3]triazole-4-carbonyl)amino]pentanoic Acid Ethyl Ester (Compound a) and (2S,4S)-2-Azetidin-1-ylmethyl-5-(5'-chloro-2'-fluorobiphenyl-4-yl)-4-[(3H-[1,2,3]triazole-4-carbonyl)amino]pentanoic Acid (Compound b)

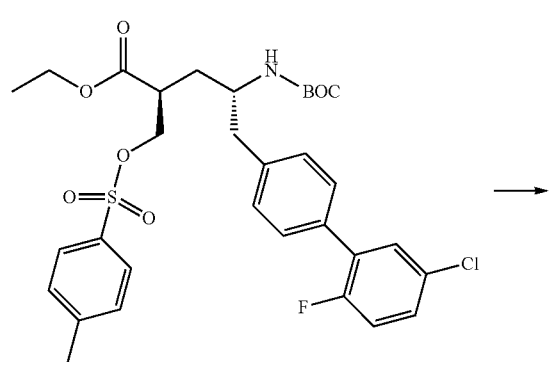

-continued

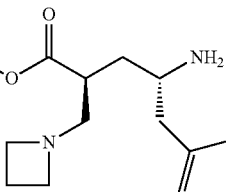

(1)

(2S,4S)-4-t-Butoxycarbonylamino-5-(5'-chloro-2'-fluorobiphenyl-4-yl)-2-(toluene-4-sulfonyloxymethyl)pentanoic acid ethyl ester (35 mg, 55 μmol) was dissolved in EtOH (2 mL), followed by addition of Na₂CO₃ (10 eq.) and azetidine (15 mg, 276 μmol). The mixture was stirred at 70° C. for 2 days, at which time LCMS indicated the mass of the desired compound. The mixture was concentrated under reduced pressure and the crude residue was purified by reverse phase chromatography to yield Compound 1 (15 mg).

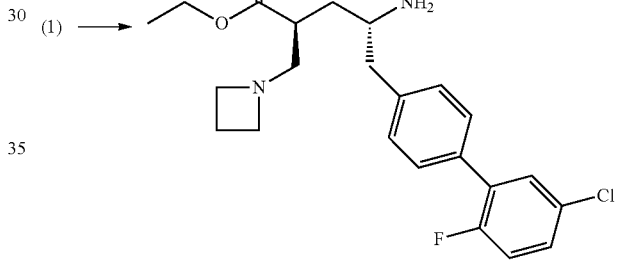

(2)

Compound 1 (15 mg, 50 μmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) ⟶

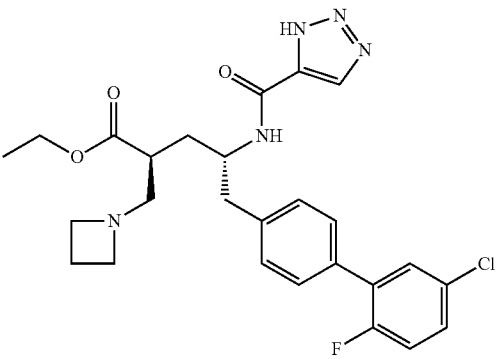

compound a 3H-1,2,3-triazole-5-carboxylic acid (2.5 mg, 22 μmol) was combined with HATU (8.4 mg, 22 μmol) in DMF (0.3 mL) and stirred for 10 minutes; Et₃N (1 eq.) was added and the mixture was stirred for 1 minute. Compound 2 (22 μmol) was dissolved in DMF (0.5 mL) and Et₃N (3.1 μL, 22 μmol) was added, followed by addition of the activated acid solution. The mixture was stirred for 30 minutes, concentrated, and purified by preparative HPLC to yield Compound a (8 mg) as a TFA salt. MS m/z [M+H]⁺ calc'd for $C_{26}H_{29}ClFN_5O_3$, 514.19. found 514.2.

compound a ⟶

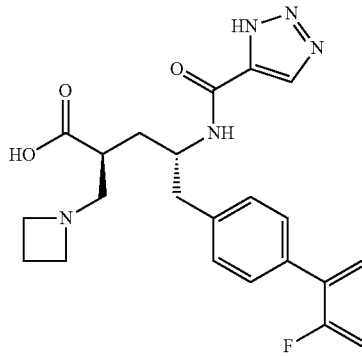

compound b

Compound a (22 μmol) was combined with 1N LiOH (88 μL, 88 μmol), THF (0.3 mL), and 2 drops of MeOH. The mixture was stirred overnight and AcOH was added. The solution was purified by purified by reverse phase chromatography to yield Compound b (3 mg) as a TFA salt. MS m/z [M+H]⁺ calc'd for $C_{24}H_{25}ClFN_5O_3$, 486.16. found 486.

Example 85

(2S,4S)-5-(5'-Chloro-2'-fluorobiphenyl-4-yl)-2-{[(2-methoxyethyl)methylamino]methyl}-4-[(3H-[1,2,3] triazole-4-carbonyl)amino]pentanoic Acid (Compound a) and (2S,4S)-5-(5'-Chloro-2'-fluorobiphenyl-4-yl)-2-{[(2-methoxyethyl) methylamino]methyl}-4-[(1H-[1,2,3]triazole-4-carbonyl)amino]pentanoic Acid Ethyl Ester (Compound b)

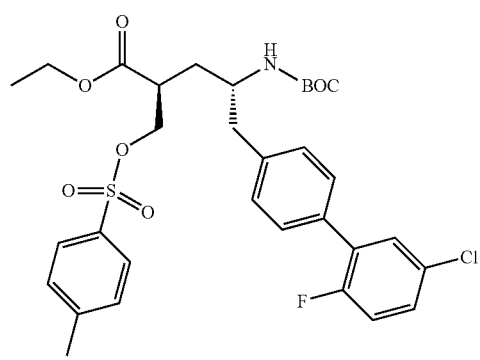

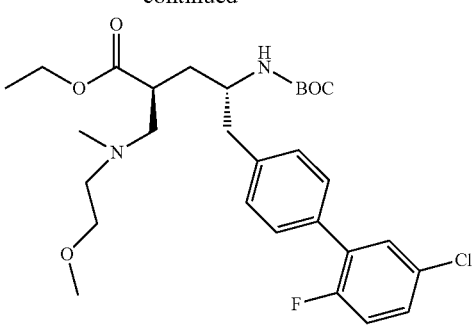

(1)

(2S,4S)-4-t-Butoxycarbonylamino-5-(5'-chloro-2'-fluoro-biphenyl-4-yl)-2-(toluene-4-sulfonyloxymethyl)pentanoic acid ethyl ester (35 mg, 55 μmol) was dissolved in EtOH (2 mL), followed by addition of Na₂CO₃ (10 eq.) and (2-methoxyethyl)methylamine (24 mg, 276 μmol). The mixture was stirred at 70° C. for 2 days, at which time LCMS indicated the mass of the desired compound. The mixture was concentrated under reduced pressure and the crude residue was purified by reverse phase chromatography to yield Compound 1 (10 mg).

(1) ⟶

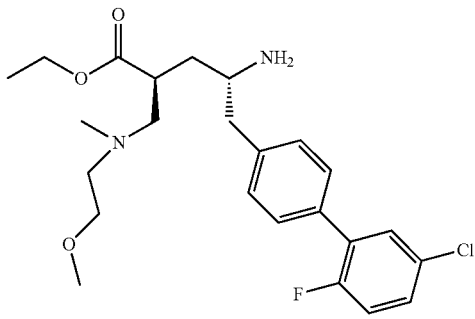

(2)

Compound 1 (10 mg, 50 μmol) was dissolved in MeCN (1 mL) and dry 4N HCl in dioxane (0.5 mL). The mixture was stirred for 10 minutes and then concentrated under reduced pressure to yield Compound 2, which was carried to the next step without purification.

(2) →

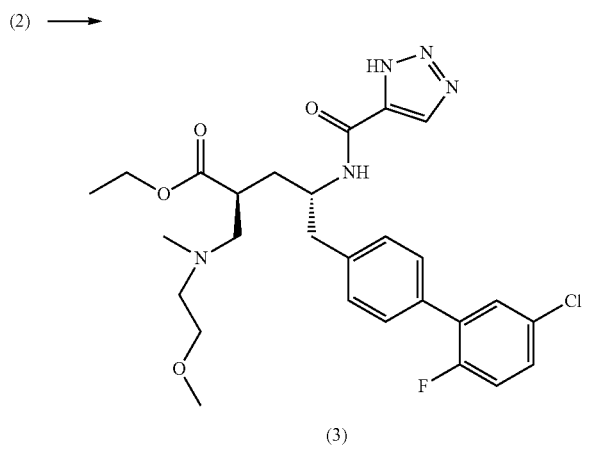

(3)

3H-1,2,3-triazole-5-carboxylic acid (2.5 mg, 22 μmol) was combined with HATU (8.4 mg, 22 μmol) in DMF (0.3 mL) and stirred for 10 minutes; $Et_3N$ (1 eq.) was added and the mixture was stirred for 1 minute. Compound 2 (22 μmol) was dissolved in DMF (0.5 mL) and $Et_3N$ (3.1 μL, 22 μmol) was added, followed by addition of the activated acid solution. The mixture was stirred for 30 minutes and concentrated to yield Compound 3, which was carried to the next step without purification.

(2) → compound b 3H-1,2,3-triazole-5-carboxylic acid (3.0 mg, 27 μmol) was combined with HATU (10.1 mg, 27 μmol) in DMF (0.5 mL); DIPEA (4.7 μL, 27 μmol) was added and the mixture was stirred for 5 minutes. Compound 2 (12 mg, 27 μmol) was dissolved in DMF (0.5 mL) and DIPEA (13.9 μL, 80 μmol) and combined with the activated acid solution. The mixture was stirred for 10 minutes, at which time LCMS indicated the mass of the desired compound. The solvent was removed under reduced pressure and the residue was purified by reverse phase chromatography to yield Compound b (8 mg) as a TFA salt. MS m/z [M+H]$^+$ calc'd for $C_{22}H_{33}ClFN_5O_4$, 546.22. found 546.

Example 86

(2S,4S)-5-(5'-Chloro-2'-fluorobiphenyl-4-yl)-2-methylaminomethyl-4-[(3H-[1,2,3]triazole-4-carbonyl)amino]pentanoic Acid Ethyl Ester (3) → compound a

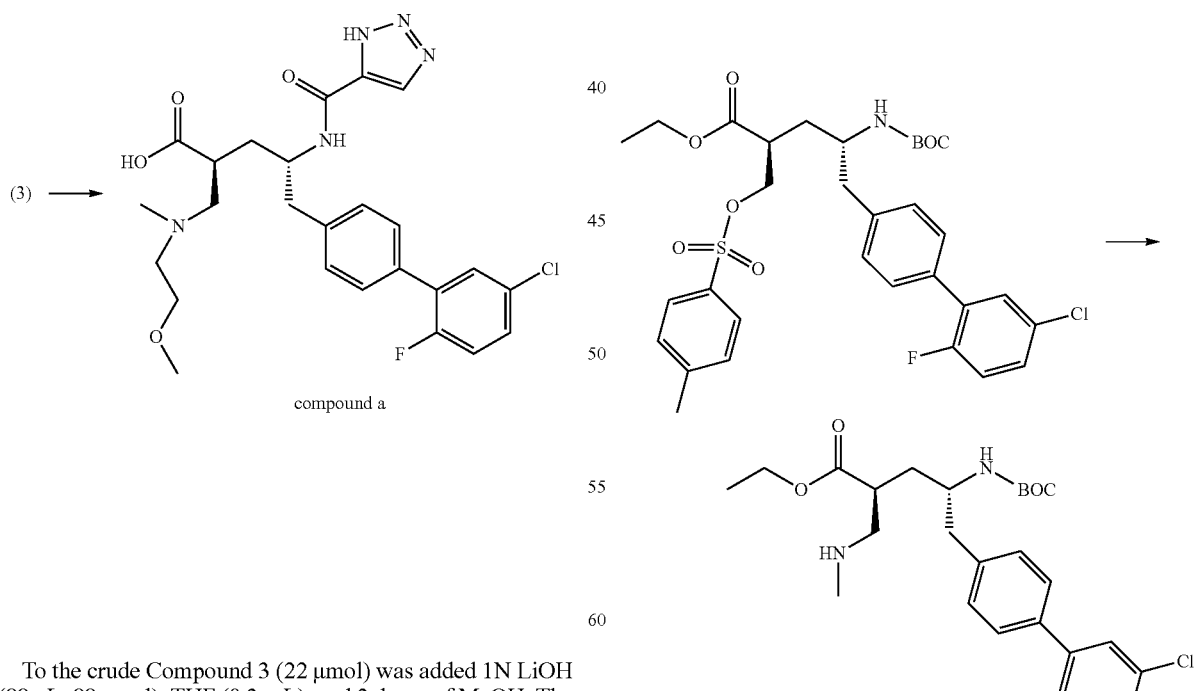

(1)

To the crude Compound 3 (22 μmol) was added 1N LiOH (88 μL, 88 μmol), THF (0.3 mL), and 2 drops of MeOH. The mixture was stirred overnight and AcOH was added. The solution was purified by purified by reverse phase chromatography to yield Compound a (3 mg). MS m/z [M+H]$^+$ calc'd for $C_{25}H_{29}ClFN_5O_4$, 518.19. found 518.

(2S,4S)-4-t-Butoxycarbonylamino-5-(5'-chloro-2'-fluoro-biphenyl-4-yl)-2-(toluene-4-sulfonyloxymethyl)pentanoic acid ethyl ester (35 mg, 55 µmol) was dissolved in EtOH (2 mL), followed by addition of $Na_2CO_3$ (10 eq.) and methylamine (8 mg, 276 µmol). The mixture was stirred at 70° C. for 2 days, at which time LCMS indicated the mass of the desired compound. The mixture was concentrated under reduced pressure and the crude residue was purified by reverse phase chromatography to yield Compound 1 (6 mg).

(1) →

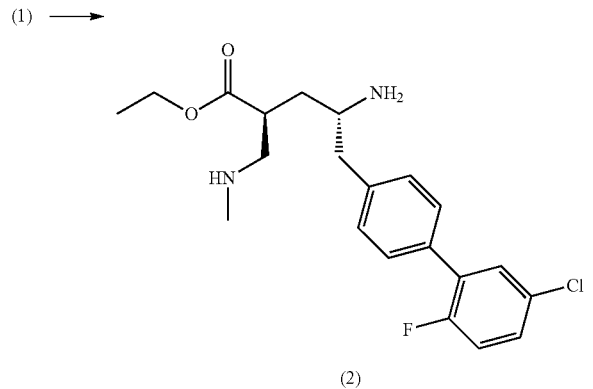 [SMILES: CCOC(=O)[C@@H](C[C@H](N)Cc1ccc(-c2cc(Cl)ccc2F)cc1)CN(C)CCOC]

(2)

Compound 1 (6 mg, 50 µmol) was dissolved in MeCN (1 mL) and dry 4N HCL in dioxane (0.5 mL). The mixture was stirred for 10 minutes and then concentrated under reduced pressure to yield Compound 2, which was carried to the next step without purification.

(2) →

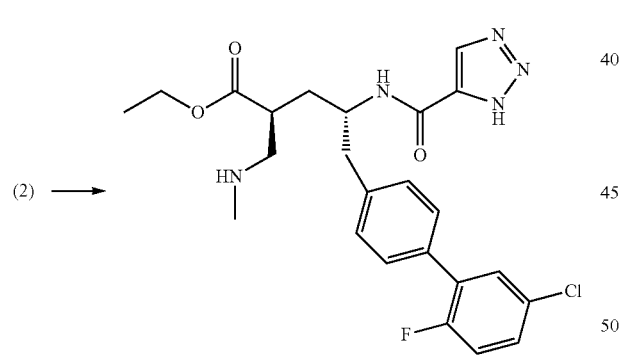

3H-1,2,3-triazole-5-carboxylic acid (2.5 mg, 22 µmol) was combined with HATU (8.4 mg, 22 µmol) in DMF (0.3 mL) and stirred for 10 minutes; $Et_3N$ (1 eq.) was added and the mixture was stirred for 1 minute. Compound 2 (22 µmol) was dissolved in DMF (0.5 mL) and $Et_3N$ (3.1 µL, 22 µmol) was added, followed by addition of the activated acid solution. The mixture was stirred for 30 minutes, concentrated, and purified by preparative HPLC to yield the title compound. MS m/z $[M+H]^+$ calc'd for $C_{24}H_{27}ClFN_5O_3$, 488.18; found 488.2.

Example 87

(2S,4S)-5-(5'-Chloro-2'-fluorobiphenyl-4-yl)-2-[(3-hydroxypropylamino)methyl]-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-[(3-hydroxypropylamino)methyl]-4-[(3H-[1,2,3]triazole-4-carbonyl)amino]pentanoic Acid (Compound b)

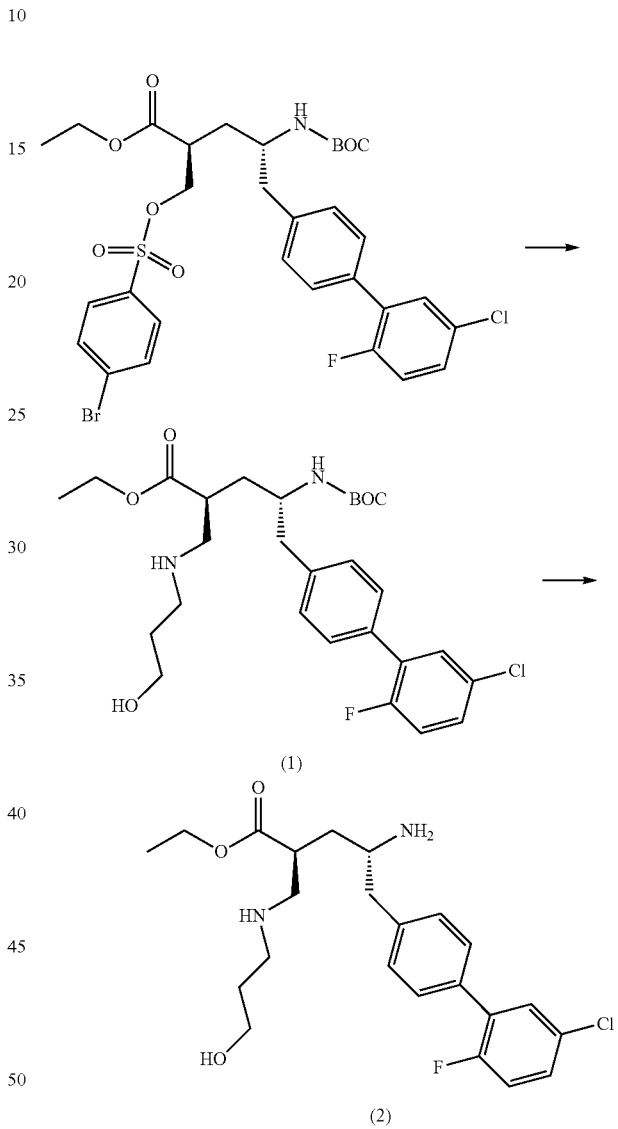

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (100 mg, 143 µmol) was dissolved in EtOH (3 mL), followed by addition of $Na_2CO_3$ (152 mg, 1.4 mmol) and 3-aminopropan-1-ol (54 mg, 715 µmol). The resulting mixture was stirred for 2 days at 70° C., at which time LCMS indicated the mass of the desired compound. The mixture was concentrated under reduced pressure and the crude residue was dissolved in AcOH (4 mL) and $H_2O$ (1 mL) and purified by reverse phase chromatography (10-80% MeCN/$H_2O$ gradient) to yield Compound 1 (25 mg).

Compound 1 (27 mg; 50 µmol) was dissolved in MeCN (1 mL) and dry 4N HCl in dioxane (0.5 mL). The mixture was stirred at room temperature for 10 minutes and then concentrated under reduced pressure to yield Compound 2 as an HCl salt, which was used in without purification.

(2) →

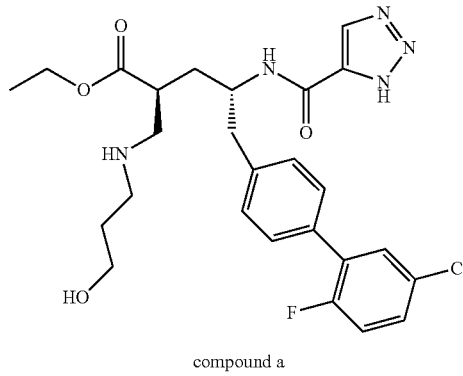

compound a 1H-1,2,3-triazole-5-carboxylic acid (3.4 mg, 30 μmol) was combined with HATU (11 mg, 30 μmol) in DMF (0.3 mL) stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a as a TFA salt (1 mg). MS m/z [M+H]$^+$ calc'd for $C_{26}H_{31}ClFN_5O_4$, 532.21. found 532. Half of the crude product was carried to the next step without further purification.

compound a →

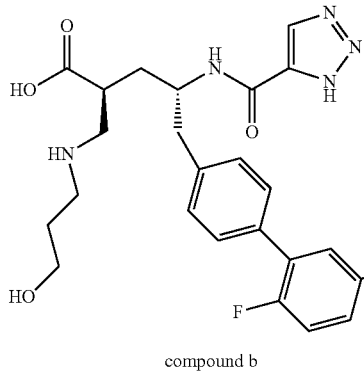

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (2 mL) was added and the solution was purified by reverse phase chromatography to yield Compound b (4 mg) as a TFA salt. MS m/z [M+H]$^+$ calc'd for $C_{24}H_{27}ClFN_5O_4$, 504.17; found 504.

Example 88

(2S,4S)-5-(5'-Chloro-2'-fluorobiphenyl-4-yl)-2-(3-cyanoazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-(3-cyanoazetidin-1-ylmethyl)-4-[(3H-[1,2,3]triazole-4-carbonyl)amino] pentanoic Acid (Compound b)

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (100 mg, 143 μmol) was dissolved in EtOH (3 mL), followed by addition of Na$_2$CO$_3$ (152 mg, 1.4 mmol) and azetidine-3-carbonitrile (59 mg, 715 μmol). The resulting mixture was stirred for 2 days at 70° C., at which time LCMS indicated the mass of the desired compound. The mixture was concentrated under reduced pressure and the crude residue was dissolved in AcOH (4 mL) and H$_2$O (1 mL) and purified by reverse phase chromatography (10-80% MeCN/H$_2$O gradient) to yield Compound 1 (30 mg).

Compound 1 (27 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was used without purification.

(2) ⟶

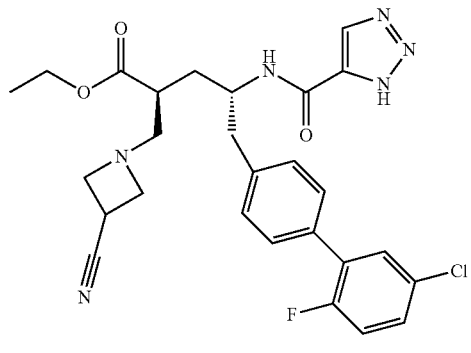

compound a 1H-1,2,3-triazole-5-carboxylic acid (3.4 mg, 30 μmol) was combined with HATU (11 mg, 30 μmol) in DMF (0.3 mL) and stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (7.7 mg) as a TFA salt. MS m/z [M+H]$^+$ calc'd for $C_{22}H_{28}ClFN_6O_3$, 539.19; found 539. Half of the crude product was carried to the next step without further purification.

compound a ⟶

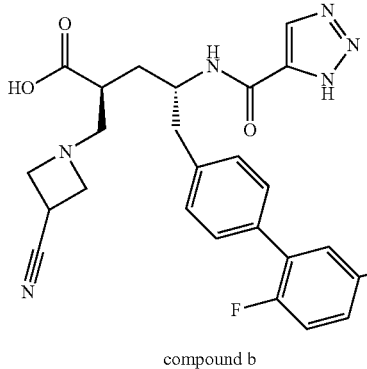

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (3 mL) was added and the solution was purified by reverse phase chromatography to yield Compound b (3 mg) as a TFA salt. MS m/z [M+H]$^+$ calc'd for $C_{25}H_{24}ClFN_6O_3$, 511.16. found 511.

Example 89

(2S,4S)-5-(5'-Chloro-2'-fluorobiphenyl-4-yl)-2-(3,3-dimethylazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-(3,3-dimethylazetidin-1-ylmethyl)-4-[(3H-[1,2,3]triazole-4-carbonyl)amino]pentanoic Acid (Compound b)

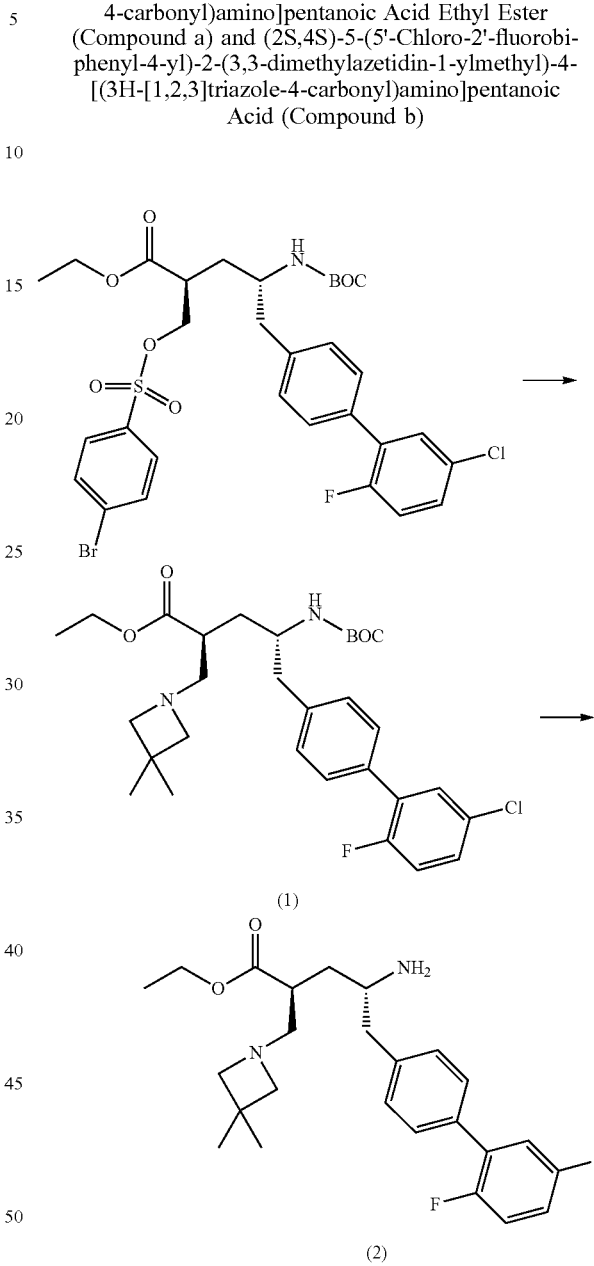

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (100 mg, 143 μmol) was dissolved in EtOH (3 mL), followed by addition of Na$_2$CO$_3$ (152 mg, 1.4 mmol) and 3,3-dimethylazetidine (61 mg, 715 μmol). The resulting mixture was stirred for 2 days at 70° C., at which time LCMS indicated the mass of the desired compound. The mixture was concentrated under reduced pressure and the crude residue was dissolved in AcOH (4 mL) and H$_2$O (1 mL) and purified by reverse phase chromatography (10-80% MeCN/H$_2$O gradient) to yield Compound 1 (40 mg).

Compound 1 (27 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was carried to the next step without purification.

(2) ⟶

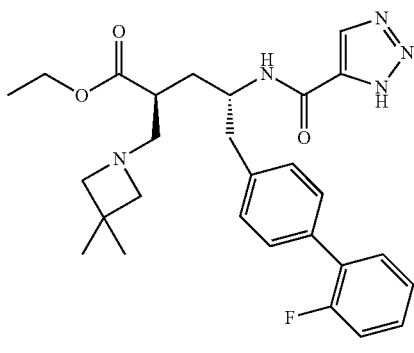

compound a 1H-1,2,3-triazole-5-carboxylic acid (3.4 mg, 30 μmol) was combined with HATU (11 mg, 30 μmol) in DMF (0.3 mL) stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (12.1 mg) as a TFA salt. MS m/z [M+H]$^+$ calc'd for $C_{28}H_{33}ClFN_5O_3$, 542.23. found 542. Half of the crude product was used in the next step without purification.

compound a ⟶

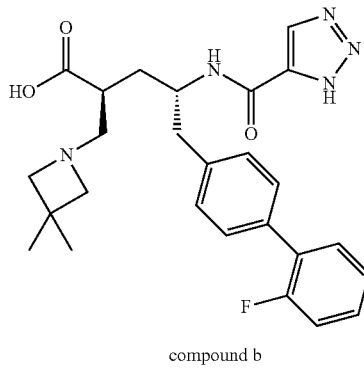

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (2 mL) was added and the solution was purified by reverse phase chromatography to yield Compound b (7 mg) as a TFA salt. MS m/z [M+H]$^+$ calc'd for $C_{26}H_{29}ClFN_5O_3$, 514.19. found 514.

Example 90

(2S,4S)-5-(5'-Chloro-2'-fluorobiphenyl-4-yl)-2-(3,3-difluoroazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-(3,3-difluoroazetidin-1-ylmethyl)-4-[(3H-[1,2,3]triazole-4-carbonyl)amino]pentanoic Acid (Compound b)

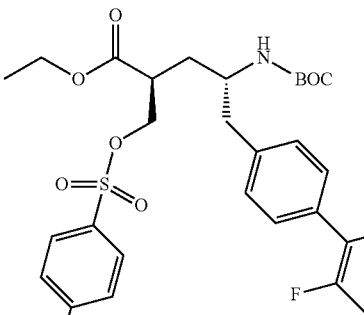

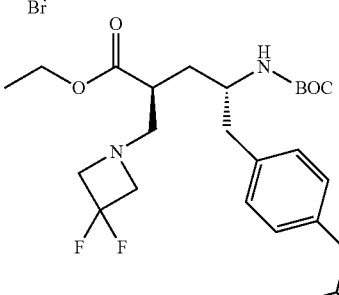

(1)

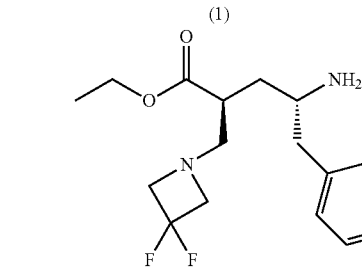

(2)

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (100 mg, 143 μmol) was dissolved in EtOH (3 mL), followed by addition of Na$_2$CO$_3$ (152 mg, 1.4 mmol) and 3,3-difluoroazetidine (67 mg, 715 μmol). The resulting mixture was stirred for 2 days at 70° C., at which time LCMS indicated the mass of the desired compound. The mixture was concentrated under reduced pressure and the crude residue was dissolved in AcOH (4 mL) and H$_2$O (1 mL) and purified by reverse phase chromatography (10-80% MeCN/H$_2$O gradient) to yield Compound 1 (8 mg).

Compound 1 (28 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without further purification.

(2) →

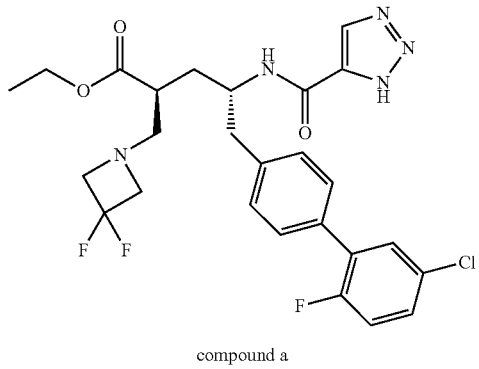

compound a 1H-1,2,3-triazole-5-carboxylic acid (3.4 mg, 30 µmol) was combined with HATU (11 mg, 30 µmol) in DMF (0.3 mL) and stirred at room temperature for 10 minutes; DIPEA (1 eq.) was added and the mixture was stirred for 1 minute. Compound 2 (10 mg, 30 µmol) was dissolved in DMF (0.5 mL) and DIPEA (5.2 µL, 30 µmol) was added, followed by addition of the activated acid solution. The mixture was stirred at room temperature for 30 minutes, after which time LCMS indicated desired product formation. Half of the crude product was purified using reverse phase chromatography to yield Compound a (1.4 mg) as a TFA salt. MS m/z [M+H]$^+$ calc'd for $C_{26}H_{22}ClF_3N_5O_3$, 550.18; found 550. Half of the crude product was used in the next step without further purification.

compound a →

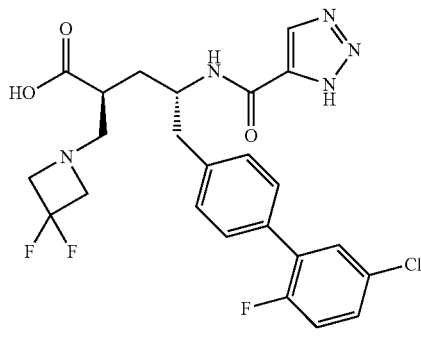

compound b

Crude Compound a (12 mg, 22 µmol) was dissolved in THF (0.3 mL), 1N LiOH (88 µL, 88 µmol) and MeOH (2 drops), and stirred for 2 hours at 50° C. AcOH (1 mL) was added and the solution was purified by reverse phase chromatography to yield Compound b (0.8 mg) as a TFA salt. MS m/z [M+H]$^+$ calc'd for $C_{24}H_{23}ClF_3N_5O_3$, 522.14. found 522.

Example 91

(2S,4S)-5-(5'-Chloro-2'-fluorobiphenyl-4-yl)-2-(3-fluoroazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-(3-fluoroazetidin-1-ylmethyl)-4-[(3H-[1,2,3]triazole-4-carbonyl)amino] pentanoic Acid (Compound b)

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (100 mg, 143 µmol) was dissolved in EtOH (3 mL), followed by addition of $Na_2CO_3$ (152 mg, 1.4 mmol) and 3-fluoroazetidine (54 mg, 715 µmol). The resulting mixture was stirred for 2 days at 70° C., at which time LCMS indicated the mass of the desired compound. The mixture was concentrated under reduced pressure and the crude residue was dissolved in AcOH (4 mL) and H$_2$O (1 mL) and purified by reverse phase chromatography (10-80% MeCN/H$_2$O gradient) to yield Compound 1 (25 mg).

Compound 1 (27 mg; 50 µmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without further purification.

(2) →

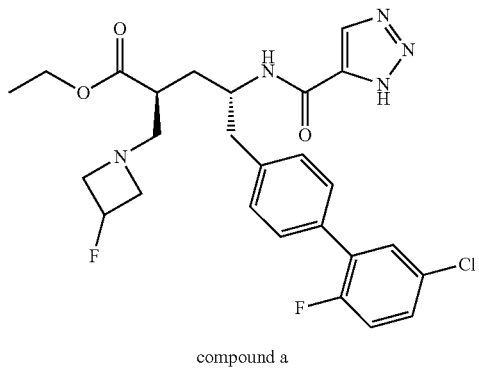

compound a 1H-1,2,3-triazole-5-carboxylic acid (3.4 mg, 30 µmol) was combined with HATU (11 mg, 30 µmol) in DMF (0.3 mL) and stirred at room temperature for 10 minutes; DIPEA (1 eq.) was added and the mixture was stirred for 1 minute. Compound 2 (10 mg, 30 µmol) was dissolved in DMF (0.5 mL) and DIPEA (5.2 µL, 30 µmol) was added, followed by addition of the activated acid solution. The mixture was stirred at room temperature for 30 minutes, after which time LCMS indicated desired product formation. Half of the crude product was purified using reverse phase chromatography to yield Compound a (3.5 mg) as a TFA salt. MS m/z [M+H]$^+$ calc'd for $C_{26}H_{28}ClF_2N_5O_3$, 532.19; found 532. Half of the crude product was carried to the next step without purification.

compound a →

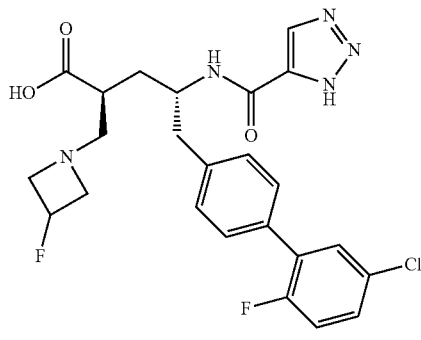

compound b

Crude Compound a (12 mg, 22 µmol) was dissolved in THF (0.3 mL), 1N LiOH (88 µL, 88 µmol) and MeOH (2 drops), and stirred for 2 hours at 50° C. AcOH (1 mL) was added and the solution was purified by reverse phase chromatography to yield Compound b (1.2 mg) as a TFA salt. MS m/z [M+H]$^+$ calc'd for $C_{24}H_{24}ClF_2N_5O_3$, 504.15. found 504.

Example 92

(2S,4S)-2-(3,3-Bis-hydroxymethylazetidin-1-ylmethyl)-5-(5'-chloro-2'-fluorobiphenyl-4-yl)-4-[(3H-[1,2,3]triazole-4-carbonyl)amino]pentanoic Acid Ethyl Ester (Compound a) and (2S,4S)-2-(3,3-Bishydroxymethylazetidin-1-ylmethyl)-5-(5'-chloro-2'-fluorobiphenyl-4-yl)-4-[(3H-[1,2,3]triazole-4-carbonyl)amino]pentanoic Acid (Compound b)

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (100 mg, 143 µmol) was dissolved in EtOH (3 mL), followed by addition of Na$_2$CO$_3$ (152 mg, 1.4 mmol) and 2-oxa-6-aza-spiro[3.3]heptane (71 mg, 715 µmol). The resulting mixture was stirred for 2 days at 70° C., at which time LCMS indicated the mass of the desired compound. The mixture was concentrated under reduced pressure and the crude residue was dissolved in AcOH (4 mL) and H$_2$O (1 mL) and purified by reverse phase chromatography (10-80% MeCN/H$_2$O gradient) to yield Compound 1 (20 mg).

Compound 1 (28 mg; 50 µmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without purification.

(2) →

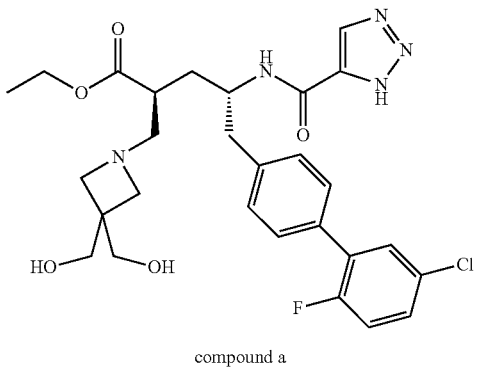

compound a 1H-1,2,3-triazole-5-carboxylic acid (3.4 mg, 30 μmol) was combined with HATU (11 mg, 30 μmol) in DMF (0.3 mL) stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (2.9 mg) as a TFA salt. MS m/z [M+H]+ calc'd for $C_{28}H_{33}ClFN_5O_5$, 574.22. found 574. Half of the crude product was used in the next step without purification.

compound a →

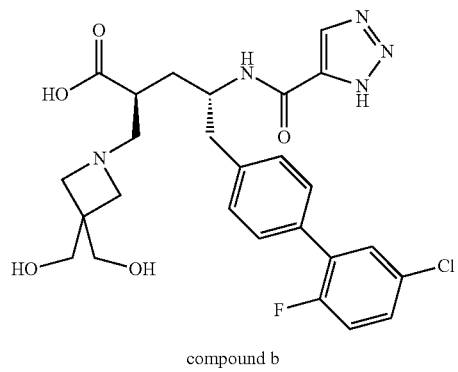

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (1 mL) was added and the solution was purified by reverse phase chromatography to yield Compound b (1 mg) as a TFA salt. MS m/z [M+H]+ calc'd for $C_{26}H_{29}ClFN_5O_5$, 546.18. found 546.

Example 93

(2S,4S)-5-(5'-Chloro-2'-fluorobiphenyl-4-yl)-2-(3-hydroxymethyl-azetidin-1-ylmethyl)-4-[(3H-[1,2,3] triazole-4-carbonyl)amino]pentanoic Acid Ethyl Ester (Compound a) and (2S,4S)-5-(5'-Chloro-2'-fluorobiphenyl-4-yl)-2-(3-hydroxymethyl-azetidin-1-ylmethyl)-4-[(3H-[1,2,3]triazole-4-carbonyl)amino] pentanoic Acid (Compound b)

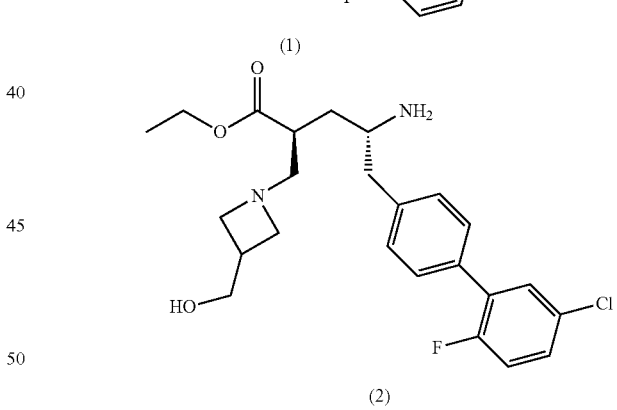

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (75 mg, 107 μmol) was dissolved in EtOH (2 mL), followed by the addition of azetidin-3-yl-methanol (9.4 mg, 107 μmol). The resulting mixture was stirred at 70° C. overnight, at which time LCMS indicated the mass of the desired compound. The organic layer was evaporated and the residue was purified by reverse phase chromatography to yield Compound 1 (30 mg).

Compound 1 (27 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without purification.

(2) →

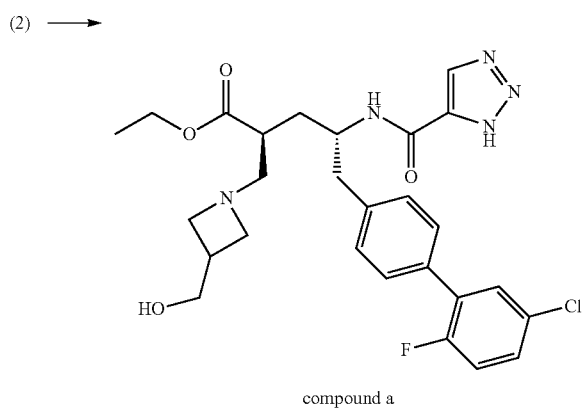

compound a 1H-1,2,3-triazole-5-carboxylic acid (3.4 mg, 30 μmol) was combined with HATU (11 mg, 30 μmol) in DMF (0.3 mL) and stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (20 mg) as a TFA salt. MS m/z [M+H]+ calc'd for $C_{27}H_{31}ClFN_5O_4$, 544.21; found 544. Half of the crude product was used in the next step without purification.

compound a →

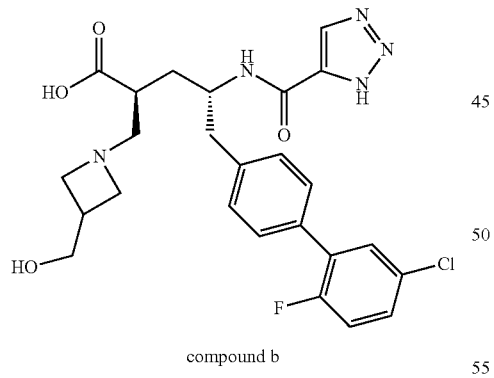

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (1 mL) was added and the solution was purified by reverse phase chromatography to yield Compound b (10 mg) as a TFA salt. MS m/z [M+H]+ calc'd for $C_{25}H_{27}ClFN_5O_4$, 516.17. found 516.

Example 94

(2S,4S)-5-(5'-Chloro-2'-fluorobiphenyl-4-yl)-24(R)-2-hydroxymethylazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-24(R)-2-hydroxymethylazetidin-1-ylmethyl)-4-[(3H-[1,2,3]triazole-4-carbonyl)amino]pentanoic Acid (Compound b)

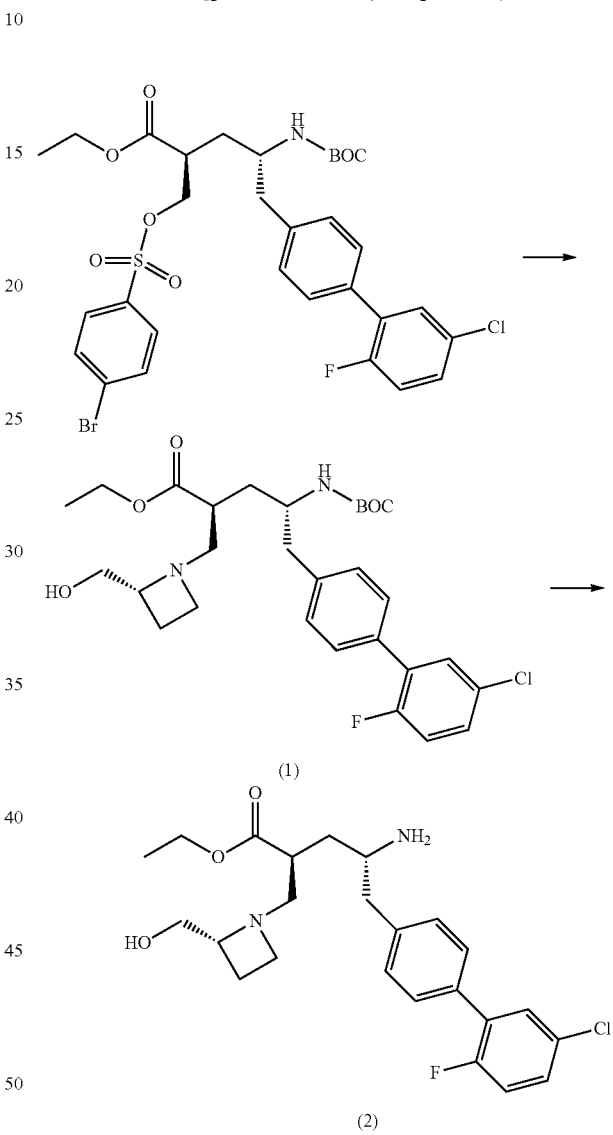

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (75 mg, 107 μmol) was dissolved in EtOH (2 mL), followed by the addition of (2R)-2-azetidinylmethanol (18.7 mg, 215 μmol). The resulting mixture was stirred at 70° C. overnight, at which time LCMS indicated the mass of the desired compound. The organic layer was evaporated and the residue was purified by reverse phase chromatography to yield Compound 1 (28 mg).

Compound 1 (27 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without purification.

(2) ⟶

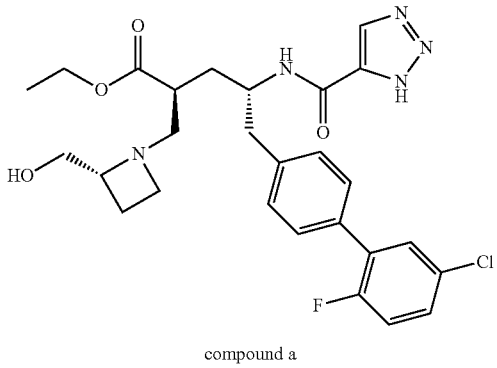

compound a 1H-1,2,3-triazole-5-carboxylic acid (3.4 mg, 30 μmol) was combined with HATU (11 mg, 30 μmol) in DMF (0.3 mL) stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (5.2 mg) as a TFA salt. MS m/z [M+H]$^+$ calc'd for $C_{27}H_{31}ClFN_5O_4$, 544.21. found 544. Half of the crude product was used in the next step without purification.

compound a ⟶

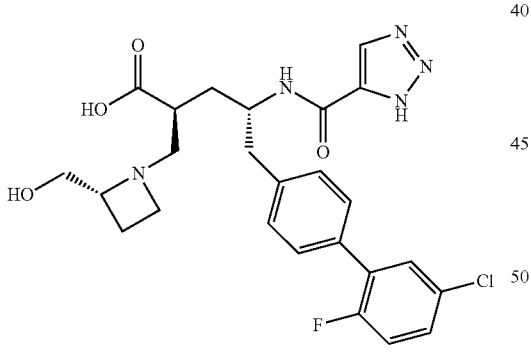

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (1 mL) was added and the solution was purified by reverse phase chromatography to yield Compound b (10 mg) as a TFA salt. MS m/z [M+H]$^+$ calc'd for $C_{25}H_{27}ClFN_5O_4$, 516.17. found 516.

Example 95

(2S,4S)-5-(5'-Chloro-2'-fluorobiphenyl-4-yl)-2-((S)-2-hydroxymethylazetidin-1-ylmethyl)-4-[(3H-[1,2,3]triazole-4-carbonyl)amino]pentanoic Acid Ethyl Ester (Compound a) and (2S,4S)-5-(5'-Chloro-2'-fluorobiphenyl-4-yl)-2-((S)-2-hydroxymethyl-azetidin-1-ylmethyl)-4-[(3H-[1,2,3]triazole-4-carbonyl)amino]pentanoic Acid (Compound b)

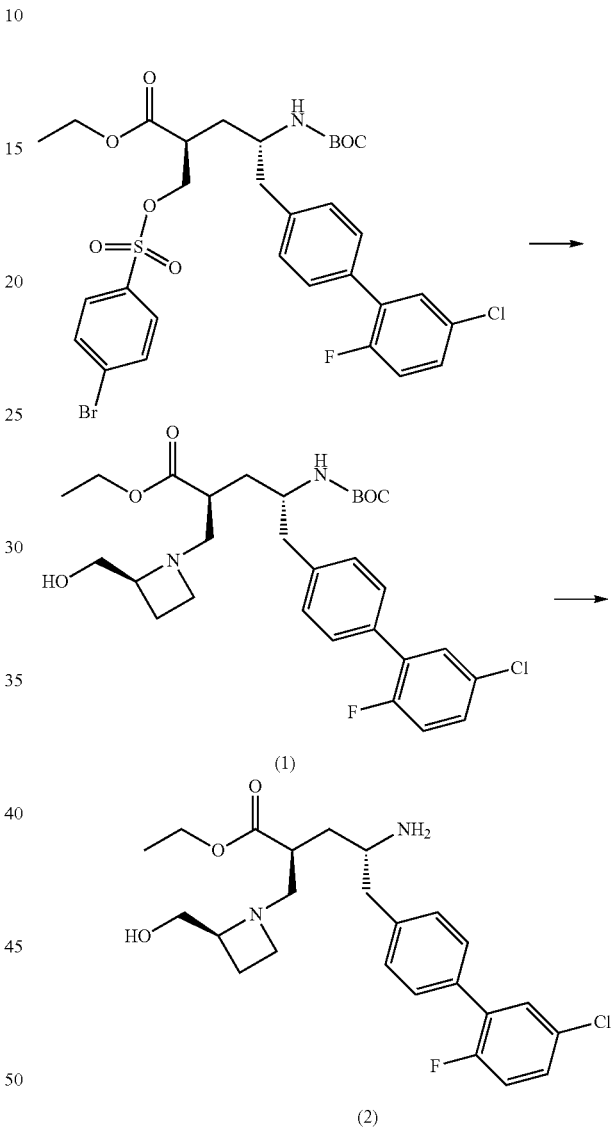

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (75 mg, 107 μmol) was dissolved in EtOH (2 mL), followed by the addition of (2S)-2-azetidinylmethanol (9.4 mg, 107 μmol). The resulting mixture was stirred at 70° C. overnight, at which time LCMS indicated the mass of the desired compound. The organic layer was evaporated and the residue was purified by reverse phase chromatography to yield Compound 1 (10 mg).

Compound 1 (27 mg; 50 μmol) was dissolved in MeCN (1 mL) and dry 4N HCl in dioxane (0.5 mL). The mixture was stirred for 10 minutes and then concentrated under reduced pressure to yield Compound 2 as an HCl salt, which was used in the next step without purification.

(2) →

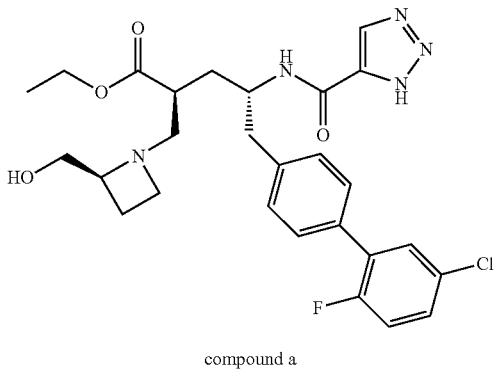

compound a 1H-1,2,3-triazole-5-carboxylic acid (3.4 mg, 30 μmol) was combined with HATU (11 mg, 30 μmol) in DMF (0.3 mL) and stirred at room temperature for 10 minutes; DIPEA (1 eq.) was added and the mixture was stirred for 1 minute. Compound 2 (10 mg, 30 μmol) was dissolved in DMF (0.5 mL) and DIPEA (5.2 μL, 30 μmol) was added, followed by addition of the activated acid solution. The mixture was stirred at room temperature for 30 minutes, after which time LCMS indicated desired product formation. Half of the crude product was purified using reverse phase chromatography to yield Compound a (4.3 mg) as a TFA salt. MS m/z [M+H]$^+$ calc'd for $C_{27}H_{31}ClFN_5O_4$, 544.21; found 544. Half of the crude product was used in the next step without purification.

compound a →

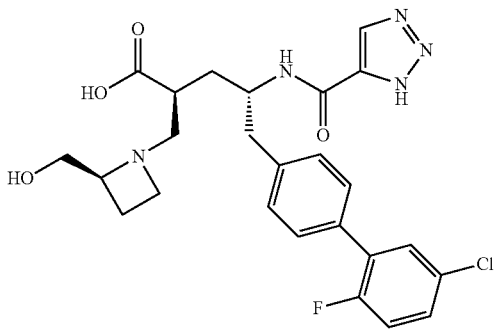

compound b

Crude Compound a (12 mg, 22 μmol) was dissolved in THF (0.3 mL), 1N LiOH (88 μL, 88 μmol) and MeOH (2 drops), and stirred for 2 hours at 50° C. AcOH (1 mL) was added and the solution was purified by reverse phase chromatography to yield Compound b (10 mg) as a TFA salt. MS m/z [M+H]$^+$ calc'd for $C_{25}H_{27}ClFN_5O_4$, 516.17. found 516.

Example 96

(2S,4S)-2-(3-Carbamoylazetidin-1-ylmethyl)-5-(5'-chloro-2'-fluorobiphenyl-4-yl)-4-[(3H-[1,2,3]triazole-4-carbonyl)amino]pentanoic Acid Ethyl Ester (Compound a) and (2S,4S)-2-(3-Carbamoylazetidin-1-ylmethyl)-5-(5'-chloro-2'-fluorobiphenyl-4-yl)-4-[(3H-[1,2,3]triazole-4-carbonyl)amino]pentanoic Acid (Compound b)

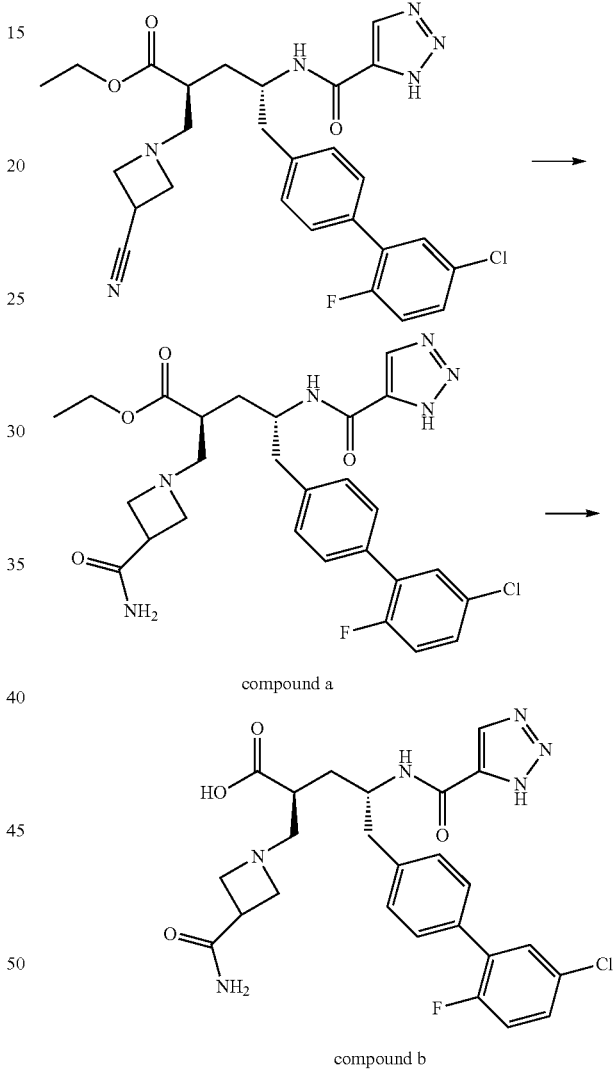

compound a compound b (2S,4S)-5-(5'-Chloro-2'-fluoro-biphenyl-4-yl)-2-(3-cyanoazetidin-1-ylmethyl)-4-[(3H-[1,2,3]triazole-4-carbonyl) amino]pentanoic acid ethyl ester (12 mg, 22 μmol) was dissolved in THF (0.3 mL), 1N LiOH (88 μL, 88 μmol) and MeOH (2 drops), and stirred for 2 hours at 50° C. to yield a mixture of the title compounds. AcOH (1 mL) was added and the solution was purified by reverse phase chromatography to yield Compound a (4.3 mg) as a TFA salt (MS m/z [M+H]$^+$ calc'd for $C_{27}H_{30}ClFN_6O_4$, 557.20. found 557) and Compound b (2 mg) as a TFA salt (MS m/z [M+H]$^+$ calc'd for $C_{25}H_{26}ClFN_6O_4$, 529.17; found 529).

Example 97

(2R,4R)-5-(5'-Chloro-2'-fluorobiphenyl-4-yl)-2-0-methoxypropylamino)-4-[(1H-[1,2,3]triazole-4-carbonyl)amino]pentanoic Acid (Compound a) and (2R,4R)-5-(5'-Chloro-2'-fluorobiphenyl-4-yl)-2-(3-methoxypropylamino)-4-[(1H-[1,2,3]triazole-4-carbonyl)amino]pentanoic Acid Ethyl Ester (Compound b)

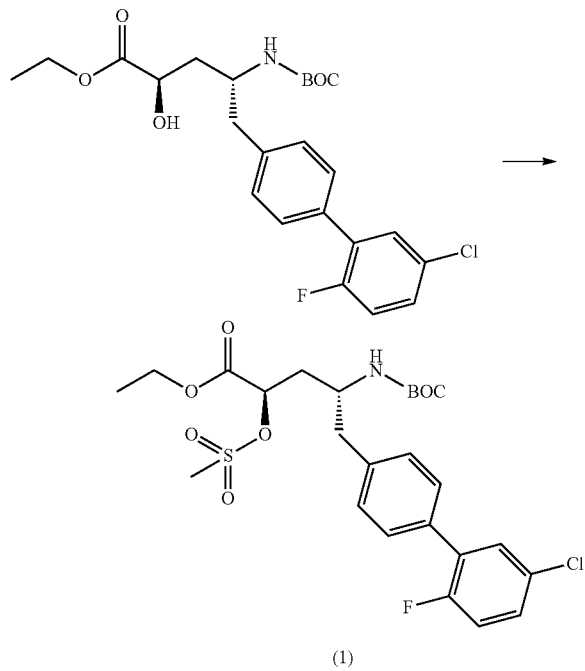

(2R,4R)-4-t-Butoxycarbonylamino-5-(5'-chloro-2'-fluorobiphenyl-4-yl)-2-hydroxypentanoic acid ethyl ester (137 mg, 294 µmol) was dissolved in DCM (5 mL). Methanesulfonyl chloride (23 µL, 294 µmol) was added, followed by Et₃N (82 µL, 0.6 mmol). The mixture was stirred at room temperature for 10 minutes, at which time LCMS indicated the mass of the desired compound. The solvent was removed in vacuo to yield crude Compound 1, which was used directly in the next step.

(1) ⟶

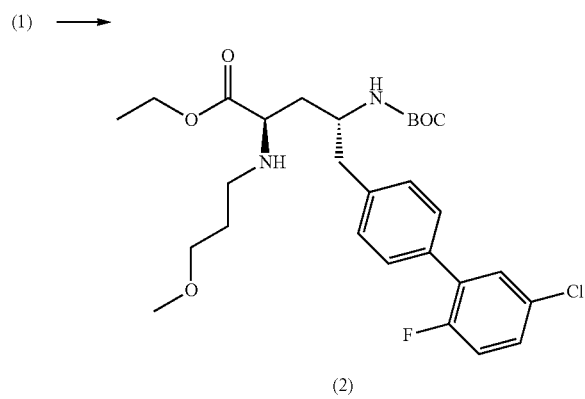

Compound 1 (53 mg, 97 µmol) was dissolved in DMF (4 mL). 3-methoxypropylamine (10.9 µL, 107 µmol) and Na₂CO₃ (31.0 mg, 292 µmol) were then added, and the resulting mixture was stirred overnight at 70° C., at which time LCMS indicated the mass of the desired compound. The solvent was removed in vacuo and the crude residue was purified by reverse phase chromatography to yield Compound 2 (10 mg).

(2) ⟶

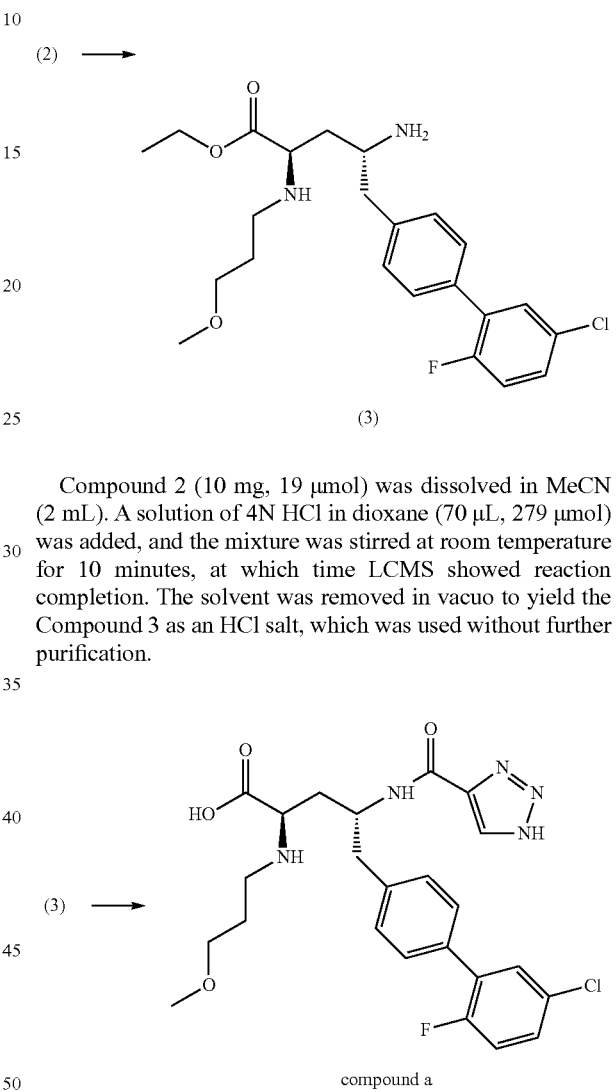

Compound 2 (10 mg, 19 µmol) was dissolved in MeCN (2 mL). A solution of 4N HCl in dioxane (70 µL, 279 µmol) was added, and the mixture was stirred at room temperature for 10 minutes, at which time LCMS showed reaction completion. The solvent was removed in vacuo to yield the Compound 3 as an HCl salt, which was used without further purification.

(3) ⟶ compound a 1H-1,2,3-triazole-4-carboxylic acid (2.3 mg, 20 µmol) was combined with HATU (7.7 mg, 20 µmol) in DMF (2 mL) and stirred at room temperature for 15 minutes. Compound 3 (8 mg, 18 µmol) and DIPEA (9.6 µL, 55 µmol) were then added. The solution was stirred at room temperature for 15 minutes, at which time LCMS showed reaction completion. The solvent was removed in vacuo and the crude residue was dissolved in EtOH (2 mL). A solution of 1N LiOH (183 µL, 183 µmol) in water was added, and the resulting solution was stirred at room temperature for 30 minutes, at which time LCMS showed reaction completion. The solvent was removed in vacuo and the crude residue was purified by reverse phase chromatography to yield Compound a (3 mg) as a TFA salt. MS m/z [M+H]⁺ calc'd for $C_{24}H_{27}ClFN_5O_4$, 504.17. found 504.

(3) ⟶

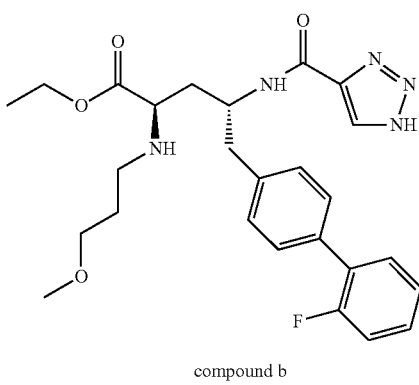

compound b 1H-1,2,3-triazole-4-carboxylic acid (3.8 mg, 34 μmol) was combined with HATU (12.9 mg, 34 μmol) in DMF (2 mL) and stirred at room temperature for 15 minutes. Compound 3 (60 mg, 137 μmol) and DIPEA (16 μL, 92 μmol) were then added. The solution was stirred at room temperature for 15 minutes, at which time LCMS showed reaction completion. The solvent was removed in vacuo and the crude residue was purified by reverse phase chromatography to yield Compound b (18.5 mg) as a TFA salt. MS m/z [M+H]+ calc'd for $C_{26}H_{31}ClFN_5O_4$, 532.21. found 532.

Example 98

(2R,4R)-5-(5'-Chloro-2'-fluorobiphenyl-4-yl)-2-(2-methoxyethylamino)-4-[(1H-[1,2,3]triazole-4-carbonyl)amino]pentanoic Acid (Compound a) and (2R,4R)-5-(5'-Chloro-2'-fluorobiphenyl-4-yl)-2-(2-methoxyethylamino)-4-[(1H-[1,2,3]triazole-4-carbonyl)amino]pentanoic Acid Ethyl Ester (Compound b)

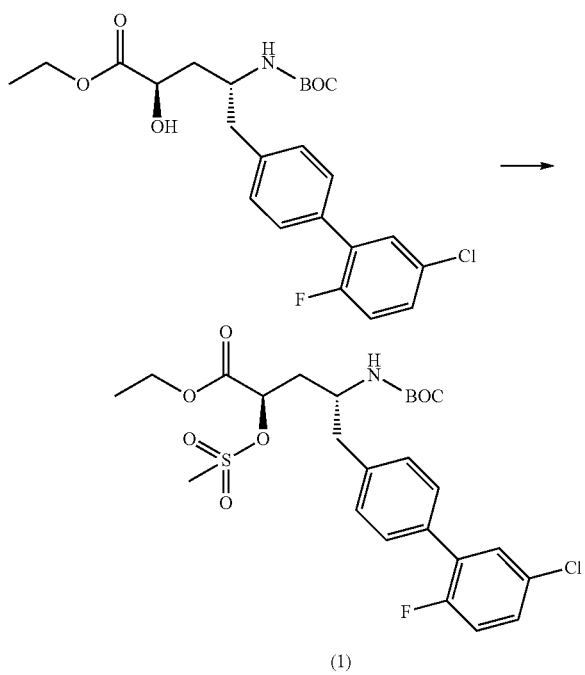

(2R,4R)-4-t-Butoxycarbonylamino-5-(5'-chloro-2'-fluorobiphenyl-4-yl)-2-hydroxypentanoic acid ethyl ester (137 mg, 294 μmol) was dissolved in DCM (5 mL). Methanesulfonyl chloride (23 μL, 294 μmol) was added, followed by Et3N (82 μL, 0.6 mmol). The mixture was stirred at room temperature for 10 minutes, at which time LCMS indicated the mass of the desired compound. The solvent was removed in vacuo to yield crude Compound 1, which was used directly in the next step.

(1) ⟶

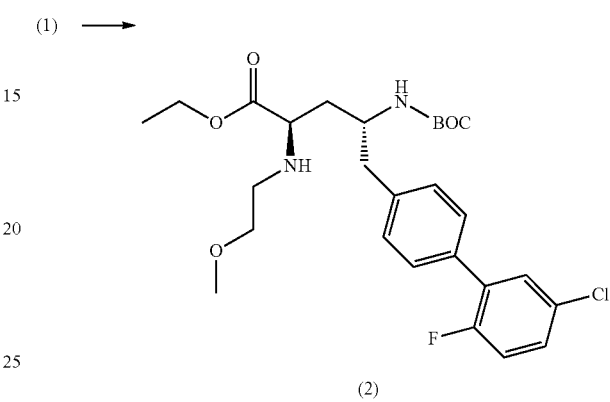

Compound 1 (53 mg, 97 μmol) was dissolved in DMF (4 mL). 2-methoxyethylamine (9.3 μL, 107 μmol) and Na2CO3 (31.0 mg, 292 μmol) were then added, and the resulting mixture was stirred overnight at 70° C., at which time LCMS indicated the mass of the desired compound. The solvent was removed in vacuo and the crude residue was purified by reverse phase chromatography to yield Compound 2 (10 mg).

(2) ⟶

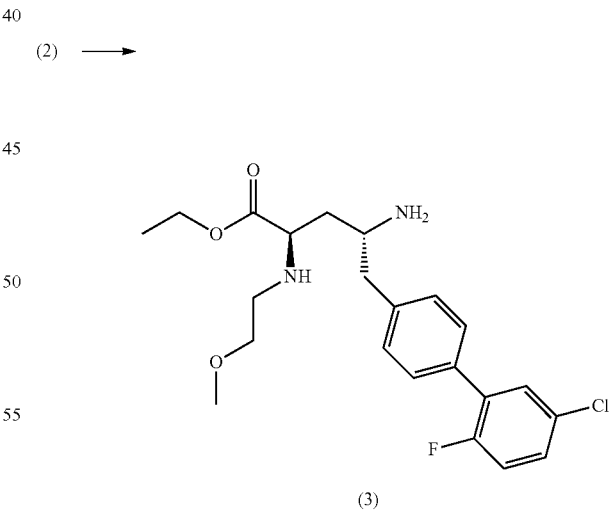

Compound 2 (10 mg, 19 μmol) was dissolved in MeCN (2 mL). A solution of 4N HCl in dioxane (70 μL, 279 μmol) was added, and the mixture was stirred at room temperature for 10 minutes, at which time LCMS showed reaction completion. The solvent was removed in vacuo to yield Compound 3 as an HCl salt, which was used without further purification.

273

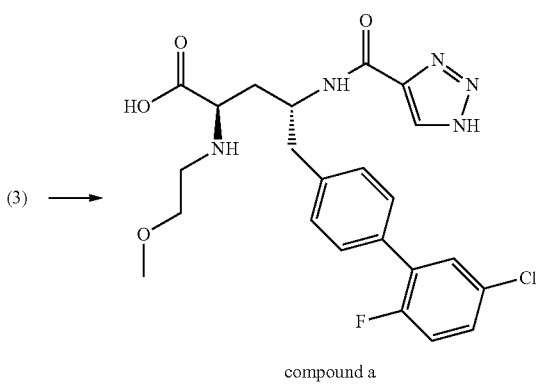 [SMILES: COCCN[C@H](C[C@@H](Cc1ccc(-c2cc(Cl)ccc2F)cc1)NC(=O)c1c[nH]nn1)C(=O)O]

compound a 1H-1,2,3-triazole-4-carboxylic acid (2.3 mg, 20 μmol) was combined with HATU (7.7 mg, 20 μmol) in DMF (2 mL) and stirred at room temperature for 15 minutes. Compound 3 (7.7 mg, 18 μmol) and DIPEA (9.6 μL, 55 μmol) were then added. The solution was stirred at room temperature for 15 minutes, at which time LCMS showed reaction completion. The solvent was removed in vacuo and the crude residue was dissolved in EtOH (2 mL). A solution of 1N LiOH (183 μL, 183 μmol) in water was added, and the resulting solution was stirred at room temperature for 30 minutes, at which time LCMS showed reaction completion. The solvent was removed in vacuo and the crude residue was purified by reverse phase chromatography to yield Compound a (3 mg) as a TFA salt. MS m/z [M+H]$^+$ calc'd for $C_{23}H_{25}ClFN_5O_4$, 490.16. found 488.

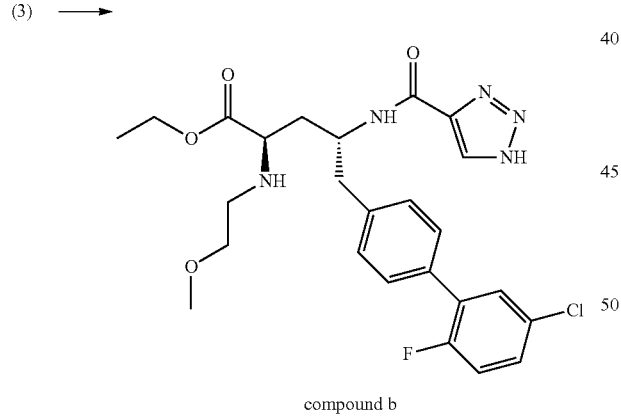

compound b 1H-1,2,3-triazole-4-carboxylic acid (3.8 mg, 34 μmol) was combined with HATU (12.9 mg, 34 μmol) in DMF (2 mL) and stirred at room temperature for 15 minutes. Compound 3 (13 mg, 31 μmol) and DIPEA (16 μL, 92 μmol) were then added. The solution was stirred at room temperature for 15 minutes, at which time LCMS showed reaction completion. The solvent was removed in vacuo and the crude residue was purified by reverse phase chromatography to yield Compound b (15 mg) as a TFA salt. MS m/z [M+H]$^+$ calc'd for $C_{25}H_{29}ClFN_5O_4$, 518.19. found 518.

274

Example 99

(2R,4R)-5-(5'-Chloro-2'-fluorobiphenyl-4-yl)-2-(1-isobutyryloxy-ethoxycarbonylamino)-4-[(3H-[1,2,3]triazole-4-carbonyl)amino]pentanoic Acid

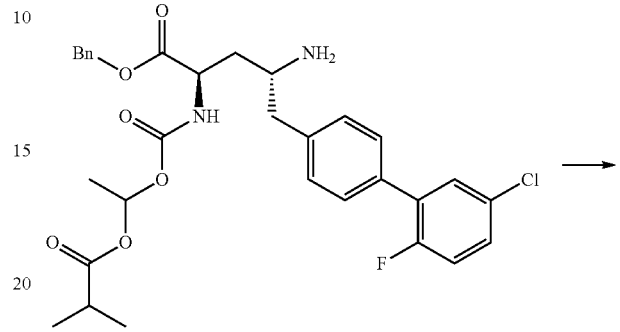

1H-1,2,3-triazole-5-carboxylic acid (3.4 mg, 30 μmol) and HATU (11.4 mg, 30 Imo') were dissolved in DMF (0.5 mL) and stirred at room temperature. A solution of (2R,4R)-4-amino-5-(5'-chloro-2'-fluorobiphenyl-4-yl)-2-(1-isobutyryloxy-ethoxycarbonylamino)pentanoic acid benzyl ester (19 mg, 27 μmol) in DMF (0.5 mL) was added to this solution, followed by DIPEA (14 μL, 82 μmol). The resulting solution was stirred at room temperature for 90 minutes and then concentrated in vacuo. The crude residue was purified by silica gel chromatography (0-100% EtOAc: hexanes) to yield Compound 1 (13 mg) as a clear oil.

(1) ⟶

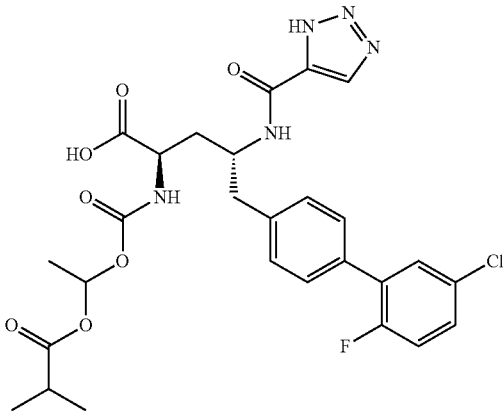

Compound 1 (13 mg, 19 μmol) and palladium (10 wt % on carbon, 20.3 mg, 19 lmo') were mixed in EtOAc (956 μL) and AcOH (956 μL). Hydrogen was bubbled through the resulting solution at room temperature for 50 minutes. The mixture was filtered through Celite® and the solution was concentrated in vacuo. The residue was diluted in a 1:1 mixture of AcOH:H$_2$O (1.5 mL) and purified by preparative HPLC to yield the title compound (6.2 mg). MS m/z [M+H]$^+$ calc'd for C$_{22}$H$_{29}$ClFN$_5$O$_2$, 590.17; found 612.2; two peaks were observed in the MS trace due to the presence of diastereomers; note that the mass of the title compound plus the mass of sodium (+23) was observed in the MS rather than the expected +1.

Example 100

(2S,4S)-5-(5'-Chloro-2'-fluorobiphenyl-4-yl)-2-(2-dimethylamino-ethoxymethyl)-4-[(1H-[1,2,3]triazole-4-carbonyl)amino]pentanoic Acid

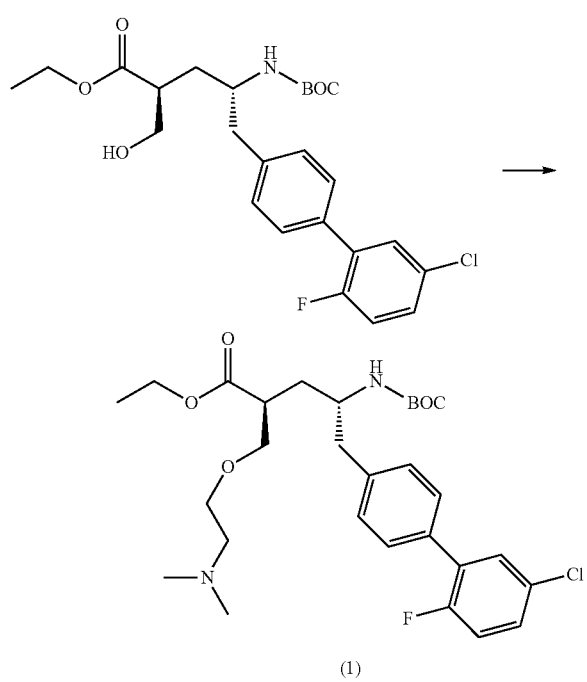

(2S,4S)-4-t-Butoxycarbonylamino-5-(5'-chloro-2'-fluoro-biphenyl-4-yl)-2-hydroxymethylpentanoic acid ethyl ester (66 mg, 138 μmol) was dissolved in dry toluene (4 mL). 2-Bromo-N,N-dimethylethanamine (418 mg, 2.8 mmol), silver oxide (382 mg, 1.7 mmol) and tetrabutylammonium iodide (25.4 mg, 69 μmol) were then added. The mixture was stirred overnight at 50° C. LC/MS showed the mass of the desired product. The solids were filtered and the solvent was removed in vacuo. The crude residue was purified by normal phase chromatography (20-95% EtOAc/hexanes) to yield Compound 1 (109 mg).

(1) ⟶

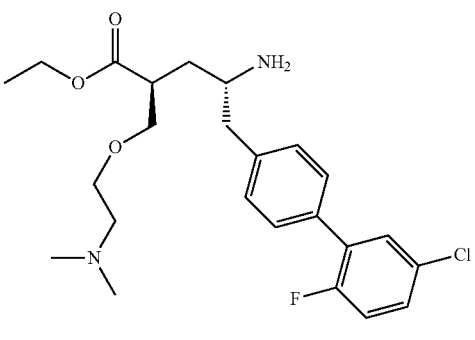

Compound 1 (109 mg, 198 μmol) was dissolved in MeCN (4.0 mL). A solution of 4N HCl in dioxane (742 μL, 3.0 mmol) was added. The solution was stirred at room temperature for 15 minutes; LC/MS showed reaction completion. The solvent was removed in vacuo, to yield Compound 2 as an HCl salt, was used in the next step without purification.

(2) ⟶

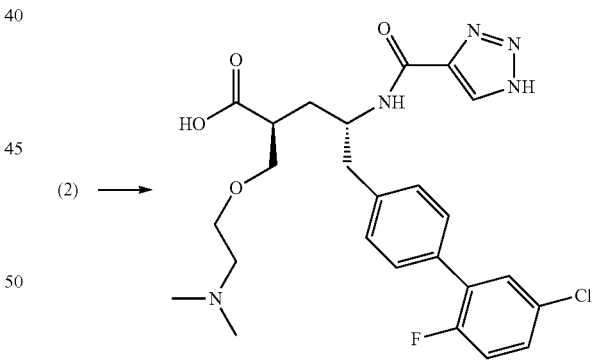

1H-1,2,3-triazole-4-carboxylic acid (24.6 mg, 217 μmol) was combined with HATU (83 mg, 217 μmol) in DMF (0.3 mL) and stirred at room temperature for 15 minutes. Compound 2 (89 mg, 197 μmol) and DIPEA (103 μL, 592 μmol) were then added. The resulting solution was stirred at room temperature for 15 minutes; LC/MS showed the mass of the desired product. The solvent was removed in vacuo and the crude residue was dissolved in EtOH (3.0 mL). A solution of 1N LiOH in water (1.6 mL, 1.6 mmol) was added, and the mixture was stirred overnight at 40° C. LC/MS showed the mass of the desired product. The solvent was removed in vacuo and the crude residue was purified by preparative HPLC to yield the title compound (5 mg) as a TFA salt. MS m/z [M+H]+ calc'd for $C_{25}H_{29}ClFN_5O_4$, 518.19. found 518.2.

Example 101

(2S,4S)-5-(5'-Chloro-2'-fluorobiphenyl-4-yl)-2-(3-hydroxy-3-methylazetidin-1-ylmethyl)-4-[(3H-[1,2,3]triazole-4-carbonyl)amino]pentanoic Acid Ethyl Ester (Compound a), (2S,4S)-5-(5'-Chloro-2'-fluorobiphenyl-4-yl)-2-(3-hydroxy-3-methylazetidin-1-ylmethyl)-4-[(1H-[1,2,3]triazole-4-carbonyl)amino]pentanoic Acid (Compound b), and (2R,4S)-5-(5'-Chloro-2'-fluorobiphenyl-4-yl)-2-(3-hydroxy-3-methylazetidin-1-ylmethyl)-4-[(1H-[1,2,3]triazole-4-carbonyl)amino]pentanoic Acid (Compound c)

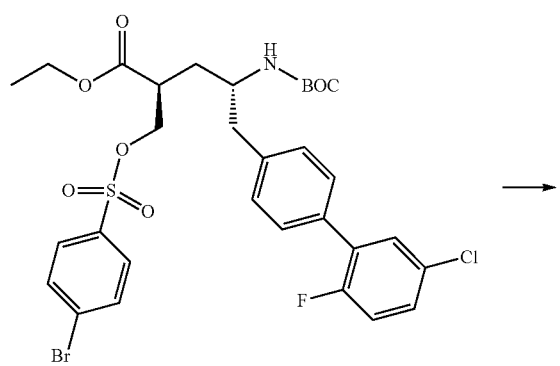

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (50 mg, 72 µmol) was dissolved in EtOH (3.0 mL). 3-Methyl-azetidin-3-ol (62 mg, 358 µmol) and Na$_2$CO$_3$ (76 mg, 715 µmol) were added, and the resulting mixture was stirred at 70° C. for 2 days, after which time LCMS indicated desired product formation. The solvent was removed under reduced pressure and the crude residue was purified by reverse phase chromatography (10-80% MeCN/H$_2$O) to yield Compound 1 (40 mg).

(1) →

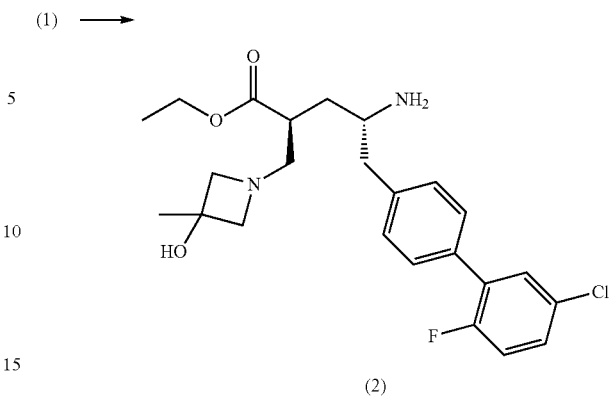

Compound 1 (16 mg) was combined with MeCN (1 mL) and 4 N HCl in dioxane (0.5 mL) and stirred for 10 minutes. The solvent was removed under reduced pressure to yield Compound 2 as an HCl salt, which was used directly in the next step.

(2) →

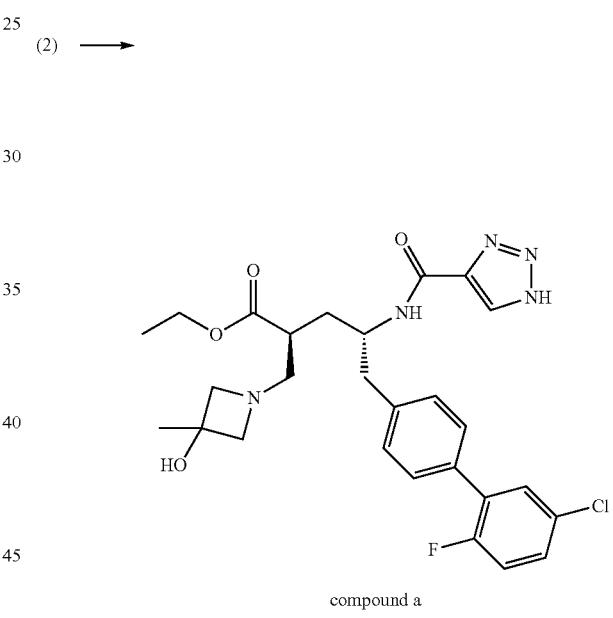

compound a 3H-1,2,3-triazole-4-carboxylic acid (3.4 mg, 30 µmol) was combined with HATU (11 mg, 30 µmol) in DMF (0.3 mL) and stirred at room temperature for 10 minutes; DIPEA (1 eq.) was added and the mixture was stirred for 1 minute. Compound 2 (10 mg, 30 µmol) in DMF (0.5 mL) was combined with DIPEA (5.2 µL, 30 µmol), then added to the activated acid solution. The resulting solution was stirred at room temperature for 30 minutes; LC/MS showed the mass of the desired product. The solvent was removed in vacuo and the crude residue was purified by reverse phase chromatography to yield Compound a (6.1 mg) as a TFA salt. MS m/z [M+H]+ calc'd for $C_{27}H_{31}ClFN_5O_4$, 544.21; found 545.2.

compound a ⟶

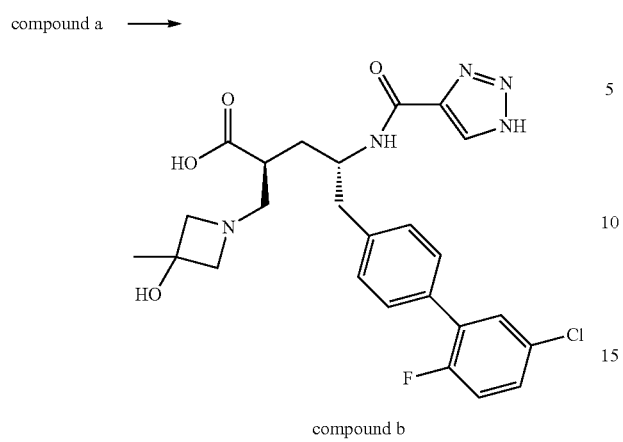

compound b

Compound a (12 mg, 22 μmol) was combined with THF (0.3 mL), 1N LiOH (88 μL, 88 μmol) and 2 drops of MeOH. The resulting mixture was stirred for 2 hours at 50° C.; LC/MS showed the mass of the desired product. The solution was then purified by reverse phase chromatography to yield Compound b as a TFA salt. MS m/z [M+H]$^+$ calc'd for $C_{25}H_{27}ClFN_5O_4$, 516.17. found 516.

Compound c was prepared in a similar manner using the appropriate starting materials. MS m/z [M+H]$^+$ calc'd for $C_{25}H_{27}ClFN_5O_4$, 516.17. found 516.

Example 102

(2S,4S)-5-(5'-Chloro-2'-fluorobiphenyl-4-yl)-2-(3-methoxyazetidin-1-ylmethyl)-4-[(3H-[1,2,3]triazole-4-carbonyl)amino]pentanoic Acid Ethyl Ester (Compound a), (2S,4S)-5-(5'-Chloro-2'-fluorobiphenyl-4-yl)-2-(3-methoxyazetidin-1-ylmethyl)-4-[(1H-[1,2,3]triazole-4-carbonyl)amino]pentanoic Acid (Compound b), and (2R,4S)-5-(5'-Chloro-2'-fluorobiphenyl-4-yl)-2-(3-methoxyazetidin-1-ylmethyl)-4-[(1H-[1,2,3]triazole-4-carbonyl)amino]pentanoic Acid (Compound c)

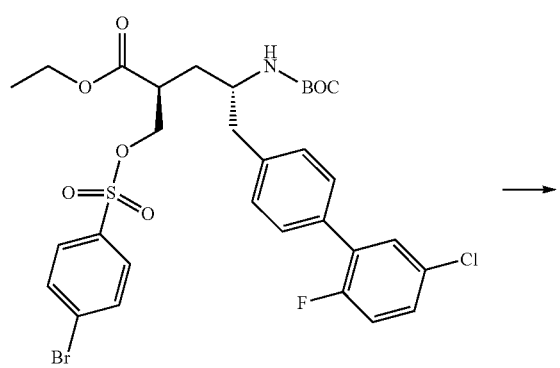

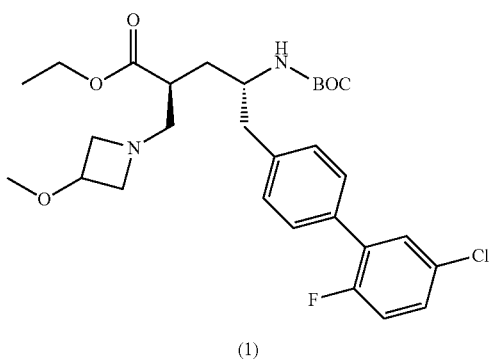

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (50 mg, 72 μmol) was dissolved in EtOH (3.0 mL). 3-Methoxy-azetidine (62 mg, 358 μmol) and $Na_2CO_3$ (76 mg, 715 μmol) were added, and the resulting mixture was stirred at 70° C. for 2 days, after which time LCMS indicated desired product formation. The solvent was removed under reduced pressure and the crude residue was purified by reverse phase chromatography (10-80% $MeCN/H_2O$) to yield Compound 1 (8 mg).

(1) ⟶

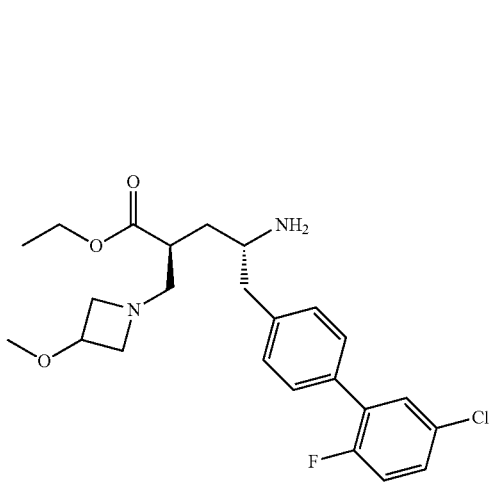

Compound 1 (16 mg) was combined with MeCN (1 mL) and 4 N HCl in dioxane (0.5 mL) and stirred for 10 minutes. The solvent was removed under reduced pressure to yield Compound 2 as an HCl salt, which was used directly in the next step.

(2) ⟶

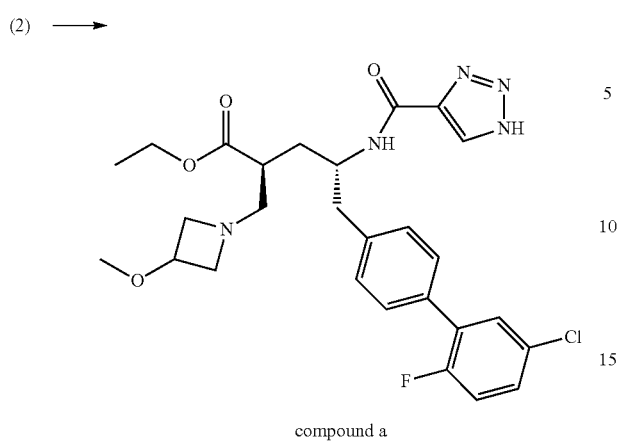

compound a 3H-1,2,3-triazole-4-carboxylic acid (3.4 mg, 30 µmol) was combined with HATU (11 mg, 30 µmol) in DMF (0.3 mL) and stirred at room temperature for 10 minutes; DIPEA (1 eq.) was added and the mixture was stirred for 1 minute. Compound 2 (10 mg, 30 µmol) in DMF (0.5 mL) was combined with DIPEA (5.2 µL, 30 µmol), then added to the activated acid solution. The resulting solution was stirred at room temperature for 30 minutes; LC/MS showed the mass of the desired product. The solvent was removed in vacuo and the crude residue was purified by reverse phase chromatography to yield Compound a (8.5 mg) as a TFA salt. MS m/z [M+H]$^+$ calc'd for $C_{27}H_{31}ClFN_5O_4$, 544.21; found 545.2.

compound a ⟶

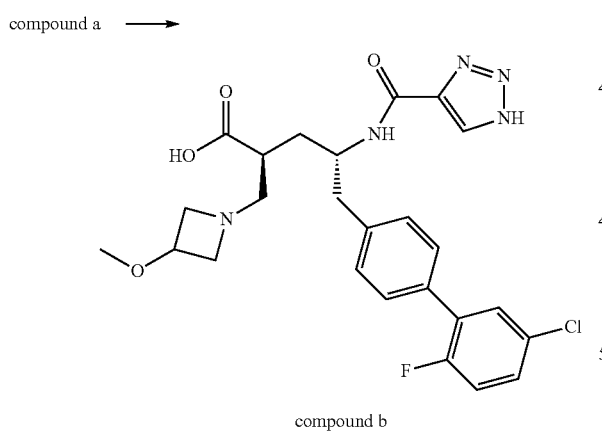

compound b

Compound a (12 mg, 22 µmol) was combined with THF (0.3 mL), 1N LiOH (88 µL, 88 µmol) and 2 drops of MeOH. The resulting mixture was stirred for 2 hours at 50° C.; LC/MS showed the mass of the desired product. The solution was then purified by reverse phase chromatography to yield Compound b as a TFA salt. MS m/z [M+H]$^+$ calc'd for $C_{25}H_{27}ClFN_5O_4$, 516.17. found 516.

Compound c was prepared in a similar manner using the appropriate starting materials. MS m/z [M+H]$^+$ calc'd for $C_{25}H_{27}ClFN_5O_4$, 516.17. found 516.

Example 103

(2S,4S)-5-(5'-Chloro-2'-fluorobiphenyl-4-yl)-24(R)-2-methoxymethylazetidin-1-ylmethyl)-4-[(1H-[1,2,3]triazole-4-carbonyl)amino]pentanoic Acid Ethyl Ester (Compound a), (2S,4S)-5-(5'-Chloro-2'-fluorobiphenyl-4-yl)-2-((R)-2-methoxymethylazetidin-1-ylmethyl)-4-[(3H-[1,2,3]triazole-4-carbonyl)amino]pentanoic Acid (Compound b), (2S,4S)-5-(5'-Chloro-2'-fluorobiphenyl-4-yl)-2-((S)-2-methoxymethylazetidin-1-ylmethyl)-4-[(1H-[1,2,3]triazole-4-carbonyl)amino]pentanoic Acid Ethyl Ester (Compound c), and (2S,4S)-5-(5'-Chloro-2'-fluorobiphenyl-4-yl)-2-((S)-2-methoxymethylazetidin-1-ylmethyl)-4-[(3H-[1,2,3]triazole-4-carbonyl)amino]pentanoic Acid (Compound d)

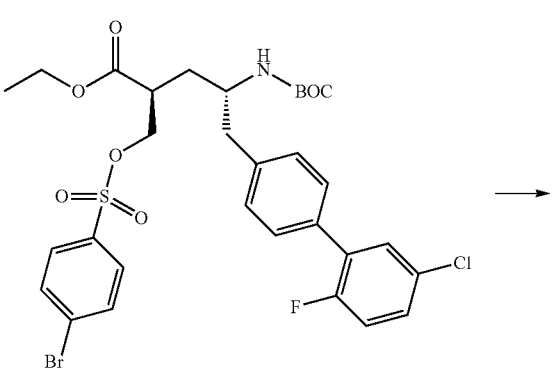

(1)

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (80 mg, 114 µmol) was dissolved in EtOH (3.0 mL). (R)-2-(methoxymethyl)azetidine (34.7 mg, 343 µmol) and Na$_2$CO$_3$ (121 mg, 1.1 mmol) were added, and the resulting mixture was stirred at 70° C. overnight, after which time LCMS indicated desired product formation. The solvent was removed in vacuo and the crude residue was purified by reverse phase chromatography (26.4 mg). The residue was dissolved in MeCN (3.0 mL). A solution of 4N HCl in dioxane (653 µL, 2.6 mmol) was added, and the resulting solution was stirred at room temperature for 20 minutes, after which time LCMS indicated desired product formation. The solvent was removed in vacuo to yield Compound 1 as an HCl salt.

(1) → 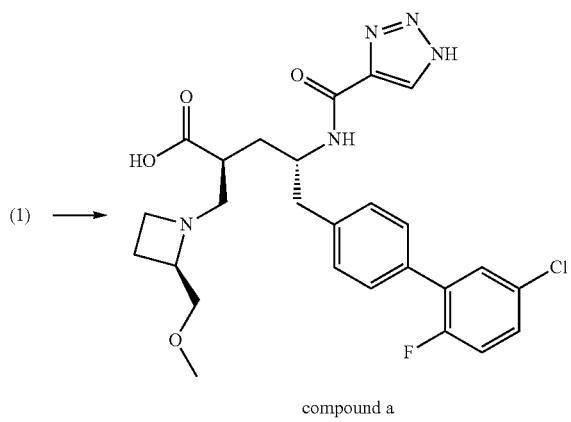 [SMILES: COC[C@H]1CCN1C[C@H](C[C@@H](Cc1ccc(-c2cc(Cl)ccc2F)cc1)NC(=O)c1c[nH]nn1)C(=O)O]

compound a 1H-1,2,3-triazole-4-carboxylic acid (9.8 mg, 87 μmol) and HATU (36.4 mg, 96 μmol) were combined in DMF (3.0 mL) and stirred at room temperature for 15 minutes. Compound 1 (40.3 mg, 87 μmol) and DIPEA (46 μL, 261 μmol) were added and the resulting solution was stirred at room temperature for 15 minutes, after which time LCMS indicated desired product formation. The solvent was removed in vacuo and the crude residue was purified by reverse phase chromatography to yield Compound a (5.2 mg) as a TFA salt. MS m/z [M+H]+ calc'd for $C_{28}H_{33}ClFN_5O_4$, 558.22. found 558.

compound a ⟶

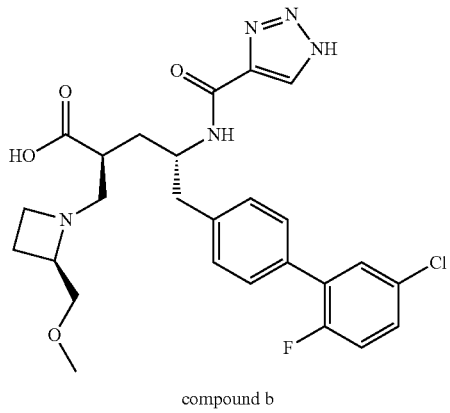

compound b

Compound a (5.2 mg, 9.3 μmol) was dissolved in EtOH (3.0 mL). A solution of 1N LiOH (75 μL, 75 μmol) in water was added, and the resulting solution was stirred at room temperature overnight, after which time LCMS indicated desired product formation. The solvent was removed in vacuo and the crude residue was purified by reverse phase chromatography to yield Compound b (4.0 mg) as a TFA salt. MS m/z [M+H]+ calc'd for $C_{26}H_{29}ClFN_5O_4$, 530.19. found 530.

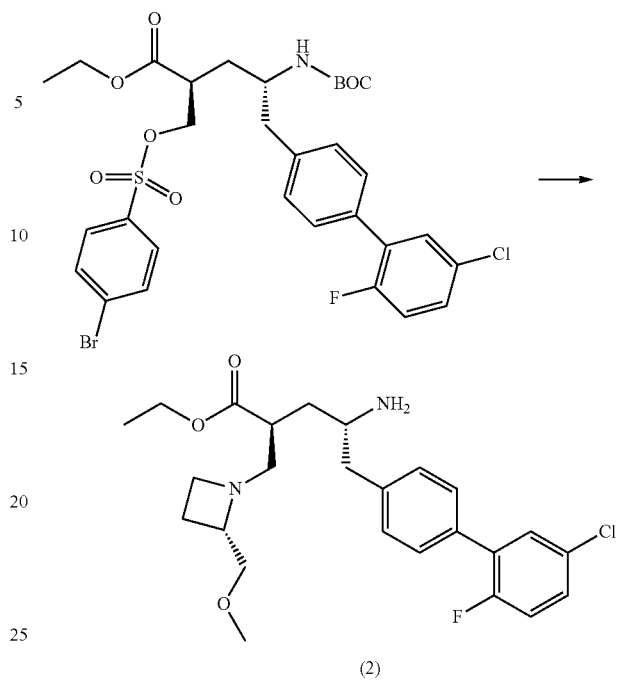

(2)

(2S,4S)-2-(4-Bromobenzenesulfonyloxymethyl)-4-t-butoxycarbonylamino-5-(5'-chloro-2'-fluorobiphenyl-4-yl) pentanoic acid ethyl ester (80 mg, 114 μmol) was dissolved in EtOH (3.0 mL). (S)-2-(methoxymethyl)azetidine (34.7 mg, 343 μmol) and $Na_2CO_3$ (121 mg, 1.1 mmol) were added, and the resulting mixture was stirred at 70° C. overnight, after which time LCMS indicated desired product formation. The solvent was removed in vacuo and the crude residue was purified by reverse phase chromatography (49 mg). The residue was dissolved in MeCN (3.0 mL). A solution of 4N HCl in dioxane (653 μL, 2.6 mmol) was added, and the resulting solution was stirred at room temperature for 20 minutes, after which time LCMS indicated desired product formation. The solvent was removed in vacuo to yield Compound 2 as an HCl salt.

(2) → 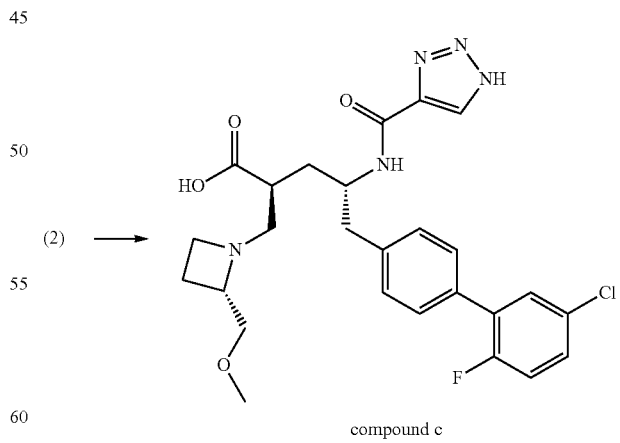

compound c 1H-1,2,3-triazole-4-carboxylic acid (9.8 mg, 87 μmol) and HATU (36.4 mg, 96 μmol) were combined in DMF (3.0 mL) and stirred at room temperature for 15 minutes. Compound 2 (40.3 mg, 87 μmol) and DIPEA (46 μL, 261 μmol) were added and the resulting solution was stirred at room temperature for 15 minutes, after which time LCMS indicated desired product formation. The solvent was removed in vacuo and the crude residue was purified by reverse phase chromatography to yield Compound c (34.5 mg) as a TFA salt. MS m/z [M+H]+ calc'd for $C_{28}H_{33}ClFN_5O_4$, 558.22. found 558.

compound c ⟶

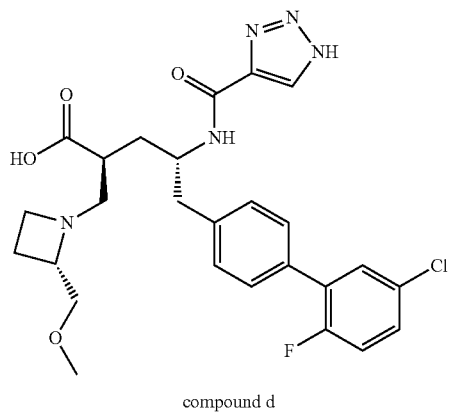

compound d

Compound c (26 mg, 47 μmol) was dissolved in EtOH (3.0 mL). A solution of 1N LiOH (75 μL, 75 μmol) in water was added, and the resulting solution was stirred at room temperature overnight, after which time LCMS indicated desired product formation. The solvent was removed in vacuo and the crude residue was purified by reverse phase chromatography to yield Compound d (15 mg) as a TFA salt. MS m/z [M+H]+ calc'd for $C_{26}H_{29}ClFN_5O_4$, 530.19. found 530.

Example 104

(2S,4S)-2-(1-Amino-1-methylethyl)-5-(5'-chloro-2'-fluorobiphenyl-4-yl)-4-[(3H-[1,2,3]triazole-4-carbonyl)amino]pentanoic Acid

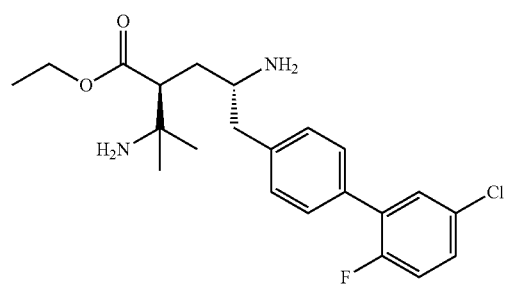

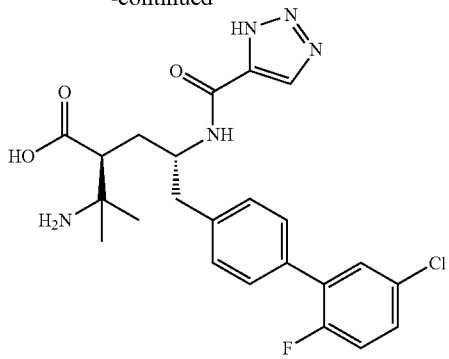

1H-1,2,3-triazole-5-carboxylic acid (15.3 mg, 135 μmol) and HATU (51.4 mg, 135 μmol) were mixed in DMF (4 mL) and stirred at room temperature for 15 minutes. (2S,4S)-4-Amino-2-(1-amino-1-methylethyl)-5-(5'-chloro-2'-fluorobiphenyl-4-yl)pentanoic acid ethyl ester (50 mg, 123 μmol) and DIPEA (64 μL, 369 μmol) were added. The resulting solution was stirred at room temperature for 15 minutes, at which point LC/MS showed reaction completion. The solvent was removed in vacuo and the crude residue was diluted in EtOH (4 mL). A solution of 1N LiOH (983 μL, 983 μmol) in water was then added. The resulting solution was stirred at 60° C. for 2 days, at which point LC/MS showed reaction completion. The solvent was removed in vacuo and the crude residue was purified by preparative HPLC to yield the title compound (4.2 mg) as a TFA salt. MS m/z [M+H]+ calc'd for $C_{23}H_{25}ClFN_5O_3$, 474.16. found 474.2.

Example 105

(2S,4S)-5-(5'-Chloro-2'-fluorobiphenyl-4-yl)-2-[3-(2-hydroxyethyl)azetidin-1-ylmethyl]-4-[(1H-[1,2,3]triazole-4-carbonyl)amino]pentanoic Acid

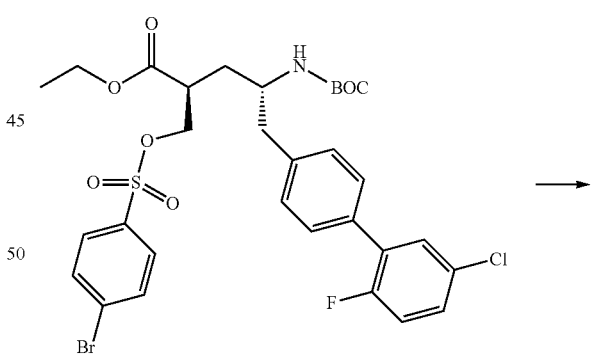

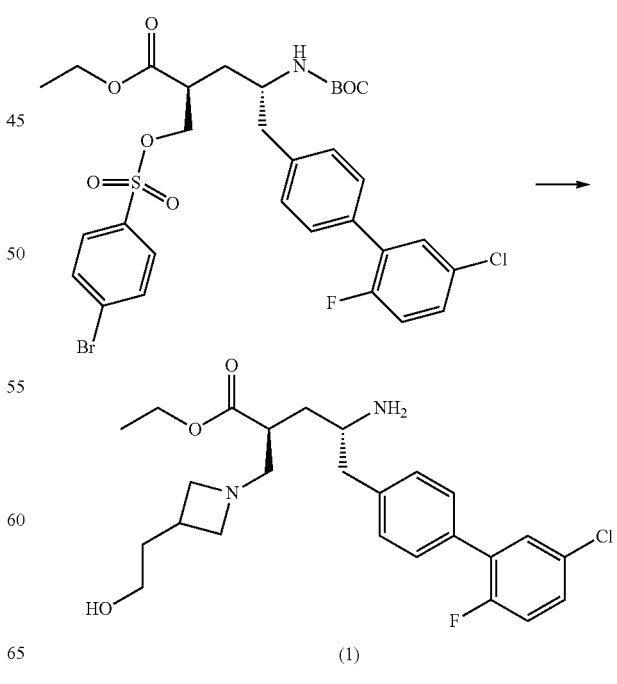

(1)

287

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (60 mg, 86 µmol) was dissolved in EtOH (3.0 mL). 2-(Azetidin-3-yl)ethan-1-ol HCl (26.0 mg, 258 µmol) and Na$_2$CO$_3$ (91 mg, 858 µmol) were added, and the resulting mixture was stirred at 70° C. overnight, after which time LCMS indicated desired product formation. The solvent was removed in vacuo and the crude residue was purified by reverse phase chromatography (60 mg). The residue (60 mg, 107 µmol) was dissolved in MeCN (3.0 mL). A solution of 4N HCl in dioxane (653 µL, 2.6 mmol) was added, and the resulting solution was stirred at room temperature for 20 minutes, after which time LCMS indicated desired product formation. The solvent was removed in vacuo to yield Compound 1 as an HCl salt.

(1) →

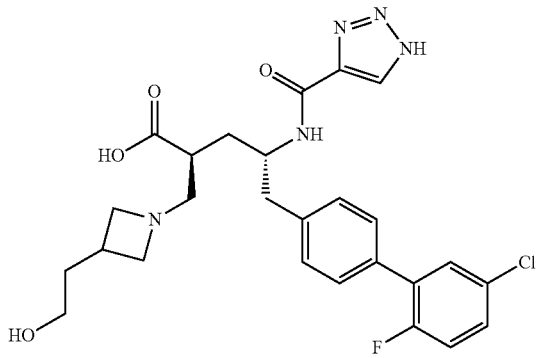

1H-1,2,3-triazole-4-carboxylic acid (9.8 mg, 87 µmol) and HATU (36.4 mg, 96 µmol) were combined in DMF (3.0 mL) and stirred at room temperature for 15 minutes. Compound 1 (49.3 mg, 106 µmol) and DIPEA (46 µL, 261 µmol) were added and the resulting solution was stirred at room temperature for 15 minutes, after which time LCMS indicated desired product formation. The solvent was removed in vacuo and the crude residue was purified by reverse phase chromatography.

The residue (56.8 mg, 87 µmol) was dissolved in EtOH (3.0 mL). A solution of 1N LiOH (696 µL, 696 µmol) in water was added, and the resulting solution was stirred at room temperature overnight, after which time LCMS indicated desired product formation. The solvent was removed in vacuo and the crude residue was purified by reverse phase chromatography to yield the title compound (36 mg) as a TFA salt. MS m/z [M+H]$^+$ calc'd for C$_{26}$H$_{29}$ClFN$_5$O$_4$, 530.19. found 530.

288

Example 106

(2S,4S)-5-(5'-Chloro-2'-fluorobiphenyl-4-yl)-2-{[(2-hydroxyethyl)-methylamino]methyl}-4-[(1H-[1,2,3]triazole-4-carbonyl)amino]pentanoic Acid

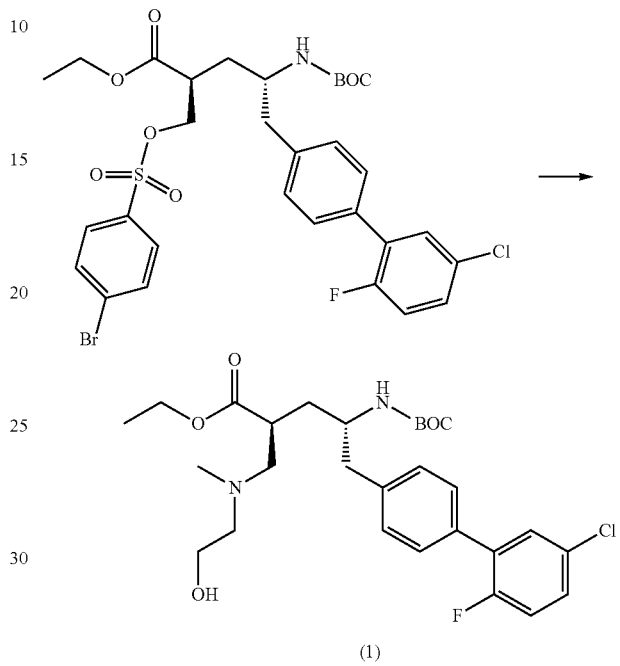

(2S,4S)-2-(4-Bromobenzenesulfonyloxymethyl)-4-t-butoxycarbonylamino-5-(5'-chloro-2'-fluorobiphenyl-4-yl)pentanoic acid ethyl ester (50 mg, 72 µmol) was dissolved in EtOH (2 mL). 2-methoxy-N-methylethanamine (19.1 mg, 215 µmol) was added and the resulting mixture was stirred at 50° C. for 2 days, after which time LCMS indicated desired product formation. The organic layer was evaporated and the crude residue was purified by reverse phase chromatography to yield Compound 1 (20 mg).

(1) →

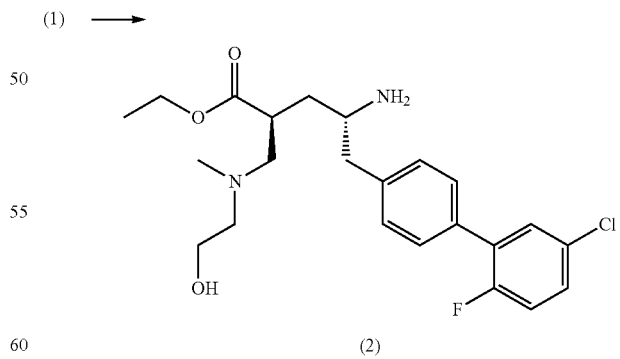

Compound 1 (15 mg, 28 µmol) was combined with MeCN (0.5 mL) and dry 4N HCl in dioxane (0.3 mL) and stirred for 10 minutes. The solvent was removed under reduced pressure to yield crude Compound 2, which was used directly in the next step.

(2) →

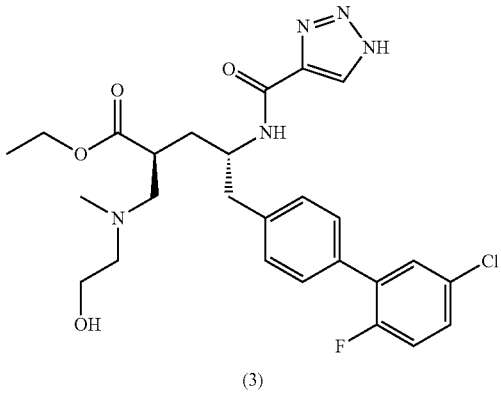

(3)

1H-1,2,3-triazole-5-carboxylic acid (3.1 mg, 27 μmol) was combined with HATU (10.4 mg, 27 μmol) in DMF (0.5 mL), and stirred for 10 minutes. DIPEA (4.8 μL, 27 Mmol) was added and the resulting mixture was stirred for 1 minute. Compound 2 (12 mg, 27 μmol) dissolved in DMF (1 mL) was combined with added DIPEA (14.4 μL, 82 μmol) followed by addition of the activated acid solution. The resulting mixture was stirred for 30 minutes then purified by reverse phase chromatography (0-100% EtOAc/hexanes to yield Compound 3 (10 mg).

(3) →

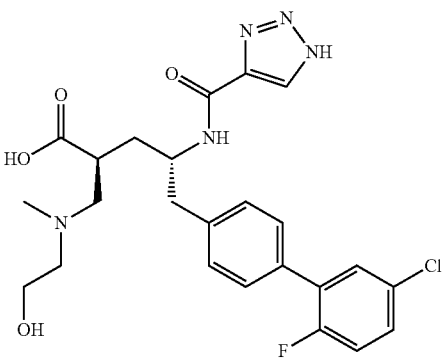

Compound 3 (9.0 mg, 17 μmol) was combined with 1N LiOH (84 μL, 84 μmol), THF (0.5 mL), and MeOH (0.1 mL). The mixture was stirred at room temperature for 1 hour, then purified by reverse phase chromatography to yield the title compound (1 mg) as a TFA salt. MS m/z [M+H]+ calc'd for $C_{24}H_{27}ClFN_5O_4$, 504.17. found 504.

Assay 1

In Vitro Assays for the Quantitation of Inhibitor Potencies at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl) aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 μM in Assay Buffer (NEP: 50 mM HEPES, pH 7.5, 100 mM NaCl, 0.01% polyethylene glycol sorbitan monolaurate (Tween-20), 10 μM $ZnSO_4$; ACE: 50 mM HEPES, pH 7.5, 100 mM NaCl, 0.01% Tween-20, 1 μM $ZnSO_4$). The respective enzymes were used at concentrations that resulted in quantitative proteolysis of 1 μM of substrate after 20 minutes at 37° C.

Test compounds were assayed over the range of concentrations from 10 μM to 20 pM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively Inhibition constants were obtained by nonlinear regression of the data using the equation (GraphPad Software, Inc., San Diego, Calif.):

$v=v_0/[1+(I/K')]$ where v is the reaction rate, $v_0$ is the uninhibited reaction rate, I is the inhibitor concentration and K' is the apparent inhibition constant.

Compounds of the invention were tested in this assay and found to have $pK_i$ values at human NEP as follows. In some instances, prodrug compounds did not inhibit the enzyme in this in vitro assay, or the prodrugs (the term "prodrug" is intended to mean an inactive or significantly less active precursor of a drug that is converted into its active form in the body under physiological conditions, for example, by normal metabolic processes; such compounds may not necessarily possess pharmacological activity at NEP, but may be administered orally or parenterally and thereafter metabolized in the body to form compounds that are pharmacologically active at NEP) were not tested (n.d.) since activity would not be expected.

| Ex. | pK$_i$ | Ex. | pK$_i$ | Ex. | pK$_i$ |
|---|---|---|---|---|---|
| 1 | ≥9.0 | 16-35 | ≥9.0 | 53 | ≥9.0 |
| 2-1 | ≥9.0 | 16-36 | n.d. | 54 | 8.5-8.9 |
| 2-2 | ≥9.0 | 17 | ≥9.0 | 55 | 8.0-8.5 |
| 2-3 | 8.5-8.9 | 18-1 | 8.0-8.5 | 56 | 8.5-8.9 |
| 2-4 | ≥9.0 | 18-2 | ≥9.0 | 57 | ≥9.0 |
| 2-5 | ≥9.0 | 18-3 | ≥9.0 | 58 | 8.0-8.5 |
| 2-6 | ≥9.0 | 18-4 | 8.0-8.5 | 59 | ≥9.0 |
| 2-7 | ≥9.0 | 18-5 | 8.5-8.9 | 60 | 8.0-8.5 |
| 2-8 | ≥9.0 | 18-6 | ≥9.0 | 61a | ≥9.0 |
| 2-9 | ≥9.0 | 18-7 | 7.5-8.0 | 61b | ≥9.0 |
| 2-10 | 8.5-8.9 | 18-8 | ≥9.0 | 62 | ≥9.0 |
| 2-11 | ≥9.0 | 18-9 | 8.0-8.5 | 63 | 8.5-8.9 |
| 2-12 | ≥9.0 | 18-10 | ≥9.0 | 64 | 8.5-8.9 |
| 2-13 | ≥9.0 | 18-11 | ≥9.0 | 65 | 8.5-8.9 |
| 2-14 | ≥9.0 | 18-12 | 8.0-8.5 | 66 | 8.5-8.9 |
| 2-15 | ≥9.0 | 19 | n.d. | 67 | ≥9.0 |
| 2-16 | ≥9.0 | 20 | ≥9.0 | 68 | 8.0-8.5 |
| 3 | ≥9.0 | 21-1 | ≥9.0 | 69a | 8.5-8.9 |
| 4-1 | ≥9.0 | 21-2 | 8.5-8.9 | 69b | n.d. |
| 4-2 | ≥9.0 | 21-3 | ≥9.0 | 70 | ≥9.0 |
| 4-3 | ≥9.0 | 21-4 | 8.5-8.9 | 71 | ≥9.0 |
| 5 | ≥9.0 | 21-5 | 8.5-8.9 | 72 | ≥9.0 |
| 6 | ≥9.0 | 21-6 | 8.5-8.9 | 73 | ≥9.0 |
| 7-1 | ≥9.0 | 21-7 | 8.5-8.9 | 74 | 8.5-8.9 |
| 7-2 | ≥9.0 | 21-8 | n.d. | 75 | 8.5-8.9 |
| 7-3 | ≥9.0 | 21-9 | n.d. | 76 | 7.5-7.9 |
| 7-4 | ≥9.0 | 21-10 | n.d. | 77a | 8.0-8.5 |
| 7-5 | ≥9.0 | 22 | 8.5-8.9 | 77b | 8.0-8.5 |
| 7-6 | ≥9.0 | 23 | 8.5-8.9 | 78 | 8.5-8.9 |
| 7-7 | 8.5-8.9 | 24-1 | 8.0-8.5 | 79 | 8.5-8.9 |
| 7-8 | 8.5-8.9 | 24-2 | 8.5-8.9 | 80 | ≥9.0 |
| 7-9 | ≥9.0 | 25 | 8.0-8.5 | 81 | 8.0-8.5 |
| 7-10 | ≥9.0 | 26 | 8.0-8.5 | 82a | ≥9.0 |
| 7-11 | ≥9.0 | 27 | 8.0-8.5 | 82b | n.d. |
| 8 | ≥9.0 | 28 | ≥9.0 | 83a | n.d. |
| 9-1 | ≥9.0 | 29 | ≥9.0 | 83b | ≥9.0 |
| 9-2 | ≥9.0 | 30-1 | ≥9.0 | 84a | n.d. |
| 9-3 | ≥9.0 | 30-2 | ≥9.0 | 84b | ≥9.0 |
| 9-4 | ≥9.0 | 30-3 | ≥9.0 | 85a | ≥9.0 |
| 9-5 | ≥9.0 | 30-4 | ≥9.0 | 85b | n.d. |
| 10 | ≥9.0 | 30-5 | ≥9.0 | 86 | n.d. |
| 11 | 8.5-8.9 | 30-6 | ≥9.0 | 87a | n.d. |
| 12 | 8.5-8.9 | 30-7 | ≥9.0 | 87b | ≥9.0 |
| 13 | ≥9.0 | 30-8 | 8.5-8.9 | 88a | n.d. |
| 14a | 7.5-8.0 | 30-9 | ≥9.0 | 88b | ≥9.0 |
| 14b | 7.0-7.5 | 30-10 | ≥9.0 | 89a | n.d. |
| 15 | ≥9.0 | 30-11 | ≥9.0 | 89b | ≥9.0 |
| 16-1 | 8.5-8.9 | 30-12 | ≥9.0 | 90a | n.d. |
| 16-2 | 8.5-8.9 | 31 | 8.5-8.9 | 90b | n.d. |
| 16-3 | 8.5-8.9 | 32 | 8.0-8.5 | 91a | n.d. |
| 16-4 | 8.5-8.9 | 33 | ≥9.0 | 91b | ≥9.0 |
| 16-5 | 8.0-8.5 | 34-1 | 8.5-8.9 | 92a | n.d. |
| 16-6 | 8.0-8.5 | 35 | 8.0-8.5 | 92b | ≥9.0 |
| 16-7 | 8.0-8.5 | 36-1 | 8.5-8.9 | 93a | n.d. |
| 16-8 | 8.0-8.5 | 36-2 | 8.5-8.9 | 93b | ≥9.0 |
| 16-9 | ≥9.0 | 37-1 | ≥9.0 | 94a | n.d. |
| 16-10 | 7.5-8.0 | 38-1 | 8.0-8.5 | 94b | ≥9.0 |
| 16-11 | 8.0-8.5 | 38-2 | 8.5-8.9 | 95a | n.d. |
| 16-12 | n.d. | 39-1 | ≥9.0 | 95b | ≥9.0 |
| 16-13 | n.d. | 40 | ≥9.0 | 96a | n.d. |
| 16-14 | n.d. | 41 | ≥9.0 | 96b | n.d. |
| 16-15 | 8.0-8.5 | 42-1 | 8.5-8.9 | 97a | ≥9.0 |
| 16-16 | ≥9.0 | 42-2 | 8.5-8.9 | 97b | n.d. |
| 16-17 | n.d. | 43 | ≥9.0 | 98a | ≥9.0 |
| 16-18 | ≥9.0 | 44-1 | ≥9.0 | 98b | n.d. |
| 16-19 | n.d. | 44-2 | n.d. | 99 | n.d. |
| 16-20 | 8.5-8.9 | 45 | ≥9.0 | 100 | ≥9.0 |
| 16-21 | ≥9.0 | 46 | 8.5-8.9 | 101a | n.d. |
| 16-22 | n.d. | 47 | 8.0-8.5 | 101b | ≥9.0 |
| 16-23 | ≥9.0 | 48a | ≥9.0 | 101c | 8.5-8.9 |
| 16-24 | ≥9.0 | 48b | 8.5-8.9 | 102a | n.d. |
| 16-25 | ≥9.0 | 48c | n.d. | 102b | ≥9.0 |
| 16-26 | 8.5-8.9 | 49a | ≥9.0 | 102c | ≥9.0 |
| 16-27 | 8.5-8.9 | 49b | ≥9.0 | 103a | n.d. |
| 16-28 | ≥9.0 | 49c | n.d. | 103b | ≥9.0 |
| 16-29 | ≥9.0 | 50 | ≥9.0 | 103c | n.d. |
| 16-30 | n.d. | 51 | 8.5-8.9 | 103d | ≥9.0 |
| 16-31 | ≥9.0 | 52-1 | ≥9.0 | 104 | ≥9.0 |
| 16-32 | n.d. | 52-2 | 8.0-8.5 | 105 | ≥9.0 |
| 16-33 | ≥9.0 | 52-3 | 8.5-8.9 | 106 | 8.5-8.9 |
| 16-34 | n.d. | | | | |

Assay 2

Pharmacodynamic (PD) Assay for ACE and NEP Activity in Anesthetized Rats

Male, Sprague Dawley, normotensive rats are anesthetized with 120 mg/kg (i.p.) of inactin. Once anesthetized, the jugular vein, carotid artery (PE 50 tubing) and bladder (flared PE 50 tubing) catheters are cannulated and a tracheotomy is performed (Teflon Needle, size 14 gauge) to facilitate spontaneous respiration. The animals are then allowed a 60 minute stabilization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of AngI (1.0 μg/kg, for ACE inhibitor activity) at 15 minutes apart. At 15 minutes post-second dose of AngI, the animals are treated with vehicle or test compound. Five minutes later, the animals are additionally treated with a bolus i.v. injection of atrial natriuretic peptide (ANP; 30 μg/kg). Urine collection (into pre-weighted eppendorf tubes) is started immediately after the ANP treatment and continued for 60 minutes. At 30 and 60 minutes into urine collection, the animals are re-challenged with AngI. Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition is assessed by quantifying the % inhibition of pressor response to AngI. NEP inhibition is assessed by quantifying the potentiation of ANP-induced elevation in urinary cGMP output.

Assay 3

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site with free access to food and water. For blood pressure recording, these animals are surgically implanted with small rodent radiotransmitters (telemetry unit; DSI Models TA11PA-C40 or C50-PXT, Data Science Inc., USA). The tip of the catheter connected to the transmitter is inserted into the descending aorta above the iliac bifurcation and secured in place with tissue adhesive. The transmitter is kept intraperitoneally and secured to the abdominal wall while closing of the abdominal incision with a non-absorbable suture. The outer skin is closed with suture and staples. The animals are allowed to recover with appropriate post-operative care. On the day of the experiment, the animals in their cages are placed on top of the telemetry receiver units to acclimate to the testing environment and baseline recording. After at least of 2 hours baseline measurement is taken, the animals are then dosed with vehicle or test compound and followed out to 24 hours post-dose blood pressure measurement. Data is recorded continuously for the duration of the study using Notocord software (Kalamazoo, Mich.) and stored as electronic digital signals. Parameters measured are blood pressure (systolic, diastolic and mean arterial pressure) and heart rate.

Assay 4

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet (8% in food or 1% NaCl in drinking water), a deoxycorticosterone acetate (DOCA) pellet (100 mg, 90 days release time, Innovative Research of America, Sarasota, Fla.) is implanted subcutaneously and unilateral nephrectomy is performed. At this time, the animals are also surgically implanted with small rodent radiotransmitters for blood pressure measurement (see Assay 3 for details). The animals are allowed to recover with appropriate post-operative care. Study design, data recording, and parameters measured is similar to that described for Assay 3.

Assay 5

In Vivo Evaluation of Antihypertensive Effects in the Conscious Dahl/SS Rat Model of Hypertension Male, Dahl salt sensitive rats (Dahl/SS, 6-7 weeks of age from Charles River Laboratory, USA) are allowed at least 48 hours of acclimation upon arrival at the testing site before they were placed on a 8% NaCl high salt diet (TD.92012, Harlan, USA) then surgically implanted with small rodent radiotransmitters for blood pressure measurement (see Assay 3 for details). The animals are allowed to recover with appropriate post-operative care. At approximately 4 to 5 weeks from the start of high salt diet, these animals are expected to become hypertensive. Once the hypertension level is confirmed, these animals are used for the study while continued with the high salt diet to maintain their hypertension level. Study design, data recording, and parameters measured is similar to that described in Assay 3.

Assay 6

Rat PO Cassette Assay

Oral bioavailability, or % F, is a measure of the percentage of a drug in an oral dose that actually reaches the systemic circulation. Compound losses can occur due to incomplete formulation dissolution, incomplete absorption due to compound insolubility or instability along the GI, or metabolism in the gut or across the gut wall. The fraction of the dose which reaches the hepatic portal vein must also then pass through the liver before reaching the systemic circulation. Compound metabolism, or "first-pass extraction," can occur during this initial passage through the liver, and this is an additional potential source of compound loss. Oral bioavailability is calculated as the dose-normalized ratio of drug exposure after an oral dose to that after an intravenous dose, wherein the entire dose is delivered directly to the systemic circulation.

Each cassette study begins with 10 mM DMSO stock solutions of up to 5 different compounds. Typically, compounds are selected such no two compounds dosed in the same cassette have a molecular weight within 5 Da of each other. This simplifies subsequent bioanalysis. Appropriate volumes of each DMSO stock are added into a volume of vehicle (5% sodium bicarbonate, 5% dextrose in $H_2O$) such that the final concentration of each compound is 0.25 mg/mL. Intravenous dosing solutions are sterile-filtered (0.2 μm) prior to dosing.

Pre-cannulated male Sprague-Dawley rats (3 per cassette per route) between 8 and 10 weeks of age were obtained from Harlan Laboratories (Indianapolis, Ind.). Rats received either a single oral gavage or a single intravenous (via lateral tail vein) dose (2 mL/kg) of the dosing solution. The final dose was 0.5 mg/kg. Serial blood samples were harvested via jugular vein cannula at 3 minutes, 15 minutes, 30 minutes, 1 hours, 2 hours, 4 hours, 6 hours, and 24 hours post-dose. Sampling was performed either manually or using automated blood samplers. Samples were collected into microtainer tubes containing EDTA as the anticoagulant and are processed to plasma by refrigerated centrifugation.

Plasma samples were extracted with 3 volumes of MeCN containing a suitable internal standard. Extracts were reconstituted into 3 volumes of water containing 1% formic acid, and analyzed via HPLC-coupled MS/MS. Plasma concentration-time data were analyzed using the Phoenix software (Pharsight Corp., St. Louis, Mo.) to calculate pharmacokinetic parameters.

Compounds of the invention of particular interest were those having a % F>10%, when tested in this assay. These include the following compounds:

| Example | Example | Example | Example |
| --- | --- | --- | --- |
| 1 | 2-16 | 14b | 30-4 |
| 2-1 | 3 | 16-10 | 30-6 |
| 2-2 | 5 | 16-23 | 30-12 |
| 2-6 | 7-1 | 16-24 | 52-1 |
| 2-8 | 7-2 | 16-32 | 69b |
| 2-9 | 7-4 | 21-1 | 84a |
| 2-13 | 14a | 29 | 91a |
| 2-15 | | | |

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A compound of formula I:

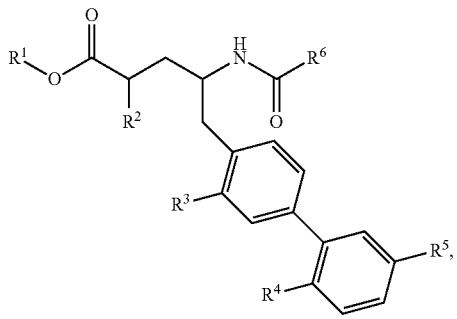

where:

R$^1$ is H, —C$_{1-8}$alkyl, —CH(CH$_3$)OC(O)—O-cyclohexyl, —(CH$_2$)$_2$-morpholinyl, or —CH$_2$-5-methyl-[1,3]dioxol-2-one;

R$^2$ is —C$_{0-3}$alkylene-NR$^{22}$R$^{23}$, R$^{22}$ is H or —C$_{1-6}$alkyl; R$^{23}$ is H, —C$_{1-6}$alkyl, —C$_{1-6}$alkyl substituted with 1 to 6 fluoro atoms, —SO$_2$—C$_{1-6}$alkyl, —CH$_2$OC(O)—C$_{1-6}$ alkyl, —C$_{2-4}$alkylene-OH, —C$_{2-4}$alkylene-O—CH$_3$, or cyclopropyl optionally substituted with one or two R$^{31}$ groups; or R$^{22}$ and R$^{23}$ are taken together to form —(CH$_2$)$_2$—O—(CH$_2$)$_2$—, a 2-oxa-6-aza-spiro[3.3]heptane ring, or an azetidine ring optionally substituted with one or two R$^{31}$ groups; and each R$^{31}$ is independently halo, —C$_{1-6}$alkyl, —C$_{0-2}$alkylene-OH, —C$_{0-2}$alkylene-OC$_{1-6}$alkyl, —CN, or —CONH$_2$;

R$^3$, R$^4$ and R$^5$ are independently H or halo;

R$^6$ is a heterocycle selected from the group consisting of 3H-oxazol-2-one, [1,2,4]oxadiazol-5-one, [1,2,3,5]oxatriazole, dihydro-[1,2,4]triazol-3-one, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an R$^{60}$ group selected from the group consisting of —OH, —(CH$_2$)$_2$OH, —C$_{0-2}$alkylene-O—C$_{1-6}$alkyl, —C$_{1-6}$alkyl, —CHF$_2$, —CF$_3$, and phenyl; and each carbon atom in the heterocycle is unsubstituted or substituted with an R$^{61}$ group independently selected from the group consisting of halo, —OH, —C$_{1-6}$alkyl, —C$_{0-2}$alkylene-O—C$_{1-6}$ alkyl, —C(O)CH$_3$, —C(O)NH(CH$_3$), —C(O)N(CH$_3$)$_2$, —C$_{3-6}$cycloalkyl, —CF$_3$, —CH$_2$SO$_2$CH$_3$, —NH$_2$, —CH$_2$NH$_2$, —CH$_2$N(CH$_3$)$_2$, pyrazine, and phenyl substituted with methyl or halo;

or a pharmaceutically acceptable salt thereof.

2. The compound of claim 1, where R$^1$ is H, —CH$_2$CH$_3$, —CH(CH$_3$)$_2$, —(CH$_2$)$_3$CH$_3$, or —(CH$_2$)$_5$CH$_3$.

3. The compound of claim 1, where R$^2$ is —NH$_2$, —CH$_2$NH$_2$, —CH(CH$_3$)NH$_2$, —C(CH$_3$)$_2$NH$_2$, —(CH$_2$)$_2$NH$_2$, —(CH$_2$)$_3$NH$_2$, —CH$_2$NH(CH$_3$), —CH$_2$N(CH$_3$)$_2$, —CH$_2$NH—CH$_2$CH$_2$F, —CH$_2$NH—CH$_2$CHF$_2$, —NH—SO$_2$CH$_3$, —NHCH$_2$OC(O)CH(CH$_3$)$_2$, —CH$_2$NHCH$_2$OC(O)CH(CH$_3$)$_2$, —CH$_2$—NH—(CH$_2$)$_2$—OH, —CH$_2$—NH—(CH$_2$)$_3$—OH, —CH$_2$—NH—(CH$_2$)$_2$—O—CH$_3$, —CH$_2$—N(CH$_3$)—(CH$_2$)$_2$—O—CH$_3$, —CH$_2$—NH—(CH$_2$)$_3$—O—CH$_3$,

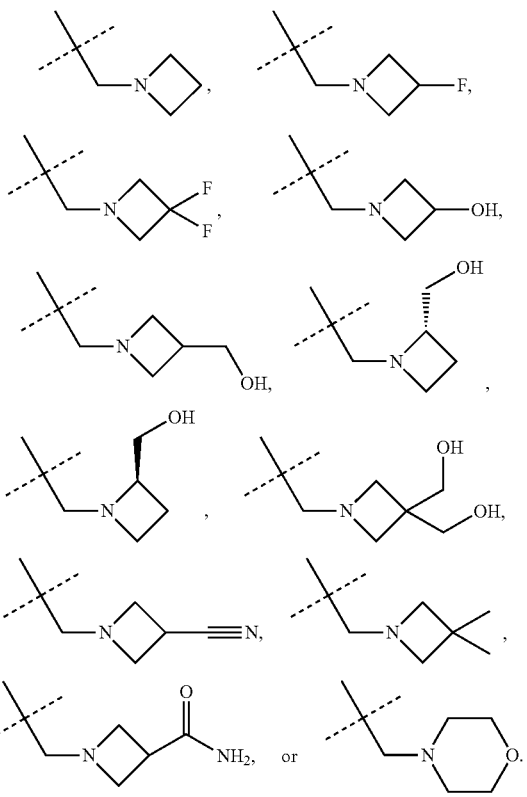

4. The compound of claim 3, where R$^2$ is —NH$_2$, —CH$_2$NH$_2$, —(CH$_2$)$_2$NH$_2$, —CH$_2$N(CH$_3$)$_2$, —CH$_2$NH—CH$_2$CH$_2$F, —CH$_2$NH—CH$_2$CHF$_2$, —NH—SO$_2$CH$_3$, —CH$_2$—NH—(CH$_2$)$_2$—OH, —CH$_2$—NH—(CH$_2$)$_2$—O—CH$_3$, —CH$_2$—N(CH$_3$)—(CH$_2$)$_2$—O—CH$_3$, —CH$_2$—NH—(CH$_2$)$_3$—O—CH$_3$,

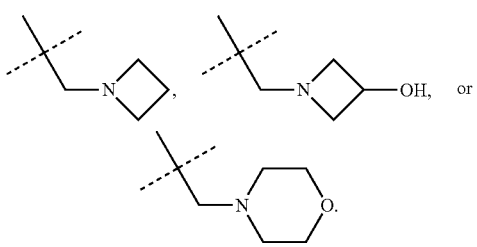

5. The compound of claim 3, where R$^2$ is —C(CH$_3$)$_2$NH$_2$, —CH$_2$—NH—(CH$_2$)$_3$—OH,

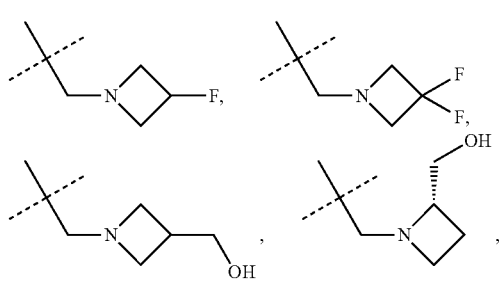

-continued

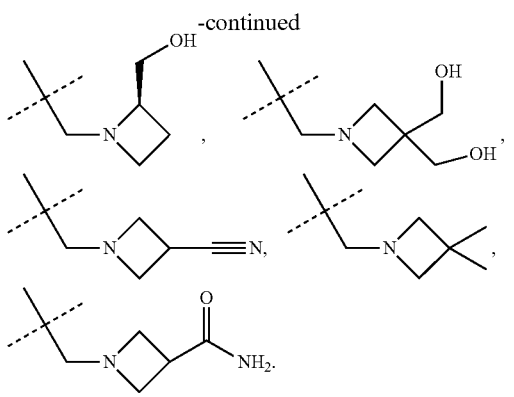

6. The compound of claim 1, where $R^2$ is —CH$_2$—N(CH$_3$)—(CH$_2$)$_2$—OH, —NH—(CH$_2$)$_2$—O—CH$_3$, —NH—(CH$_2$)$_3$—O—CH$_3$,

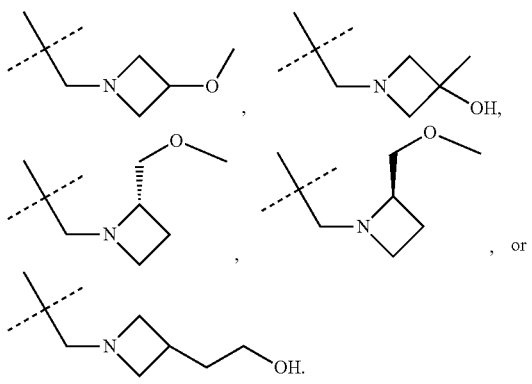

7. The compound of claim 1, where $R^3$ is H or Cl.
8. The compound of claim 1, where $R^4$ is H or F.
9. The compound of claim 1, where $R^5$ is H or Cl.
10. The compound of claim 1, where $R^3$ is H, $R^4$ is F, and $R^5$ is Cl; or $R^3$ and $R^4$ are H and $R^5$ is Br or Cl; or $R^3$, $R^4$, and $R^5$ are H; or $R^3$ is Cl, $R^4$ is F, and $R^5$ is Cl; or $R^3$ is H, $R^4$ is F, and $R^5$ is H.
11. The compound of claim 10, where $R^3$ is H, $R^4$ is F, and $R^5$ is Cl; or $R^3$ and $R^4$ are H, and $R^5$ is Cl; or $R^3$, $R^4$, and $R^5$ are H; or $R^3$ is Cl, $R^4$ is F, and $R^5$ is Cl; or $R^3$ is H, $R^4$ is F, and $R^5$ is H.
12. The compound of claim 1, where $R^6$ is 3H-oxazol-2-one, 4H-[1,2,4]oxadiazol-5-one, [1,2,3,5]oxatriazole, [1,2,4]triazolo[1,5-α]pyridine, [1,2,3]triazole, [1,2,4]triazole, pyrazole, imidazole, oxazole, isoxazole, isothiazole, pyridine, oxadiazole, or pyrimidine.
13. The compound of claim 12, where $R^6$ is 3H-oxazol-2-one, 4H-[1,2,4]oxadiazol-5-one, [1,2,4]triazolo[1,5-α]pyridine, [1,2,3]triazole, [1,2,4]triazole, pyrazole, oxazole, isoxazole, isothiazole, pyridine, or pyrimidine.
14. The compound of claim 1, where the nitrogen atoms in the heterocycle are unsubstituted.
15. The compound of claim 1, where $R^{60}$ is —OH, —(CH$_2$)$_2$OH, —OCH$_3$, —OCH$_2$CH$_3$, —CH$_3$, —CHF$_2$, or —CF$_3$.
16. The compound of claim 1, where $R^{60}$ is phenyl.
17. The compound of claim 1, where the carbon atoms in the heterocycle are unsubstituted.
18. The compound of claim 1, where $R^{61}$ is chloro, fluoro, —OH, —CH$_3$, —CH$_2$CH$_3$, —(CH$_2$)$_2$CH$_3$, —CH(CH$_3$)$_2$, —OCH$_3$, —OCH$_2$CH$_3$, —CH$_2$—OCH$_3$, —C(O)CH$_3$, —C(O)NH(CH$_3$), —C(O)N(CH$_3$)$_2$, cyclopropyl, —CF$_3$, —CH$_2$SO$_2$CH$_3$, —NH$_2$, —CH$_2$NH$_2$, —CH$_2$N(CH$_3$)$_2$, pyrazine, or phenyl substituted with methyl or fluoro.
19. The compound of claim 18, where $R^{61}$ is chloro, fluoro, —OH, —CH$_3$, —CH$_2$CH$_3$, —(CH$_2$)$_2$CH$_3$, —CH(CH$_3$)$_2$, —OCH$_3$, —OCH$_2$CH$_3$, —C(O)CH$_3$, —C(O)NH(CH$_3$), —C(O)N(CH$_3$)$_2$, cyclopropyl, —CF$_3$, or phenyl substituted with methyl or fluoro.
20. The compound of claim 1, where a first carbon atom in the heterocycle is substituted with an $R^{61}$ group selected from the group consisting of fluoro, —OH, —CH$_3$, —C$_{0-2}$alkylene-O—C$_{1-6}$alkyl, —C(O)CH$_3$, —C$_{3-6}$cycloalkyl, —CF$_3$, —CH$_2$SO$_2$CH$_3$, —NH$_2$, and —CH$_2$N(CH$_3$)$_2$; and a second carbon atom in the heterocycle is substituted with an $R^{61}$ group selected from the group consisting of halo, —OH, —CH$_3$, —O—CH$_2$CH$_3$, —C(O)CH$_3$, cyclopropyl, —CF$_3$, —CH$_2$SO$_2$CH$_3$, —NH$_2$, —CH$_2$N(CH$_3$)$_2$, and phenyl substituted with methyl or halo.
21. The compound of claim 20, where a first carbon atom in the heterocycle is substituted with an $R^{61}$ group selected from the group consisting of fluoro and —CH$_3$; and a second carbon atom in the heterocycle is substituted with an $R^{61}$ group selected from the group consisting of —CH$_3$, —O—CH$_2$CH$_3$, cyclopropyl, and phenyl substituted with methyl.
22. A pharmaceutical composition comprising a pharmaceutically acceptable carrier and the compound of claim 1.
23. The pharmaceutical composition of claim 22, further comprising a therapeutic agent selected from the group consisting of adenosine receptor antagonists, α-adrenergic receptor antagonists, β$_1$-adrenergic receptor antagonists, β$_2$-adrenergic receptor agonists, dual-acting β-adrenergic receptor antagonist/α$_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, antidiabetic agents, antidiarrheal agents, anti-glaucoma agents, anti-lipid agents, antinociceptive agents, anti-thrombotic agents, AT$_1$ receptor antagonists and dual-acting AT$_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, and vasopressin receptor antagonists, or combinations thereof.
24. The pharmaceutical composition of claim 23, wherein the therapeutic agent is an AT$_1$ receptor antagonist.
25. A method for treating hypertension, heart failure, or renal disease, comprising administering to a patient having said hypertension, heart failure, or renal disease, a therapeutically effective amount of the compound of claim 1.

\* \* \* \* \*